(12) United States Patent
Iwakuma et al.

(10) Patent No.: US 9,126,887 B2
(45) Date of Patent: Sep. 8, 2015

(54) ORGANIC ELECTROLUMINESCENT ELEMENT MATERIAL AND ORGANIC ELECTROLUMINESCENT ELEMENT COMPRISING SAME

(75) Inventors: Toshihiro Iwakuma, Chiba (JP); Yoriyuki Takashima, Chiba (JP); Toshinari Ogiwara, Chiba (JP)

(73) Assignee: IDEMITSU KOSAN CO., LTD., Tokyo (JP)

(*) Notice: Subject to any disclaimer, the term of this patent is extended or adjusted under 35 U.S.C. 154(b) by 350 days.

(21) Appl. No.: 13/143,097

(22) PCT Filed: Dec. 25, 2009

(86) PCT No.: PCT/JP2009/071675
§ 371 (c)(1),
(2), (4) Date: Aug. 30, 2011

(87) PCT Pub. No.: WO2010/076878
PCT Pub. Date: Jul. 8, 2010

(65) Prior Publication Data
US 2011/0303907 A1 Dec. 15, 2011

(30) Foreign Application Priority Data
Jan. 5, 2009 (JP) .................. 2009-000332

(51) Int. Cl.
*H01L 51/54* (2006.01)
*C07C 13/60* (2006.01)
(Continued)

(52) U.S. Cl.
CPC ............... *C07C 13/66* (2013.01); *C07C 15/20* (2013.01); *C07C 15/30* (2013.01); *C07C 15/38* (2013.01);
(Continued)

(58) Field of Classification Search
None
See application file for complete search history.

(56) References Cited

U.S. PATENT DOCUMENTS

2004/0151943 A1* 8/2004 Lee et al. ............... 428/690
2007/0252516 A1* 11/2007 Kondakova et al. ....... 313/504
(Continued)

FOREIGN PATENT DOCUMENTS

JP   2005 302657   10/2005
JP   2007 84485    4/2007
(Continued)

OTHER PUBLICATIONS

International Search Report issued Mar. 9, 2010 in PCT/JP09/071675 filed Dec. 25, 2009.

*Primary Examiner* — J. L. Yang
(74) *Attorney, Agent, or Firm* — Oblon, McClelland, Maier & Neustadt, L.L.P.

(57) ABSTRACT

A material for organic electroluminescent devices including a 2,7-disubstituted naphthalene ring in its molecule of formulas (1) and (2):

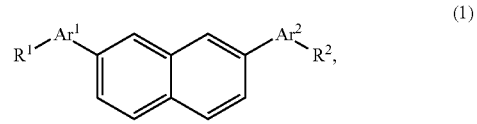

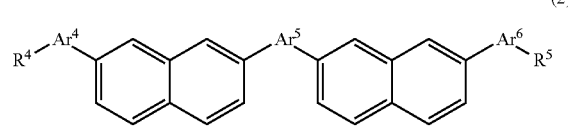

and an organic electroluminescent device including an organic thin film layer having one or more layers between a cathode and an anode. An organic electroluminescence device having the organic thin film layer which includes the material for organic electroluminescent devices and at least one kind of phosphorescent emitting materials has long lifetime and high current efficiency.

27 Claims, 1 Drawing Sheet

(51) Int. Cl.

| | |
|---|---|
| *C07C 13/48* | (2006.01) |
| *C07D 307/91* | (2006.01) |
| *C07C 13/66* | (2006.01) |
| *C07C 15/20* | (2006.01) |
| *C07C 15/30* | (2006.01) |
| *C07C 15/38* | (2006.01) |
| *C07D 407/10* | (2006.01) |
| *C09K 11/06* | (2006.01) |
| *H01L 51/00* | (2006.01) |
| *H05B 33/14* | (2006.01) |
| *H01L 51/50* | (2006.01) |

(52) U.S. Cl.
CPC ............ *C07D 307/91* (2013.01); *C07D 407/10* (2013.01); *C09K 11/06* (2013.01); *H01L 51/0058* (2013.01); *H01L 51/0065* (2013.01); *H05B 33/14* (2013.01); *C07C 2102/28* (2013.01); *C07C 2103/26* (2013.01); *C07C 2103/42* (2013.01); *C07C 2103/52* (2013.01); *C09K 2211/1011* (2013.01); *H01L 51/5016* (2013.01)

(56) References Cited

U.S. PATENT DOCUMENTS

| | | | |
|---|---|---|---|
| 2008/0224603 A1* | 9/2008 | Hashimoto et al. | 313/504 |
| 2008/0286611 A1 | 11/2008 | Muratsubaki et al. | |
| 2009/0108734 A1* | 4/2009 | Begley et al. | 313/504 |
| 2009/0230852 A1* | 9/2009 | Lee et al. | 313/504 |

FOREIGN PATENT DOCUMENTS

| | | |
|---|---|---|
| JP | 2008 255099 | 10/2008 |
| JP | 2008 280312 | 11/2008 |
| JP | 2009 212201 | 9/2009 |
| JP | 2009 272144 | 11/2009 |

\* cited by examiner

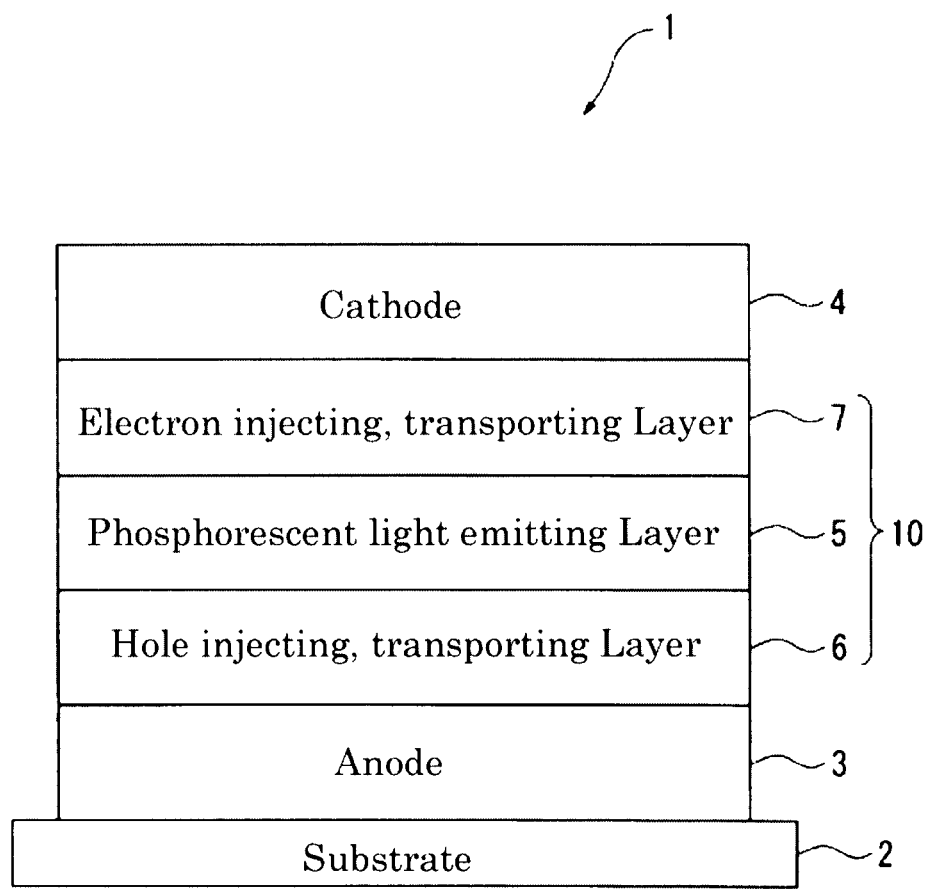

ORGANIC ELECTROLUMINESCENT ELEMENT MATERIAL AND ORGANIC ELECTROLUMINESCENT ELEMENT COMPRISING SAME

TECHNICAL FIELD

The present invention relates to a material for organic electroluminescence devices and an organic electroluminescence device (hereinafter, sometimes referred to as "organic EL device") using the material, in particular, a material for organic electroluminescence devices each including a red-emitting layer and an organic electroluminescence device using the material.

BACKGROUND ART

An organic electroluminescence device, which has an organic thin film layer including a light emitting layer between an anode and a cathode and which emits light from an exciton energy resulted from the recombination of holes and electrons injected into the light emitting layer, has been known.

Sine the organic electroluminescence device is a spontaneous emitting device, it has been expected to be applicable, using its advantages, to a light emitting device with high current efficiency, high image quality, low power consumption and wide design freedom for thinner products.

The organic electroluminescence device has been still required to be further improved in its properties, for example, in the current efficiency.

In this regard, to enhance the internal quantum efficiency, a light emitting material (phosphorescent emitting material) which emits light from triplet exciton has been developed, and a phosphorescent organic electroluminescence device are reported in recent years.

By forming a light emitting layer (phosphorescent emitting layer) using the above phosphorescent emitting material, an internal quantum efficiency of 75% or more, theoretically about 100% is obtained, to realize an organic electroluminescence device having high efficiency and low power consumption.

Further, a doping method in which a light emitting material is doped as a dopant into a host material for forming a light emitting layer is known.

In a doped light emitting layer, excitons can be efficiently generated from charges injected into a host material. The exciton energy of generated excitons is transferred to a dopant, and this allows the dopant to emit light in high efficiency.

To intermolecularly transfer the energy from a host material to a phosphorescent dopant, the excited triplet energy $Eg_H$ of the host material has to be larger than the excited triplet energy $Eg_D$ of the phosphorescent dopant.

CBP (4,4'-bis(N-carbazolyl)biphenyl) is a well known material which has an effectively large excited triplet energy (Patent Document 1).

If CBP is used as a host material, the energy can be transferred to a phosphorescent dopant which emits light with a specific wavelength (for example, green and red), and an organic electroluminescence device having high efficiency can be obtained.

When CBP is used as a host material, the current efficiency is drastically enhanced by phosphorescent emission on one hand, but the lifetime is very short to make the device unsuitable for practical use on the other hand.

This may be because that CBP has a molecular structure less resistant to oxidation and therefore its molecule is largely degraded by holes.

Patent Document 2 discloses a technique in which a condensed ring derivative having a nitrogen-containing ring such as carbazole is used as a host material for a red-emitting phosphorescent layer. This technique enables the improvement of current efficiency and lifetime, but is not satisfactory for practical application in some cases.

A wide variety of fluorescent host materials (fluorescent hosts) for a fluorescent dopant is known, and various host materials which can form, in combination with a fluorescent dopant, a fluorescent layer excellent in current efficiency and lifetime are proposed.

The excited singlet energy Eg (S) of a fluorescent host is larger than that of a fluorescent dopant, but its excited triplet energy Eg (T) is not necessarily large. Therefore, the fluorescent host cannot be simply used as a host material (phosphorescent host) for a phosphorescent emitting layer.

For example, an anthracene derivative is well known as a fluorescent host. However, the excited triplet energy Eg (T) of anthracene derivative is as relatively small as about 1.9 eV. Therefore, the energy transfer to a phosphorescent dopant having an emission wavelength in a visible light region of 520 to 720 nm can not be secured. Further, the anthracene derivative cannot confine the excited triplet energy within a light emitting layer.

Therefore, the anthracene derivative is unsuitable as a phosphorescent host.

Further, perylene derivatives, pyrene derivatives and naphthacene derivatives are not preferred as a phosphorescent host for the same reason.

Patent Document 3 proposes to use an aromatic hydrocarbon compound as a phosphorescent host, which has a central benzene skeleton having two aromatic substituents at its meta positions.

However, the aromatic hydrocarbon compound described in Patent Document 3 has a molecular structure which bilaterally symmetrically extends with respect to the central benzene skeleton. Therefore, the light emitting layer would be likely to crystallize.

Patent Documents 4 to 9 disclose organic electroluminescence devices each employing an aromatic hydrocarbon compound. However, these documents are completely silent about the effectiveness of these compounds as a phosphorescent host.

Further, Patent Document 10 discloses a compound having a naphthalene ring substituted at its 2- and 7-positions with condensed aromatic hydrocarbon rings. Patent Document 11 discloses a compound having a naphthalene ring substituted at its 2- and 7-positions with nitrogen-containing heterorings such as phenanthroline rings. Patent Document 12 discloses a compound having a naphthalene ring substituted at its 2- and 7-positions with aromatic substituents each essentially having an anthracene ring.

PRIOR ART DOCUMENTS

Patent Documents

Patent Document 1: US 2002/182441
Patent Document 2: WO 2005/112519
Patent Document 3: JP 2003-142267A
Patent Document 4: WO 2007/046658
Patent Document 5: JP2006-151966A
Patent Document 6: JP2005-8588A
Patent Document 7: JP2005-19219A
Patent Document 8: JP2005-197262A
Patent Document 9: JP2004-75567A
Patent Document 10: US 2008/0224603
Patent Document 11: JP 2004-281390A
Patent Document 12: JP 2006-045503A

DISCLOSURE OF THE INVENTION

Problems to be Solved by the Invention

The inventors have found that the film of the compound described in Patent Document 10 is less stable, because the highly planar aromatic hydrocarbon rings which are composed of four or more rings and bilaterally symmetrically positioned at 2- and 7-positions of the naphthalene ring increase the intermolecular overlap to make the compound highly crystallizable. The inventors have further found that since the anthracene ring of the compound described in Patent Document 12 has an excited triplet energy of 1.9 eV or less, the energy level is too small for a phosphorescent device and the compound cannot ensure an efficient organic electroluminescent emission even for red emission of low energy, particularly when used as a host for a phosphorescent emitting material in a light emitting layer.

As described above, a host material capable of efficiently transferring energy to a phosphorescent emitting material and having a long practical lifetime has not yet been known, thereby preventing the application of the phosphorescent emitting material to practical devices.

An object of the invention is to provide a material for a highly efficient phosphorescent organic electroluminescence device with long lifetime and an organic electroluminescence device using the material.

Means for Solving the Problems

As a result of extensive research for achieving the above object, the inventors have found that a phosphorescent organic electroluminescence device with high efficiency and long lifetime is obtained by using a material for organic electroluminescence devices (which may hereinafter be referred to as "material for organic EL devices") represented by the following formula (1) or (2). The present invention is based on this finding.

The present invention provides:
1. A material for organic electroluminescence devices represented by formula (1):

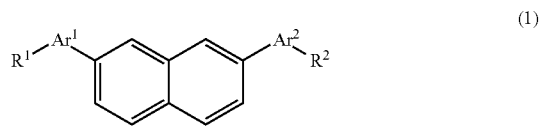

(1)

wherein $R^2$ represents a hydrogen atom, a benzene ring, a condensed aromatic hydrocarbon ring, a dibenzofuran ring or a group represented by $—Ar^3—R^3$;

$Ar^1$ to $Ar^3$ each independently represent a benzene ring, a condensed aromatic hydrocarbon ring or a dibenzofuran ring;

$R^1$ and $R^3$ each independently represent a hydrogen atom, a benzene ring, a condensed aromatic hydrocarbon ring, or a dibenzofuran ring;

the condensed aromatic hydrocarbon ring represented by $R^1$ to $R^3$ and $Ar^1$ to $Ar^3$ is selected from the group consisting of a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring; and $R^1$ to $R^3$, $Ar^1$ to $Ar^3$ and 2,7-disubstituted naphthalene ring each independently may have one or more substituents;

with the proviso that:

when each of $Ar^1$ and $Ar^2$ represents a condensed aromatic hydrocarbon constituted by four or more rings, $Ar^1$ and $Ar^2$ are different from each other;

when each of $Ar^1$ and $Ar^2$ represents a benzene ring, $R^1$ and $R^2$ cannot both be a hydrogen atom or a naphthalene ring at the same time;

when each of $R^1$ and $R^2$ represents a hydrogen atom, $Ar^1$ and $Ar^2$ cannot both be a naphthalene ring at the same time or a combination of a naphthalene ring and a benzene ring; and a material represented by any one of formulae (x-1) to (x-16) is excluded:

(x-1)

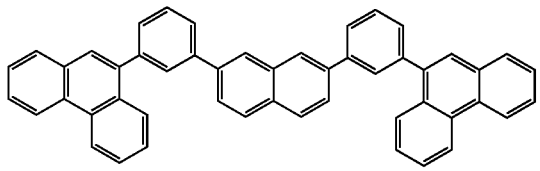

(x-2)

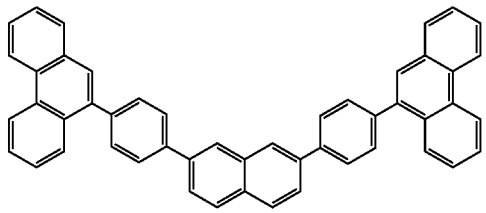

(x-3)

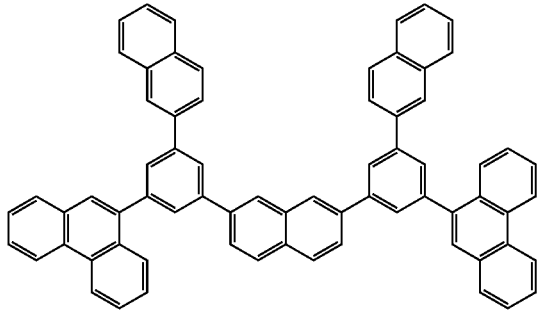

(x-4)

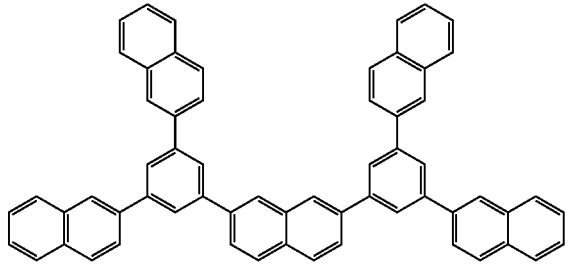

-continued
(x-5)
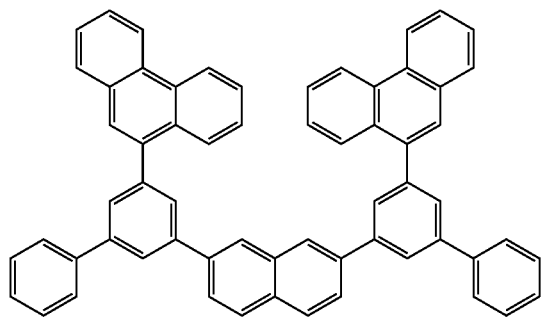
(x-6)
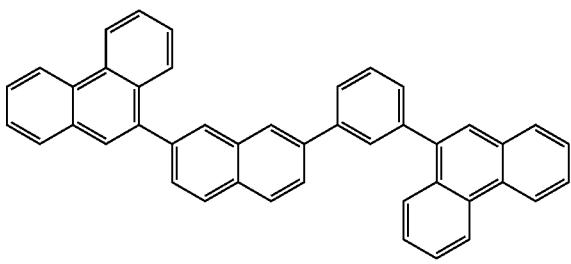
(x-7)
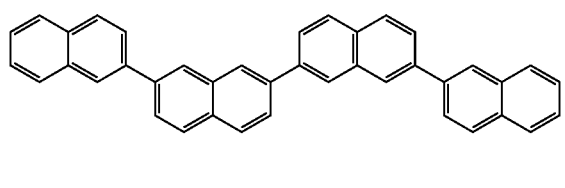
(x-8)
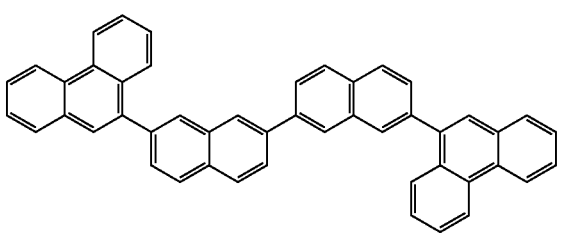
(x-9)
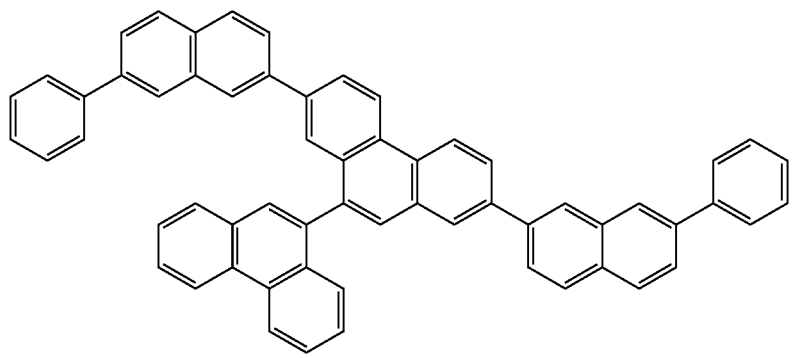
(x-10)
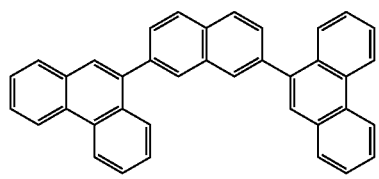
(x-11)
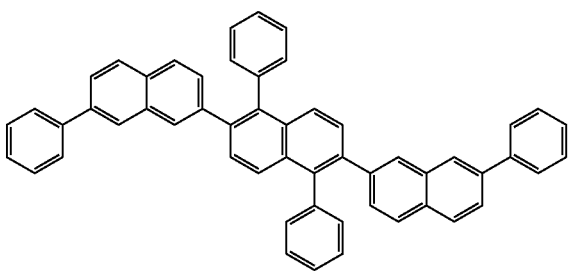
(x-12)
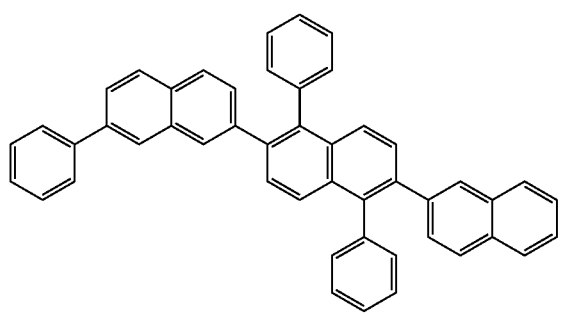
(x-13)
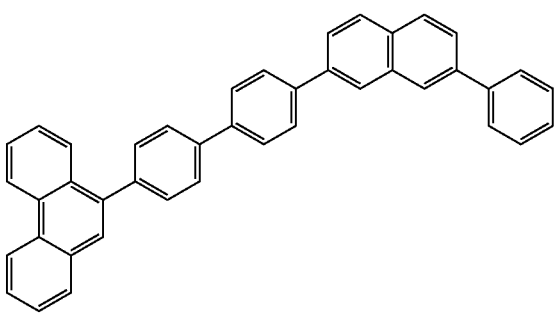

(x-14)

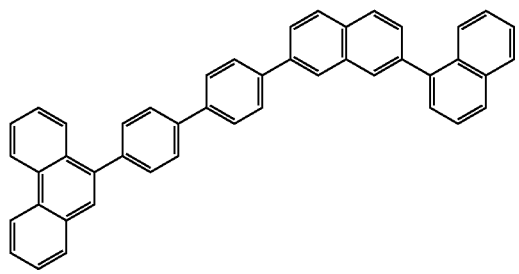

(x-15)

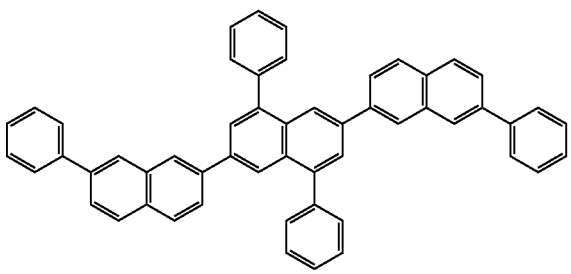

(x-16)

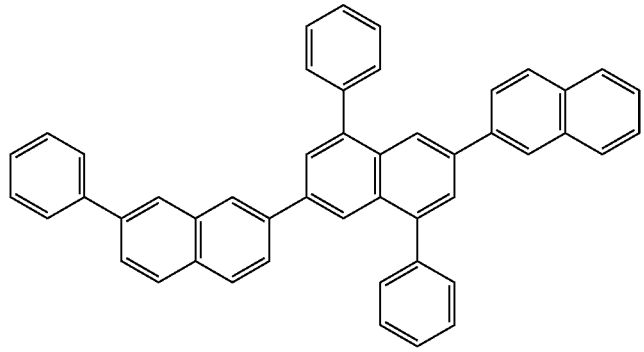

;

2. The material for organic electroluminescence devices 1, wherein the optional substituent of $R^1$ to $R^3$, $Ar^1$ to $Ar^3$, and the 2,7-disubstituted naphthalene ring is an aryl group having 6 to 14 carbon atoms other than an anthracene ring, an alkyl group having 1 to 20 carbon atoms, a haloalkyl group having 1 to 20 carbon atoms, a cycloalkyl group having 5 to 18 carbon atoms, or a silyl group having 3 to 20 carbon atoms;

3. The material for organic electroluminescence devices 1 or 2, wherein $Ar^1$ and $Ar^2$ each independently represent a benzene ring or the condensed aromatic hydrocarbon ring;

4. The material for organic electroluminescence devices 3, wherein $Ar^1$ and $Ar^2$ represent condensed aromatic hydrocarbon rings different from each other;

5. The material for organic electroluminescence devices 3, wherein $Ar^1$ is a ring selected from a phenanthrene ring, a fluoranthene ring, a benzophenanthrene ring, and a benzochrysene ring;

6. The material for organic electroluminescence devices 5, wherein $Ar^1$ represents a ring selected from a phenanthrene ring, a fluoranthene ring, a benzophenanthrene ring, and a benzochrysene ring; and $Ar^2$ represents a benzene ring or a naphthalene ring;

7. The material for organic electroluminescence devices 5, wherein $Ar^1$ and $Ar^2$ each independently represent a ring selected from a phenanthrene ring, a fluoranthene ring, a benzophenanthrene ring, and a benzochrysene ring; and $Ar^1$ and $Ar^2$ represent rings different from each other;

8. A material for organic electroluminescence devices represented by formula (2):

(2)

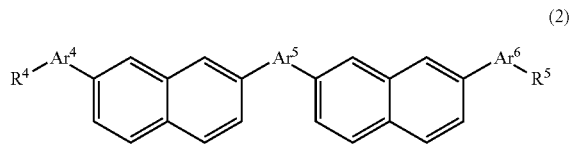

wherein $Ar^4$ to $Ar^6$ each independently represent a benzene ring, a condensed aromatic hydrocarbon ring, or a dibenzofuran ring;

$R^4$ and $R^5$ each independently represent a hydrogen atom, a benzene ring, a condensed aromatic hydrocarbon ring, or a dibenzofuran ring;

the condensed aromatic hydrocarbon rings represented by $R^4$, $R^5$, and $Ar^4$ to $Ar^6$ are each independently selected from a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring;

$R^4$, $R^5$, $Ar^4$ to $Ar^6$, and two 2,7-disubstituted naphthalene rings may each independently have one or more substituents; and when $Ar^5$ represents a benzene ring, $Ar^4$ and $Ar^6$ cannot both be a benzene ring at the same time;

9. The material for organic electroluminescence devices 8, wherein when $Ar^5$ of formula (2) represents a benzene ring, $Ar^4$ and $Ar^6$ each independently represent a condensed aromatic hydrocarbon ring selected from a chrysene ring, a fluoranthene ring, a benzophenanthrene ring, a dibenzophenanthrene ring, a benzotriphenylene ring, a benzochrysene ring, a benzo[b]fluoranthene ring, and a picene ring;

10. The material for organic electroluminescence devices 8, wherein when $Ar^5$ of formula (2) represents a benzene ring, $Ar^4$ and $Ar^6$ represent condensed aromatic hydrocarbon rings different from each other;

11. The material for organic electroluminescence devices 8, wherein the optional substituent of $R^4$, $R^5$, $Ar^4$ to $Ar^6$, and the 2,7-disubstituted naphthalene ring is an aryl group having 6 to 14 carbon atoms other than an anthracene ring, an alkyl group having 1 to 20 carbon atoms, a haloalkyl group having 1 to 20 carbon atoms, a cycloalkyl group having 5 to 18 carbon atoms, or a silyl group having 3 to 20 carbon atoms;

12. The material for organic electroluminescence devices 8, wherein $R^4$ and $R^5$ represent hydrogen atoms; and $Ar^4$ or $Ar^6$ represents a ring selected from a phenanthrene ring, a fluoranthene ring, a benzophenanthrene ring, and a benzochrysene ring;

13. The material for organic electroluminescence devices 8, wherein $R^4$ and $R^5$ represent hydrogen atoms; $Ar^5$ is a ring having 10 or more ring carbon atoms; and $Ar^4$ or $Ar^6$ represents a ring selected from a phenanthrene ring, a fluoranthene ring, a benzophenanthrene ring, and a benzochrysene ring;

14. The material for organic electroluminescence devices 8, wherein $Ar^5$ represents a dibenzofuran ring;

15. An organic electroluminescence device comprising an organic thin film layer formed of one or more layers between a cathode and an anode, wherein the organic thin film layer comprises a material for organic electroluminescence devices and at least one kind of a phosphorescent emitting material, the material for organic electroluminescence devices being represented by formula (1):

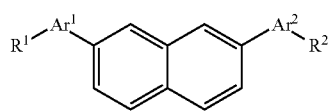

(1)

wherein $R^2$ represents a hydrogen atom, a benzene ring, a condensed aromatic hydrocarbon ring, a dibenzofuran ring or a group represented by —$Ar^3$—$R^3$;

$Ar^1$ to $Ar^3$ each independently represent a benzene ring, a condensed aromatic hydrocarbon ring or a dibenzofuran ring;

$R^1$ and $R^3$ each independently represent a hydrogen atom, a benzene ring, a condensed aromatic hydrocarbon ring, or a dibenzofuran ring;

the condensed aromatic hydrocarbon ring represented by $R^1$ to $R^3$ and $Ar^1$ to $Ar^3$ is selected from the group consisting of a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring; and $R^1$ to $R^3$, $Ar^1$ to $Ar^3$ and 2,7-disubstituted naphthalene ring each independently may have one or more substituents;

with the proviso that:

when each of $Ar^1$ and $Ar^2$ represents a condensed aromatic hydrocarbon constituted by four or more rings, $Ar^1$ and $Ar^2$ are different from each other;

when each of $Ar^1$ and $Ar^2$ represents a benzene ring, $R^1$ and $R^2$ cannot both be a hydrogen atom or a naphthalene ring at the same time;

when each of $R^1$ and $R^2$ represents a hydrogen atom, $Ar^1$ and $Ar^2$ cannot both be a naphthalene ring at the same time or a combination of a naphthalene ring and a benzene ring; and a material represented by any one of formulae (x-1) to (x-16) is excluded:

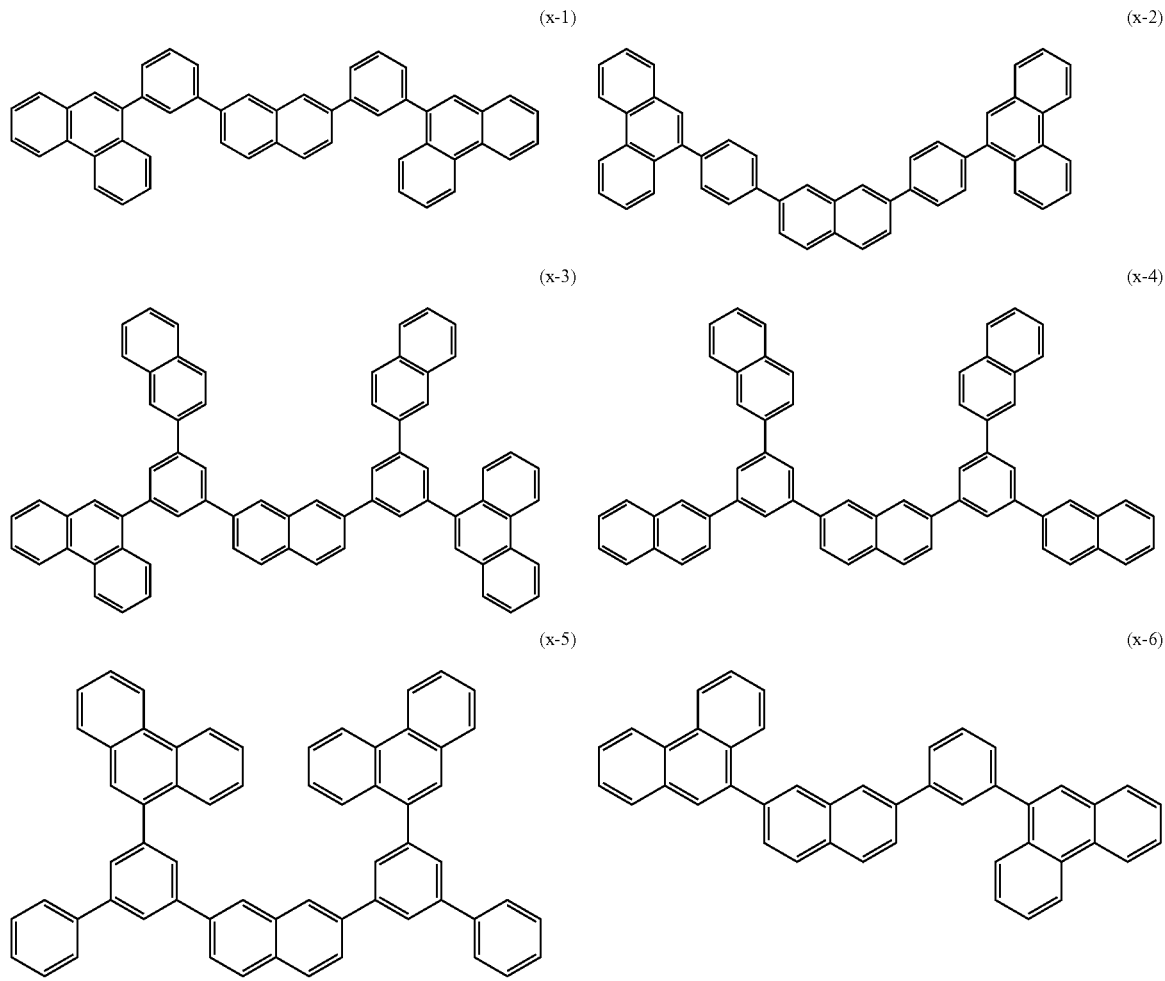

-continued
(x-7)
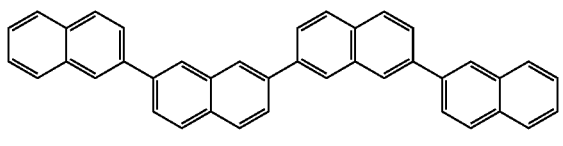
(x-8)
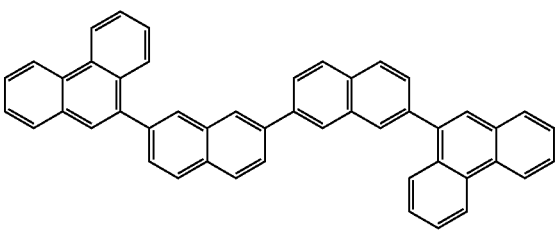
(x-9)
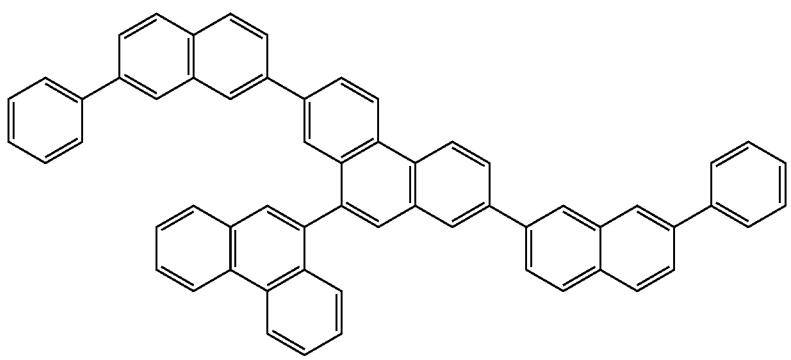
(x-10)
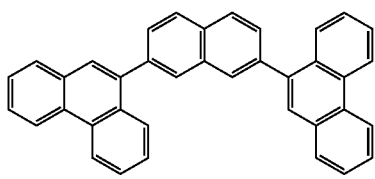
(x-11)
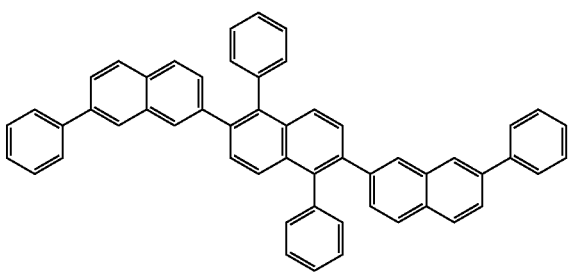
(x-12)
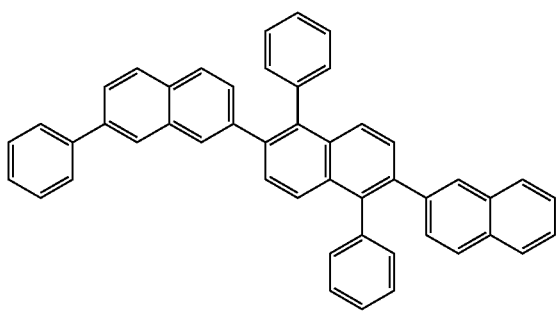
(x-13)
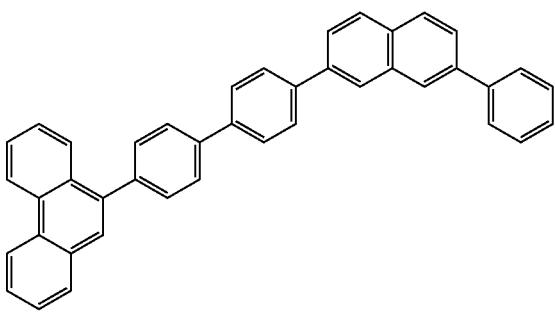
(x-14)
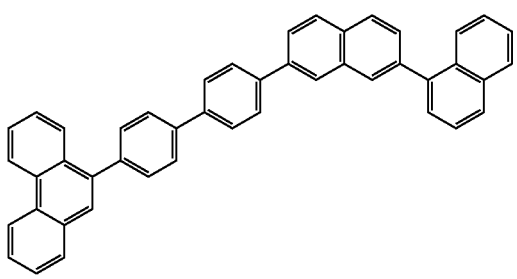
(x-15)
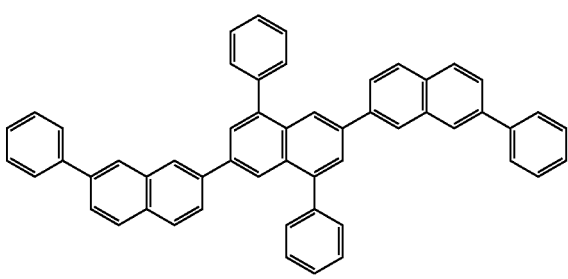

(x-16)

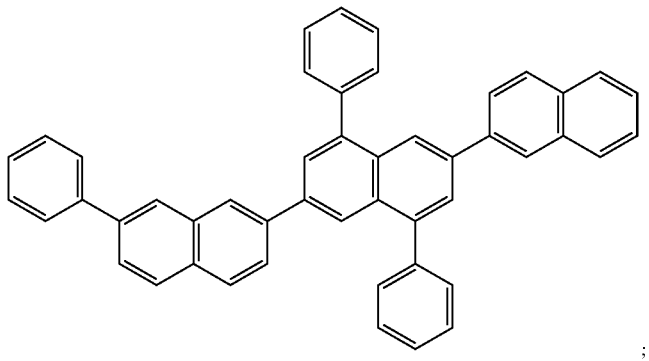

;

16. The organic electroluminescence device 15, wherein the optional substituent of $R^1$ to $R^3$, $Ar^1$ to $Ar^3$, and the 2,7-disubstituted naphthalene ring is an aryl group having 6 to 14 carbon atoms other than an anthracene ring, an alkyl group having 1 to 20 carbon atoms, a haloalkyl group having 1 to 20 carbon atoms, a cycloalkyl group having 5 to 18 carbon atoms, or a silyl group having 3 to 20 carbon atoms;

17. The organic electroluminescence device 15, wherein $Ar^1$ and $Ar^2$ each independently represent a benzene ring or the condensed aromatic hydrocarbon ring;

18. The organic electroluminescence device 17, wherein $Ar^1$ and $Ar^2$ represent condensed aromatic hydrocarbon rings different from each other;

19. The organic electroluminescence device 17, wherein $Ar^1$ is a ring selected from a phenanthrene ring, a fluoranthene ring, a benzophenanthrene ring, and a benzochrysene ring;

20. The organic electroluminescence device 19, wherein $Ar^1$ represents a ring selected from a phenanthrene ring, a fluoranthene ring, a benzophenanthrene ring, and a benzochrysene ring; and $Ar^2$ represents a benzene ring or a naphthalene ring;

21. The organic electroluminescence device 19, wherein $Ar^1$ and $Ar^2$ each independently represent a ring selected from a phenanthrene ring, a fluoranthene ring, a benzophenanthrene ring, and a benzochrysene ring; and $Ar^1$ and $Ar^2$ represent rings different from each other;

22. An organic electroluminescence device comprising an organic thin film layer formed of one or more layers between a cathode and an anode, wherein the organic thin film layer comprises a material for organic electroluminescence devices and at least one kind of a phosphorescent emitting material, the material for organic electroluminescence devices being represented by formula (2):

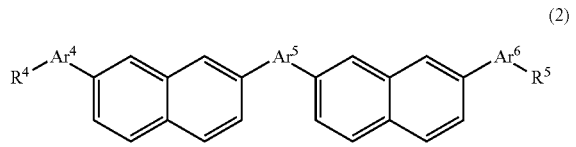

(2)

wherein $Ar^4$ to $Ar^6$ each independently represent a benzene ring, a condensed aromatic hydrocarbon ring, or a dibenzofuran ring;

$R^4$ and $R^5$ each independently represent a hydrogen atom, a benzene ring, a condensed aromatic hydrocarbon ring, or a dibenzofuran ring;

the condensed aromatic hydrocarbon rings represented by $R^4$, $R^5$, and $Ar^4$ to $Ar^6$ are each independently selected from a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring;

$R^4$, $R^5$, $Ar^4$ to $Ar^6$, and two 2,7-disubstituted naphthalene rings may each independently have one or more substituents; and when $Ar^5$ represents a benzene ring, $Ar^4$ and $Ar^6$ cannot both be a benzene ring at the same time;

23. The organic electroluminescence device 22, wherein when $Ar^5$ of formula (2) represents a benzene ring, $Ar^4$ and $Ar^6$ each independently represent a condensed aromatic hydrocarbon ring selected from a chrysene ring, a fluoranthene ring, a benzophenanthrene ring, a dibenzophenanthrene ring, a benzotriphenylene ring, a benzochrysene ring, a benzo[b]fluoranthene ring, and a picene ring;

24. The organic electroluminescence device 22, wherein when $Ar^5$ of formula (2) represents a benzene ring, $Ar^4$ and $Ar^6$ represent condensed aromatic hydrocarbon rings different from each other;

25. The organic electroluminescence device 22, wherein the optional substituent of $R^4$, $R^5$, $Ar^4$ to $Ar^6$, and the 2,7-disubstituted naphthalene ring is an aryl group having 6 to 14 carbon atoms other than an anthracene ring, an alkyl group having 1 to 20 carbon atoms, a haloalkyl group having 1 to 20 carbon atoms, a cycloalkyl group having 5 to 18 carbon atoms, or a silyl group having 3 to 20 carbon atoms;

26. The organic electroluminescence device 22, wherein $R^4$ and $R^5$ represent hydrogen atoms; and $Ar^4$ or $Ar^6$ represents a ring selected from a phenanthrene ring, a fluoranthene ring, a benzophenanthrene ring, and a benzochrysene ring;

27. The organic electroluminescence device 22, wherein $R^4$ and $R^5$ represent hydrogen atoms; $Ar^5$ is a ring having 10 or more ring carbon atoms; and $Ar^4$ or $Ar^6$ represents a ring selected from a phenanthrene ring, a fluoranthene ring, a benzophenanthrene ring, and a benzochrysene ring;

28. The organic electroluminescence 22, wherein $Ar^5$ represents a dibenzofuran ring;

29. The organic electroluminescence device 15 or 22, wherein the material for organic electroluminescence devices represented by formula (1) or (2) has an excited triplet energy of 2.0 eV or more and 2.8 eV or less;

30. The organic electroluminescence device 15 or 22, wherein the organic thin film layer comprises a light emitting layer; and at least one light emitting layer comprises the material for organic electroluminescence devices represented by formula (1) or (2) and at least one kind of a phosphorescent emitting material;

31. The organic electroluminescence device 30, wherein the phosphorescent emitting material comprises a metal complex; and the metal complex comprises a metal atom selected from Ir, Pt, Os, Au, Cu, Re, and Ru, and a ligand;

32. The organic electroluminescence device 31, wherein the ligand has an ortho-metallated bond;

33. The organic electroluminescence device 32, wherein a wavelength of a maximum emission of at least one of the phosphorescent emitting materials is 520 nm or more and 720 nm or less;

34. The organic electroluminescence device 15 or 22, wherein the organic thin film layer comprises an electron transporting layer or an electron injecting layer between the cathode and the light emitting layer; and the electron transporting layer or the electron injecting layer comprises any one of the materials for organic electroluminescence devices 1 to 10;

35. The organic electroluminescence device 15 or 22, wherein the organic thin film layer comprises an electron transporting layer or an electron injecting layer between the cathode and the light emitting layer; and the electron transporting layer or the electron injecting layer comprises an aromatic ring compound having a nitrogen-containing six- or five-membered ring or a condensed aromatic ring compound having a nitrogen-containing six- or five-membered ring; and 36. The organic electroluminescence device 15 or 22, wherein a reduction-causing dopant is added to an interfacial region between the cathode and the organic thin film layer.

Effect of the Invention

According to the present invention, a phosphorescent organic electroluminescence device with high efficiency and long lifetime is obtained by using the material for organic electroluminescence devices represented by formula (1) or (2).

BRIEF DESCRIPTION OF THE DRAWINGS

FIG. 1 is a schematic illustration showing an embodiment of architecture of the organic electroluminescence device according to the present invention.

REFERENCE NUMERALS

1: Organic electroluminescence device
2: Substrate
3: Anode
4: Cathode
5: Phosphorescent emitting layer
6: Hole injecting/transporting layer
7: Electron injecting/transporting layer
10: Organic thin film layer

EMBODIMENTS FOR CARRYING OUT THE INVENTION

The embodiment of the present invention will be described bellow.

Material for Organic Electroluminescence Devices

The present invention provides a material for organic electroluminescence devices represented by formula (1) (material (1) for organic EL devices) and a material for organic electroluminescence devices represented by formula (2) (material (2) for organic EL devices).

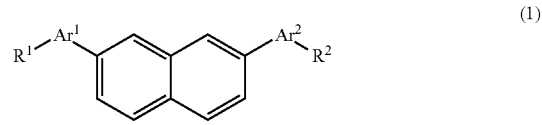

(1)

wherein $R^2$ represents a hydrogen atom, a benzene ring, a condensed aromatic hydrocarbon ring, a dibenzofuran ring or a group represented by —$Ar^3$—$R^3$;

$Ar^1$ to $Ar^3$ each independently represent a benzene ring, a condensed aromatic hydrocarbon ring or a dibenzofuran ring;

$R^1$ and $R^3$ each independently represent a hydrogen atom, a benzene ring, a condensed aromatic hydrocarbon ring, or a dibenzofuran ring;

the condensed aromatic hydrocarbon ring represented by $R^1$ to $R^3$ and $Ar^1$ to $Ar^3$ is selected from the group consisting of a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring; and $R^1$ to $R^3$, $Ar^1$ to $Ar^3$ and 2,7-disubstituted naphthalene ring each independently may have one or more substituents;

with the proviso that:

when each of $Ar^1$ and $Ar^2$ represents a condensed aromatic hydrocarbon constituted by four or more rings, $Ar^1$ and $Ar^2$ are different from each other;

when each of $Ar^1$ and $Ar^2$ represents a benzene ring, $R^1$ and $R^2$ cannot both be a hydrogen atom or a naphthalene ring at the same time;

when each of $R^1$ and $R^2$ represents a hydrogen atom, $Ar^1$ and $Ar^2$ cannot both be a naphthalene ring at the same time or a combination of a naphthalene ring and a benzene ring; and a material represented by any one of formulae (x-1) to (x-16) is excluded.

Examples of the condensed aromatic hydrocarbon ring constituted by four or more rings include a chrysene ring, a fluoranthene ring, a triphenylene ring, a benzophenanthrene ring, a dibenzophenanthrene ring, a benzotriphenylene ring, a benzochrysene ring, a benzo[b]fluoranthene ring, and a picene ring.

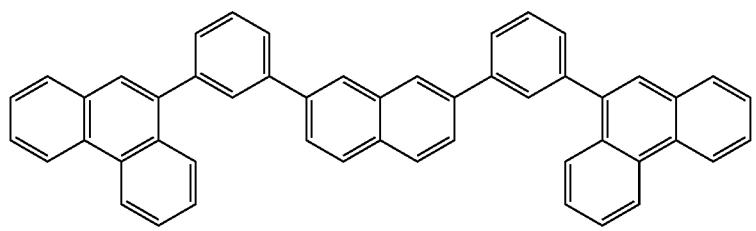

(x-1)

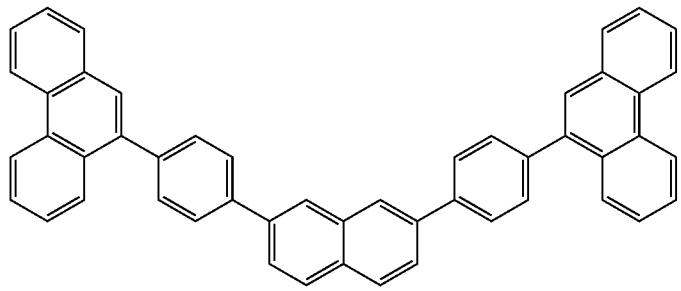
(x-2)
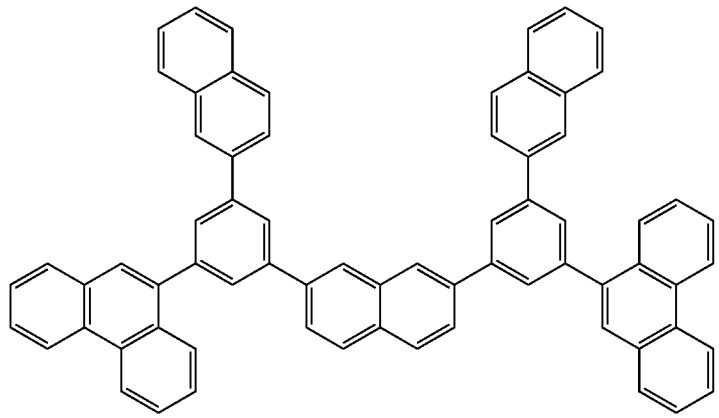
(x-3)
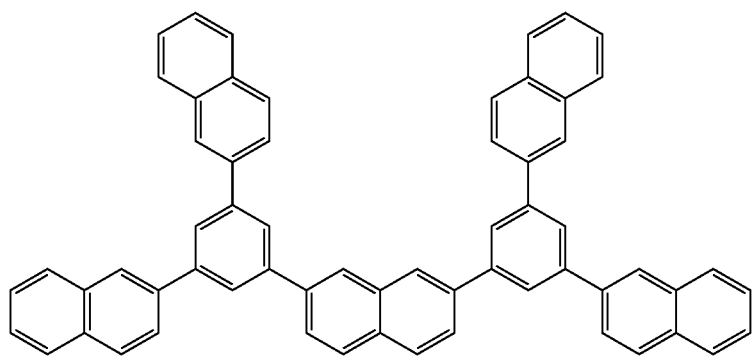
(x-4)
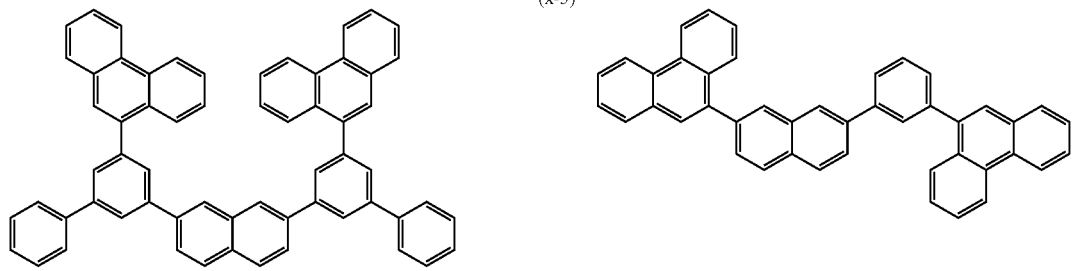
(x-5)            (x-6)
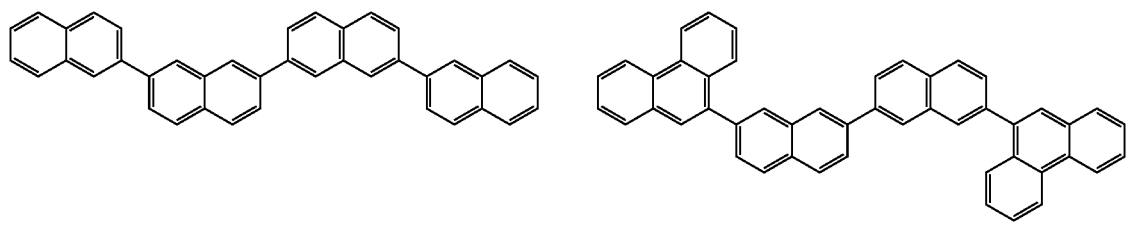
(x-7)            (x-8)

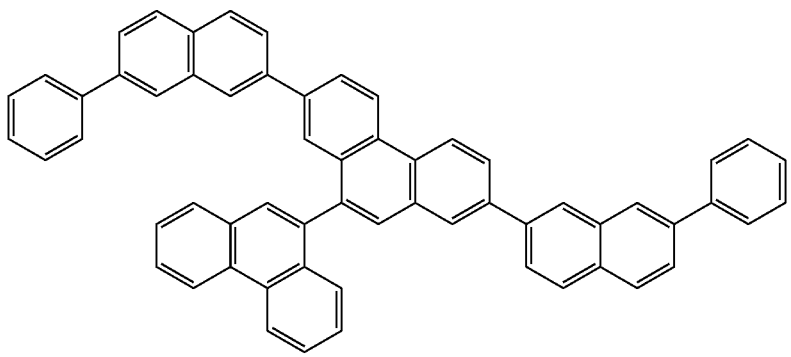
(x-9)
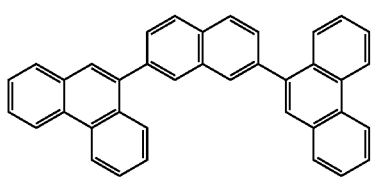
(x-10)
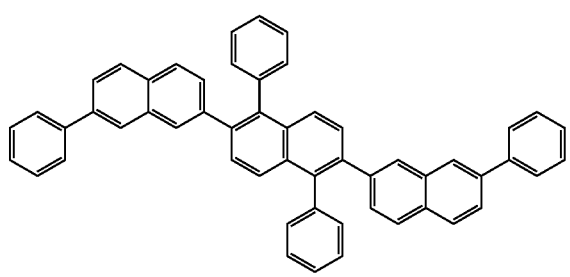
(x-11)
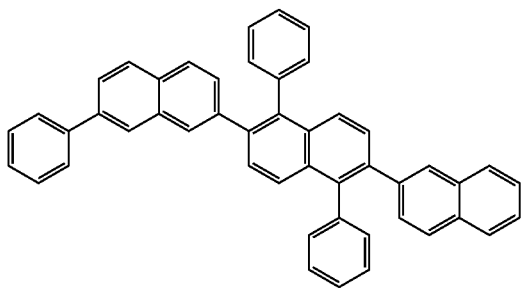
(x-12)
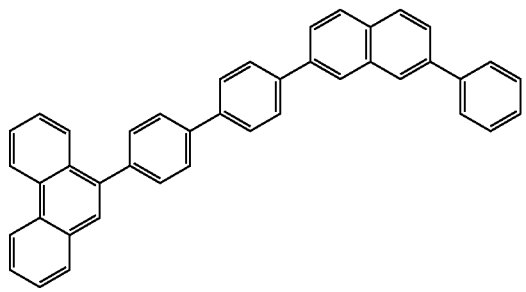
(x-13)
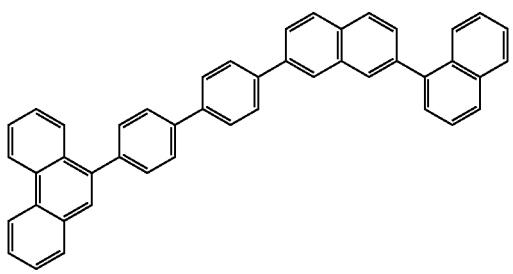
(x-14)
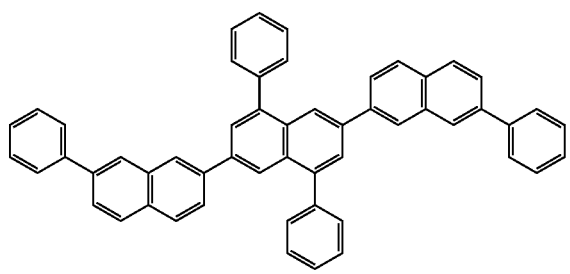
(x-15)
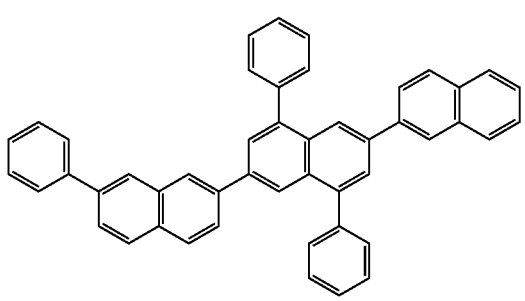
(x-16)
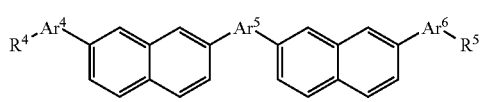
(2)

wherein $Ar^4$ to $Ar^6$ each independently represent a benzene ring, a condensed aromatic hydrocarbon ring, or a dibenzofuran ring;

$R^4$ and $R^5$ each independently represent a hydrogen atom, a benzene ring, a condensed aromatic hydrocarbon ring, or a dibenzofuran ring;

the condensed aromatic hydrocarbon rings represented by $R^4$, $R^5$, and $Ar^4$ to $Ar^6$ are each independently selected from a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring;

$R^4$, $R^5$, $Ar^4$ to $Ar^6$, and two 2,7-disubstituted naphthalene rings may each independently have one or more substituents; and when $Ar^5$ represents a benzene ring, $Ar^4$ and $Ar^6$ cannot both be a benzene ring at the same time.

The material (1) for organic EL devices represented by formula (1) is asymmetric with respect to the 2,7-disubstituted naphthalene ring and the material (2) for organic EL devices represented by formula (2) is asymmetric with respect to the structure of 2,7-disubstituted naphthalene ring-$Ar^5$-2,7-disubstituted naphthalene ring. Accordingly, the lifetime of organic EL devices having those materials in their light emitting layers are dramatically improved.

As the material (1) for organic EL devices and material (2) for organic EL devices of the invention have a large triplet energy gap (excited triplet energy), each of the materials can transfer energy to a phosphorescent dopant to cause the dopant to emit phosphorescent light.

An anthracene derivative well known as a fluorescent host is unsuitable as a host of a red-emitting phosphorescent dopant. In contrast, the materials for organic EL devices allows a red-emitting phosphorescent dopant to effectively emit because of its large triplet energy gap.

CBP, a well-known phosphorescent host, is usable as a host of a phosphorescent dopant which emits light having a wavelength shorter than that of green light. However, the materials for organic EL devices of the invention are usable as a host of a phosphorescent dopant which emits green light or light having a longer wavelength.

In the present invention, the stability of molecule is enhanced to prolong the lifetime of device by constituting the skeleton of the materials for organic EL devices from polycondensed rings containing no nitrogen atom.

When the number of ring atoms of the skeleton is excessively small, the stability of the compound is not sufficient. When the number of rings in the polycondensed rings constituting the skeleton is excessively large, the triplet energy gap is narrow for the wavelength of desired emission, because the HOMO to LUMO gap is narrow because of a long conjugated system. In this regard, since each of the material (1) for organic EL devices and the material (2) for organic EL devices has a moderate number of ring atoms, the compound is suitably used as a phosphorescent host for a phosphorescent emitting layer, which allows the emission of desired wavelength and is highly stable.

Conventionally, a host material applicable to a wide range of phosphorescent dopants emitting lights of wide range of wavelengths from green to red has been selected. Therefore, a compound, such as CBP, having a wide triplet energy gap has been used as the host material.

Although the triplet energy gap Eg(T) of CBP is wide, CBP involves a problem of short lifetime.

Although not applicable as a host of a phosphorescent dopant having a wide gap corresponding to blue light, the materials of the invention work as a host of a red- or green-emitting phosphorescent dopant. If the triplet energy gap is excessively wide as in CBP, the energy is not effectively transferred to a red-emitting phosphorescent dopant because of an excessively large difference in the energy gaps. In contrast, when the host of the invention is used, the energy is effectively transferred from the exciton of host to a red- or green-emitting phosphorescent dopant because their energy gaps are matched, giving a phosphorescent emitting layer with extremely high efficiency.

Thus, according to the present invention, a phosphorescent emitting layer with high efficiency and long lifetime is obtained.

The triplet energy gap Eg(T) of the material for an organic electroluminescence device is determined, for example, from the phosphorescent emission spectrum. In the present invention, it is determined, for example, as described below.

A sample for phosphorescent measurement is prepared by dissolving a test material in EPA solvent (diethyl ether:isopentane:ethanol=5:5:2 by volume) at 10 μmol/L.

The sample for phosphorescent measurement is charged into a quartz cell, cooled to 77 K, and irradiated with exciting light, and the wavelength of emitted phosphorescent light was measured.

A line tangent to the rising portion at the short-wavelength side of the obtained phosphorescent emission spectrum is drawn, and the wavelength at the intersection of the tangent line and the base line is converted to a value of energy unit, employing the converted value as the triplet energy gap Eg(T).

The phosphorescent measurement is carried out, for example, by using a commercially available apparatus, such as F-4500 (manufactured by Hitachi, Ltd.).

The triplet energy gap may be determined in different manner without departing from the spirit and scope of the present invention.

$Ar^1$ and $Ar^2$ in formula (1) each independently represent preferably a benzene ring or the condensed aromatic hydrocarbon ring and more preferably represent condensed aromatic hydrocarbon rings different from each other. $Ar^1$ preferably represent a ring selected from a phenanthrene ring, a fluoranthene ring, a benzophenanthrene ring, and a benzochrysene ring. More preferably, $Ar^1$ represent a ring selected from a phenanthrene ring, a fluoranthene ring, a benzophenanthrene ring, and a benzochrysene ring, and $Ar^2$ represent a benzene ring or a naphthalene ring.

When $Ar^5$ in formula (2) represents a benzene ring, $Ar^4$ and $Ar^6$ preferably each independently represent a condensed aromatic hydrocarbon ring selected from a chrysene ring, a fluoranthene ring, a benzophenanthrene ring, a dibenzophenanthrene ring, a benzotriphenylene ring, a benzochrysene ring, a benzo[b]fluoranthene ring, and a picene ring. More preferably, $Ar^4$ and $Ar^6$ each independently represent condensed aromatic hydrocarbon rings different from each other. In addition, in formula (2), it is preferred that $R^4$ and $R^5$ each represent a hydrogen atom, and $Ar^4$ or $Ar^6$ represent a group selected from a phenanthrene ring, a fluoranthene ring, a benzophenanthrene ring, and a benzochrysene ring, and it is more preferred that $Ar^5$ is a ring having 10 or more ring carbon atoms, and $Ar^4$ or $Ar^6$ represent a ring selected from a phenanthrene ring, a fluoranthene ring, a benzophenanthrene ring, and a benzochrysene ring.

In addition, $Ar^5$ preferably represents a dibenzofuran ring.

Particularly preferred in the asymmetric materials of the present invention is a material wherein $Ar_1$ to $Ar_3$, and $Ar_4$ and $Ar_6$ each independently represent a group excellent in heat resistance, such as a substituted or unsubstituted phenanthrene ring, a substituted or unsubstituted fluoranthene ring, a substituted or unsubstituted benzophenanthrene ring, or a substituted or unsubstituted benzochrysene ring.

The one or more optional substituents of $R^1$ to $R^3$, $Ar^1$ to $Ar^3$, and the 2,7-disubstituted naphthalene ring in formula (1), and $R^4$ and $R^5$, $Ar^4$ to $Ar^6$, and two 2,7-disubstituted naphthalene rings in formula (2) are preferably an aryl group having 6 to 22 carbon atoms, an alkyl group having 1 to 20 carbon atoms, a haloalkyl group having 1 to 20 carbon atoms, a cycloalkyl group having 5 to 18 carbon atoms, a silyl group having 3 to 20 carbon atoms, a cyano group, or a halogen atom, and more preferably an aryl group having 6 to 14 carbon atoms other than an anthracene ring, an alkyl group having 1 to 20 carbon atoms, a haloalkyl group having 1 to 20 carbon atoms, a cycloalkyl group having 5 to 18 carbon atoms, or a silyl group having 3 to 20 carbon atoms.

As those substituents are free of nitrogen atoms, the stability of each of the materials for organic EL devices can be additionally improved and the device lifetime can be additionally lengthened.

The number of substituents of $R^1$ to $R^3$, $Ar^1$ to $Ar^3$, and the 2,7-disubstituted naphthalene ring in formula (1), and $R^4$ and $R^5$, $Ar^4$ to $Ar^6$, and two 2,7-disubstituted naphthalene rings in formula (2) is preferably 2 or less, and more preferably 1 or less.

Preferred examples of the aryl group having 6 to 22 carbon atoms include a phenyl group, a biphenyl group, a terphenyl group, a naphthyl group, a phenylnaphthyl group, a naphthylphenyl group, a naphthylnaphthyl group, a phenylphenanthrenyl group, a chrysenyl group, a fluoranthenyl group, a 9,10-dialkylfluorenyl group, a 9,10-diarylfluorenyl group, a triphenylenyl group, a phenanthrenyl group, a benzophenanthrenyl group, a dibenzophenanthrenyl group, a benzotriphenylenyl group, a benzochrysenyl group, and a dibenzofuranyl group. More preferred are aryl groups having 6 to 18 carbon atoms, such as a phenyl group, a biphenyl group, a terphenyl group, a naphthyl group, a chrysenyl group, a phenylnaphthyl group, a naphthylphenyl group, a fluoranthenyl group, a 9,10-dimethylfluorenyl group, a triphenylenyl group, a phenanthrenyl group, a benzophenanthrenyl group, and a dibenzofuranyl group. Still more preferred are aryl groups having 6 to 14 carbon atoms, such as a phenyl group, a biphenyl group, a naphthyl group, a phenanthrenyl group, and a dibenzofuranyl group.

Examples of the alkyl group having 1 to 20 carbon atoms include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group.

Examples of the haloalkyl group having 1 to 20 carbon atoms include a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, and a 1,2,3-triiodopropyl group.

Examples of the cycloalkyl group having 5 to 18 carbon atoms include a cyclopentyl group, a cyclohexyl group, a cyclooctyl group, and a 3,5-tetramethylcyclohexyl group, with a cyclohexyl group, a cyclooctyl group, and a 3,5-tetramethylcyclohexyl group being preferred.

Preferred examples of the silyl group having 3 to 20 carbon atoms include an alkylsilyl group, an arylsilyl group, and an aralkylsilyl group. Examples thereof include a trimethylsilyl group, a triethylsilyl group, a tributylsilyl group, a trioctylsilyl group, a triisobutylsilyl group, a dimethylethylsilyl group, a dimethylisopropylsilyl group, a dimethylpropylsilyl group, a dimethylbutylsilyl group, a dimethyl-t-butylsilyl group, a diethylisopropylsilyl group, a phenyldimethylsilyl group, a diphenylmethylsilyl group, a diphenyl-t-butylsilyl group, and a triphenylsilyl group.

Examples of the halogen atom include a fluorine atom, a chlorine atom, a bromine atom, and an iodine atom.

$Ar^3$ in formula (1) preferably represents a ring selected from a substituted or unsubstituted phenanthrene ring, a substituted or unsubstituted fluoranthene ring, and a substituted or unsubstituted benzophenanthrene ring.

When these ring structures are selected, the material forms a thin film for organic electroluminescence devices excellent in stability and provides a high-efficiency, long-lifetime device particularly when used in combination with a red-emitting phosphorescent material.

The excited triplet energy of the material (1) for organic EL devices and material (2) for organic EL devices is preferably 2.0 eV or more and 2.8 eV or less.

If being 2.0 eV or more, the energy can be transferred to a phosphorescent emitting material which emits light of 520 nm or longer and 720 nm or shorter. If being 2.8 eV or less, the problem of failing to efficient emission due the energy gap excessively large for a red-emitting phosphorescent dopant is avoided.

The excited triplet energy of the materials for organic EL devices of the invention is more preferably 2.0 eV or more and 2.7 eV or less, and still more preferably 2.1 eV or more and 2.7 eV or less.

Specific examples of the material (1) for organic EL devices include the following compounds.

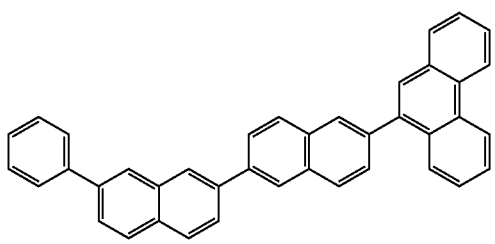

(1-1)

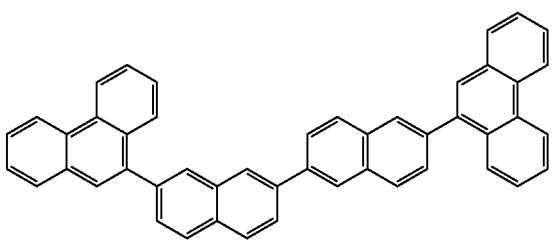

(1-2)

-continued
(1-3)
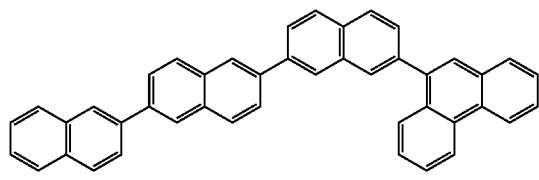
(1-4)
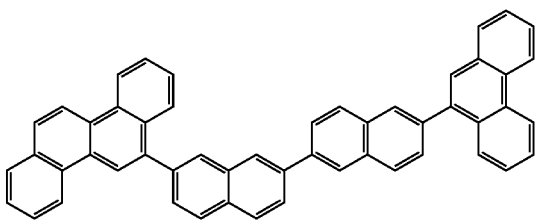
(1-5)
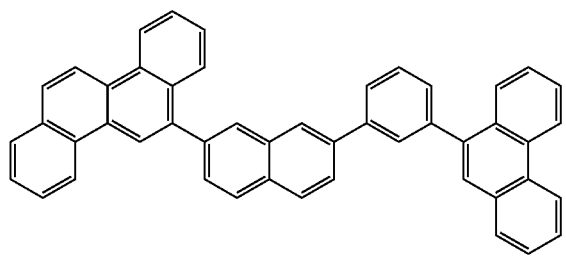
(1-6)
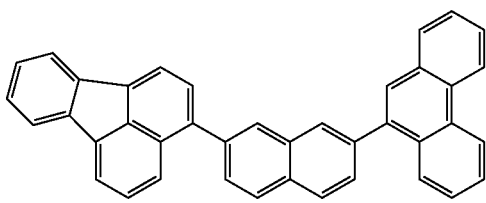
(1-7)
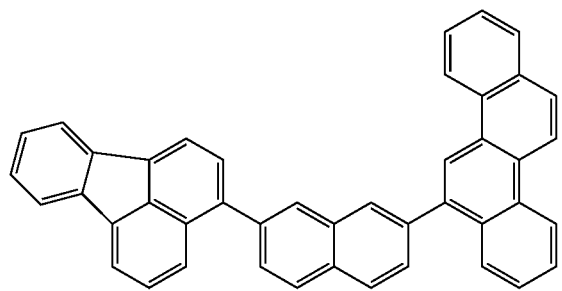
(1-8)
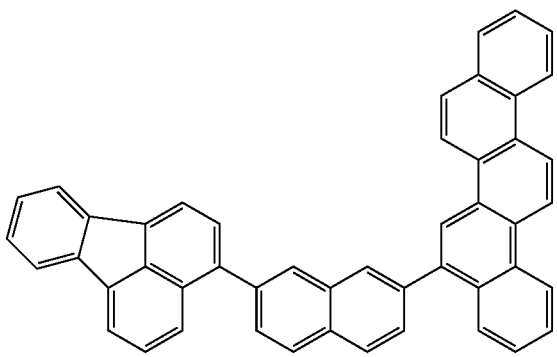
(1-9)
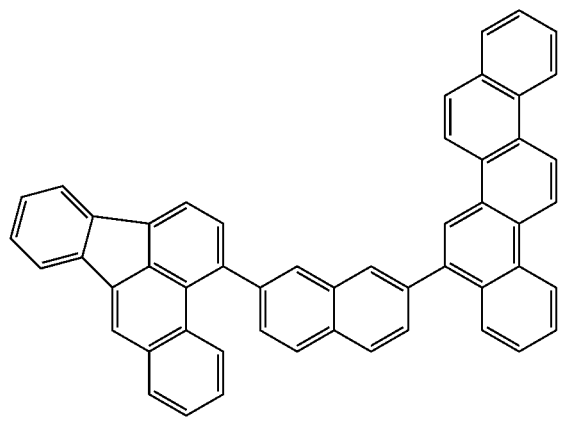
(1-10)
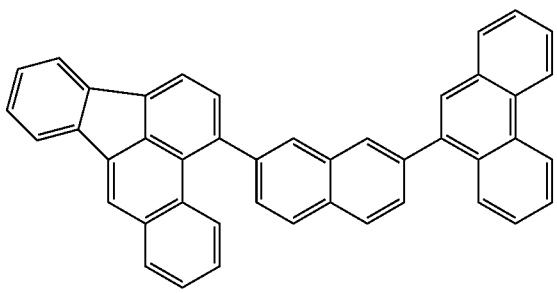

-continued
(1-11)
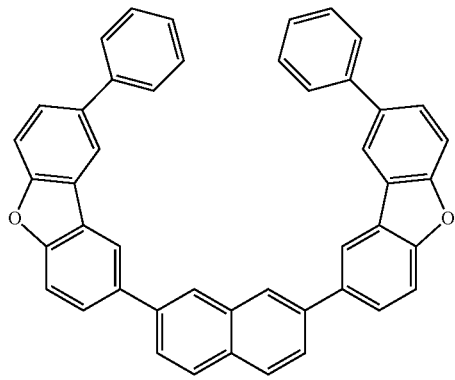
(1-12)
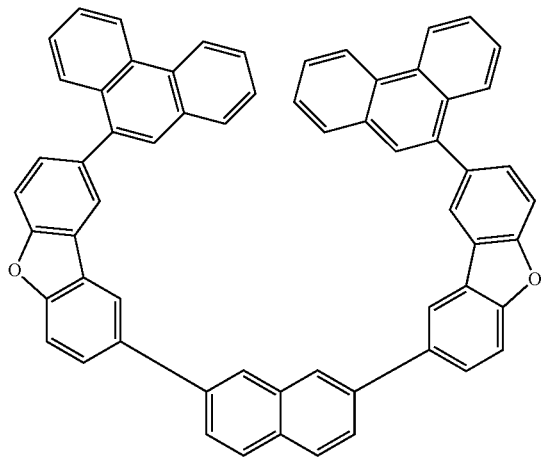
(1-13)
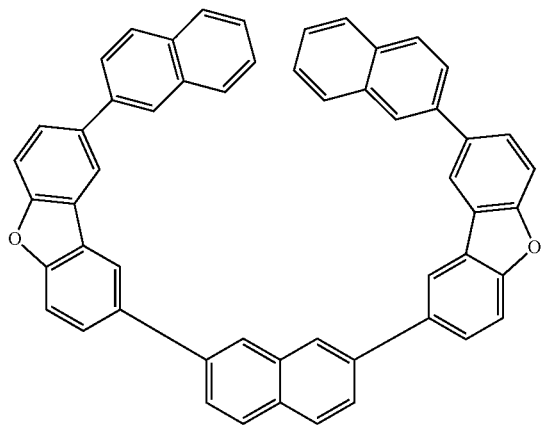
(1-14)
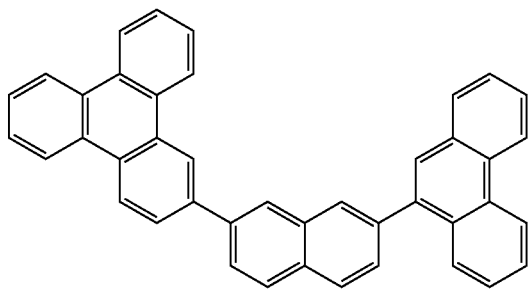
(1-15)
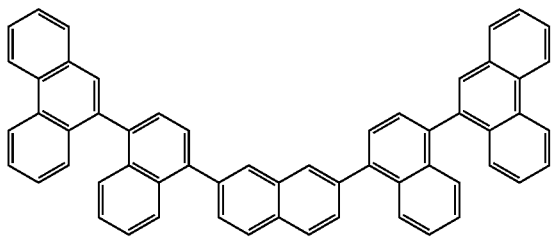
(1-16)
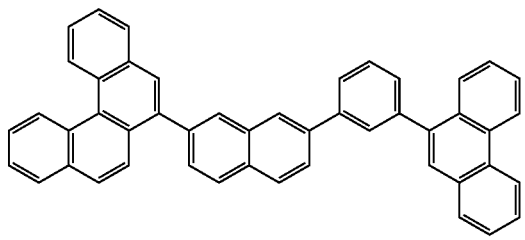
(1-17)
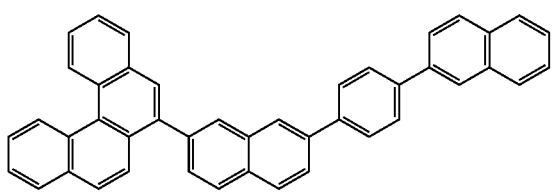
(1-18)
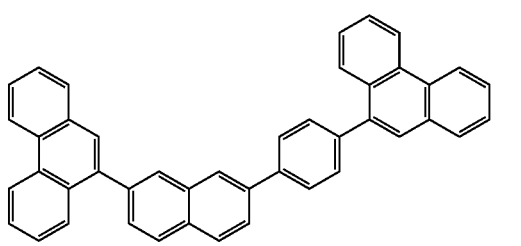
(1-19)
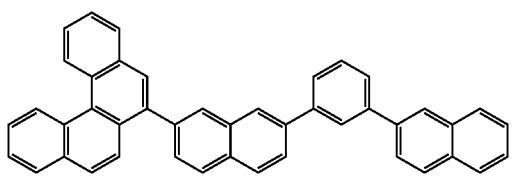
(1-20)
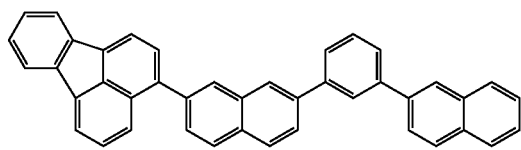

(1-21)
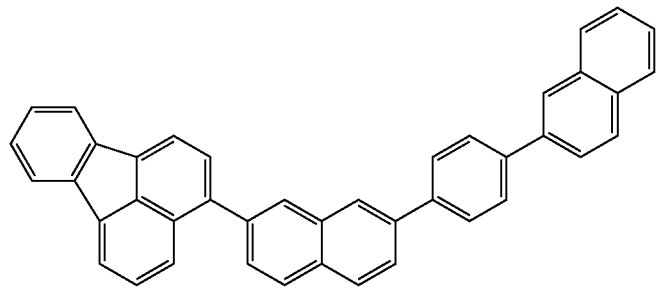
(1-22)
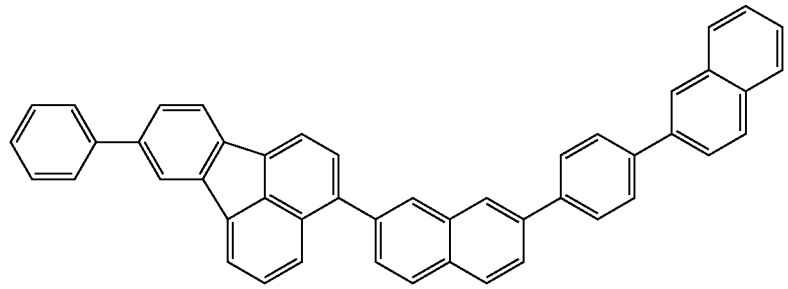
(1-23)
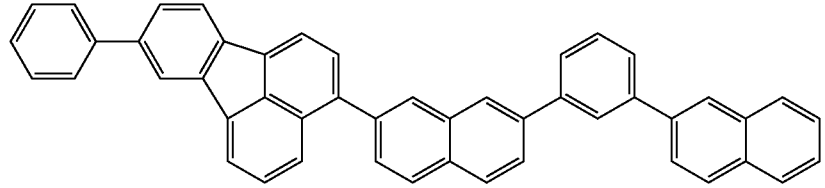
(1-24)
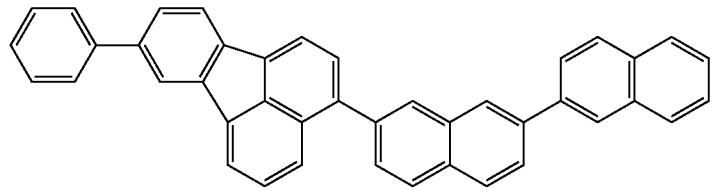
(1-25)
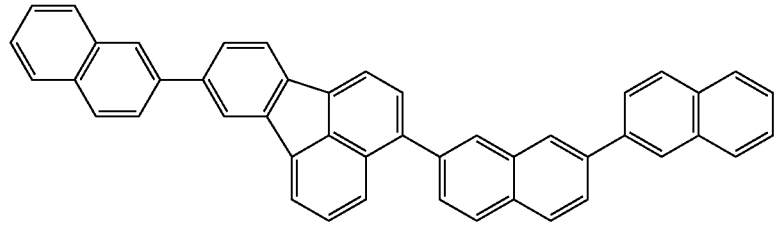
(1-26) (1-27)
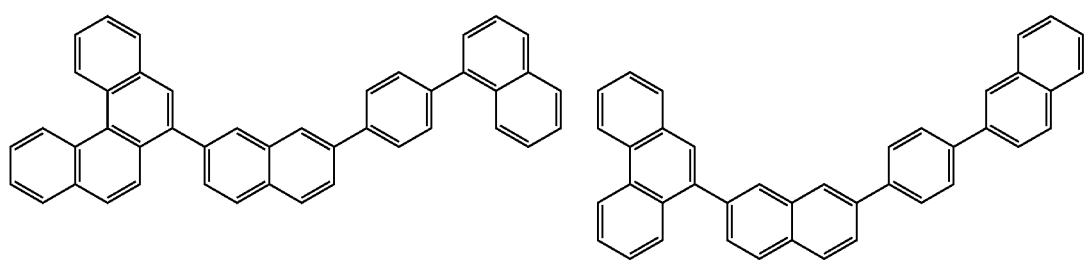

-continued
(1-28)
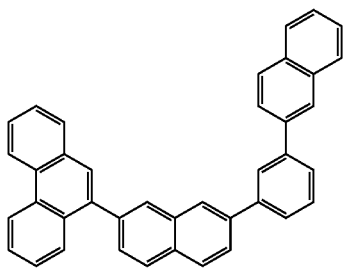
(1-29)
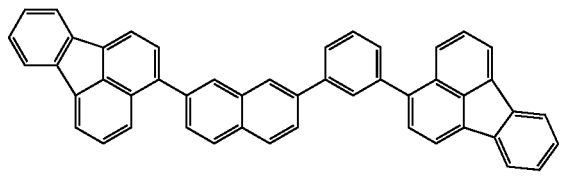
(1-30)
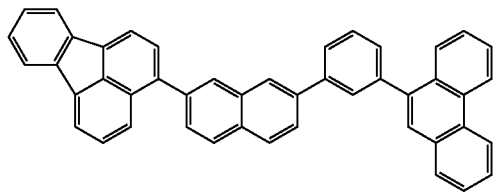
(1-31)
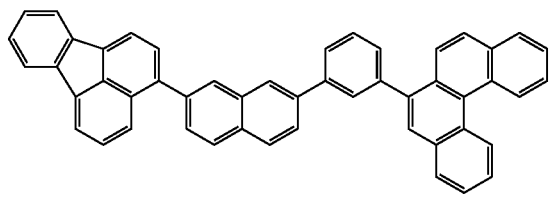
(1-32)
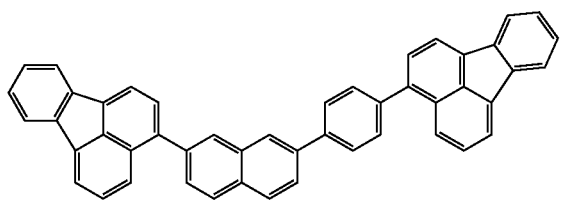
(1-33)
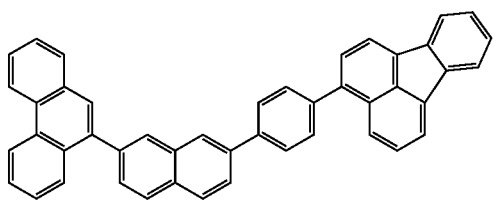
(1-34)
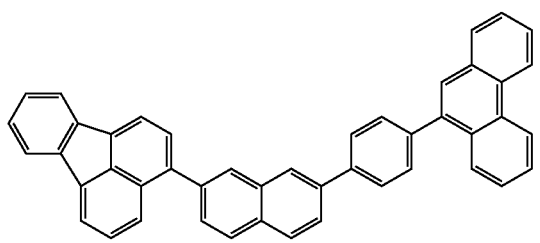
(1-35)
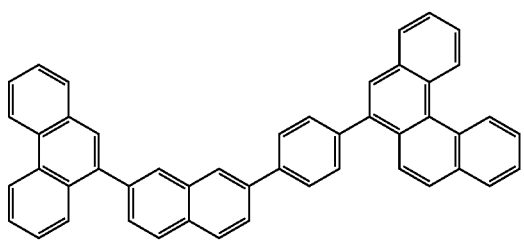
(1-36)
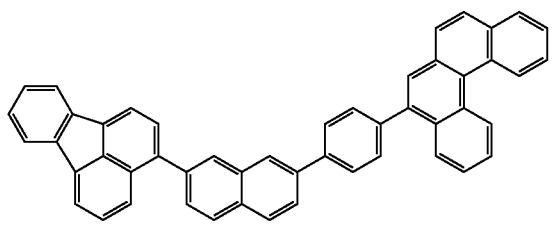
(1-37)
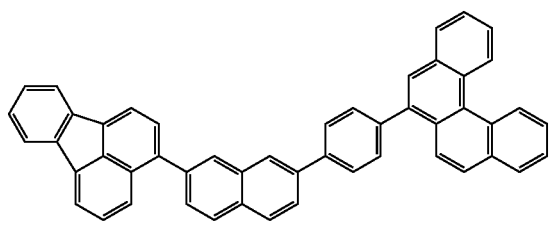
(1-38)
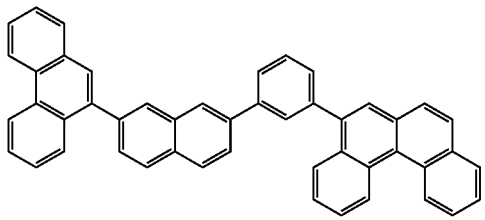
(1-39)
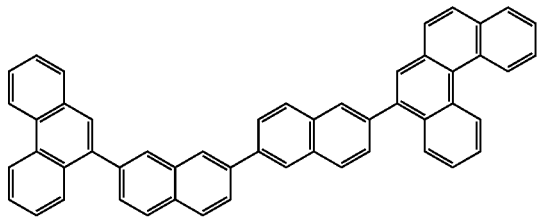

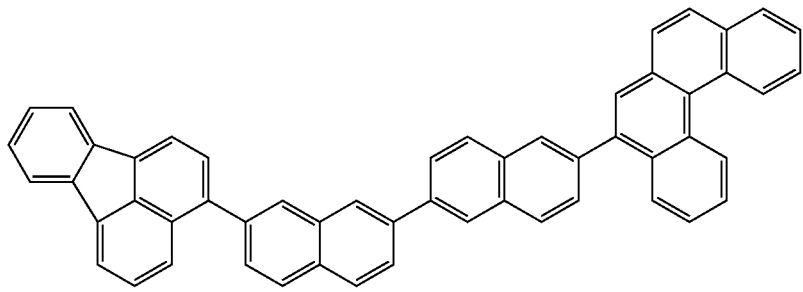
(1-40)
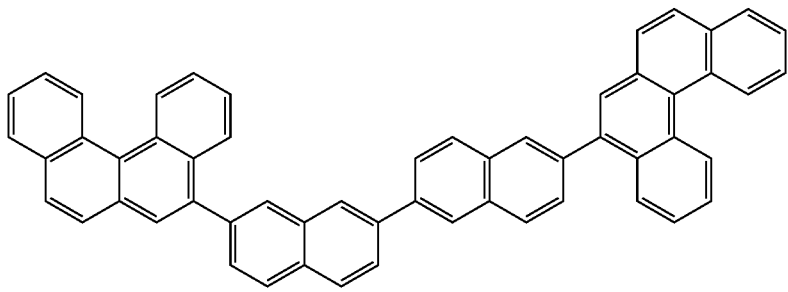
(1-41)
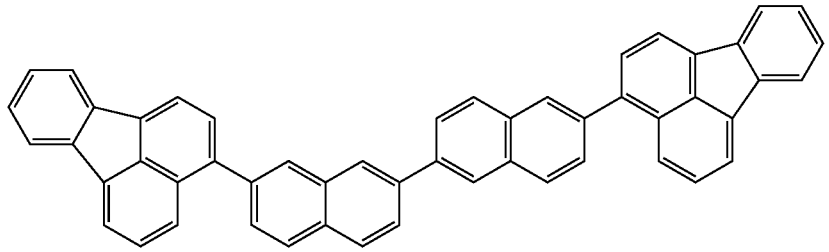
(1-42)
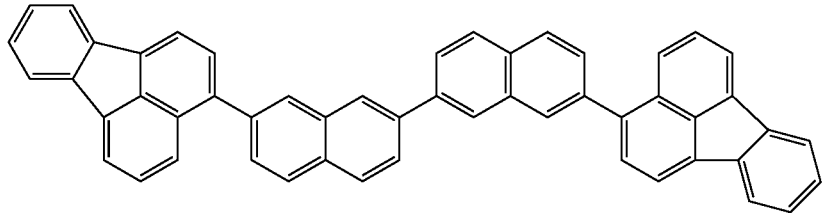
(1-43)
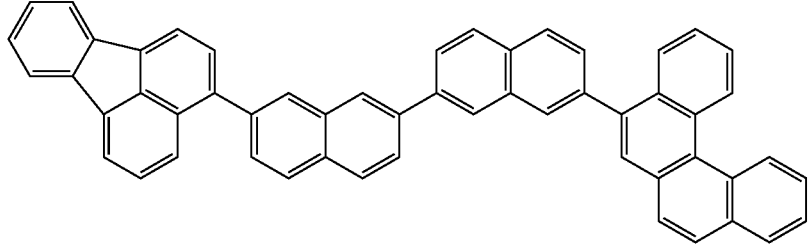
(1-44)
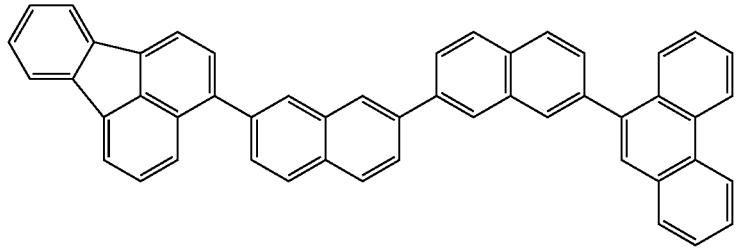
(1-45)

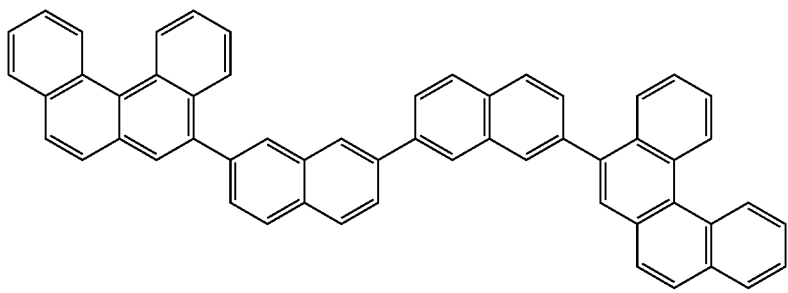
(1-46)
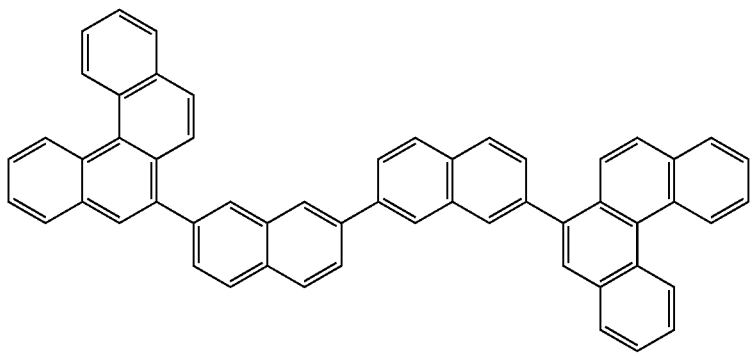
(1-47)
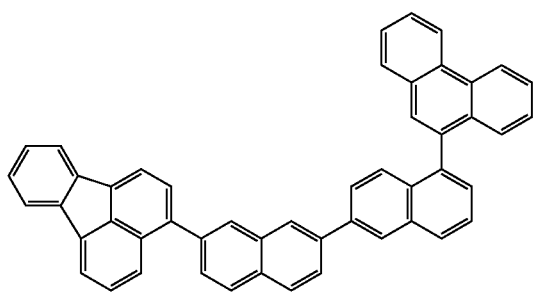
(1-48)
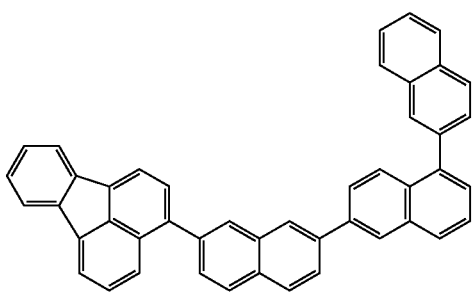
(1-49)
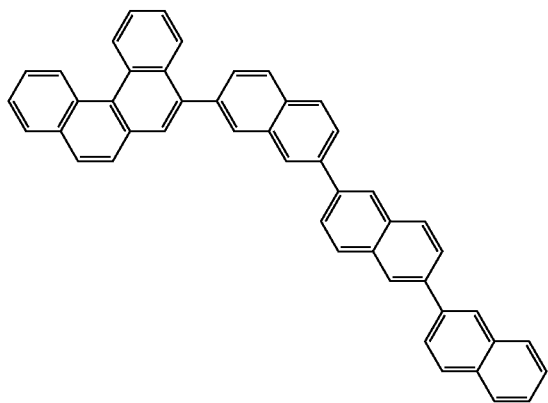
(1-50)
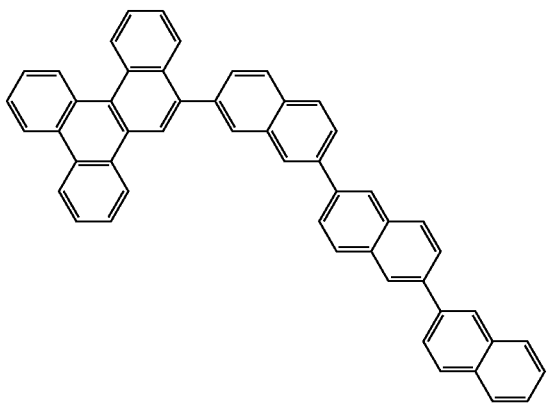
(1-51)

-continued
(1-52)
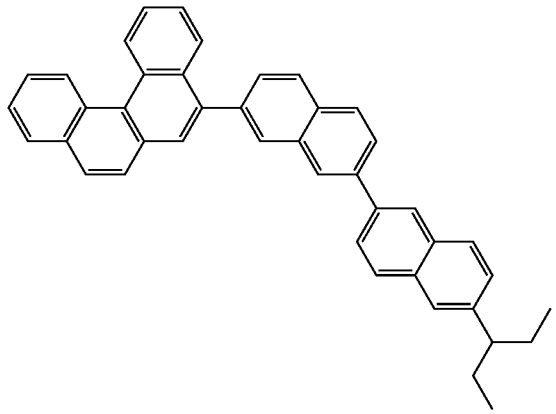
(1-53)
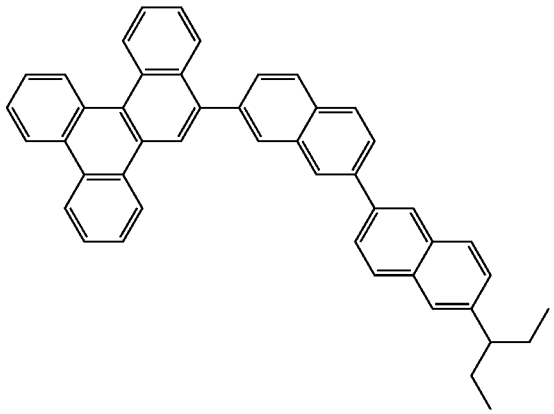
(1-54)
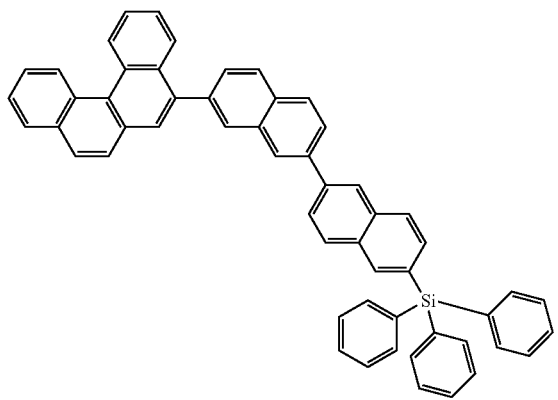
(1-55)
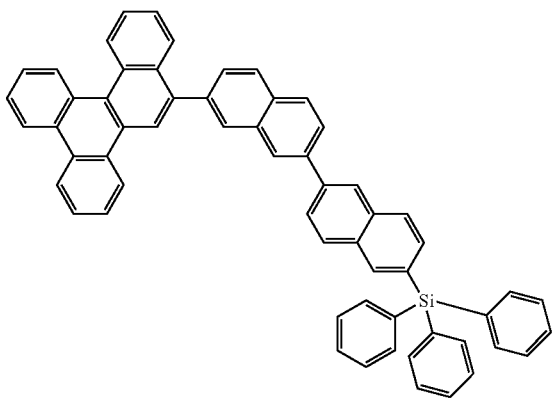
(1-56)
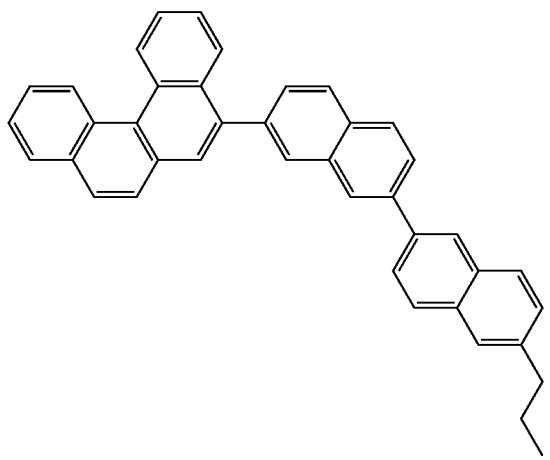
(1-57)
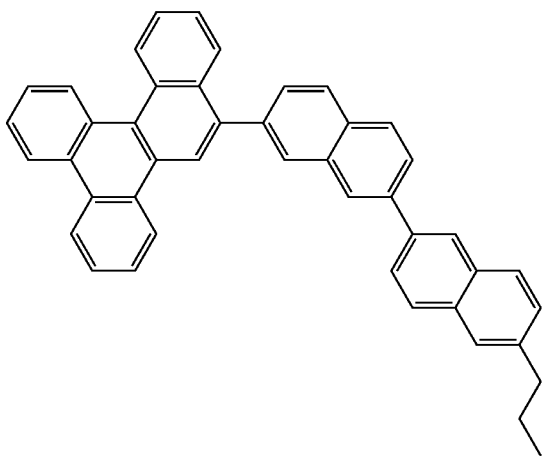

-continued
(1-58) (1-59)
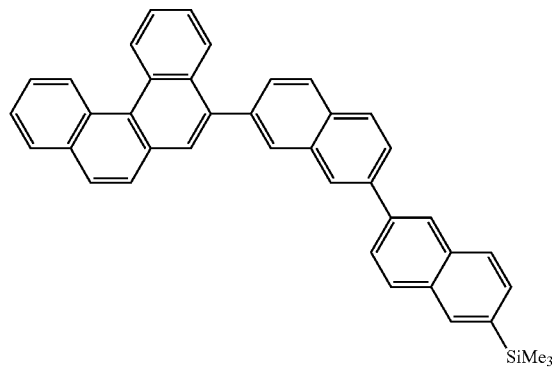
(1-60) (1-61)
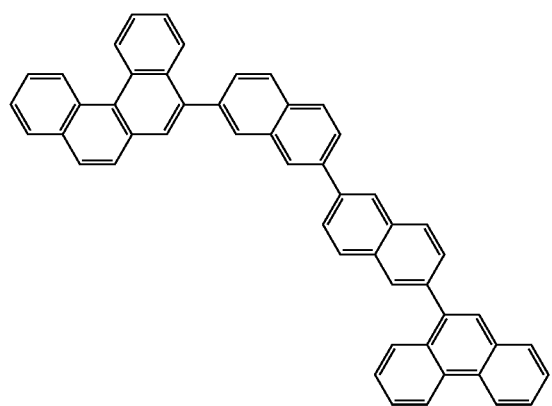
(1-62) (1-63)

(1-64)
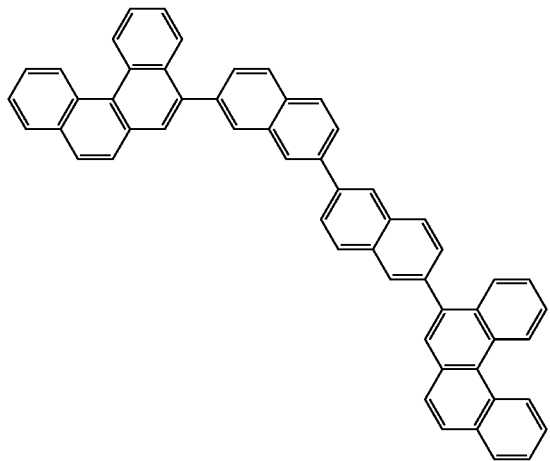
(1-65)
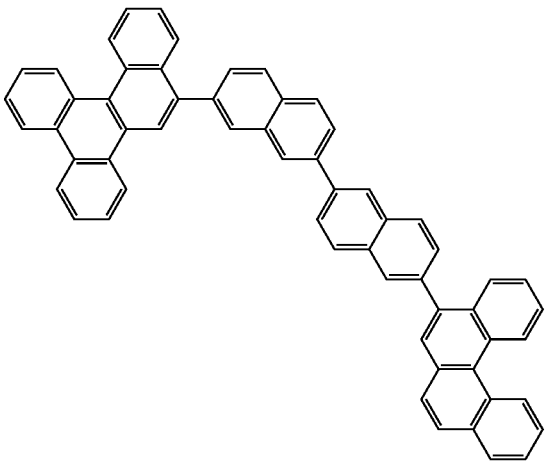
(1-66)
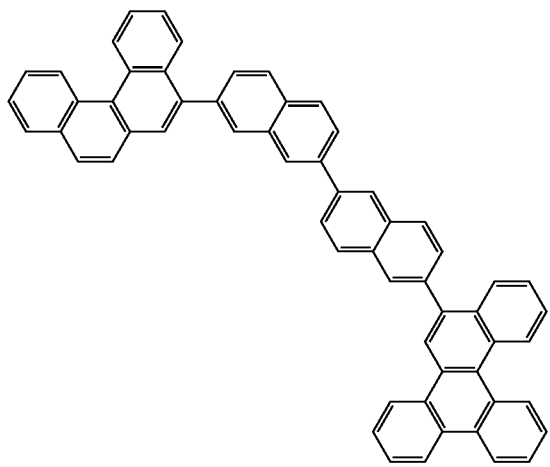
(1-67)
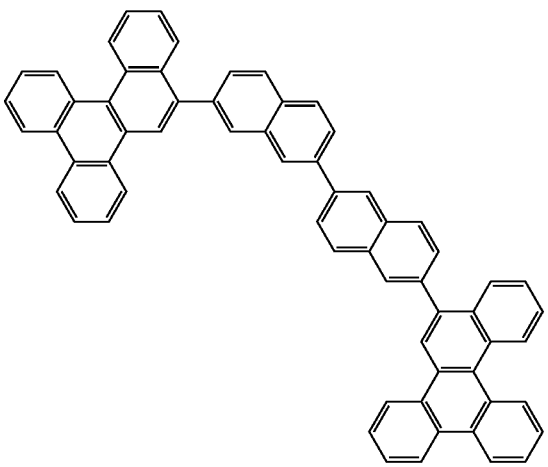
(1-68)
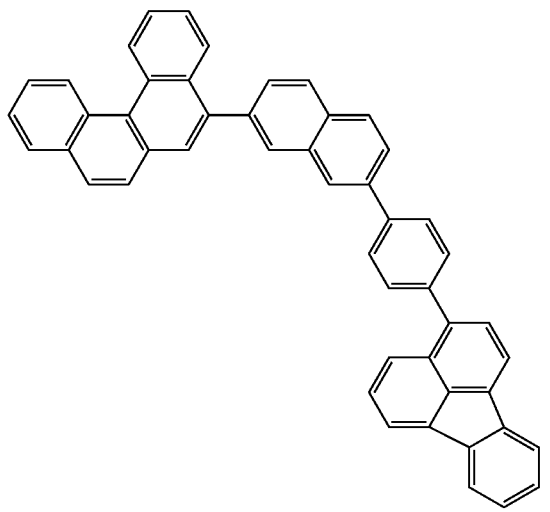
(1-69)
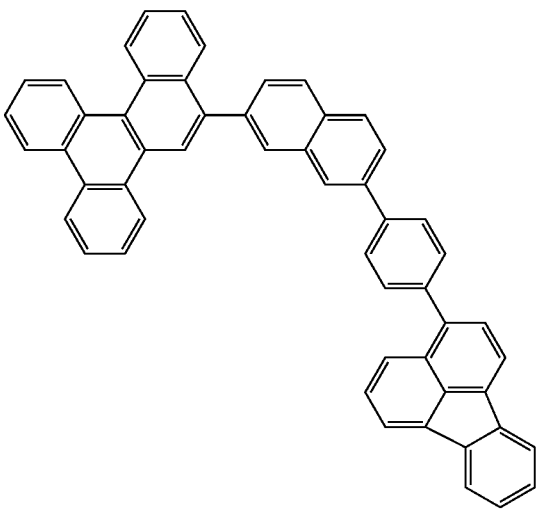

(1-70) 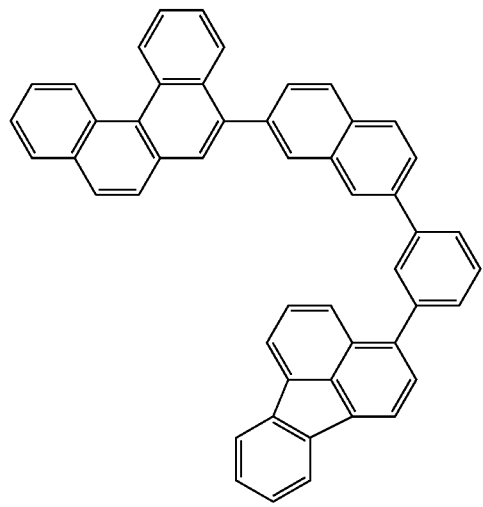
(1-71) 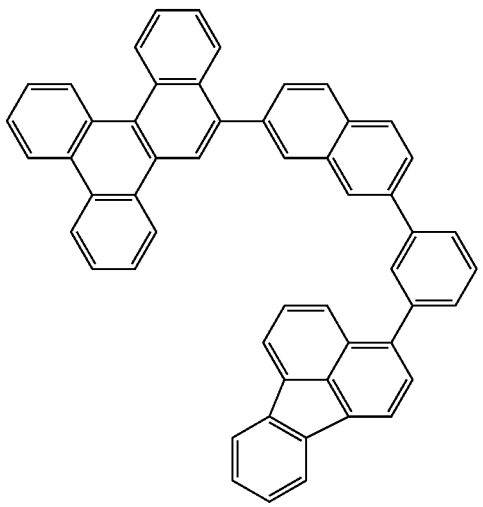
(1-72) 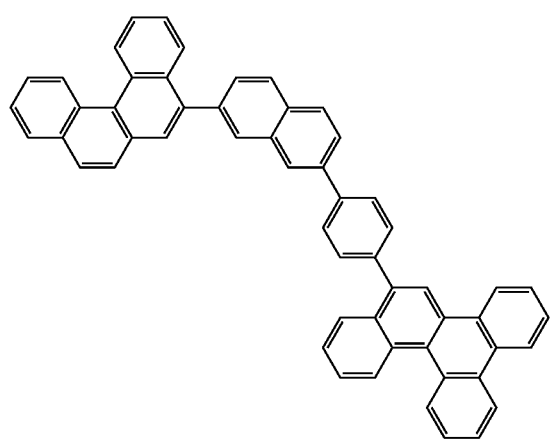
(1-73) 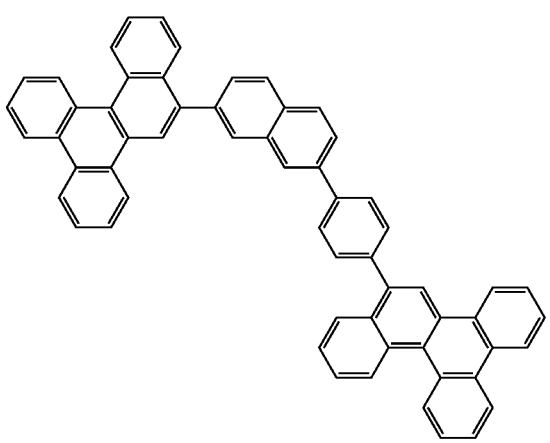
(1-74) 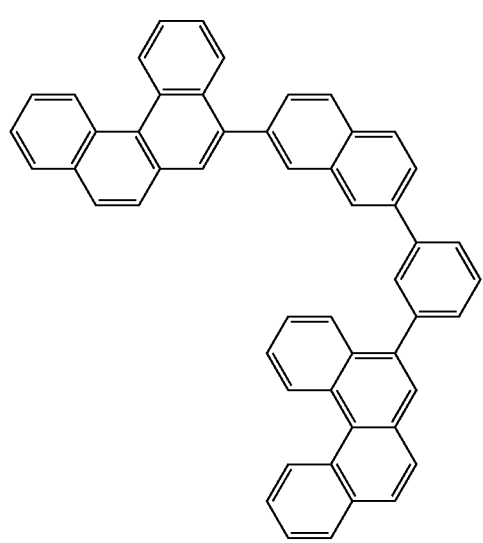
(1-75) 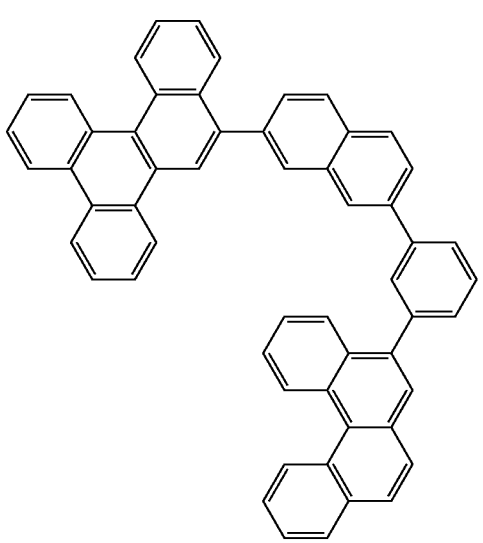

-continued
(1-76)
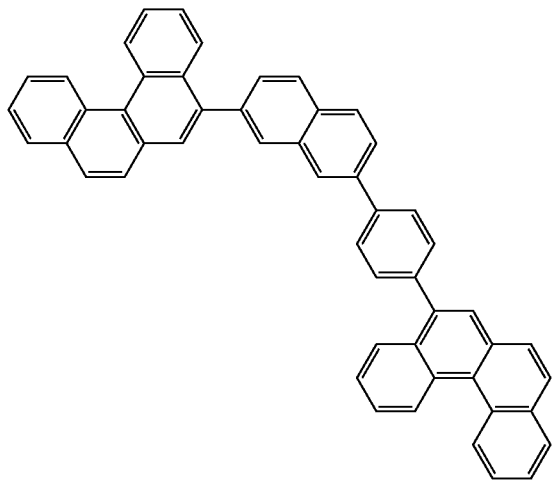
(1-77)
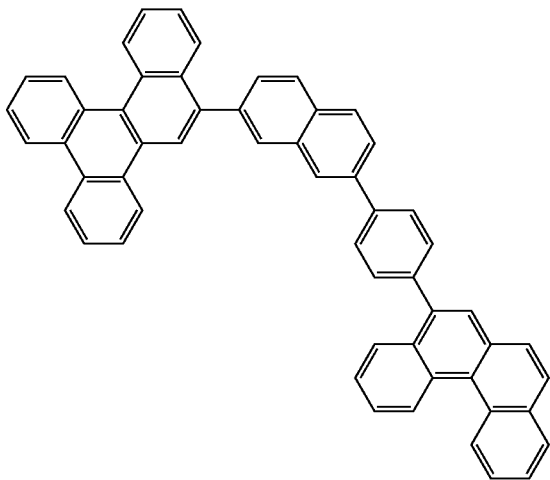
Specific examples of the material (2) for organic EL devices include the following compounds.
(2-1)
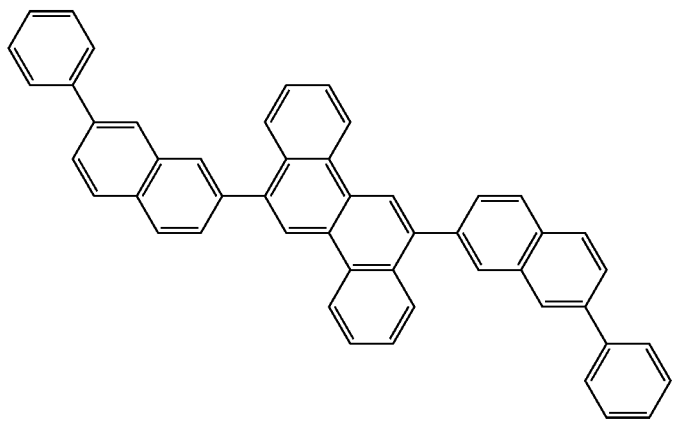
(2-2)
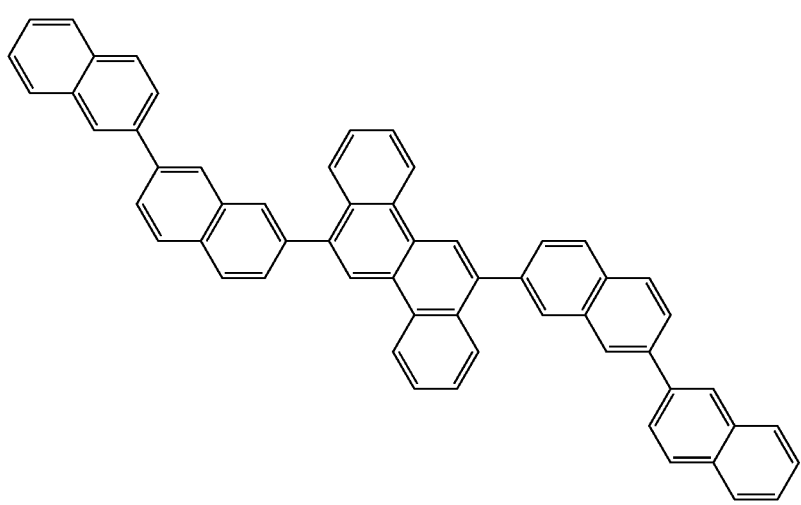

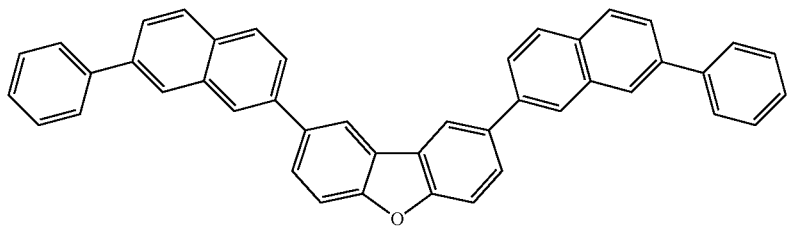
(2-3)
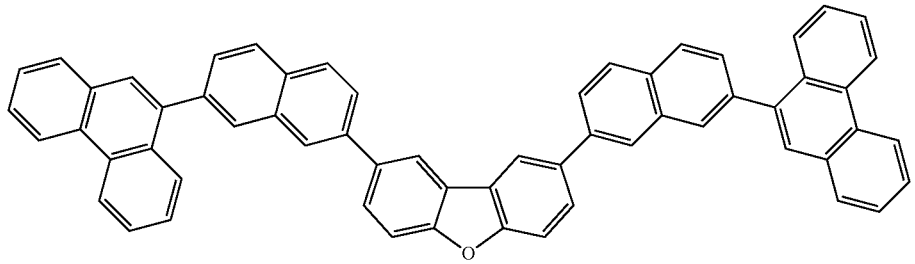
(2-4)
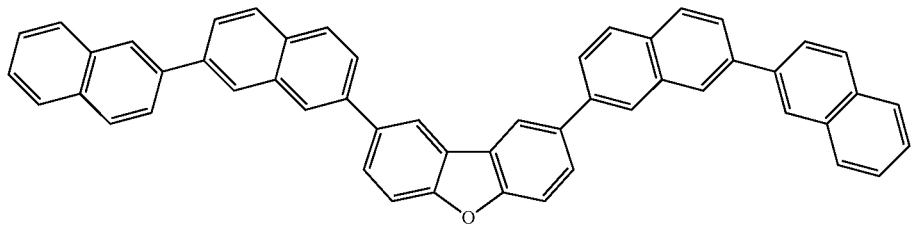
(2-5)
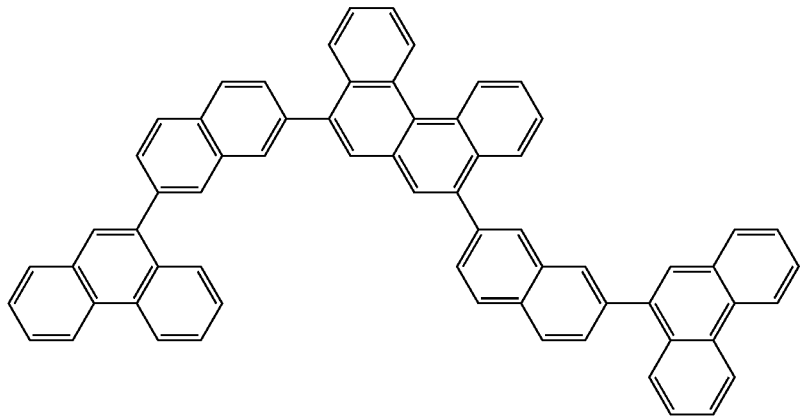
(2-6)
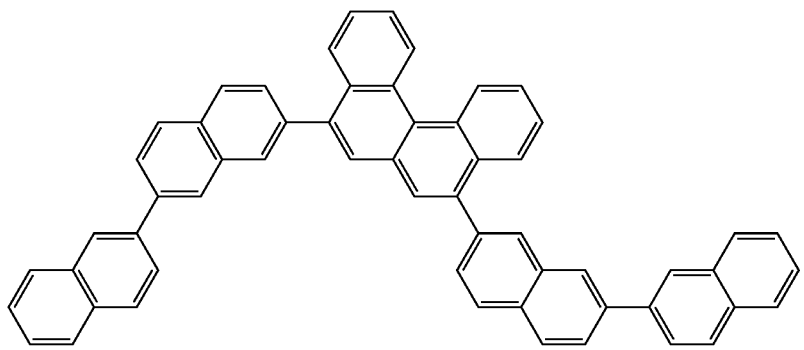
(2-7)

(2-8)
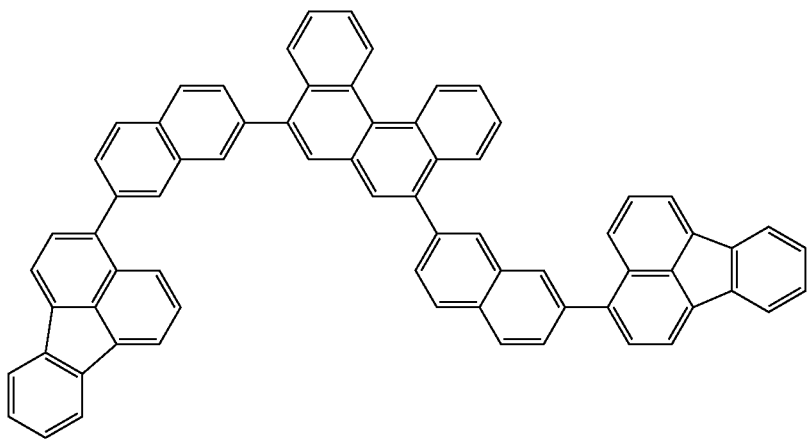
(2-9)
(2-10)
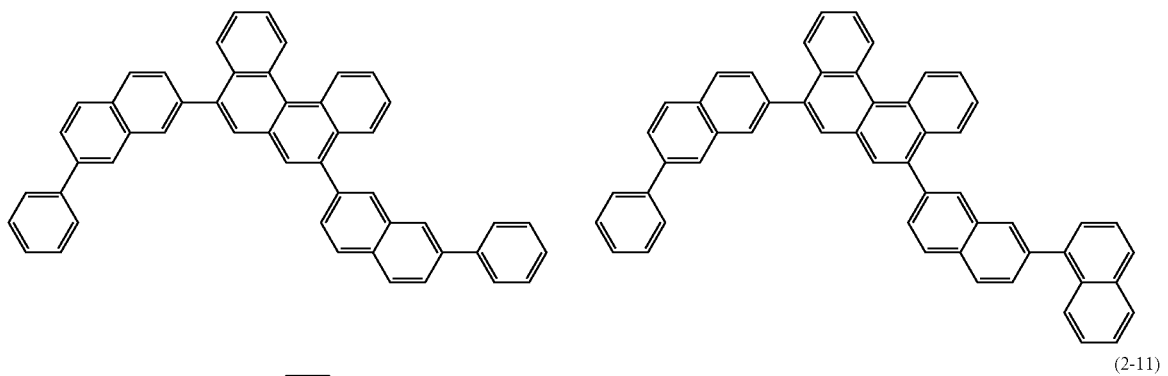
(2-11)
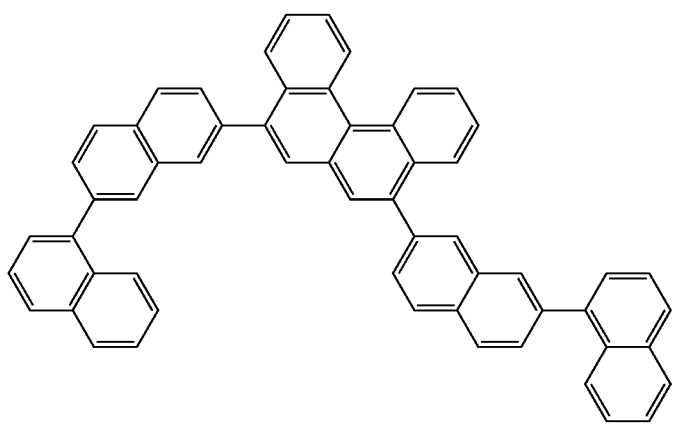
(2-12)
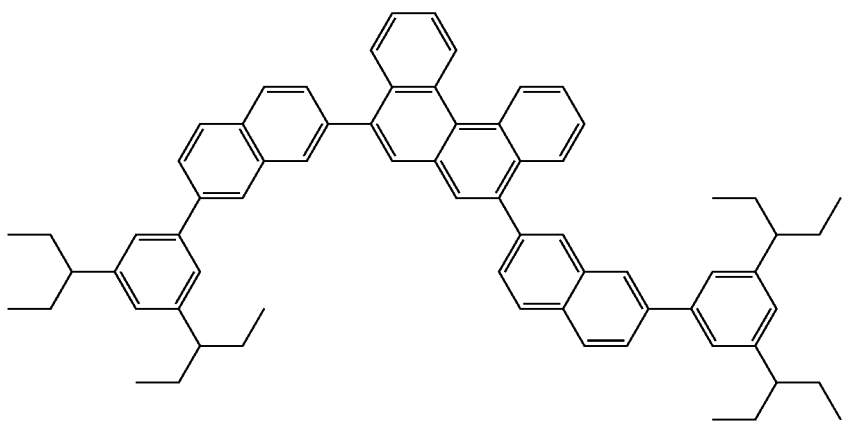

(2-13)
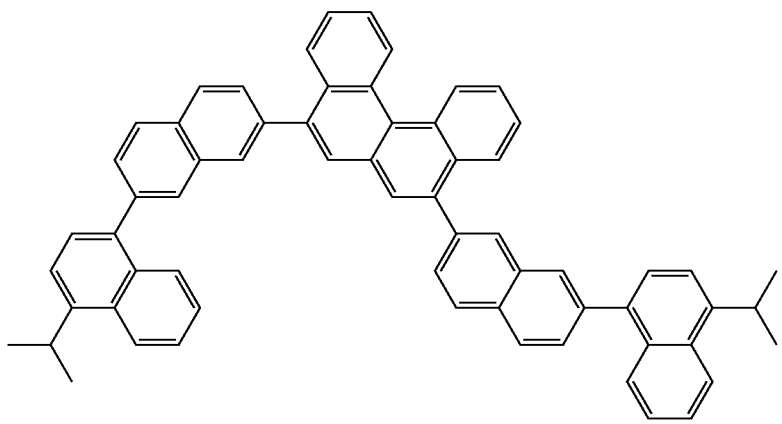
(2-14)
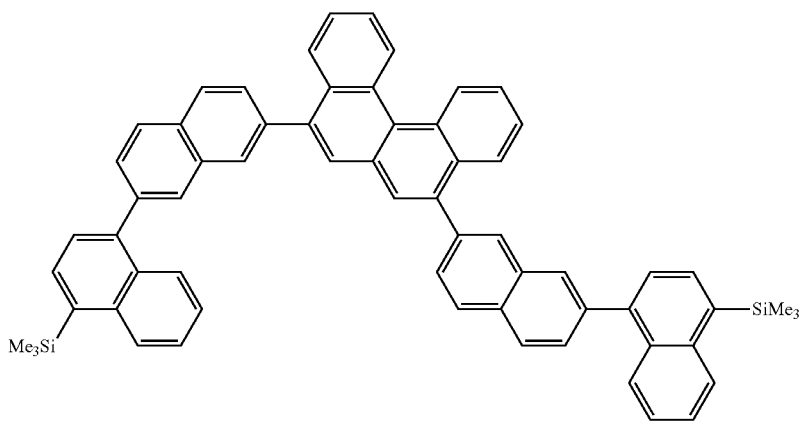
(2-15)
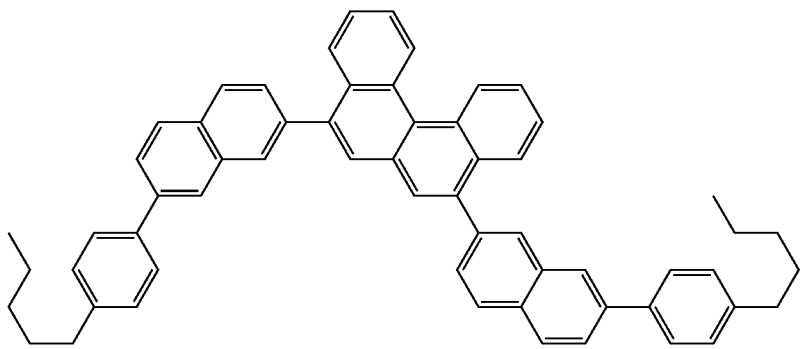
(2-16)
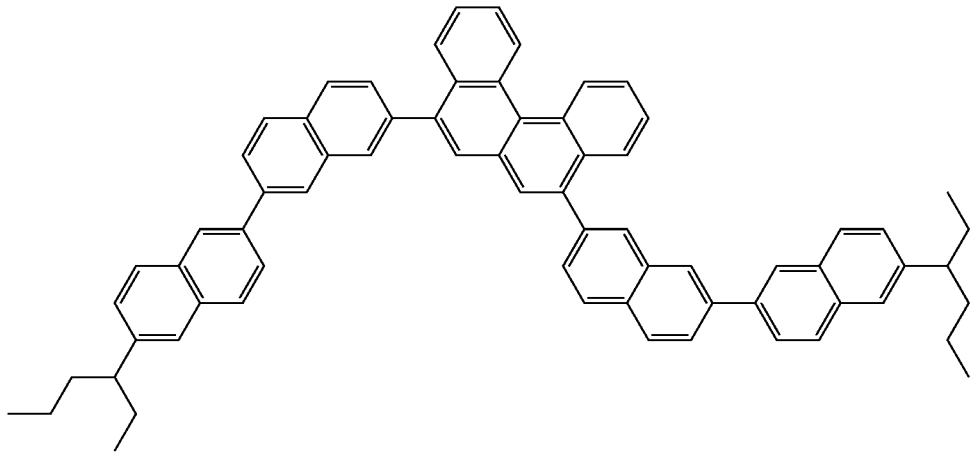

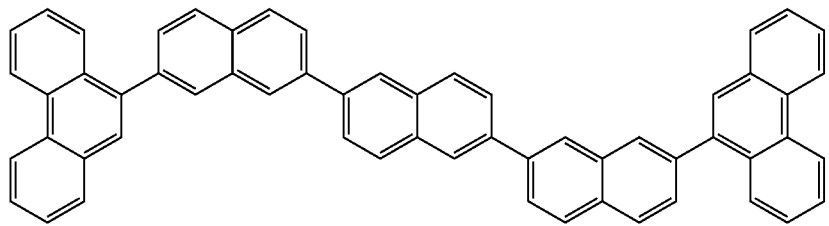
(2-17)
(2-18)
(2-19)
(2-20)
(2-21)
(2-22)

Organic Electroluminescence Device

The present invention further provides an organic electroluminescence device comprising an organic thin film layer formed of one or more layers between a cathode and an anode, wherein the organic thin film layer comprises the material (1) for organic EL devices or material (2) for organic EL devices and at least one kind of a phosphorescent emitting material.

Device Architecture

The architecture of the organic electroluminescence device will be described.

Representative architecture of the organic electroluminescence device includes:
(1) anode/light emitting layer/cathode,
(2) anode/hole injecting layer/light emitting layer/cathode,
(3) anode/light emitting layer/electron injecting/transporting layer/cathode,
(4) anode/hole injecting layer/light emitting layer/electron injecting/transporting layer/cathode,
(5) anode/organic semiconductor layer/light emitting layer/cathode,
(6) anode/organic semiconductor layer/electron blocking layer/light emitting layer/cathode,
(7) anode/organic semiconductor layer/light emitting layer/adhesion improving layer/cathode,
(8) anode/hole injecting/transporting layer/light emitting layer/electron injecting/transporting layer/cathode,
(9) anode/insulating layer/light emitting layer/insulating layer/cathode,
(10) anode/inorganic semiconductor layer/insulating layer/light emitting layer/insulating layer/cathode,
(11) anode/organic semiconductor layer/insulating layer/light emitting layer/insulating layer/cathode,
(12) anode/insulating layer/hole injecting/transporting layer/light emitting layer/insulating layer/cathode, and
(13) anode/insulating layer/hole injecting/transporting layer/light emitting layer/electron injecting/transporting layer/cathode, with the device architecture (8) being preferably used, but not limited thereto.

An example of the architecture of the organic electroluminescence device according to the present invention is schematically shown in FIG. 1.

The organic electroluminescence device 1 comprises a transparent substrate 2, an anode 3, a cathode 4, and an organic thin film layer 10 disposed between the anode 3 and the cathode 4.

The organic thin film layer 10 includes a phosphorescent emitting layer 5 comprising a phosphorescent host and a phosphorescent dopant. A hole injecting/transporting layer 6 may be disposed between the phosphorescent emitting layer 5 and the anode 3, and an electron injecting/transporting layer 7 may be disposed between the phosphorescent emitting layer 5 and the cathode 4.

An electron blocking layer may be formed on the side of the phosphorescent emitting layer 5 facing the anode 3, and a hole blocking layer may be formed on the side of the phosphorescent emitting layer 5 facing the cathode 4.

With such layers, electrons and holes are confined in the phosphorescent emitting layer 5, to facilitate the formation of excitons in the phosphorescent emitting layer 5.

In the present invention, the host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures.

Namely, the term "fluorescent host" means a material for constituting a fluorescent emitting layer containing a fluorescent dopant and does not mean a material usable only as a host of a fluorescent material.

Similarly, the term "phosphorescent host" means a material for constituting a phosphorescent emitting layer containing a phosphorescent dopant and does not mean a material usable only as a host of a phosphorescent emitting material.

In the present invention, the term "hole injecting/transporting layer" means a hole injecting layer, a hole transporting layer, or both, and the term "electron injecting/transporting layer" means an electron injecting layer, an electron transporting layer, or both.

Light-Transmissive Substrate

The organic electroluminescence device of the invention is formed on a light-transmissive substrate. The light-transmissive substrate serves as a support for the organic electroluminescence device and preferably a flat substrate having a transmittance of 50% or more to 400 to 700 nm visible light.

Examples of the substrate include a plate of glass and a plate of polymer.

The plate of glass may include a plate made of soda-lime glass, barium-strontium-containing glass, lead glass, aluminosilicate glass, borosilicate glass, barium borosilicate glass, or quartz.

The plate of polymer may include a plate made of polycarbonate resin, acrylic resin, polyethylene terephthalate resin, polyether sulfide resin, or polysulfone resin.

Anode and Cathode

The anode of the organic electroluminescence device injects holes to the hole injecting layer, the hole transporting layer or the light emitting layer, and an anode having a work function of 4.5 eV or more is effective.

Examples of material for anode include indium tin oxide alloy (ITO), tin oxide (NESA), indium zinc oxide alloy, gold, silver, platinum, and cupper.

The anode is formed by making the electrode material into a thin film by a method, such as a vapor deposition method or a sputtering method.

When getting the light emitted from the light emitting layer through the anode as employed in the embodiments of the present invention, the transmittance of anode to visible light is preferably 10% or more. The sheet resistance of anode is preferably several hundreds $\Omega/\square$ or less. The film thickness of anode depends upon the kind of material and generally 10 nm to 1 μm, preferably 10 to 200 nm.

The cathode is formed preferably from a material having a small work function in view of injecting electrons to the electron injecting layer, the electron transporting layer or the light emitting layer.

Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy.

Like the anode, the cathode is formed by making the material into a thin film by a method, such as the vapor deposition method and the sputtering method. The emitted light may be taken from the side of cathode.

Light Emitting Layer

The light emitting layer of organic electroluminescence device combines the following functions:
(1) Injection function: allowing holes to be injected from the anode or hole injecting layer, and allowing electrons to be injected from the cathode or electron injecting layer, by the action of electric field;

(2) Transporting function: transporting the injected charges (holes and electrons) by the force of electric field; and
(iii) Emission function: providing a zone for recombination of electrons and holes to cause the emission.

The light emitting layer may be different in the hole injection ability and the electron injection ability, and also in the hole transporting ability and the electron transporting ability each being expressed by mobility.

The light emitting layer is formed, for example, by a known method, such as a vapor deposition method, a spin coating method, and LB method.

The light emitting layer is preferably a molecular deposit film.

The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The light emitting layer can be also formed by making a solution of a binder, such as a resin, and its material in a solvent into a thin film by a spin coating method, as disclosed in JP 57-51781A.

The thickness of the light emitting layer is preferably 5 to 50 nm, more preferably 7 to 50 nm, and most preferably 10 to 50 nm. If being less than 5 nm, the light emitting layer is difficult to form and the control of color is difficult. If exceeding 50 nm, the driving voltage may increase.

It is preferred that the organic thin film layer in the organic EL device of the invention have at least one light emitting layer, and at least one light emitting layer contains the material (1) or (2) for organic EL devices and at least one kind of a phosphorescent emitting material.

Phosphorescent Emitting Material

The phosphorescent emitting material used in the invention preferably comprises a metal complex. The metal complex preferably comprises a metal atom selected from Ir, Pt, Os, Au, Cu, Re, and Ru and a ligand. A ligand having an ortho metal bond is particularly preferred.

In view of obtaining a high phosphorescent quantum efficiency and further improving the external quantum efficiency of electroluminescence device, a compound comprising a metal selected from iridium (Ir), osmium (Os), and platinum (Pt) is preferred, with a metal complex, such as iridium complex, osmium complex, and platinum, being more preferred, iridium complex and platinum complex being still more preferred, and an ortho metallated iridium complex being most preferred.

Examples of the metal complex are shown below, among which green- to red-emitting metal complexes are preferred.

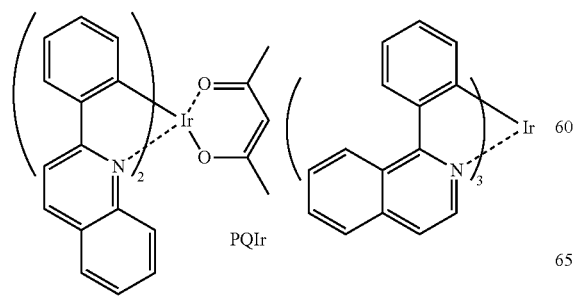

PQIr

-continued

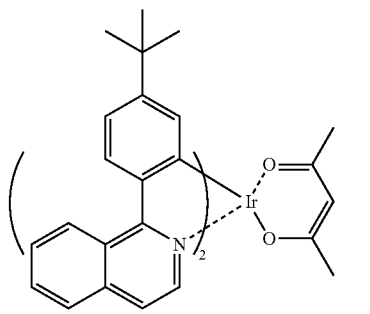

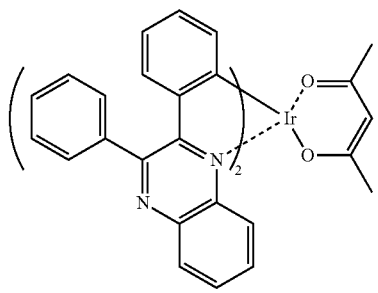

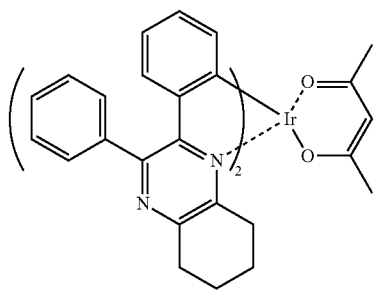

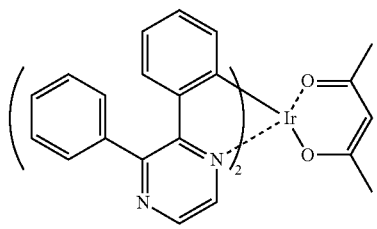

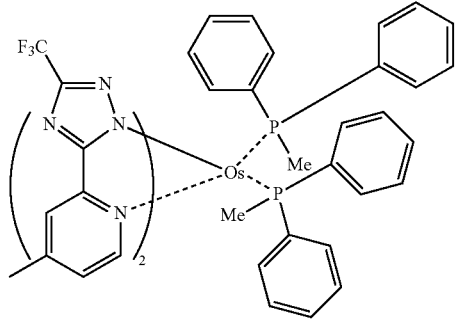

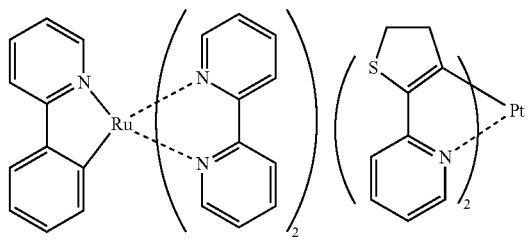

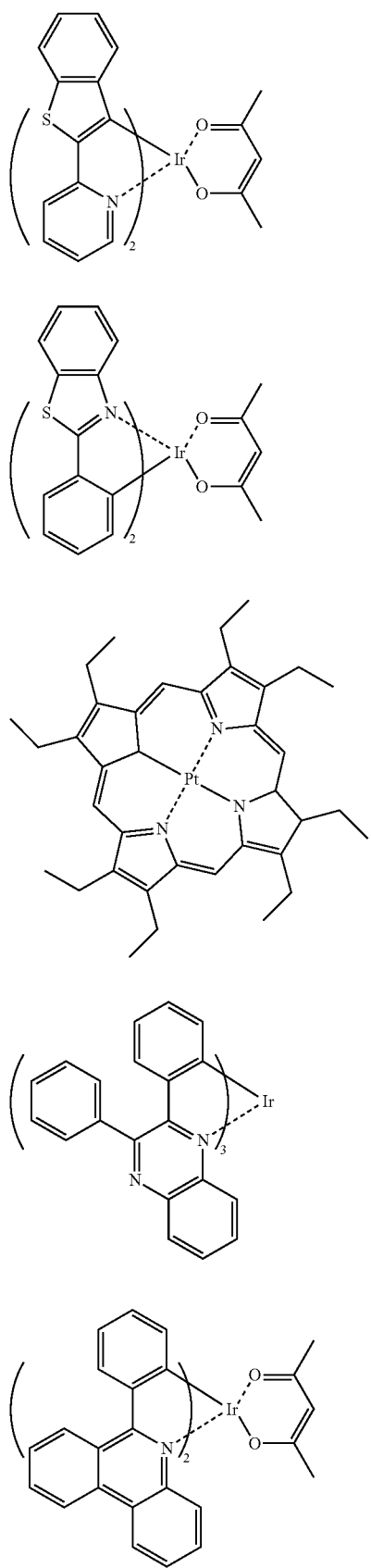
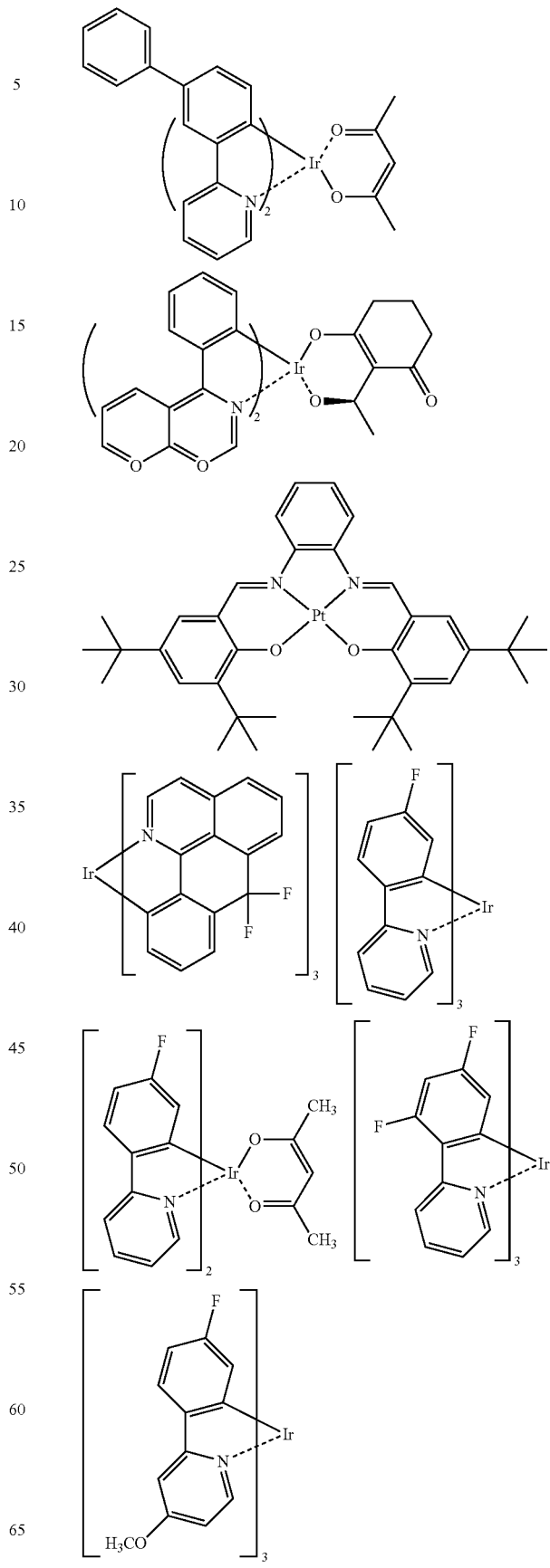

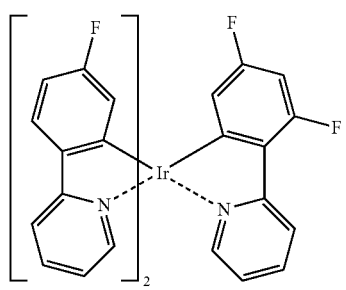
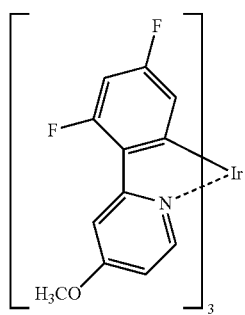
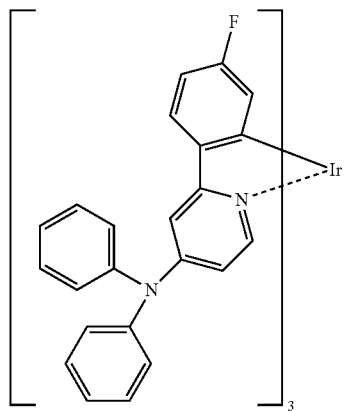
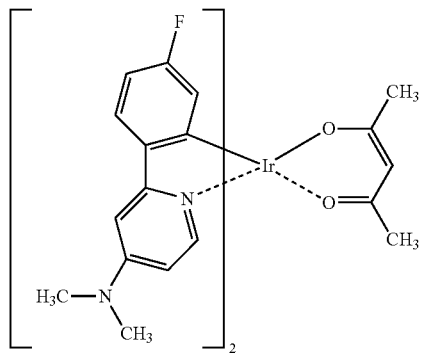
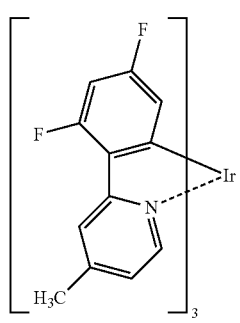
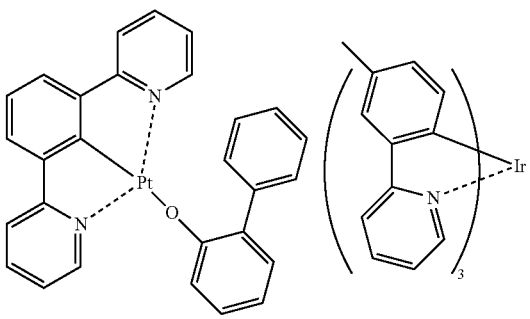
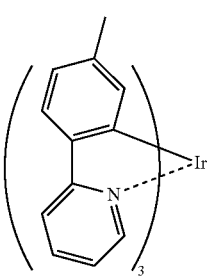
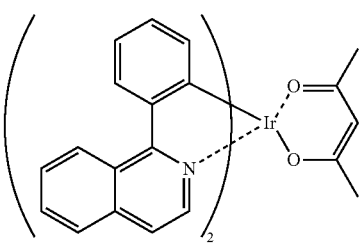
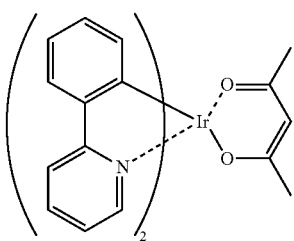
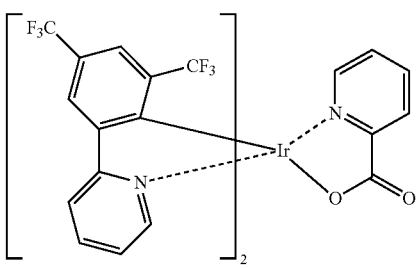
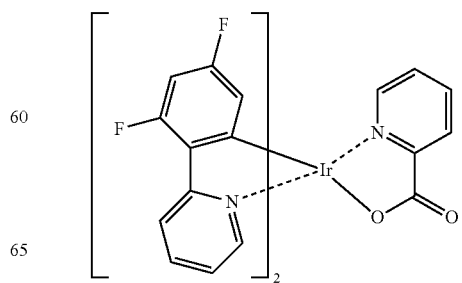

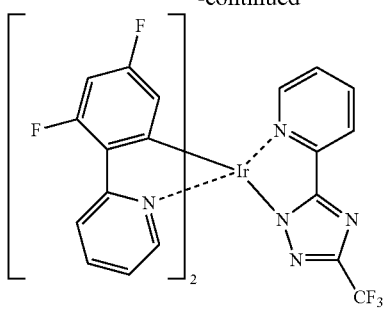
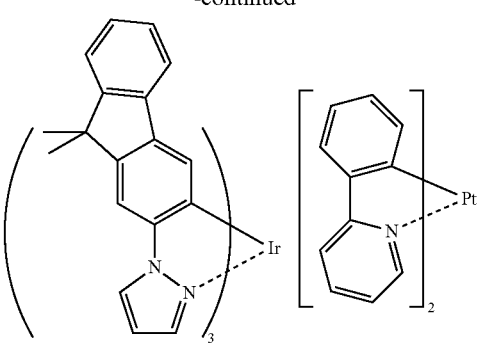
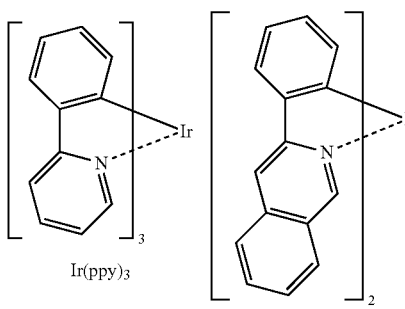
Ir(ppy)₃
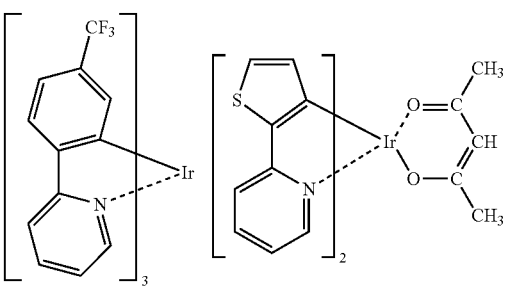
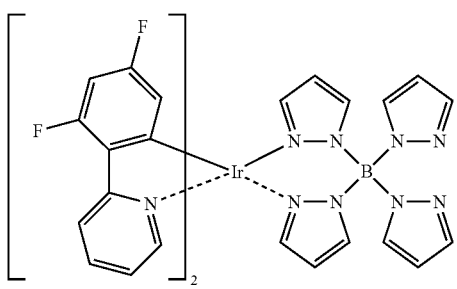
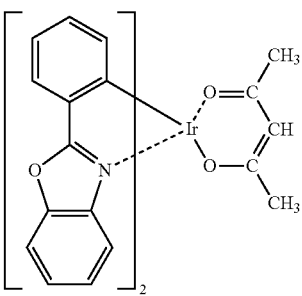
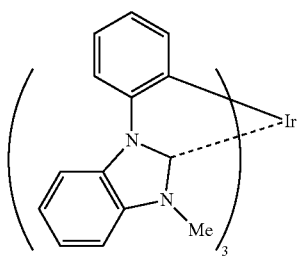
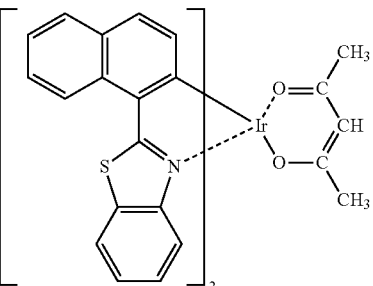
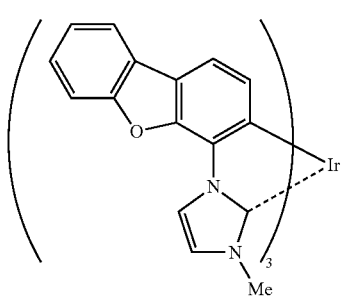
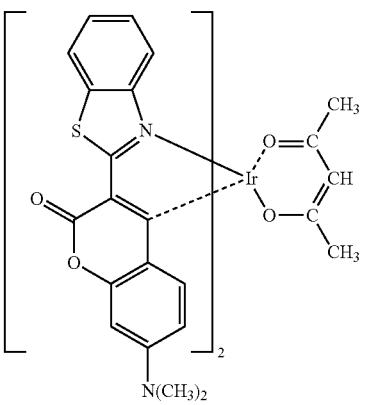

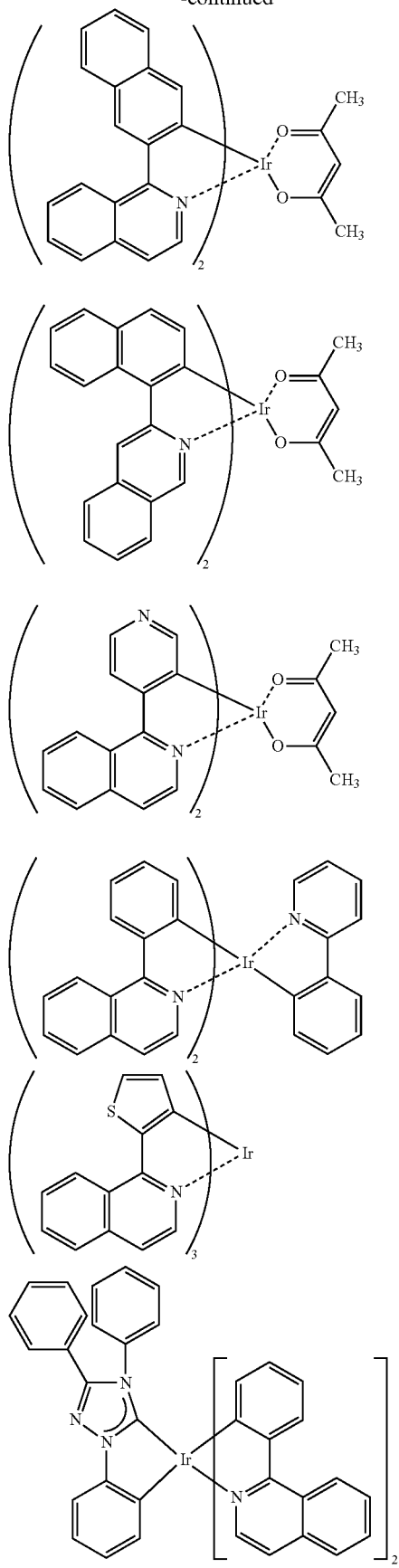

In the present invention, at least one of the phosphorescent emitting materials in the light emitting layer shows emission maximum in a range preferably 520 nm or more and 720 nm or less and more preferably 570 nm or more and 720 nm or less.

A highly efficient organic electroluminescence device is obtained by forming the light emitting layer comprising the specific compound of the invention which is doped with the phosphorescent emitting material (phosphorescent dopant) showing such emission wavelength.

The organic electroluminescence device of the invention may have a hole transporting layer (hole injecting layer), and the hole transporting layer (hole injecting layer), each preferably containing the material for organic electroluminescence devices represented by formula (1). In addition, the organic electroluminescence device of the invention may have an electron transporting layer and/or a hole blocking layer, and the electron transporting layer and/or the hole blocking layer preferably contains the material for organic electroluminescence devices represented by formula (1).

It is also preferred for the organic electroluminescence device of the invention to contain a reduction-causing dopant in the interfacial region between the cathode and the organic thin film layer.

With such a construction, the organic electroluminescence device has an improved luminance and an elongated lifetime.

Examples of the reduction-causing dopant include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs.

Examples of the alkaline earth metal include Ca (work function: 2.9 eV), Sr (work function: 2.0 to 2.5 eV), and Ba (work function: 2.52 eV), with those having a work function of 2.9 eV or less being particularly preferred.

Examples of the rare earth metal include Sc, Y, Ce, Tb, and Yb, with those having a work function of 2.9 eV or less being particularly preferred.

Since the preferred metals mentioned above has a particularly high reductivity, an organic electroluminescence device having an improved luminance and an elongated lifetime ban be obtained by its addition to the electron injecting region in a relatively small amount.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred.

Examples of the alkaline earth metal compound include BaO, SrO, CaO, and mixture thereof, such as $Ba_xSr_{1-x}O$ (0<x<1) and $Ba_xCa_{1-x}O$ (0<x<1), with BaO, SrO, and CaO being preferred.

Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, rare earth metal ions, respectively. The ligand is preferably, but limited to, quinolinol, benzoquinolinol, acridinol, phenanthridinol, hydroxyphenyloxazole, hydroxyphenyl-thiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The reduction-causing dopant is formed in the interfacial region preferably into a form of layer or island. The reduction-causing dopant is added preferably by co-depositing the reduction-causing dopant and the organic material for forming the interfacial region, such as a light emitting material and an electron injecting material, by a resistance heating deposition method, thereby dispersing the reduction-causing dopant into the organic material. The disperse concentration expressed by the molar ratio of the organic material and the reduction-causing dopant is 100:1 to 1:100 and preferably 5:1 to 1:5.

When the reduction-causing dopant is formed into a form of layer, a light emitting material or an electron injecting material is made into a layer which serves as an organic layer in the interface, and then, the reduction-causing dopant alone is deposited by a resistance heating deposition method into a layer having a thickness preferably 0.1 to 15 nm.

When the reduction-causing dopant is formed into a form of island, a light emitting material or an electron injecting material is made into a form of island which serves as an organic layer in the interface, and then, the reduction-causing dopant alone is deposited by a resistance heating deposition method into a form of island having a thickness preferably 0.05 to 1 nm.

The molar ratio of the main component and the reduction-causing dopant in the organic electroluminescence device of the invention is preferably 5:1 to 1:5 and more preferably 2:1 to 1:2.

It is preferred for the organic electroluminescence device of the invention that an electron transporting layer or electron injecting layer is disposed between the light emitting layer and the cathode, and the electron transporting layer or electron injecting layer contains the material for organic electroluminescence devices, preferably as a main component. The electron injecting layer may work as an electron transporting layer The term "main component" referred to herein means that 50% by mass or more of the electron injecting layer is the material for organic electroluminescence devices.

The electron injecting layer or the electron transporting layer is a layer for facilitating the injection of electrons into the light emitting layer and has large electron mobility. The electron injecting layer is formed to adjust the energy level, for example, by reducing the abrupt change in energy level.

An aromatic heterocyclic compound having one or more heteroatoms in its molecule is preferably used as the electron injecting material for the electron transporting layer or electron injecting layer, with a nitrogen-containing ring derivative being particularly preferred. The nitrogen-containing ring derivative is preferably an aromatic ring compound having a nitrogen-containing 6- or 5-membered ring or a condensed aromatic ring compound having a nitrogen-containing 6- or 5-membered ring.

The nitrogen-containing ring derivative is preferably, for example, a chelate metal complex having a nitrogen-containing ring represented by formula (A):

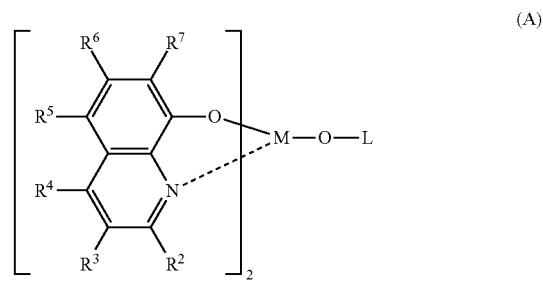

$R^2$ to $R^7$ are each independently hydrogen atom, a halogen atom, hydroxyl group, amino group, a hydrocarbon group having 1 to 40 carbon atoms, an alkoxy group, an aryloxy group, an alkoxycarbonyl group, or a heterocyclic group, each being optionally substituted.

The halogen atom may include fluorine, chlorine, bromine, and iodine. The substituted amino group may include an alkylamino group, an arylamino group, and an aralkylamino group.

The hydrocarbon group having 1 to 40 carbon atoms may include an alkyl group, an alkenyl group, a cycloalkyl group, an aryl group, and an aralkyl group, each being substituted or unsubstituted.

Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxyt-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromot-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodot-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, and 1,2,3-trinitropropyl group.

Of the above, preferred are methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 1-pentylhexyl group, 1-butylpentyl group, and 1-heptyloctyl group.

Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl1-butenyl group, with styryl group, 2,2-diphenylvinyl group, and 1,2-diphenylvinyl group being preferred.

Examples of the cycloalkyl group include cyclopentyl group, cyclohexyl group, cyclooctyl group, and 3,5-tetramethylcyclohexyl group, with cyclohexyl group, cyclooctyl group, and 3,5-tetramethylcyclohexyl group being preferred.

The alkoxy group is represented by —OY, wherein Y is an alkyl group. Examples and preferred examples thereof are the same as those described above.

Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quaterphenyl group.

Of the above, preferred are phenyl group, biphenyl-2-yl group, biphenyl-3-yl group, biphenyl-4-yl group, m-terphenyl-4-yl group, m-terphenyl-3-yl group, m-terphenyl-2-yl group, p-tolyl group, 3,4-xylyl group, and m-quaterphenyl-2-yl group.

Examples of the condensed aryl group include 1-naphthyl group, 2-naphthyl group.

The heterocyclic group may be monocyclic or condensed and has preferably 1 to 20 ring carbon atoms, more pre 1 to 12 ring carbon atoms, and more preferably 1 to 10 ring carbon atoms. The heterocyclic group is preferably an aromatic heterocyclic group having at least one heteroatom selected from nitrogen atom, oxygen atom, sulfur atom, and selenium atom. Examples of the heterocyclic group include the residues derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, tetrazaindene, carbazole, and azepine, with the residues of furan, thiophene, pyridine, pyrazine, pyrimidine, pyridazine, triazine, quinoline, phthalazine, naphthyridine, quinoxaline, and quinazoline being preferred, the residues derived from furan, thiophene, pyridine, and quinoline being more preferred, and quinolinyl group being still more preferred.

Examples of the aralkyl group include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group.

Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The aryloxy group is represented by —OY' wherein Y' is phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, or 4"-t-butyl-p-terphenyl-4-yl group.

The aryloxy group includes a heteroaryloxy group represented by —OZ', wherein Z' is 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1 isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The alkoxycarbonyl group is represented by —COOY', wherein Y' is an alkyl group and examples thereof are selected from those described above.

The alkylamino group and the aralkylamino group are represented by —NQ$^1$Q$^2$, wherein Q$^1$ and Q$^2$ are each independently an alkyl group or an aralkyl group, examples and preferred examples being the same as those described above. One of Q$^1$ and Q$^2$ may be hydrogen atom.

The arylamino group represented by —NAr$^1$Ar$^2$, wherein Ar$^1$ and Ar$^2$ are each independently a non-condensed aryl group or a condensed aryl group, examples thereof being the same as those described above. One of Ar$^1$ and Ar$^2$ may be hydrogen atom.

M is aluminum (Al), gallium (Ga), or indium (In), with In being preferred.

L in formula (A) is a group represented by formula (A') or (A"):

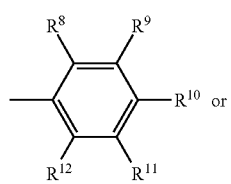

(A')

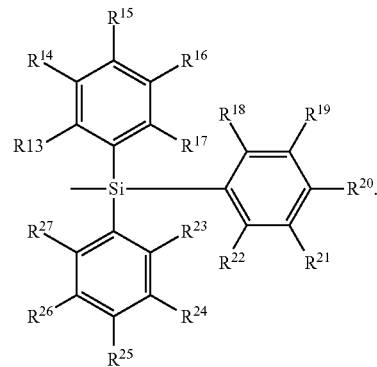

(A")

In the above formulae, $R^8$ to $R^{12}$ are each independently hydrogen atom or a substituted or unsubstituted hydrocarbon group having 1 to 40 carbon atoms. The adjacent two groups may form a ring structure. $R^{13}$ to $R^{27}$ are each independently hydrogen atom or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$.

Examples of the divalent group formed by the adjacent groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

Specific examples of the chelate metal complex having a nitrogen-containing ring represented by formula (A) are shown below, although not limited thereto.

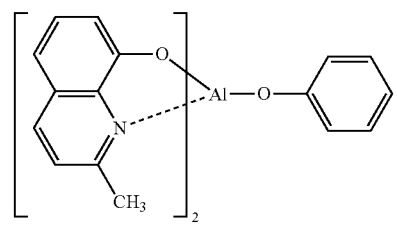

(A-1)

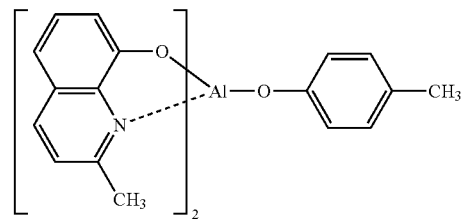

(A-2)

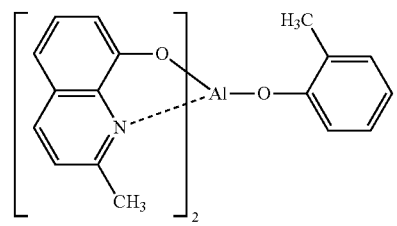

(A-3)

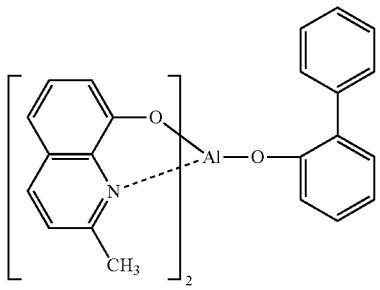 (A-4)
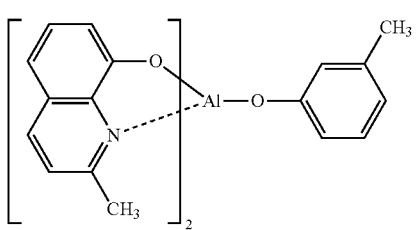 (A-5)
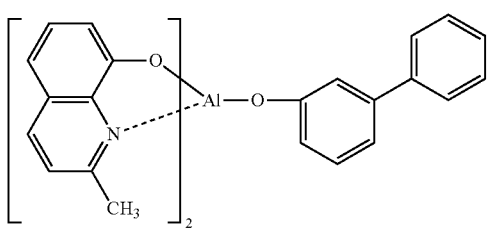 (A-6)
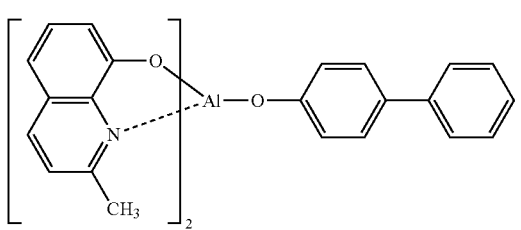 (A-7)
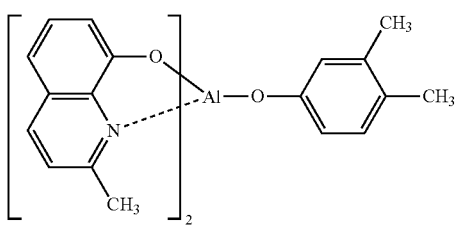 (A-8)
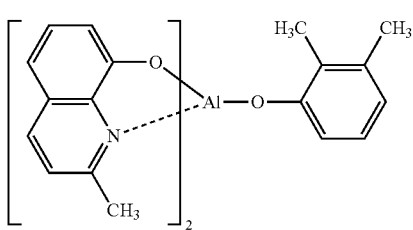 (A-9)
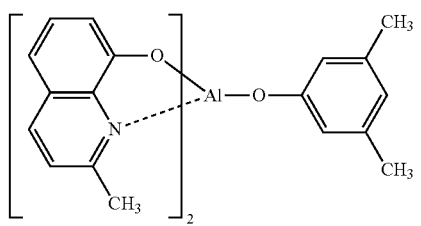 (A-10)
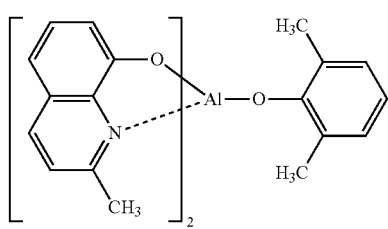 (A-11)
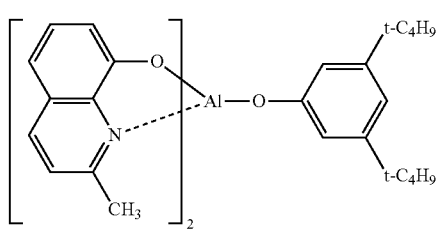 (A-12)
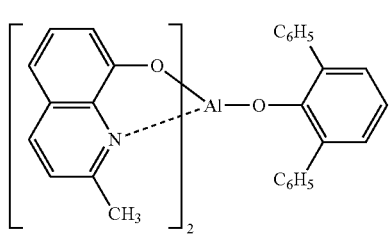 (A-13)
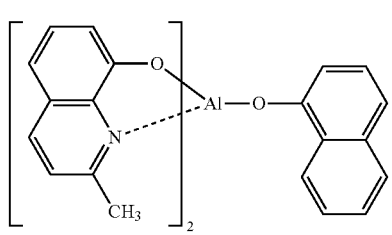 (A-14)
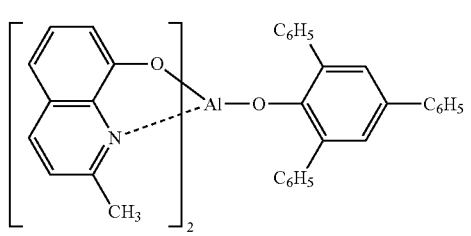 (A-15)
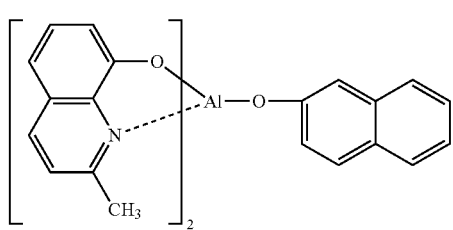 (A-16)

(A-17)
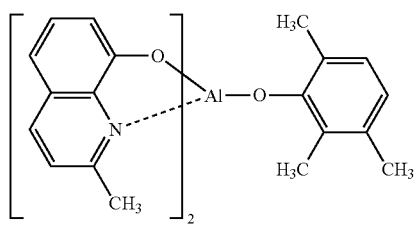
(A-18)
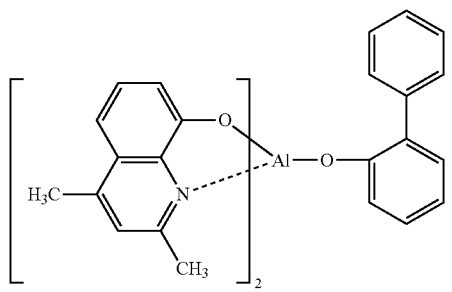
(A-19)
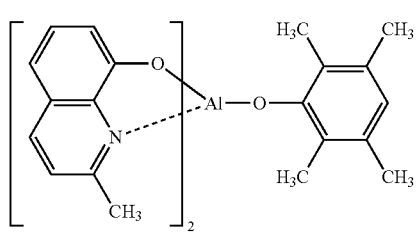
(A-20)
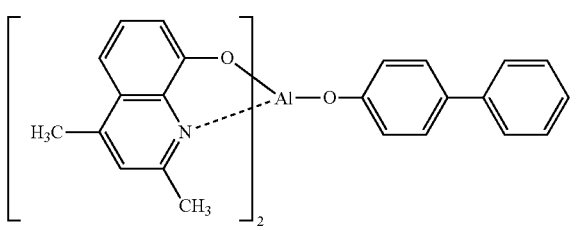
(A-21)
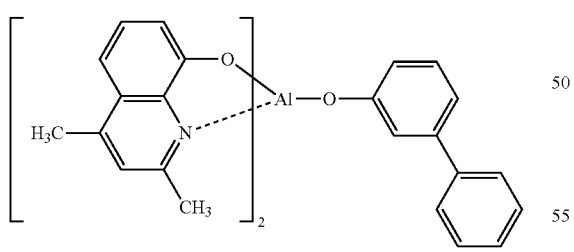
(A-22)
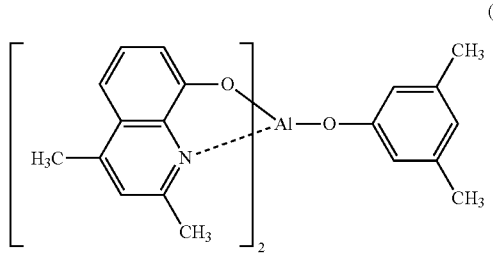
(A-23)
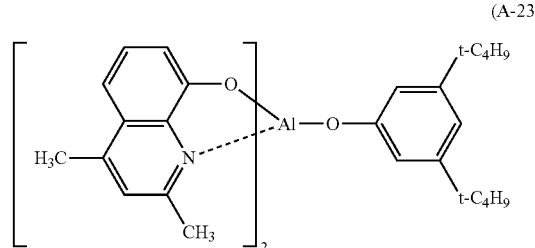
(A-24)
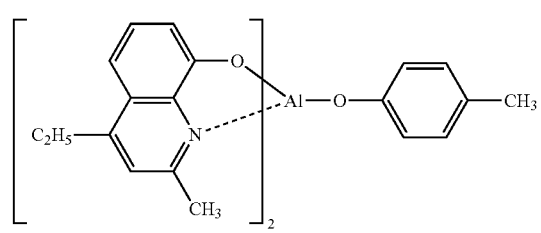
(A-25)
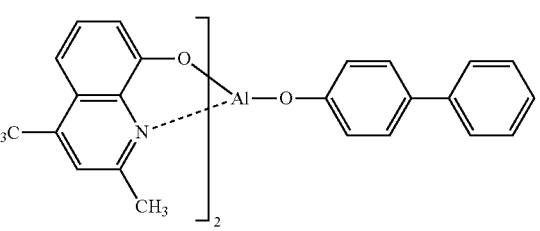
(A-26)
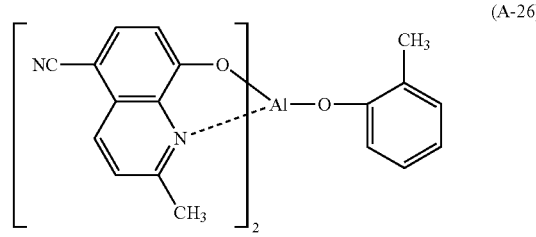
(A-27)
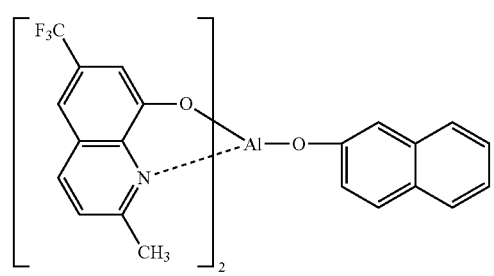
(A-28)
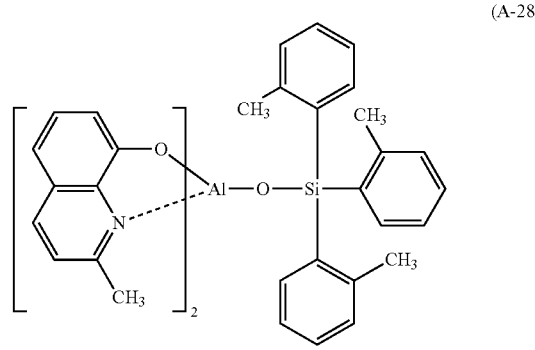

(A-29)

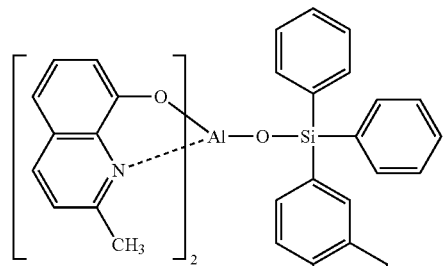

(A-30)

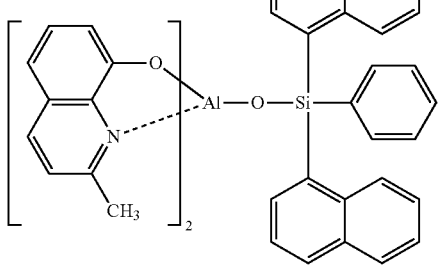

(A-31)

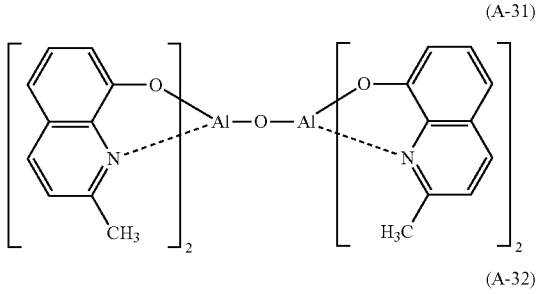

(A-32)

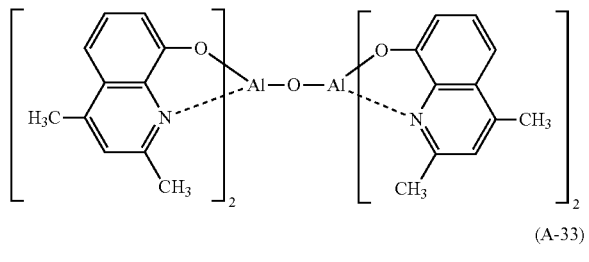

(A-33)

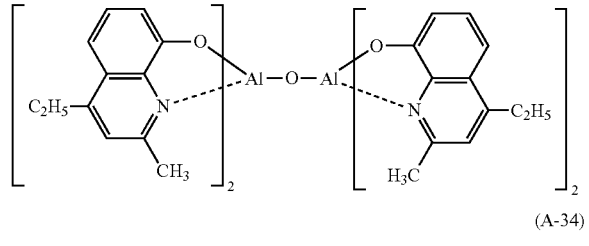

(A-34)

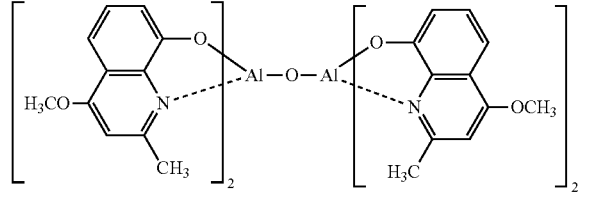

(A-35)

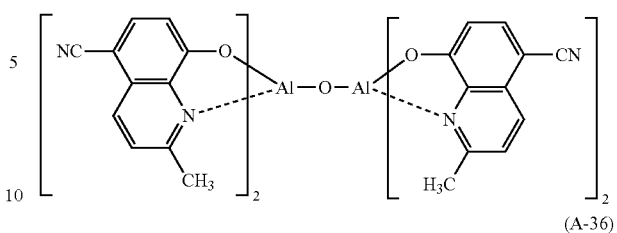

(A-36)

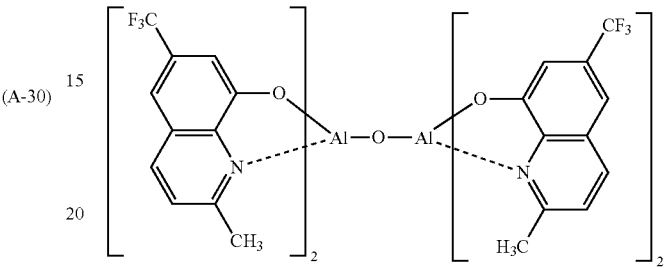

In the present invention, the electron injecting layer and the electron transporting layer preferably contain a nitrogen-containing heterocyclic derivative.

The electron injecting layer or the electron transporting layer is a layer for facilitating the injection of electrons into the light emitting layer and have large electron mobility. The electron injecting layer is formed to adjust the energy level, for example, by reducing the abrupt change in energy level. The material for the electron injecting layer or the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below.

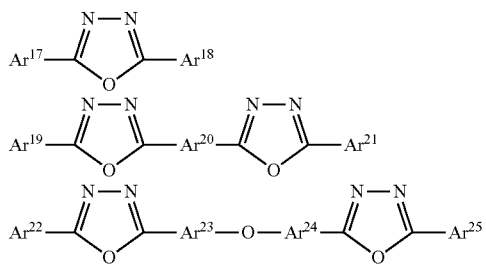

In the above formulae, each of $Ar^{17}$, $Ar^{18}$, $Ar^{19}$, $Ar^{21}$, and $Ar^{25}$ is a substituted or unsubstituted aryl group, and $Ar^{17}$ and $Ar^{18}$, $Ar^{19}$ and $Ar^{21}$, and $Ar^{22}$ and $Ar^{25}$ may be the same or different. Each of $Ar^{20}$, $Ar^{23}$, and $Ar^{24}$ is a substituted or unsubstituted arylene group, and $Ar^{23}$ and $Ar^{24}$ may be the same or different.

Examples of the arylene group include phenylene group, naphthylene group, biphenylene group, anthracenylene group, perylenylene group, and pyrenylene group. Examples of the substituent include an alkyl group having 1 to 10 carbon atoms, an alkoxy group having 1 to 10 carbon atoms, and cyano group. Electron transporting compounds which have a good thin film-forming property are preferably used. Examples of the electron transporting compound are shown below.

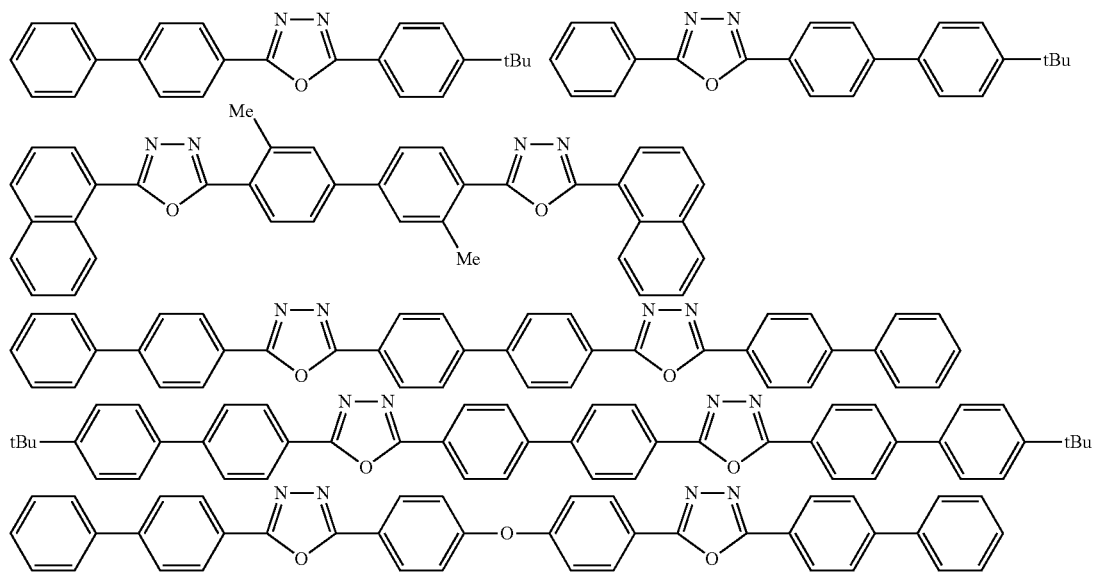

Examples of the nitrogen-containing heterocyclic derivative include a nitrogen-containing heterocyclic derivative having the following formulae but exclusive of metal complex, for example, a nitrogen-containing having a 5- or 6-membered ring having the skeleton represented by formula (A) or having the structure represented by formula (B).

(A)

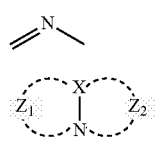

(B)

In formula (B), X is carbon atom or nitrogen atom. $Z_1$ and $Z_2$ are each independently a group of atoms for completing the nitrogen-containing heteroring.

(C)

A nitrogen-containing aromatic polycyclic compound having a 5- or 6-membered ring is preferred. If two or more nitrogen atoms are included, the nitrogen-containing aromatic polycyclic compound preferably has a skeleton of a combination of (A) and (B) or a combination of (A) and (C).

The nitrogen-containing group of the nitrogen-containing organic compound is selected from the nitrogen-containing heterocyclic groups shown below.

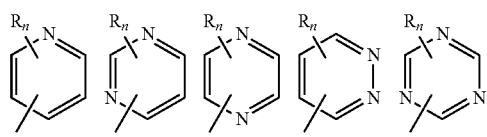

-continued

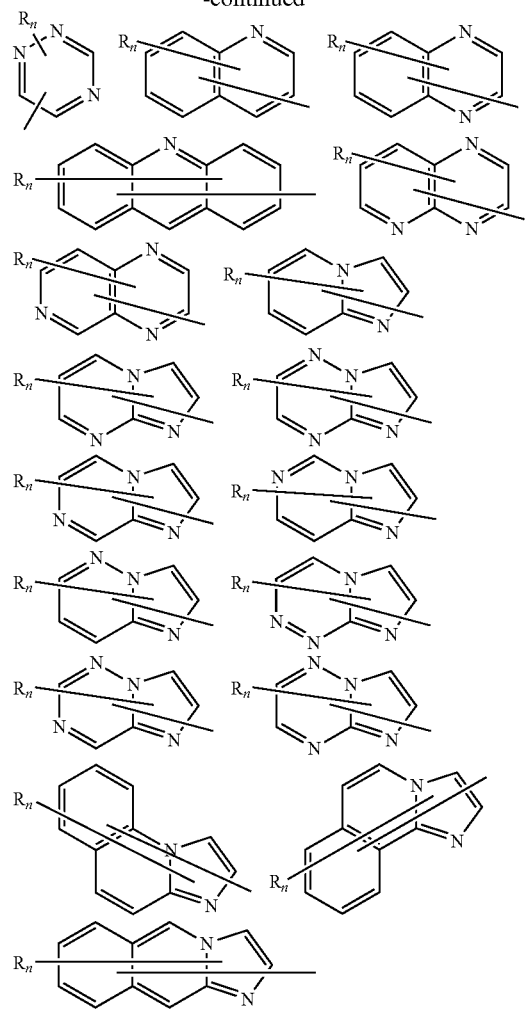

In the above formulae, R is an aryl group having 6 to 40 carbon atoms, a heteroaryl group having 3 to 40 carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by the following formula:

HAr-L$^1$-Ar$^1$—Ar$^2$

In the above formula, HAr is a substitute or unsubstituted nitrogen-containing heteroring having 3 to 40 carbon atoms; L$^1$ is a single bond, a substituted or unsubstituted arylene group having 6 to 40 carbon atoms, or a substituted or unsubstituted heteroarylene group having 3 to 40 carbon atoms; Ar$^1$ is a substitute or unsubstituted divalent aromatic hydrocarbon group having 6 to 40 carbon atoms; and Ar$^2$ is a substitute or unsubstituted aryl group having 6 to 40 carbon atoms or a substituted or unsubstituted heteroaryl group having 3 to 40 carbon atoms.

HAr is selected, for example, from the following group:

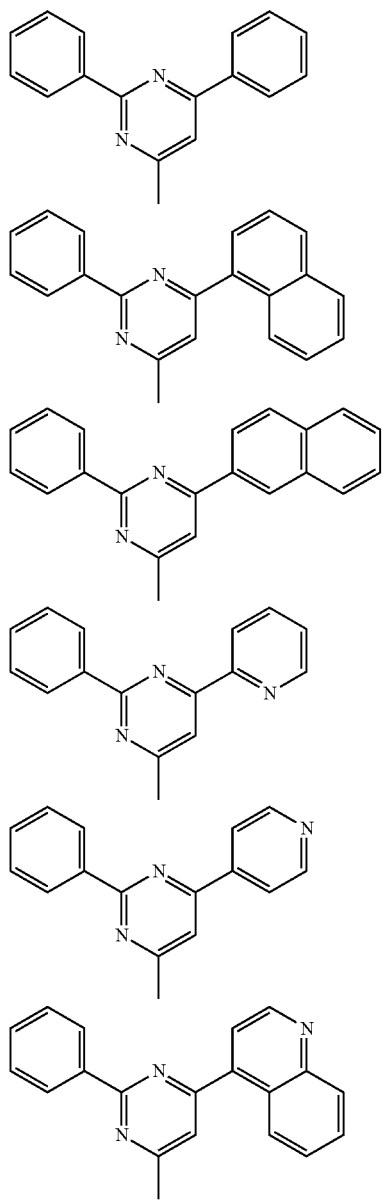

-continued

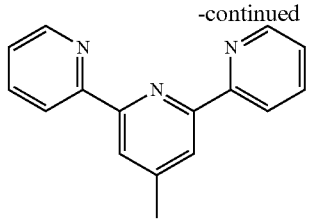

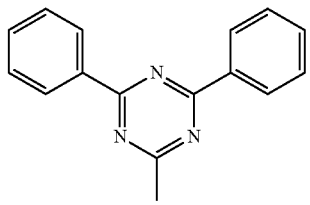

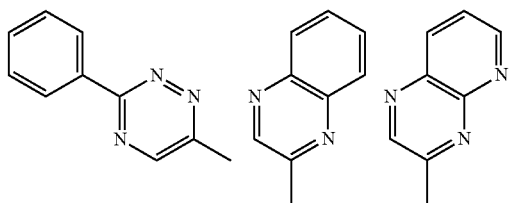

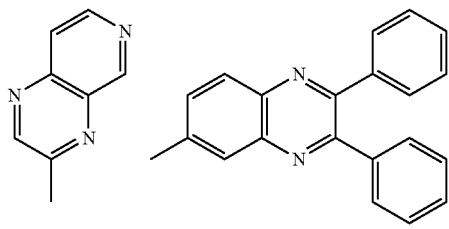

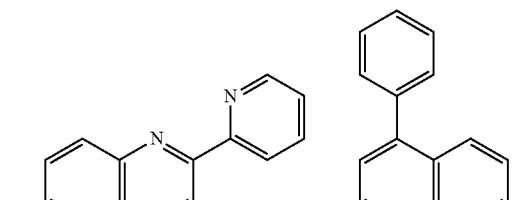

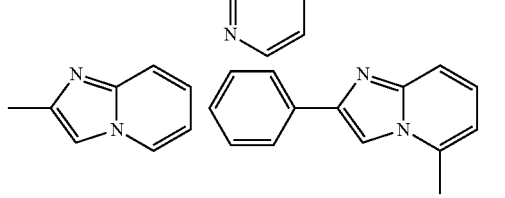

$L^1$ is selected, for example, from the following group:

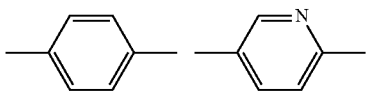

$Ar^2$ is selected, for example, from the following group:

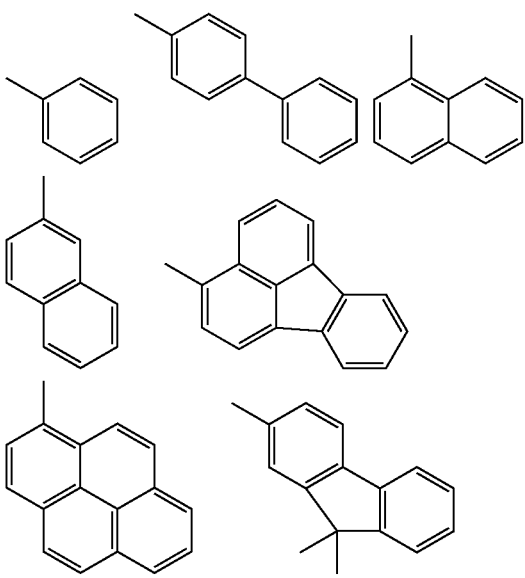

$Ar^1$ is selected, for example, from the following arylanthranyl groups:

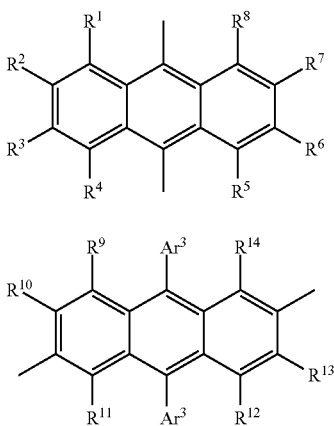

In the above formulae, $R^1$ to $R^{14}$ are each independently hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aryl group having 6 to 40 carbon atoms, or a heteroaryl group having 3 to 40 carbon atoms; and $Ar^3$ is a substituted or unsubstituted aryl group having 6 to 40 carbon atoms or a substituted or unsubstituted heteroaryl group having 3 to 40 carbon atoms.

A nitrogen-containing heterocyclic derivative having $Ar^1$ wherein $R^1$ to $R^8$ are all hydrogen atoms is preferred.

In addition, the following compound (JP 9-3448A) is preferred.

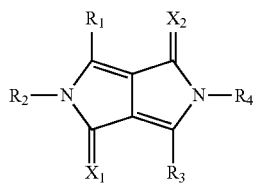

In the above formula, $R_1$ to $R_4$ are each independently hydrogen atom, a substituted or unsubstituted aliphatic group, a substituted or unsubstituted alicyclic group, a substituted or unsubstituted carbocyclic aromatic group, or a substituted or unsubstituted heterocyclic group; and $X_1$ and $X_2$ are each independently oxygen atom, sulfur atom, or dicyanomethylene group.

Further, the following compound (JP 2000-173774A) is also preferred.

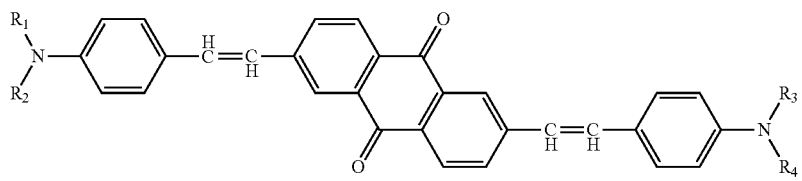

In the above formula, $R^1$, $R^2$, $R^3$, and $R^4$ may be the same or different and each represents an aryl group represented by the following formula:

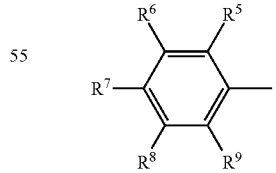

wherein $R^5$, $R^6$, $R^7$, $R^8$, and $R^9$ may be the same or different and represent hydrogen atoms or at least one thereof is a saturated or unsaturated alkoxy group, an alkyl group, amino group, or an alkylamino group.

Further, a high molecular compound having the nitrogen-containing heterocyclic group or the nitrogen-containing heterocyclic derivative is also usable.

It is preferred for the electron transporting layer to contain any one of the nitrogen-containing heterocyclic derivatives represented by the following formulae (201) to (203):

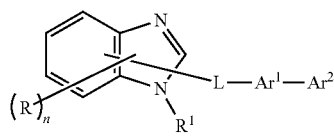
(201)

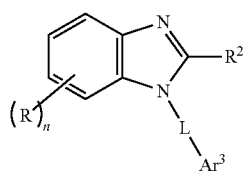
(202)

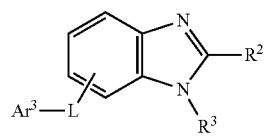
(203)

wherein R is hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms; n is an integer of 0 to 4; $R^1$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms; $R^2$ and $R^3$ are each independently hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms; L is a substituted or unsubstituted arylene group having 6 to 60 carbon atoms, a substituted or unsubstituted pyridinylene group, a substituted or unsubstituted quinolinylene group, or a substituted or unsubstituted fluorenylene group; $Ar^1$ is a substituted or unsubstituted arylene group having 6 to 60 carbon atoms, a substituted or unsubstituted pyridinylene group, or a substituted or unsubstituted quinolinylene group; and $Ar^2$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms.

$Ar^3$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by —$Ar^1$—$Ar^2$ wherein $Ar^1$ and $Ar^2$ are as defined above.

In formulae (201) to (203), R is hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of the aryl group having 6 to 60 carbon atoms, preferably 6 to 40 carbon atoms, and more preferably 6 to 20 carbon atoms include phenyl group, naphthyl group, anthryl group, phenanthryl group, naphthacenyl group, chrysenyl group, pyrenyl group, biphenyl group, terphenyl group, tolyl group, t-butylphenyl group, (2-phenylpropyl)phenyl group, fluoranthenyl group, fluorenyl group, a monovalent residue of spirobifluorene, perfluorophenyl group, perfluoronaphthyl group, perfluoroanthryl group, perfluorobiphenyl group, a monovalent residue of 9-phenylanthracene, a monovalent residue of 9-(1'-naphthyl)anthracene, a monovalent residue of 9-(2'-naphthyl)anthracene, a monovalent residue of 6-phenylchrysene, and a monovalent residue of 9-[4-(diphenylamino)phenyl]anthracene, with phenyl group, naphthyl group, biphenyl group, terphenyl group, 9-(10-phenyl)anthryl group, 9-[10-(1'-naphthyl)]anthryl group, and 9-[10-(2'-naphthyl)]anthryl group being preferred.

Examples of the alkyl group having 1 to 20 carbon atoms, preferably 1 to 6 carbon atoms include methyl group, ethyl group, propyl group, butyl group, pentyl group, hexyl group, and a haloalkyl group, such as trifluoromethyl group. The alkyl group having 3 or more carbon atoms may be linear, cyclic or branched.

Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Examples of the substituent represented by R include a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, and a substituted or unsubstituted heteroaryl group having 3 to 40 carbon atoms.

Examples of the halogen atom include fluorine, chlorine, bromine, and iodine.

Examples of the alkyl group having 1 to 20 carbon atoms, the alkoxy group having 1 to 20 carbon atoms, and the aryl group having 6 to 40 carbon atoms are the same as those described above.

Examples of the aryloxy group having 6 to 40 carbon atoms include phenoxy group and biphenyloxy group.

Examples of the heteroaryl group having 3 to 40 carbon atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, and triazolyl group.

n is an integer of 0 to 4, preferably 0 to 2.

In formula (201), $R^1$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms.

Examples, preferred examples, and preferred carbon numbers of the above groups are the same as those described with respect to R.

In formulae (202) and (203), $R^2$ and $R^3$ are each independently hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of each group, preferred carbon numbers, and examples of substituent are the same as those described with respect to R.

In formulae (201) to (203), L is a substituted or unsubstituted arylene group having 6 to 60 carbon atoms, a substituted or unsubstituted pyridinylene group, a substituted or unsubstituted quinolinylene group, or a substituted or unsubstituted fluorenylene group.

Preferably the arylene group has 6 to 40 carbon atoms and more preferably 6 to 20 carbon atoms. Examples thereof include divalent groups formed by removing one hydrogen atom from the aryl groups described with respect to R. Examples of the substituent of each group represented by L are the same as those described with respect to R.

L is preferably selected from the following group:

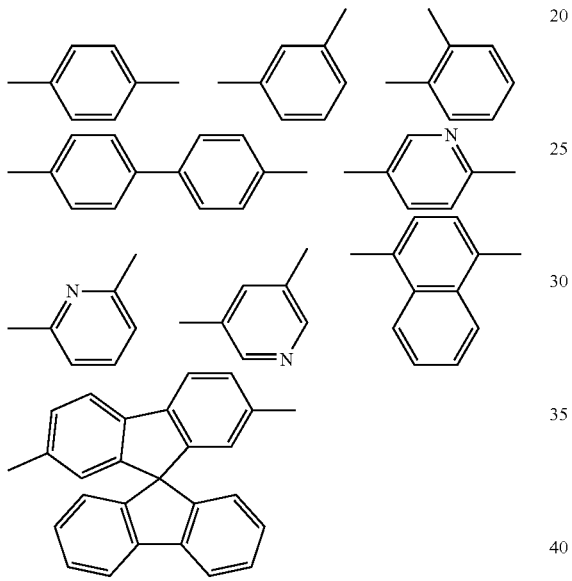

In formula (201), Ar¹ is a substituted or unsubstituted arylene group having 6 to 60 carbon atoms, a substituted or unsubstituted pyridinylene group, or a substituted or unsubstituted quinolinylene group. Examples of the substituent of each group represented by Ar¹ and Ar³ are the same as those described with respect to R.

Ar¹ is preferably any one of condensed groups represented by the following formulae (101) to (110):

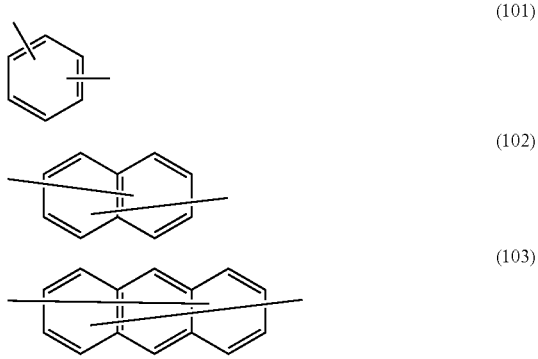

(101)
(102)
(103)

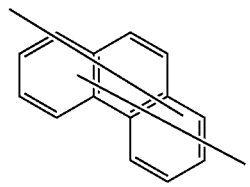

(104)
(105)

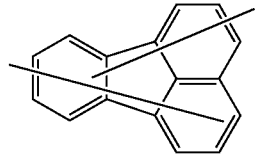

(106)

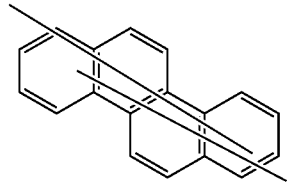

(107)

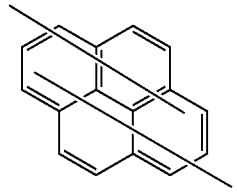

(108)

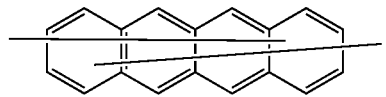

(109)

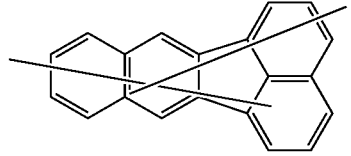

(110)

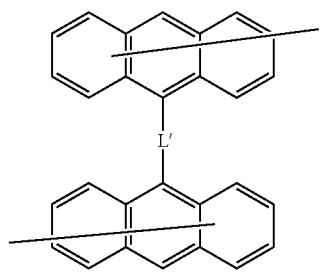

In formulae (101) to (110), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more groups, the substituents may be the same or different. Examples of the substituent are the same as those described above.

In formula (110), L' is a single bond or a group selected from the following group:
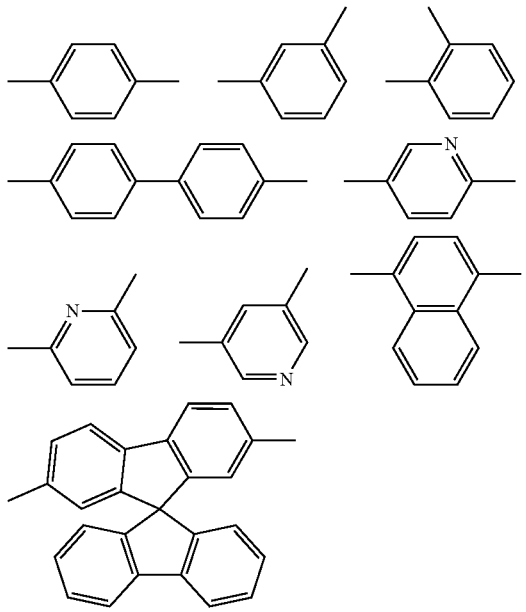
Formula (103) represented by Ar¹ is preferably the condensed ring group represented by the following formulae (111) to (125):
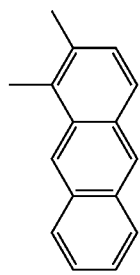
(111)
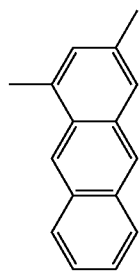
(112)
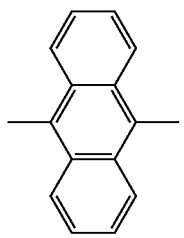
(113)
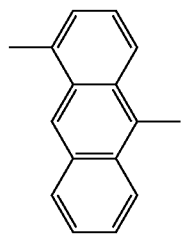
(114)
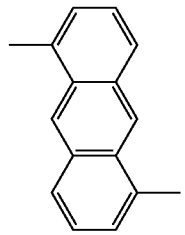
(115)
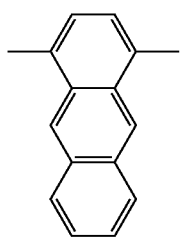
(116)
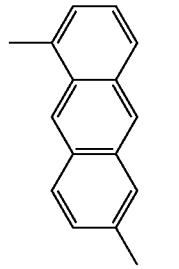
(117)
(118)
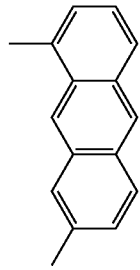
(119)

(120) 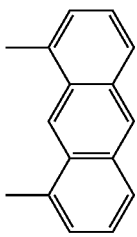

(121) 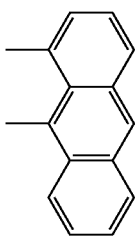

(122) 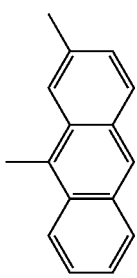

(123) 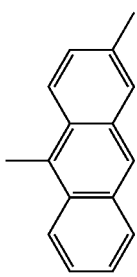

(124) 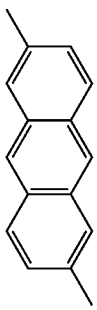

(125) 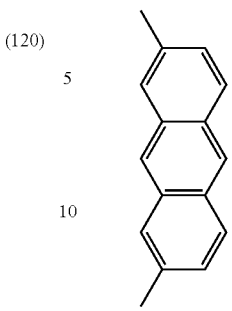

In formulae (111) to (125), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more groups, the substituents may be the same or different. Examples of the substituent are the same as those described above.

In formula (201), $Ar^2$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

Examples of each group, preferred carbon numbers, and examples of substituent are the same as those described with respect to R.

In formulae (202) and (203), $Ar^3$ is a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by $-Ar^1-Ar^2$ wherein $Ar^1$ and $Ar^2$ are as defined above.

Examples of each group, preferred carbon numbers, and examples of substituent are the same as those described with respect to R.

$Ar^3$ is preferably any one of condensed ring groups represented by the following formulae (126) to (135):

(126) 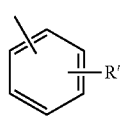

(127) 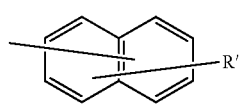

(128) 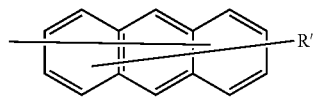

-continued

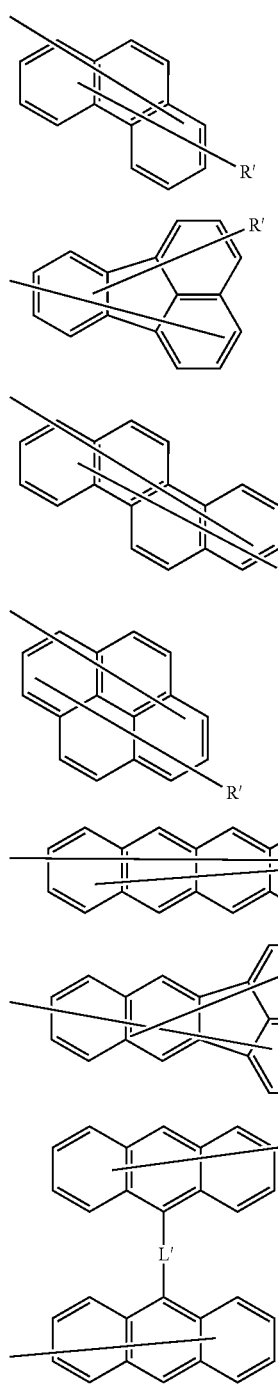

(129)
(130)
(131)
(132)
(133)
(134)
(135)

In formulae (126) to (135), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more groups, the substituents may be the same or different. Examples of the substituent are the same as those described above.

In formula (135), L' is as defined above.

In formulae (126) to (135), R' is hydrogen atom, a substituted or unsubstituted alkyl group having 1 to 20 carbon atoms, a substituted or unsubstituted aryl group having 6 to 40 carbon atoms, or a substituted or unsubstituted heteroaryl group having 3 to 40 carbon atoms. Examples thereof are the same as those described above.

Formula (128) represented by Ar³ is preferably the condensed ring group represented by the following formulae (136) to (158):

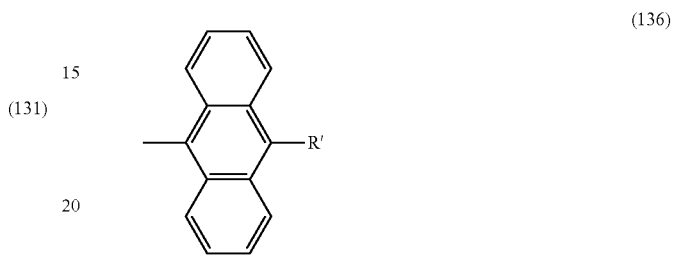

(136)

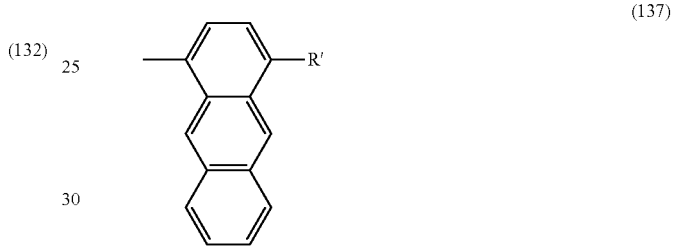

(137)

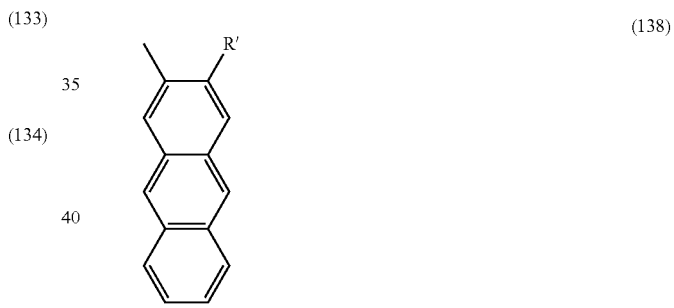

(138)

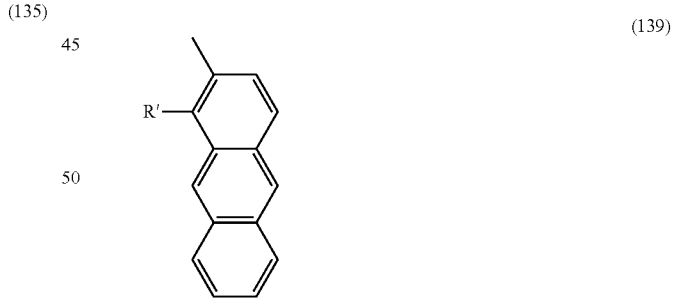

(139)

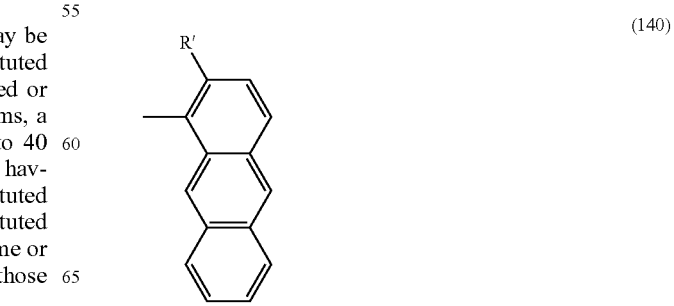

(140)

-continued
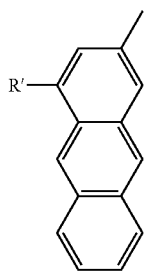
(141)
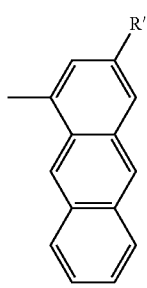
(142)
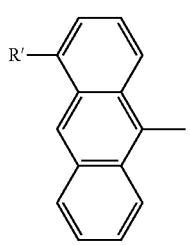
(143)
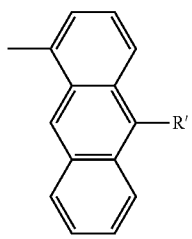
(144)
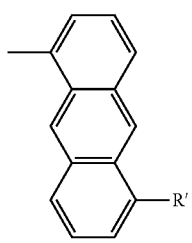
(145)
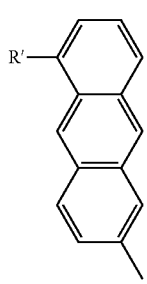
(146)
-continued
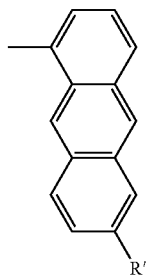
(147)
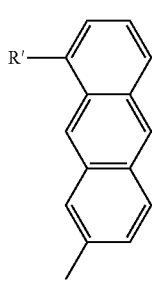
(148)
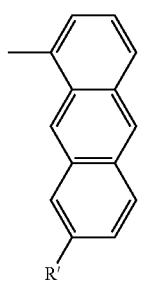
(149)
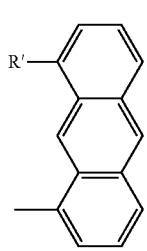
(150)
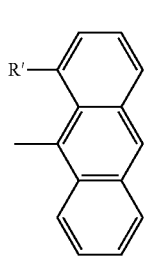
(151)
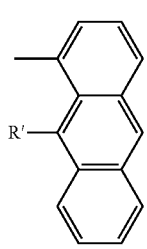
(152)

(153) 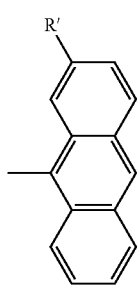

(154) 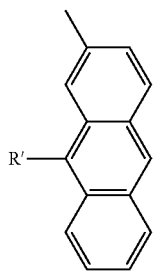

(155) 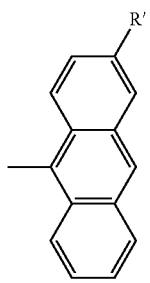

(156) 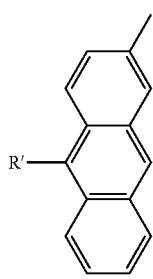

(157) 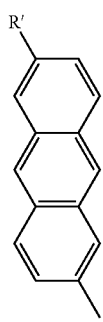

(158) 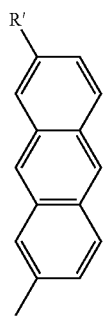

In formulae (136) to (158), each condensed ring may be substituted by a halogen atom, a substituted or unsubstituted alkyl group having 1 to 20 carbon atoms, a substituted or unsubstituted alkoxy group having 1 to 20 carbon atoms, a substituted or unsubstituted aryloxy group having 6 to 40 carbon atoms, a substituted or unsubstituted aryl group having 6 to 40 carbon atoms, or a substituted or unsubstituted heteroaryl group having 3 to 40 carbon atoms. If substituted by two or more groups, the substituents may be the same or different. Examples of the substituent are the same as those described above.

Each of $Ar^2$ and $Ar^3$ is preferably selected from the following group:

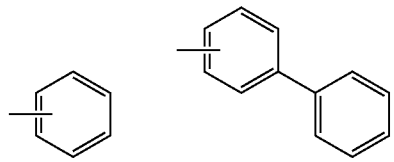

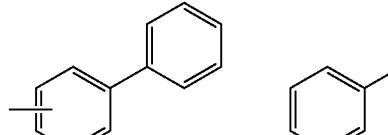

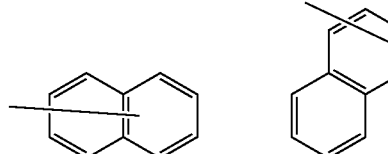

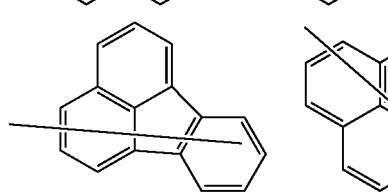

-continued
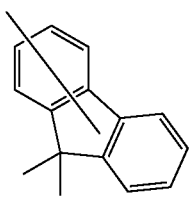
Examples of the nitrogen-containing heterocyclic derivative represented by formulae (201) to (203) are shown below. The nitrogen-containing heterocyclic derivative is, however, not limited to the following exemplary compounds.
In the following tables, HAr is the following structure in formulae (201) to (203).
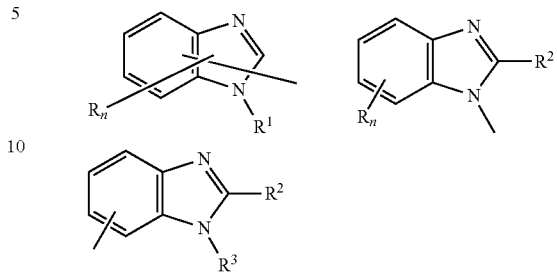
| | HAr | L | Ar$^1$ | Ar$^2$ |
|---|---|---|---|---|
| 1-1 | | | | |
| 2 | | | | |
| 3 | | | | |
| 4 | | | | |

-continued

| HAr | L | Ar¹ | Ar² |
|---|---|---|---|

Rows 5–10: each HAr is 1-phenyl-2-methyl-benzimidazole; each L is para-phenylene; each Ar¹ is 9,10-disubstituted anthracene (with methyl shown at 10-position).

- 5: Ar² = 3,5-diphenylphenyl
- 6: Ar² = 1-naphthyl
- 7: Ar² = 2-naphthyl
- 8: Ar² = phenanthrenyl
- 9: Ar² = fluoranthenyl
- 10: Ar² = pyrenyl -continued
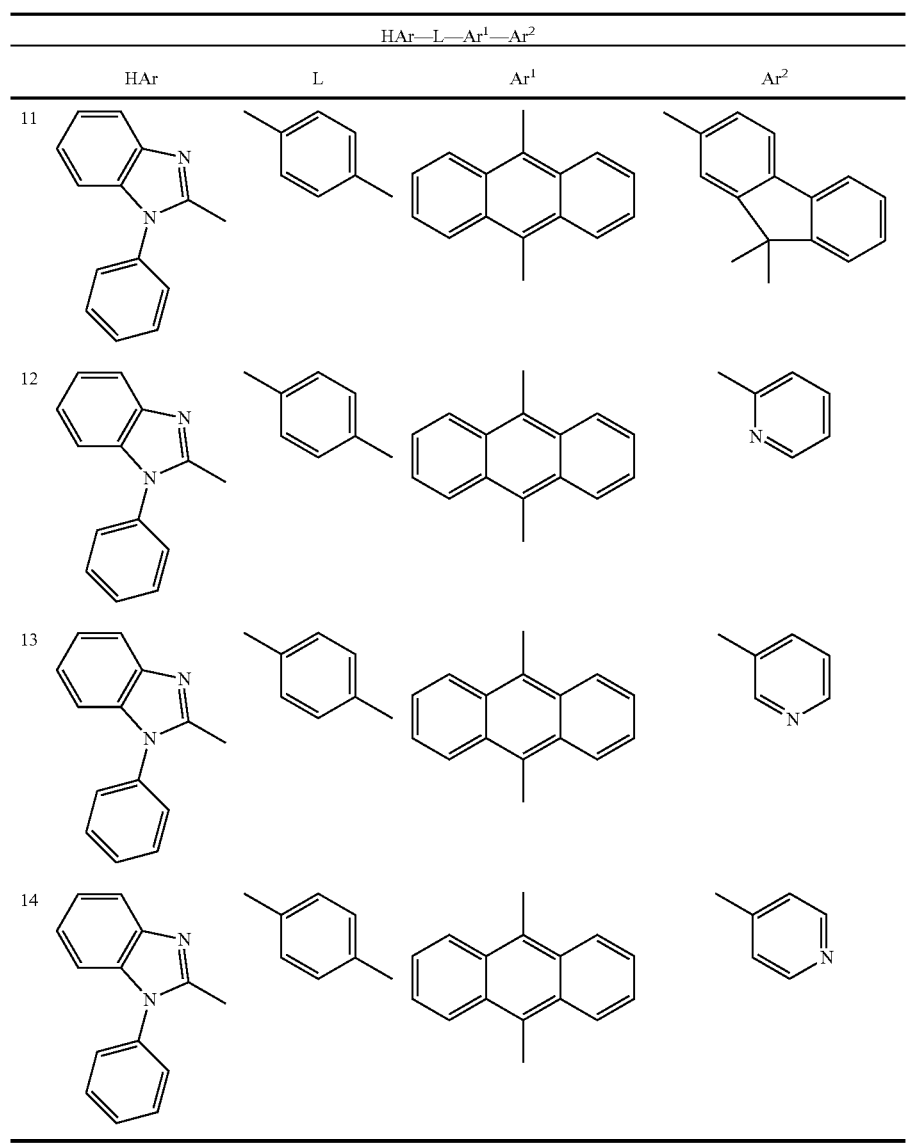
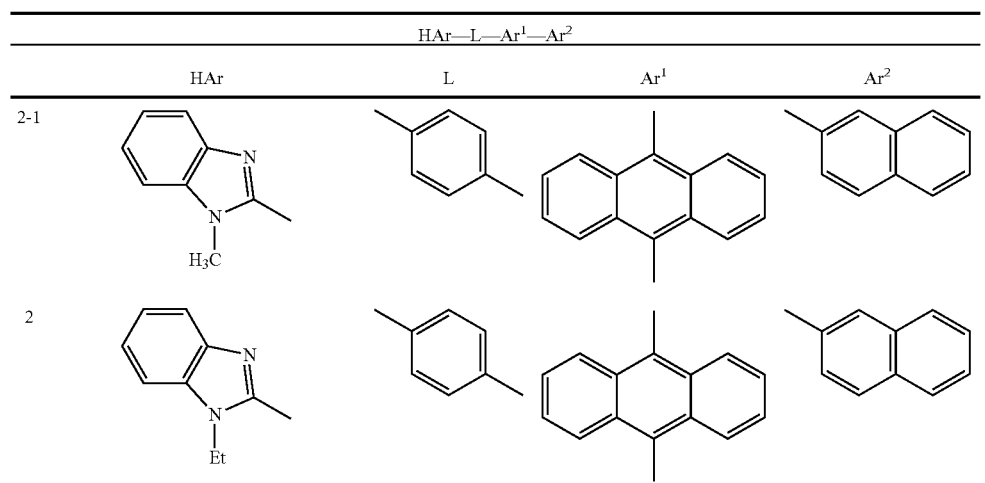

-continued

| | HAr | L | Ar¹ | Ar² |
|---|---|---|---|---|
| 3 | | | | |
| 4 | | | | |
| 5 | | | | |
| 6 | | | | |
| 7 | | | | |

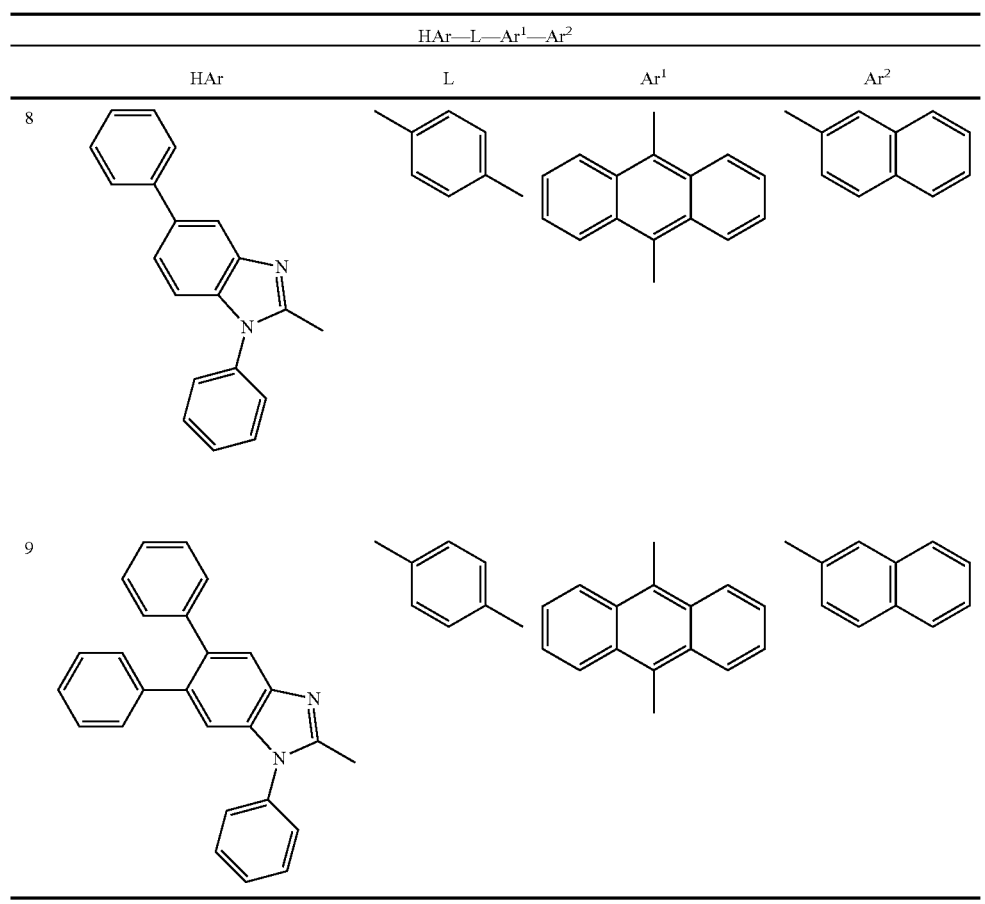
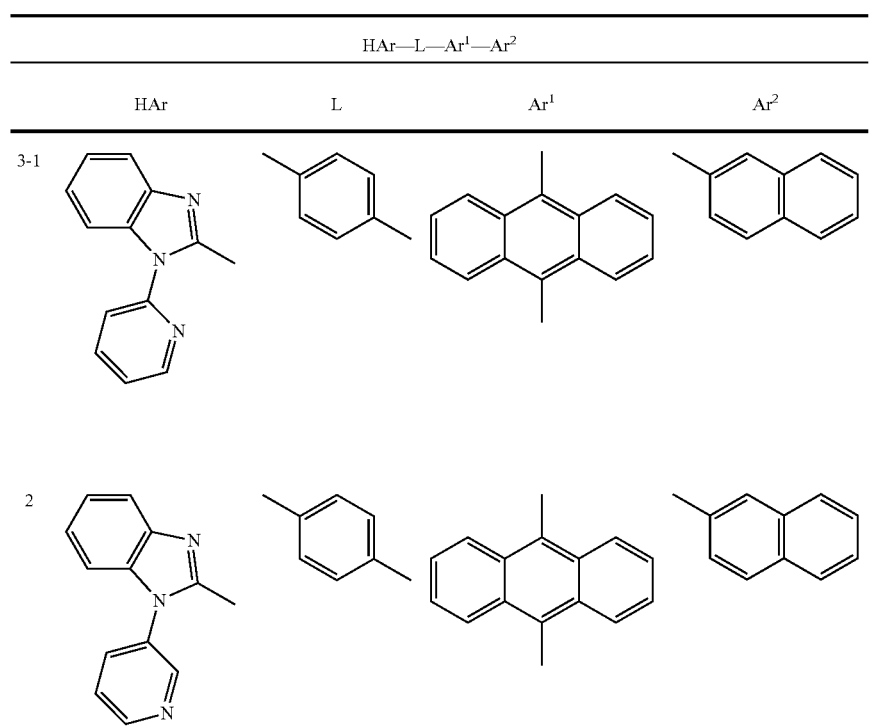

-continued
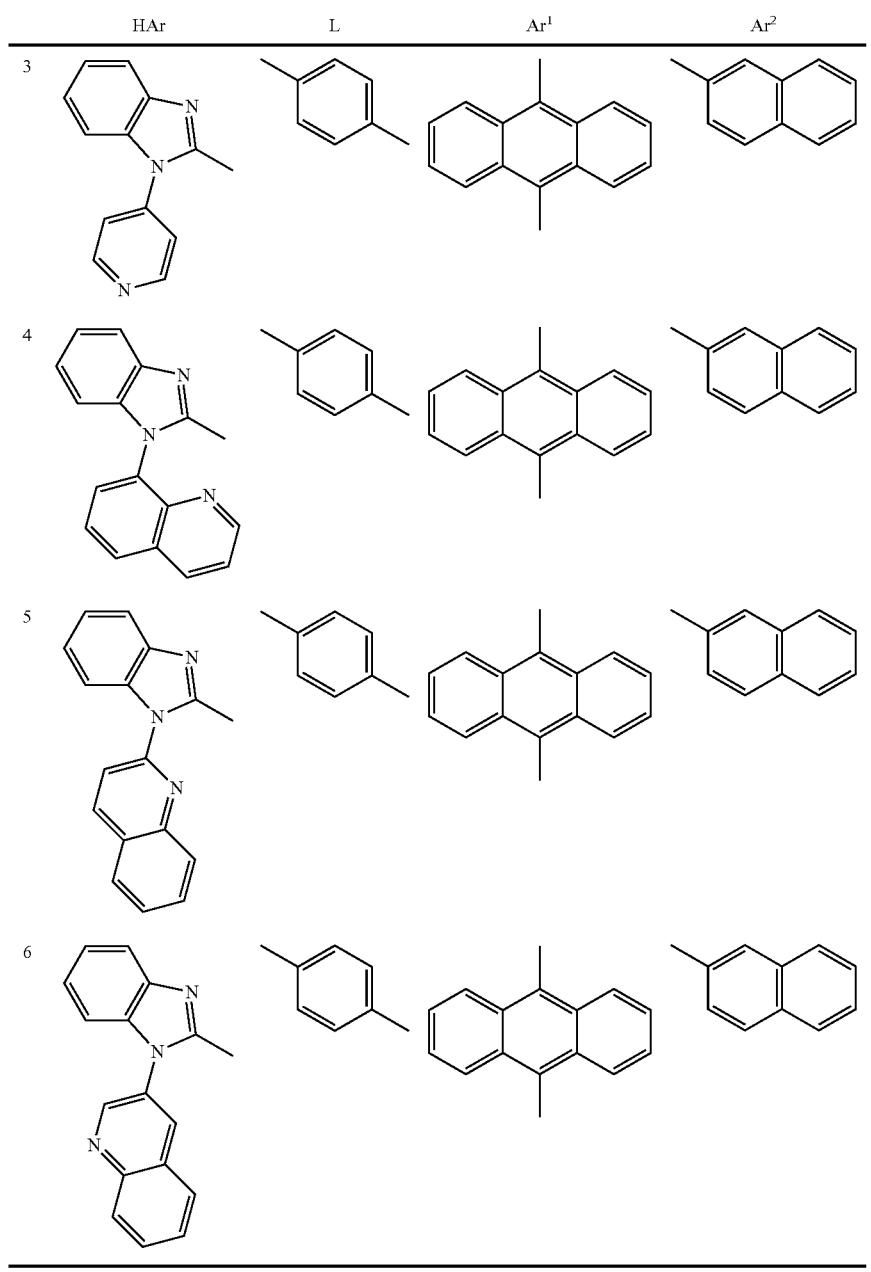
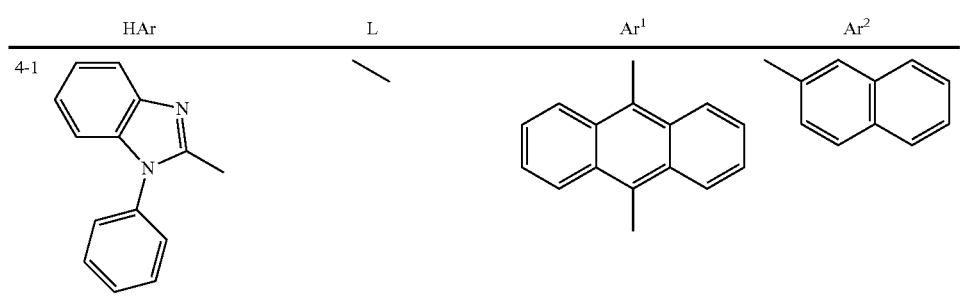

-continued
| | HAr—L—Ar¹—Ar² | | |
|---|---|---|---|
| HAr | L | Ar¹ | Ar² |
| | | | | |
|---|---|---|---|---|
| 2 | 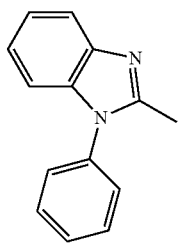 | 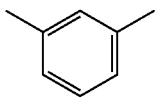 | 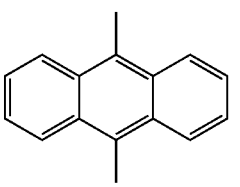 | 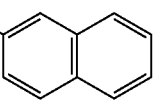 |
| 3 | 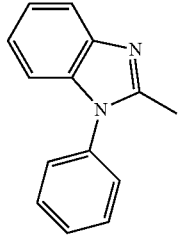 | 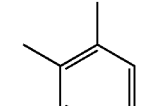 | 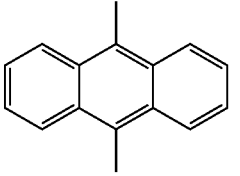 | 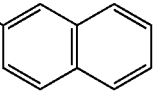 |
| 4 | 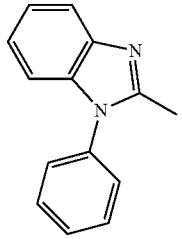 | 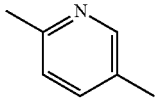 | 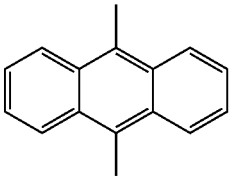 | 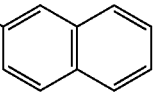 |
| 5 | 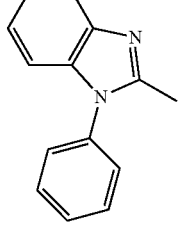 | 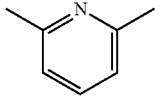 | 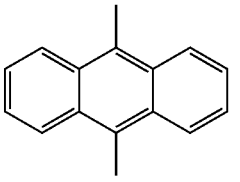 | 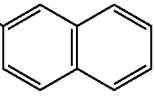 |
| 6 | 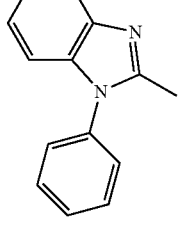 | 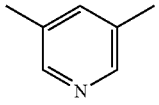 | 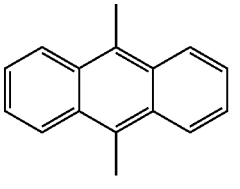 | 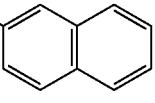 |
| 7 | 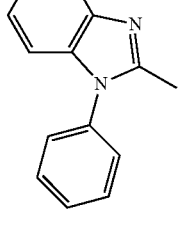 | 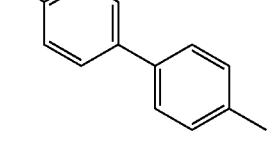 | 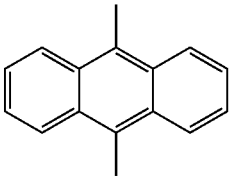 | 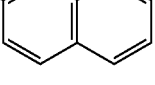 |

-continued
| | HAr | L | Ar¹ | Ar² |
|---|---|---|---|---|
| 8 | 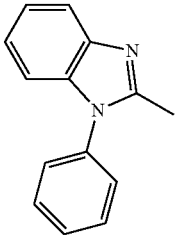 | 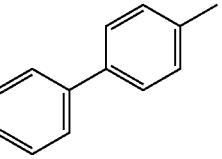 | 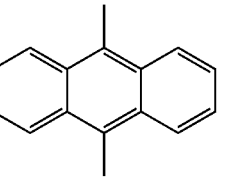 | 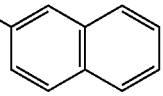 |
| 9 | 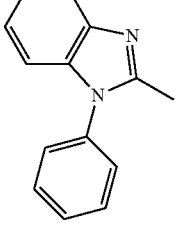 | 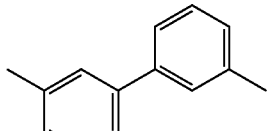 | 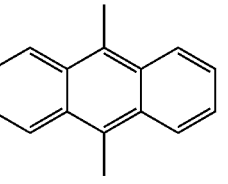 | 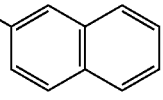 |
| 10 | 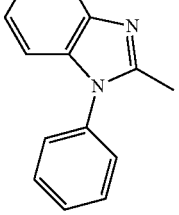 | 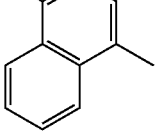 | 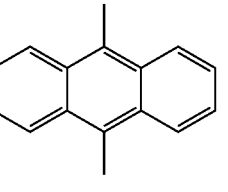 | 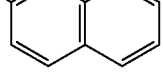 |
| 11 | 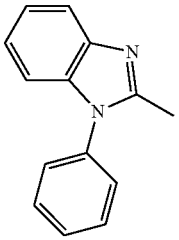 | 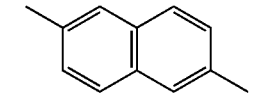 | 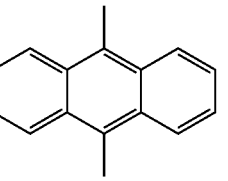 | 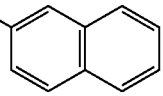 |
| 12 | 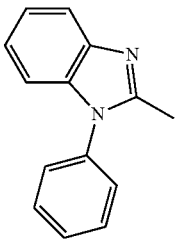 | 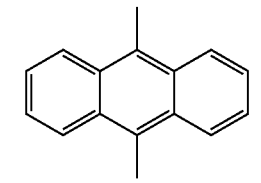 | 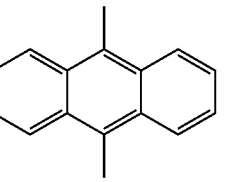 | 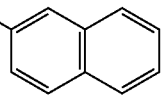 |

| | HAr | L | Ar¹ | Ar² |
|---|---|---|---|---|
| 5-1 | 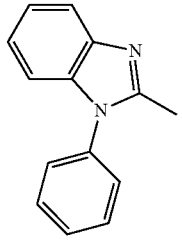 | 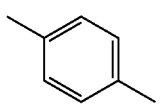 | 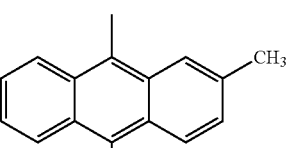 | 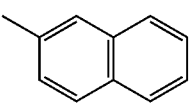 |
| 2 | 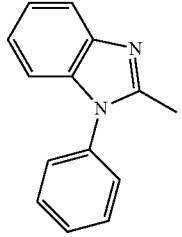 | 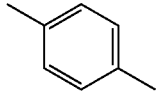 | 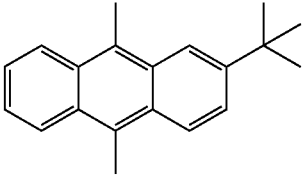 | 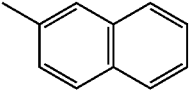 |
| 3 | 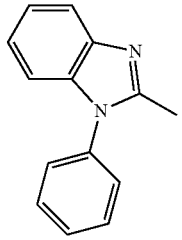 | 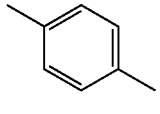 | 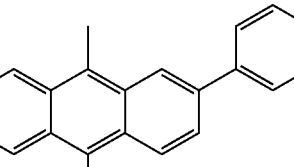 | 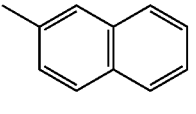 |
| 4 | 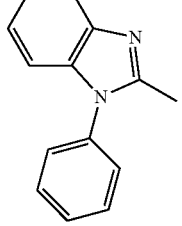 | 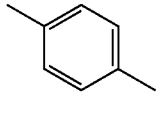 | 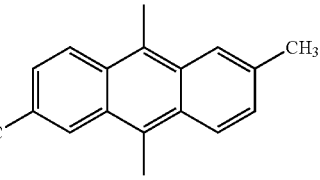 | 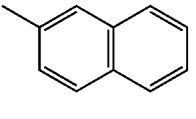 |
| 5 | 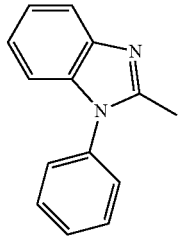 | 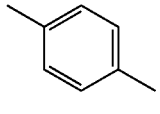 | 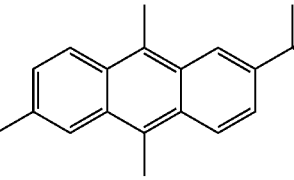 | 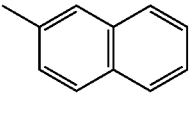 |
| 6 | 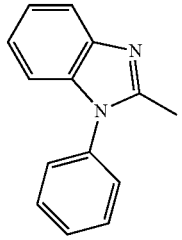 | 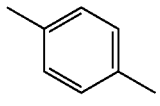 | 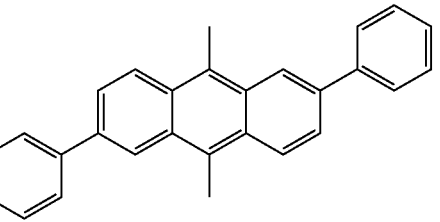 | 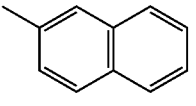 |

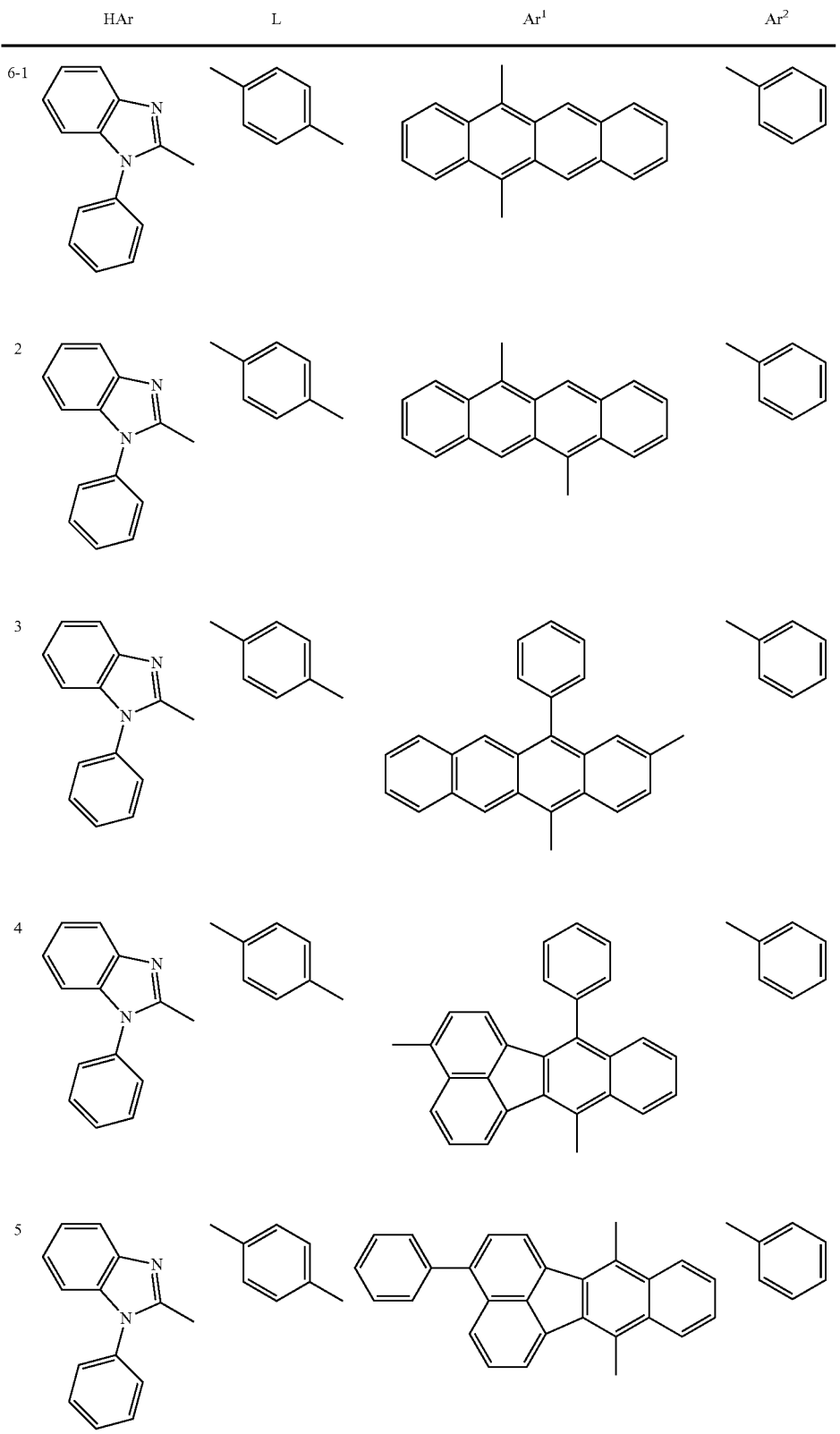

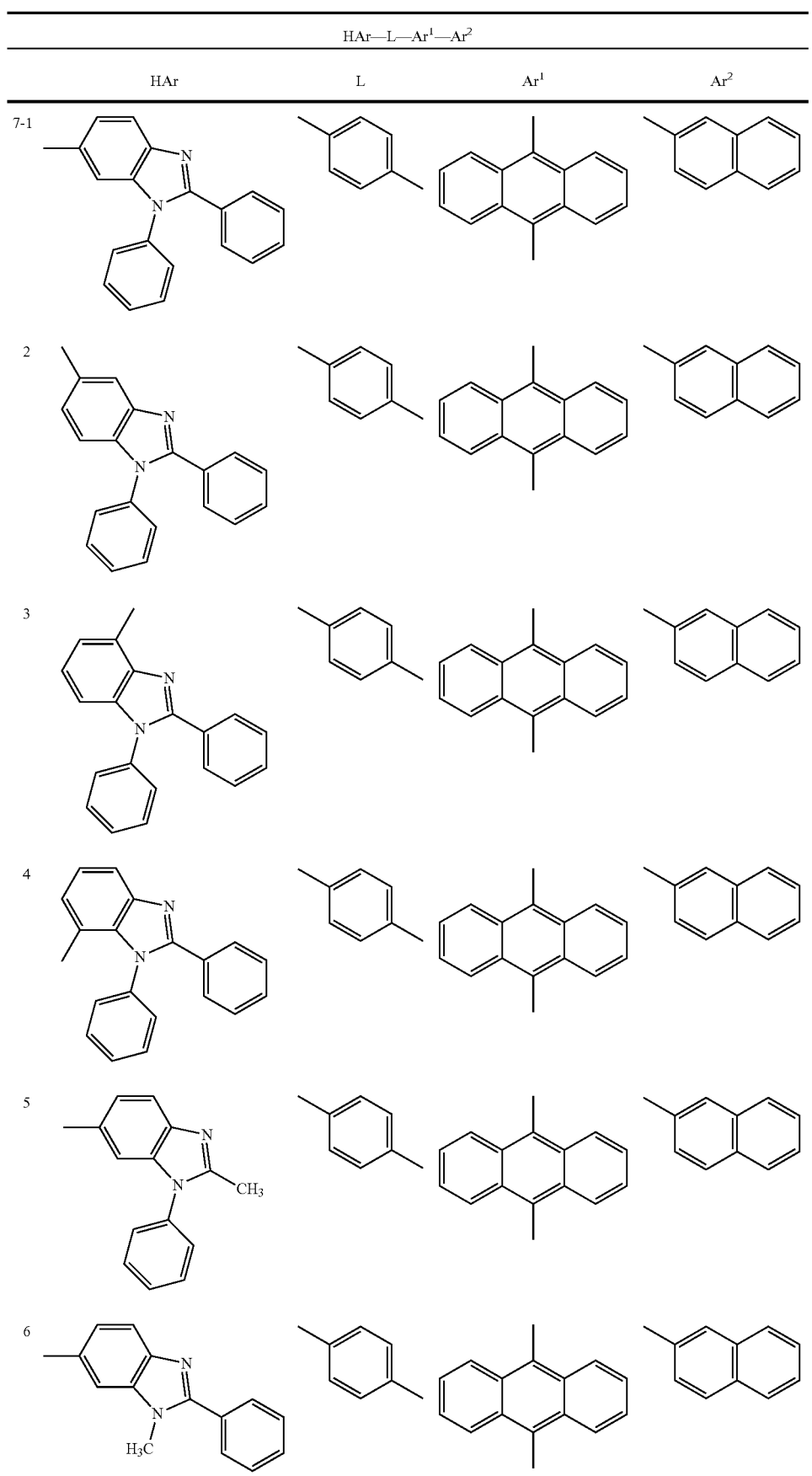

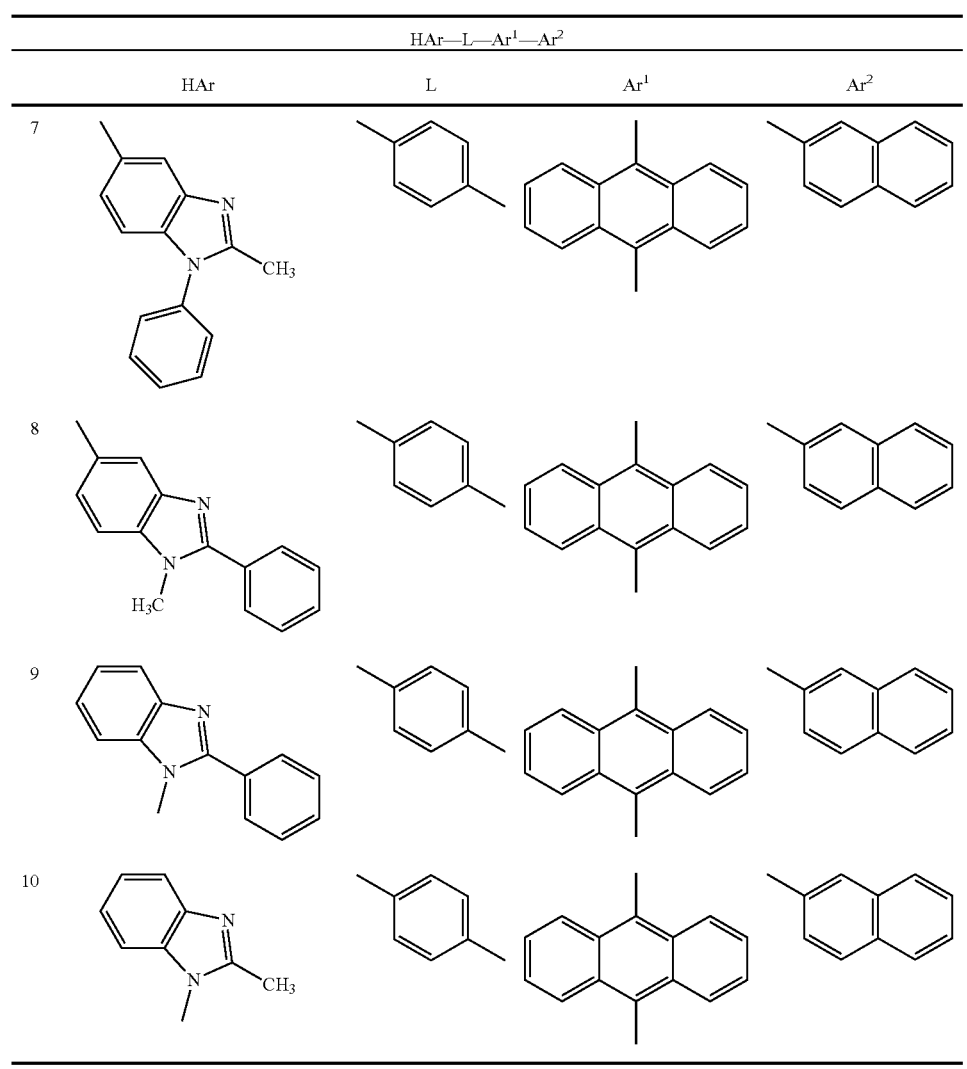
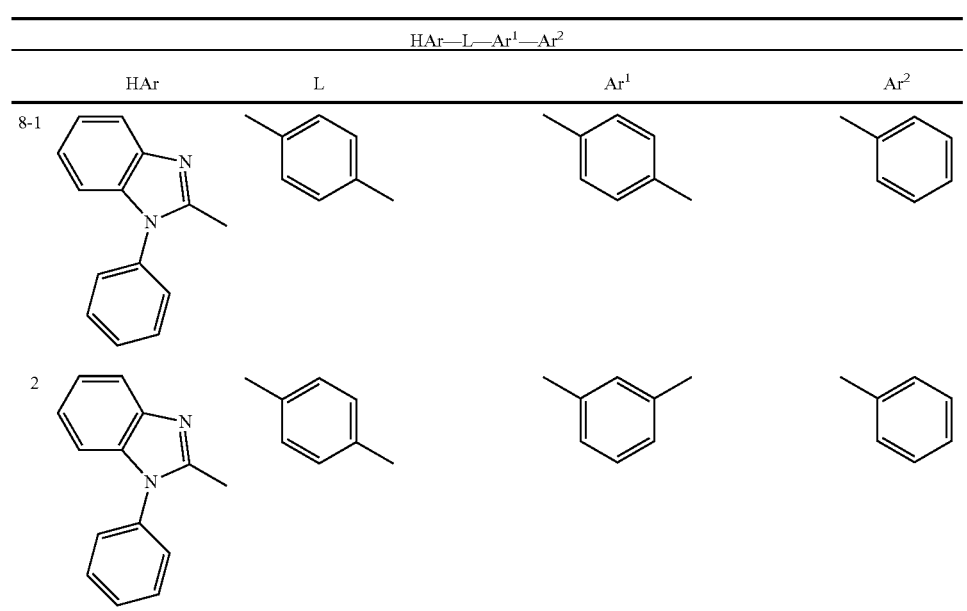

-continued

| HAr | L | Ar¹ | Ar² |
|---|---|---|---|
| 3 | | | |
| 4 | | | |
| 5 | | | |
| 6 | | | |
| 7 | | | H |
| 8 | | | |

-continued
| | HAr | L | Ar¹ | Ar² |
|---|---|---|---|---|
| 9 | 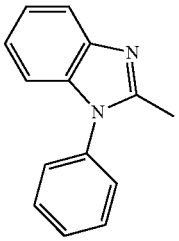 | 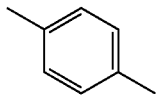 | 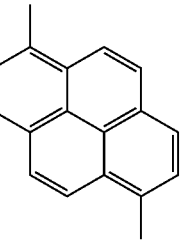 | 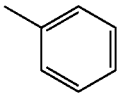 |
| 10 | 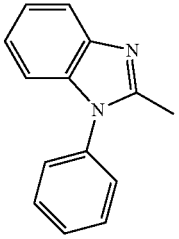 | 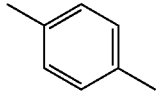 | 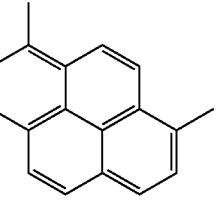 | 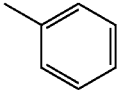 |
| 11 | 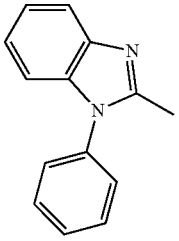 | 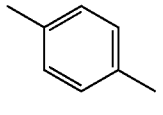 | 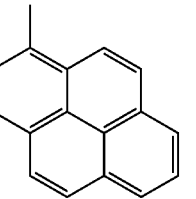 | —H |
| 12 |  | 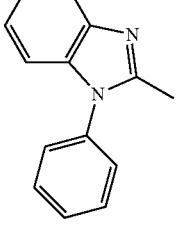 | 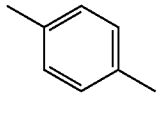 | 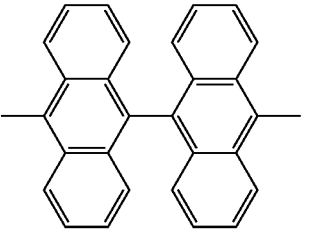 |
| 13 | 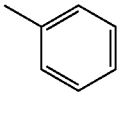 | 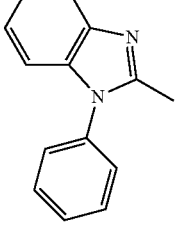 | 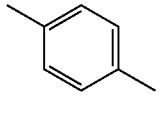 | 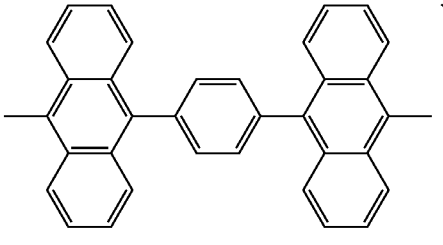 |

| HAr—L—Ar¹—Ar² | | | |
|---|---|---|---|
| HAr | L | Ar¹ | Ar² |

-continued
| | HAr—L—Ar¹—Ar² | | | |
|---|---|---|---|---|
| | HAr | L | Ar¹ | Ar² |
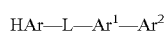

| | HAr—L—Ar¹—Ar² | | | |
|---|---|---|---|---|
| | HAr | L | Ar¹ | Ar² |
| 10-1 | 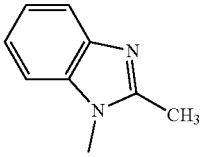 | 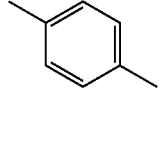 | 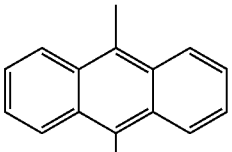 | 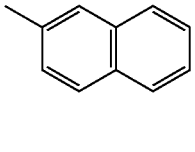 |
| 2 | 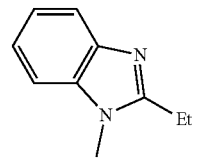 | 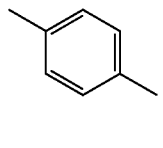 | 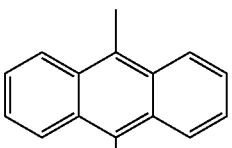 | 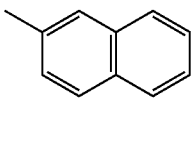 |
| 3 | 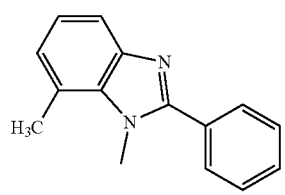 | 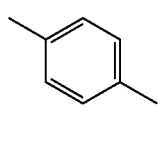 | 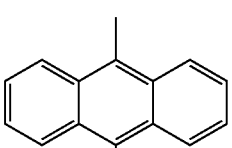 | 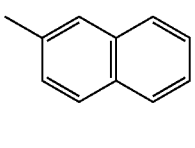 |
| 4 | 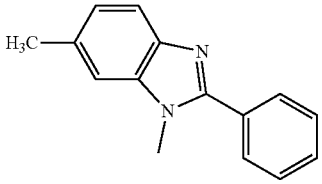 | 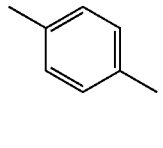 | 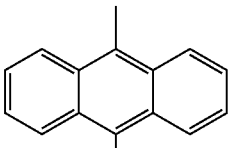 | 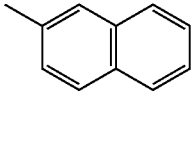 |
| 5 | 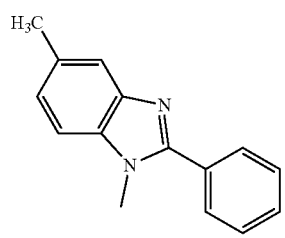 | 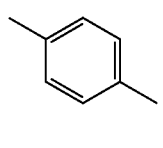 | 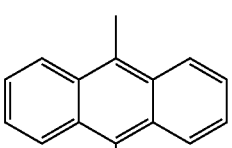 | 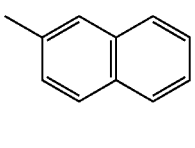 |
| 6 | 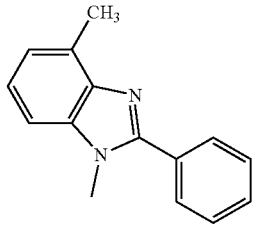 | 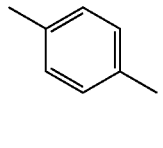 | 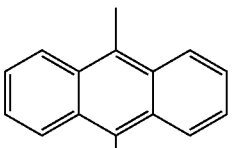 | 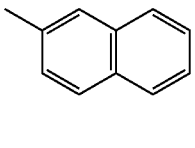 |
| 7 | 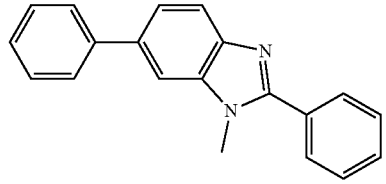 | 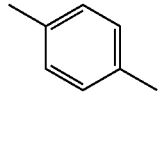 | 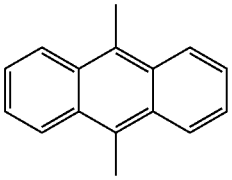 | 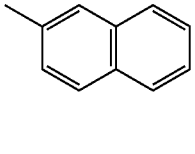 |

-continued
| | HAr | L | Ar¹ | Ar² |
|---|---|---|---|---|
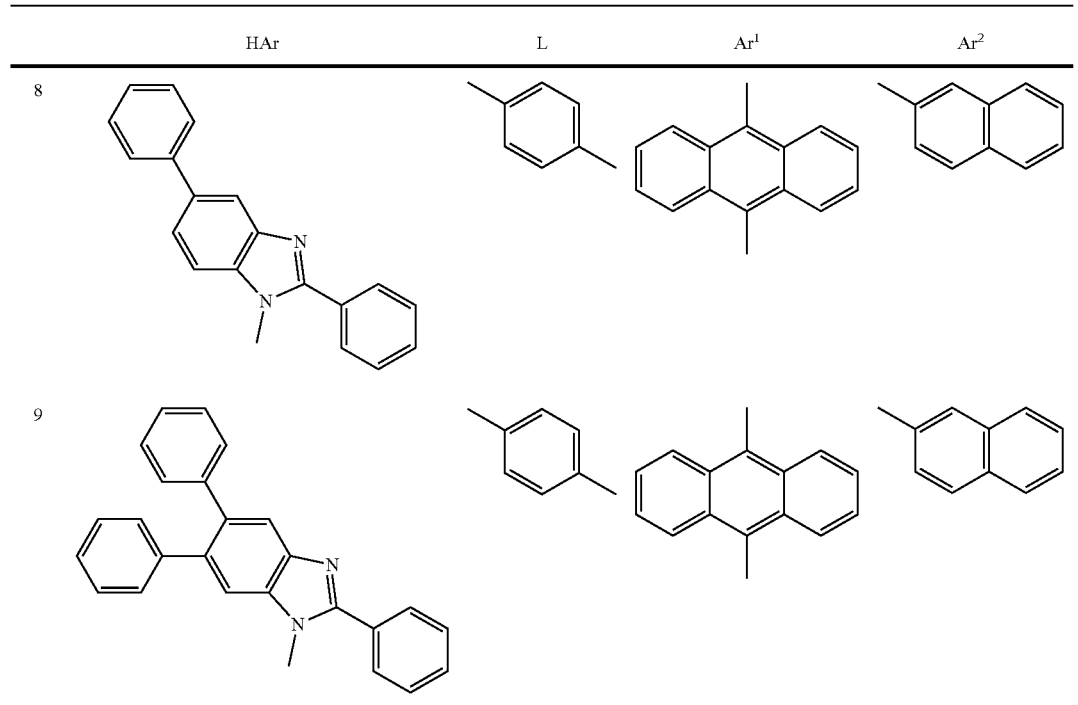
| | HAr | L | Ar¹ | Ar² |
|---|---|---|---|---|
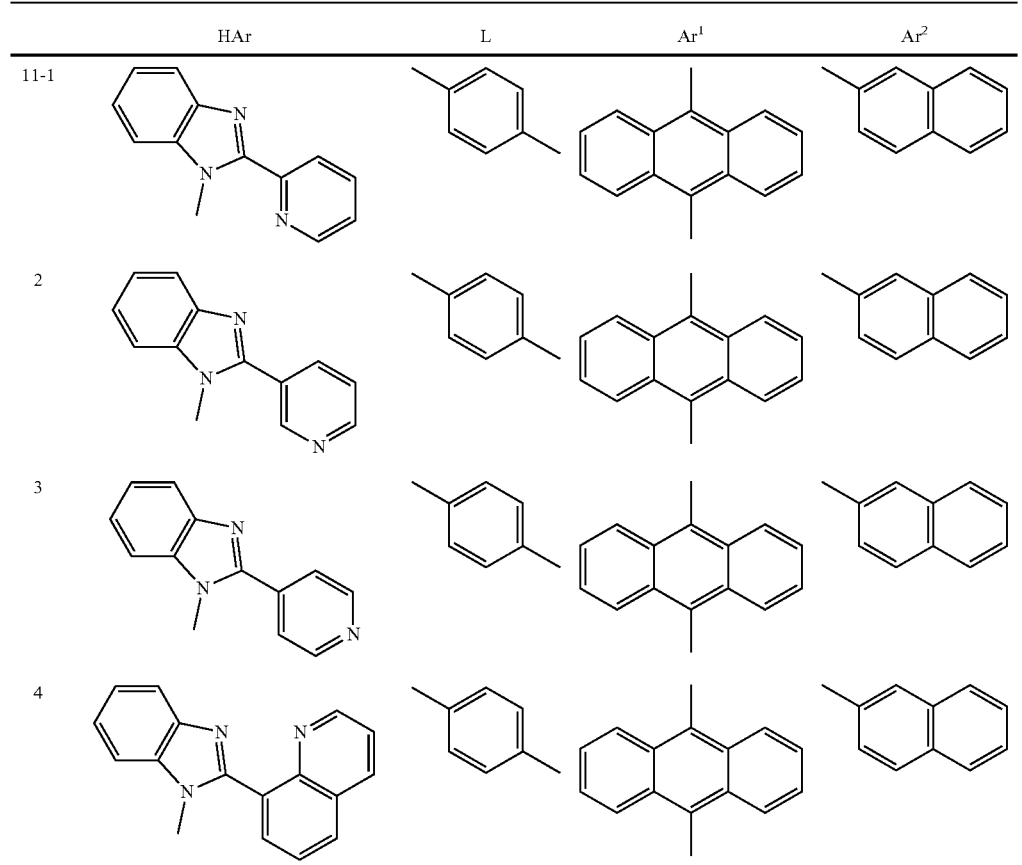

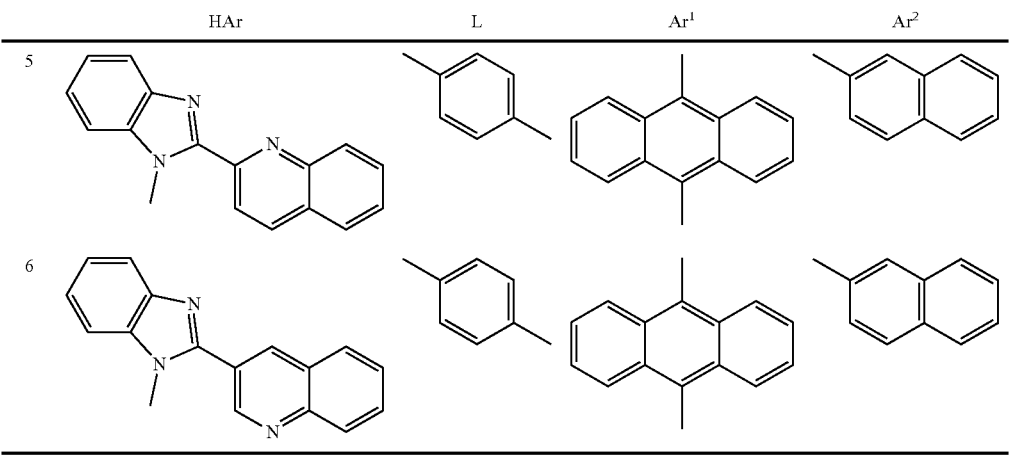
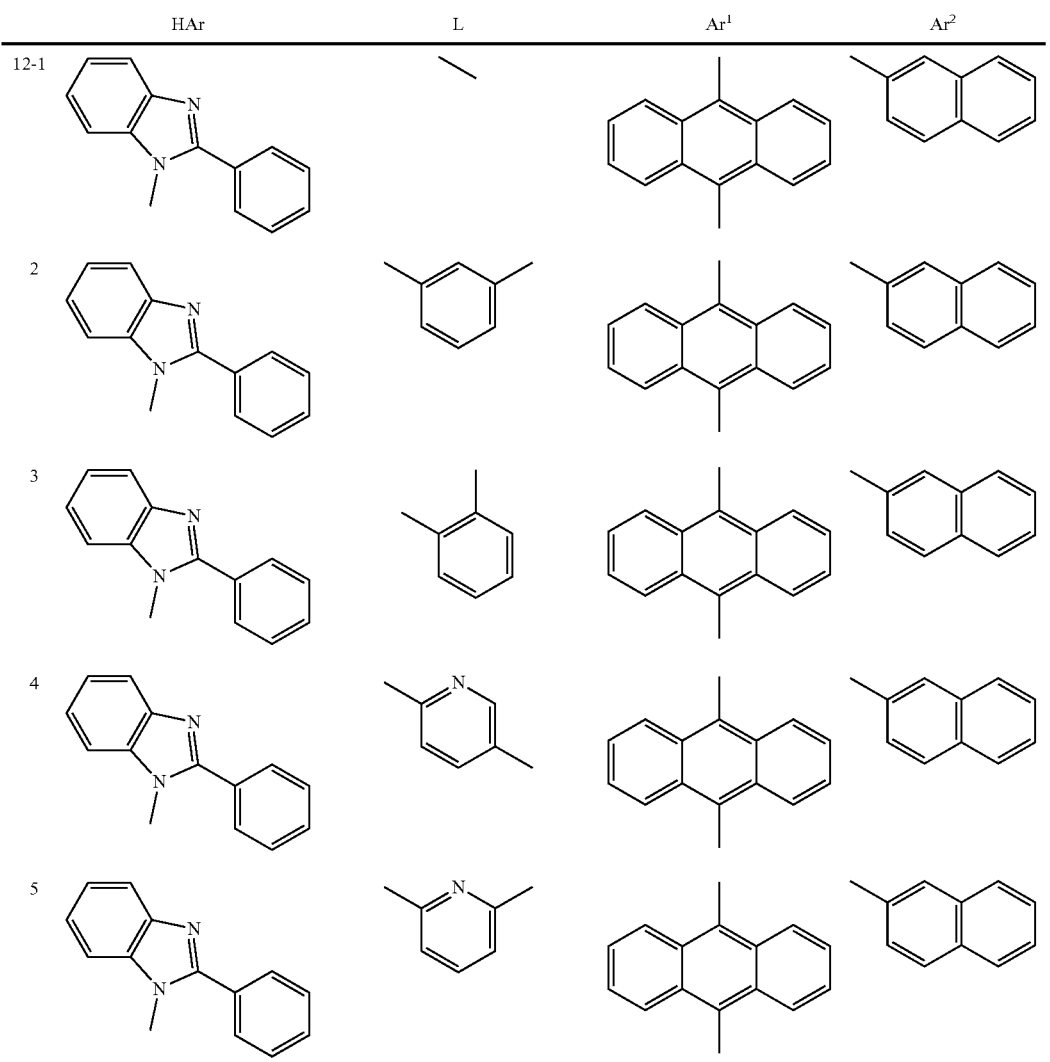

-continued
| | HAr | L | Ar¹ | Ar² |
|---|---|---|---|---|
| 6 | 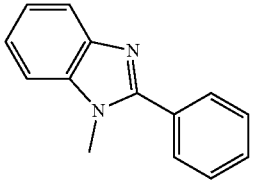 | 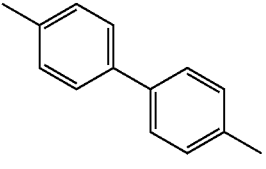 | 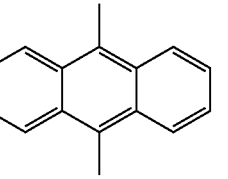 | 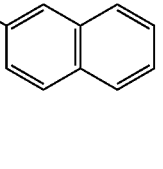 |
| 7 | 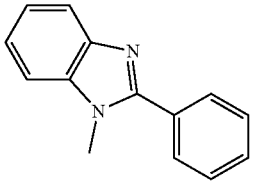 | 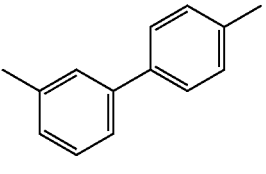 | 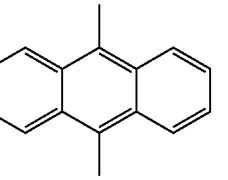 | 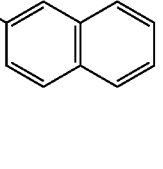 |
| 8 | 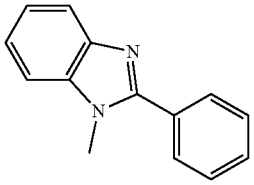 | 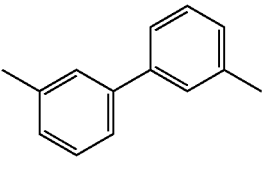 | 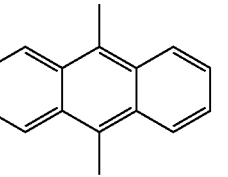 | 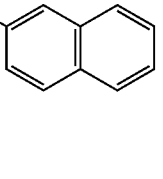 |
| 9 | 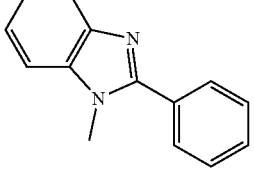 | 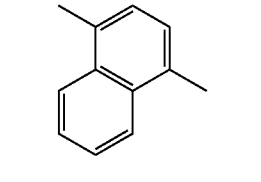 | 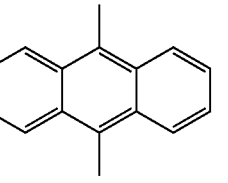 | 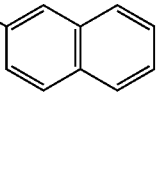 |
| 10 | 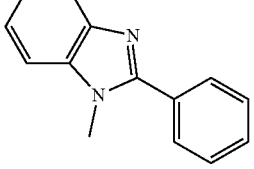 | 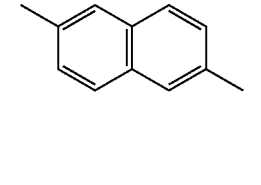 | 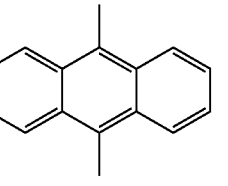 | 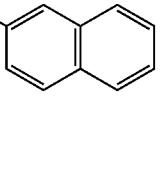 |
| 11 | 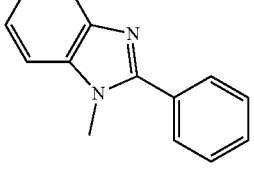 | 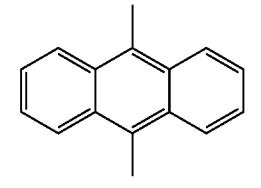 | 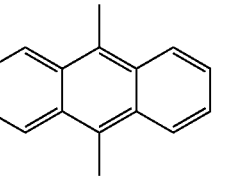 | 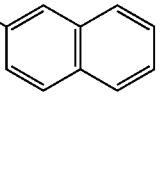 |
| | HAr | L | Ar¹ | Ar² |
|---|---|---|---|---|
| 13-1 | 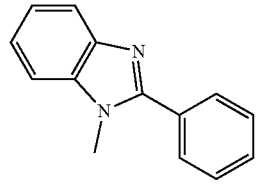 | 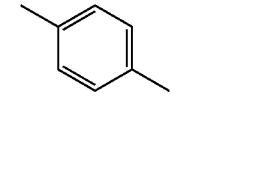 | 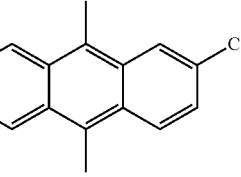 | 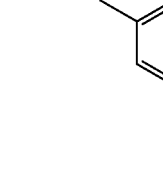 |

-continued
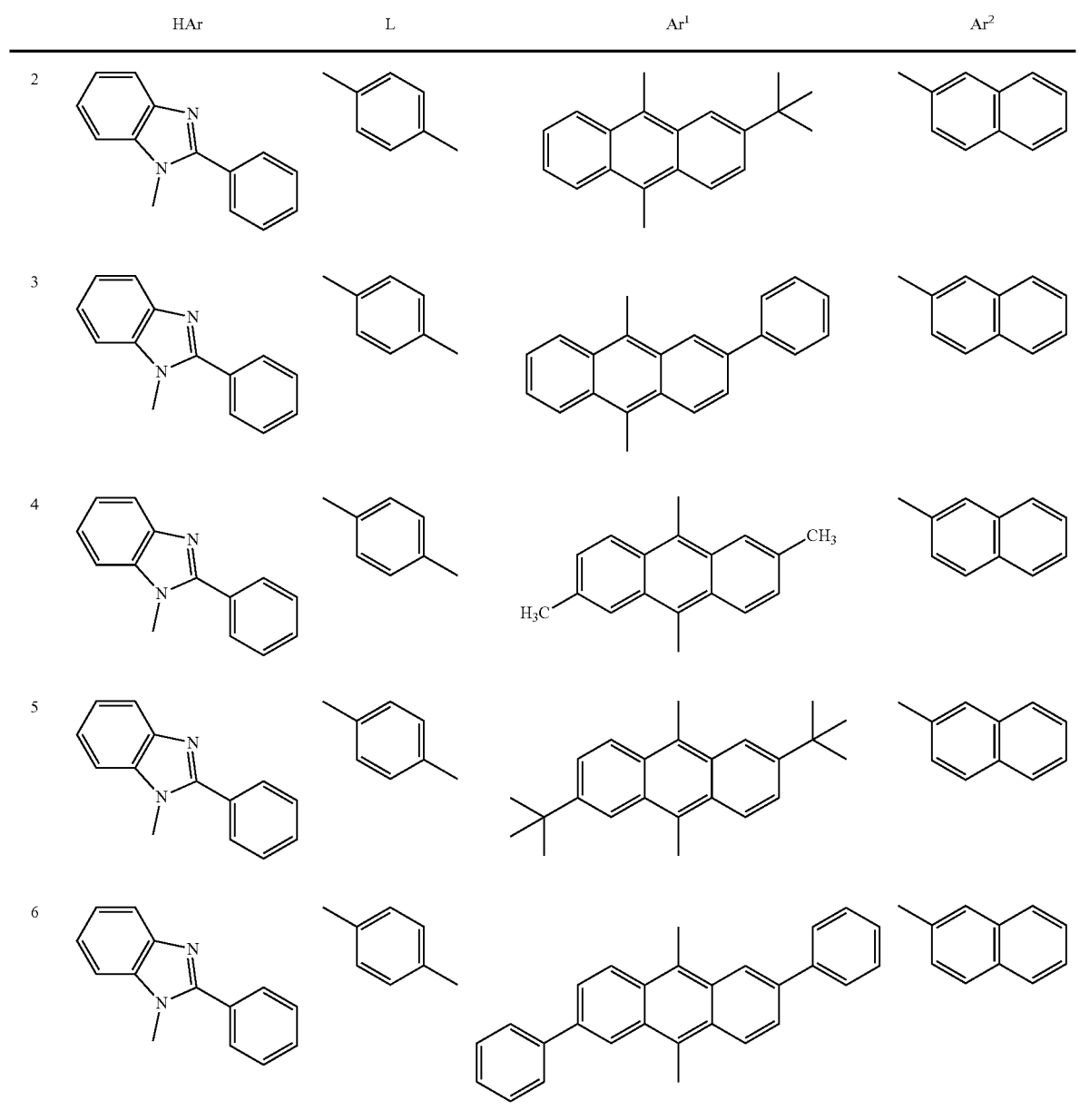
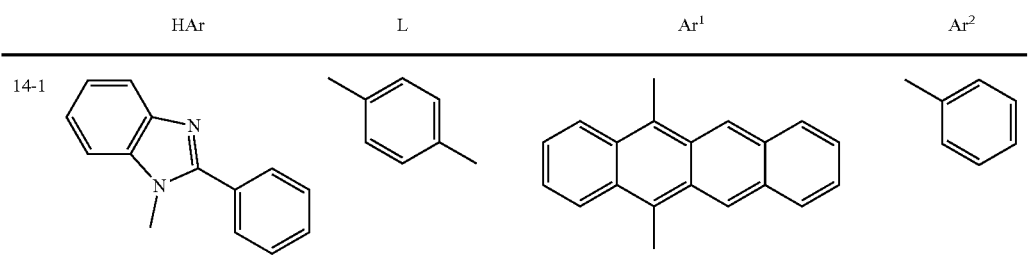

-continued
| HAr—L—Ar¹—Ar² | | | |
|---|---|---|---|
| HAr | L | Ar¹ | Ar² |
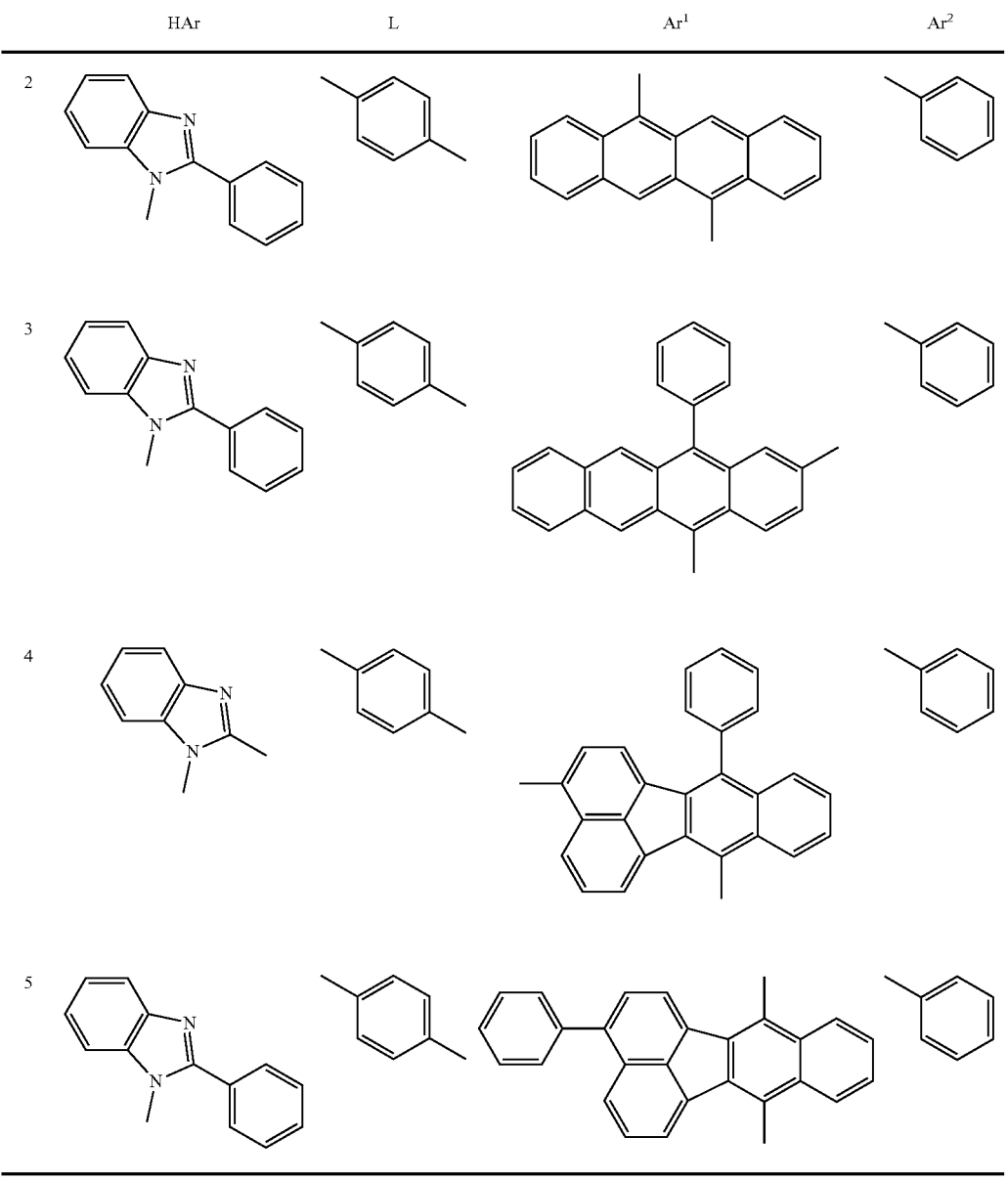
| HAr—L—Ar¹—Ar² | | | |
|---|---|---|---|
| HAr | L | Ar¹ | Ar² |
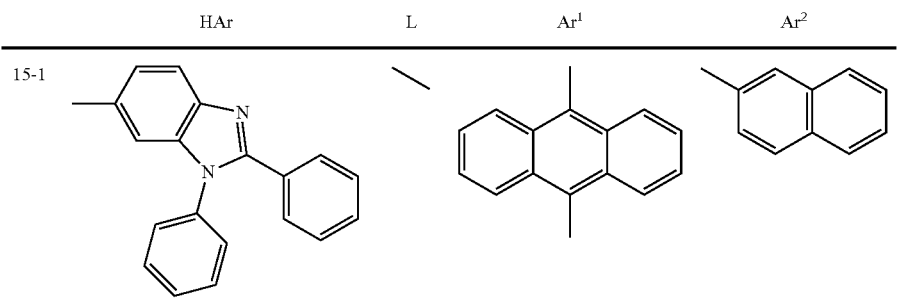

-continued
| | HAr | L | Ar¹ | Ar² |
|---|---|---|---|---|
| 2 | 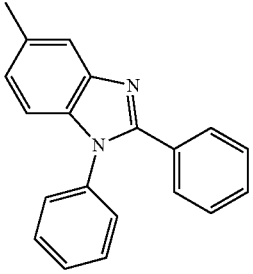 | 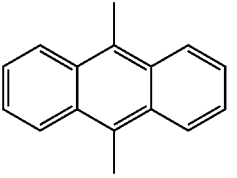 |  | 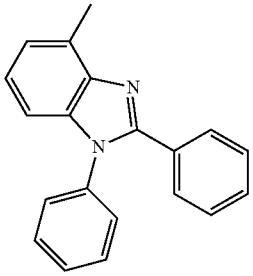 |
| 3 | 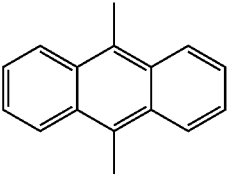 | |  | 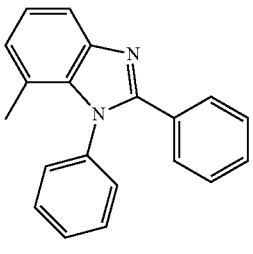 |
| 4 | 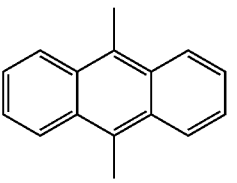 | |  | 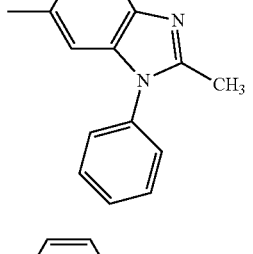 |
| 5 | 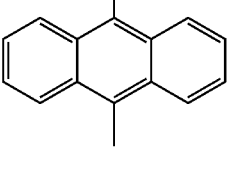 | |  | 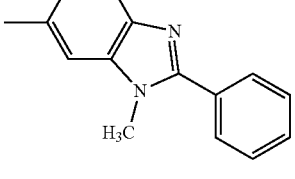 |
| 6 | 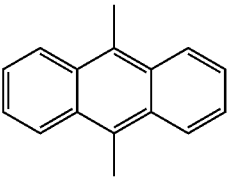 | |  | 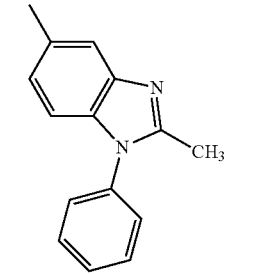 |
| 7 | 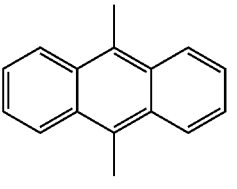 | |  | |

-continued
| | HAr | L | Ar¹ | Ar² |
|---|---|---|---|---|
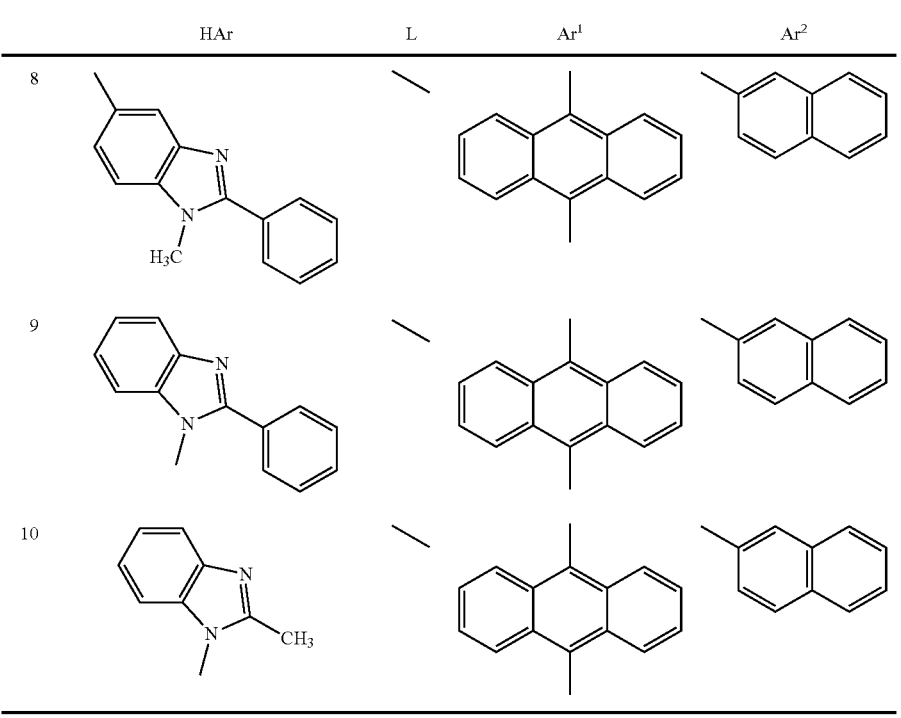
| | HAr | L | Ar¹ | Ar² |
|---|---|---|---|---|
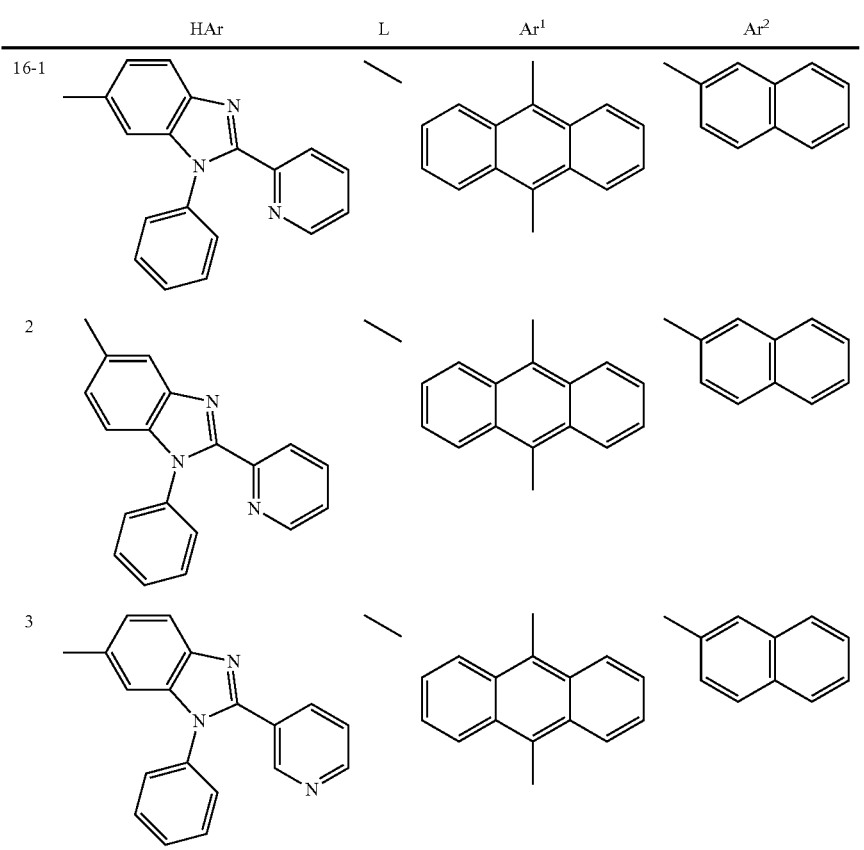

-continued
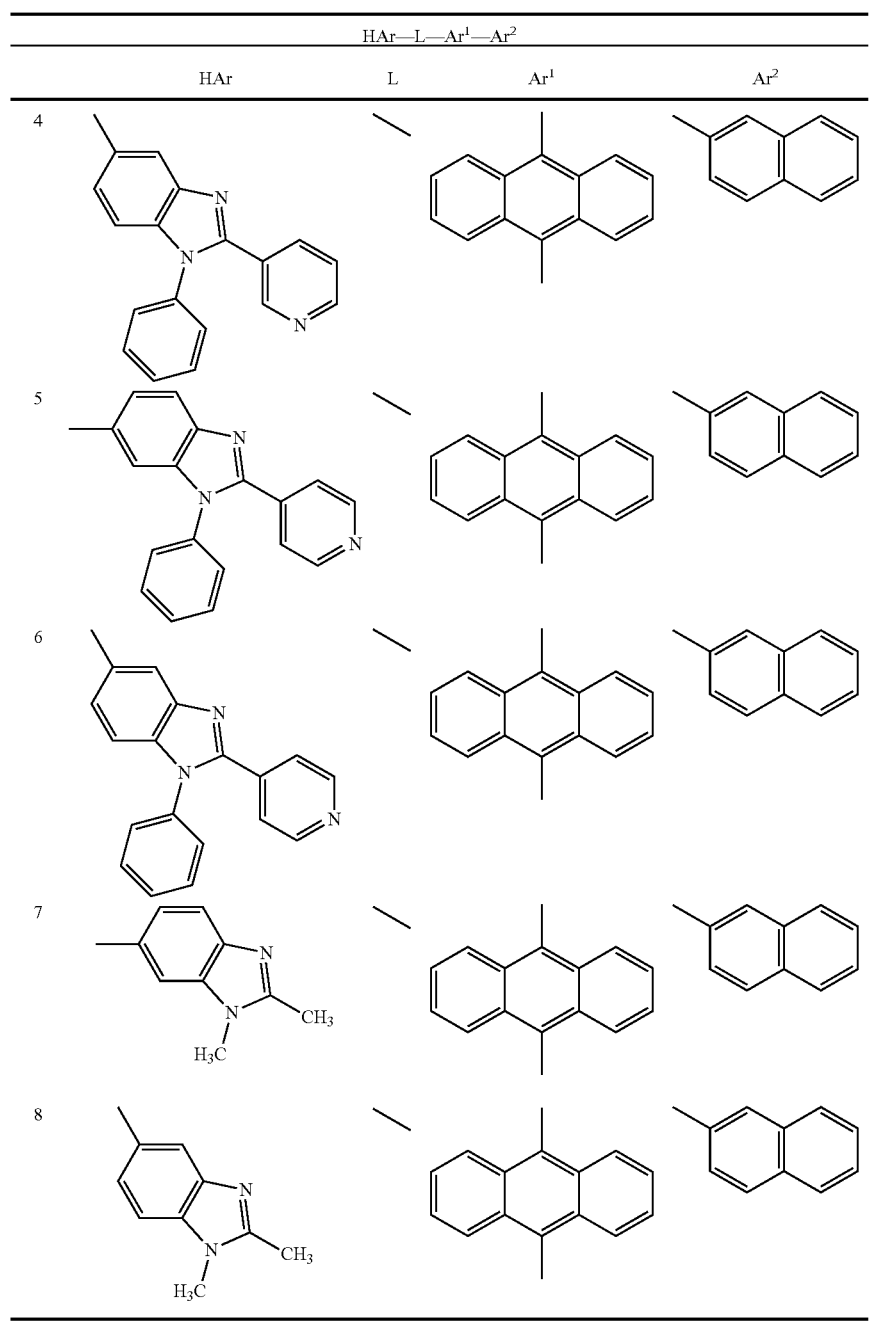
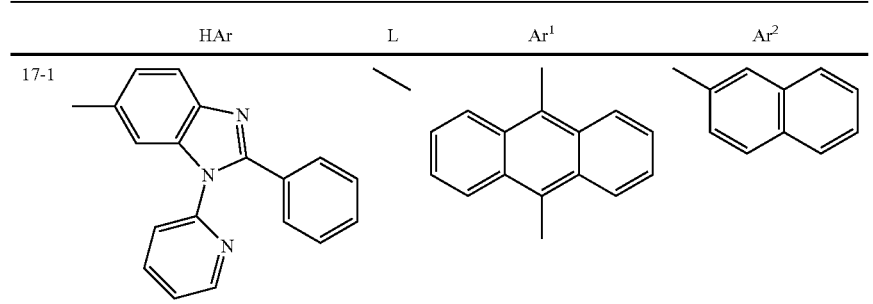

-continued

| HAr | L | Ar¹ | Ar² |
|---|---|---|---|
| 2 | — | | |
| 3 | — | | |
| 4 | — | | |
| 5 | — | | |
| 6 | — | | |

-continued

| HAr—L—Ar¹—Ar² | | | |
|---|---|---|---|
| HAr | L | Ar¹ | Ar² |
| 7 | | | |
| 8 | | | |

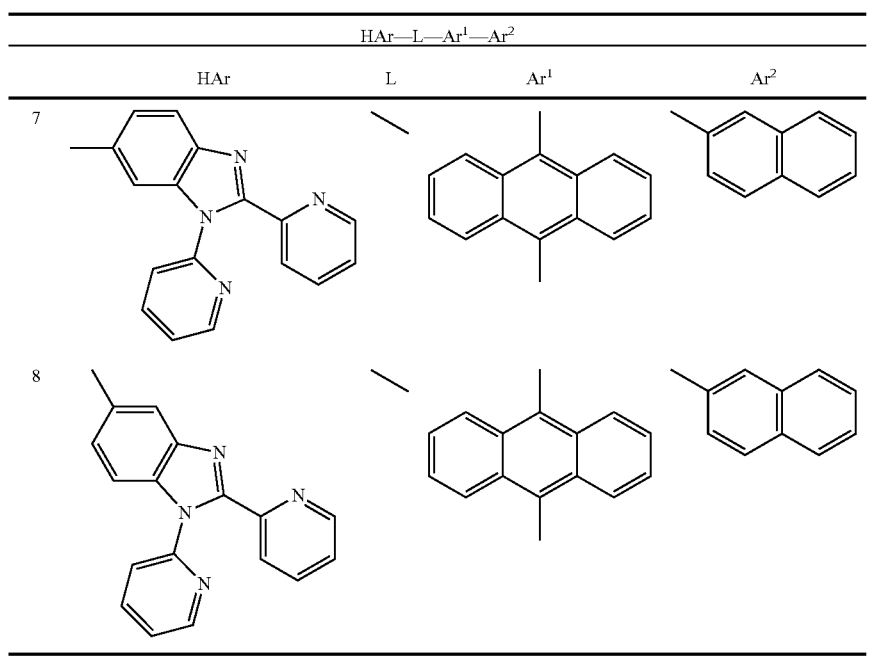

Of the above exemplary compounds, particularly preferred are the compounds (1-1), (1-5), (1-7), (2-1), (3-1), (4-2), (4-6), (7-2), (7-7), (7-8), (7-9), (9-1), and (9-7).

The thickness of the electron injecting layer and the electron transporting layer is preferably, but not particularly limited to, 1 to 100 nm.

It is preferred that the electron injecting layer is constituted by an inorganic compound, such as an insulating material and a semiconductor, in addition to the nitrogen-containing ring derivative. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhance. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer in the invention may contain the reduction-causing dopant mentioned above.

The hole injecting layer or the hole transporting layer (inclusive of a hole injecting/transporting layer) is preferably formed from an aromatic amine compound, for example, an aromatic amine derivative represented by the following formula (I):

(I)

In formula (I), each of $Ar^1$ to $Ar^4$ is a substituted or unsubstituted aryl group having 6 to 50 ring carbon atoms or a substituted or unsubstituted heteroaryl group having 5 to 50 ring atoms.

Examples of the substituted or unsubstituted aryl group having 6 to 50 ring carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, and fluorenyl group.

Examples of the substituted or unsubstituted heteroaryl group having 5 to 50 ring atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group, with phenyl group, naphthyl group, biphenyl group, anthranyl group, phenanthryl group, pyrenyl group, chrysenyl group, fluoranthenyl group, and fluorenyl group being preferred.

L is a linking group, for example, a substituted or unsubstituted arylene group having 6 to 50 ring carbon atoms, a substituted or unsubstituted heteroarylene group having 5 to 50 ring atoms, or a divalent group derived from two or more arylene groups or heteroarylene groups by bonding these groups vis a single bond, an ether bond, a thioether bond, an alkylene group having 1 to 20 carbon atoms, an alkenylene group having 2 to 20 carbon atoms, or amino group. Examples of the arylene group having 6 to 50 ring carbon atoms include 1,4-phenylene group, 1,2-phenylene group, 1,3-phenylene group, 1,4-naphthylene group, 2,6-naphthylene group, 1,5-naphthylene group, 9,10-anthracenylene group, 9,10-phenanthrenylene group, 3,6-phenanthrenylene group, 1,6-pyrenylene group, 2,7-pyrenylene group, 6,12-chrysenylene group, 4,4'-biphenylene group, 3,3'-biphenylene group, 2,2'-biphenylene group, and 2,7-fluorenylene group. Examples of the heteroarylene group having 5 to 50 ring atoms include 2,5-thiophenylene group, 2,5-silolylene group, and 2,5-oxadiazolylene group. Of the above groups, preferred are 1,4-phenylene group, 1,2-phenylene group, 1,3-phenylene group, 1,4-naphthylene group, 9,10-anthracenylene group, 6,12-chrysenylene group, 4,4'-biphenylene group, 3,3'-biphenylene group, 2,2'-biphenylene group, and 2,7-fluorenylene group.

If L is a linking group having two or more arylene groups or heteroarylene groups, adjacent arylene groups or adjacent heteroarylene group may bond to each other via a divalent group to form a ring. Examples of the divalent group for completing such ring include tetramethylene group, pentamethylene group, hexamethylene group, diphenylmethane-2,2'-diyl group, diphenylethane-3,3'-diyl group, and diphenylpropane-4,4'-diyl group.

Examples of the substituent of $Ar^1$ to $Ar^4$ and L include a substituted or unsubstituted aryl group having 6 to 50 ring carbon atoms, a substituted or unsubstituted heteroaryl group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted heteroaryloxy group having 5 to 50 ring atoms, a substituted or unsubstituted arylthio group having 6 to 50 ring carbon atoms, a substituted or unsubstituted heteroarylthio group having 5 to 50 ring atoms, a substituted or unsubstituted alkoxycarbonyl group having 2 to 50 carbon atoms, an amino group substituted by a substituted or unsubstituted aryl group having 6 to 50 ring carbon atoms or a substituted or unsubstituted heteroaryl group having 5 to 50 ring atoms, halogen atom, cyano group, nitro group, and hydroxyl group.

Examples of the substituted or unsubstituted aryl group having 6 to 50 ring carbon atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthylgroup, 4-methyl-1-naphthyl group, 4-methyl-1-anthryl group, 4'-methylbiphenylyl group, 4"-t-butyl-p-terphenyl-4-yl group, fluoranthenyl group, and fluorenyl group.

Examples of the substituted or unsubstituted heteroaryl group having 5 to 50 ring atoms include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Examples of the substituted or unsubstituted alkyl group having 1 to 50 carbon atoms include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxyt-butyl group, 1,2,3-trihydroxypropyl group, chloromethyl group, 1-chloroethyl group, 2-chloroethyl group, 2-chloroisobutyl group, 1,2-dichloroethyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromot-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodot-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

Examples of the substituted or unsubstituted cycloalkyl group having 3 to 50 carbon atoms include cyclopropyl group, cyclobutyl group, cyclopentyl group, cyclohexyl group, 4-methylcyclohexyl group, 1-adamantyl group, 2-adamantyl group, 1-norbornyl group, and 2-norbornyl group.

The substituted or unsubstituted alkoxy group having 1 to 50 carbon atoms is represented by —OY. Examples of Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxyt-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromot-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodotbutyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

Examples of the substituted or unsubstituted aralkyl group having 7 to 50 carbon atoms include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

The substituted or unsubstituted aryloxy group having 6 to 50 ring carbon atoms is represented by —OY'. Examples of Y' include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

The substituted or unsubstituted heteroaryloxy group having 5 to 50 ring atoms is represented by —OZ'. Examples of Z' include 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The substituted or unsubstituted arylthio group having 6 to 50 ring carbon atoms is represented by —SY". Examples of Y" include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

The substituted or unsubstituted heteroarylthio group having 5 to 50 ring atoms is represented by —SZ". Examples of Z" include 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

The substituted or unsubstituted alkoxycarbonyl group having 2 to 50 carbon atoms is represented by —COOZ. Examples of Z include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxyt-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichlorot-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromot-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodot-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, and 1,2,3-trinitropropyl group.

The amino group substituted by a substituted or unsubstituted aryl group having 6 to 50 ring carbon atoms or a substituted or unsubstituted heteroaryl group having 5 to 50 ring atoms is represented by —NPQ. Examples of P and Q include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Examples of the compound represented by formula (I) are shown below, although not limited thereto.

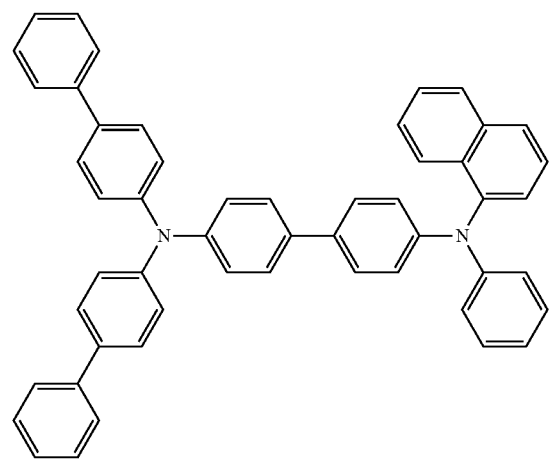

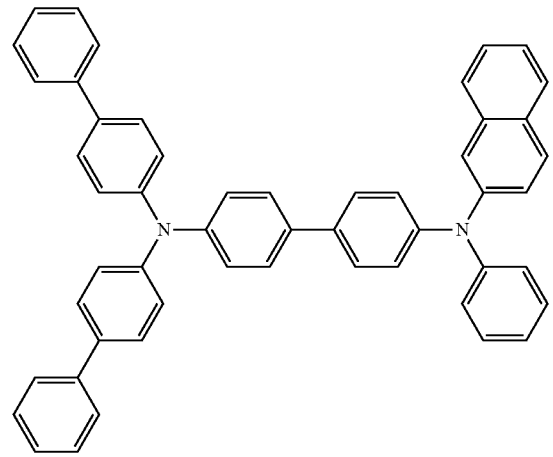

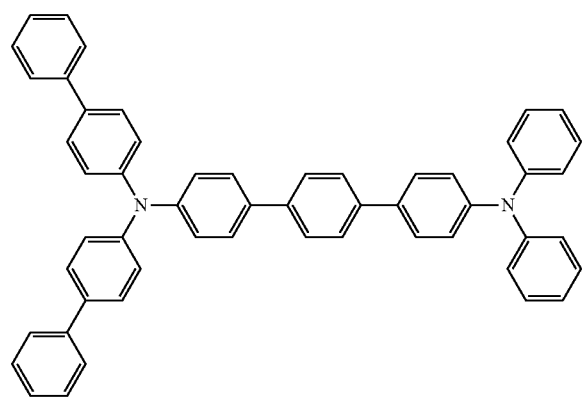

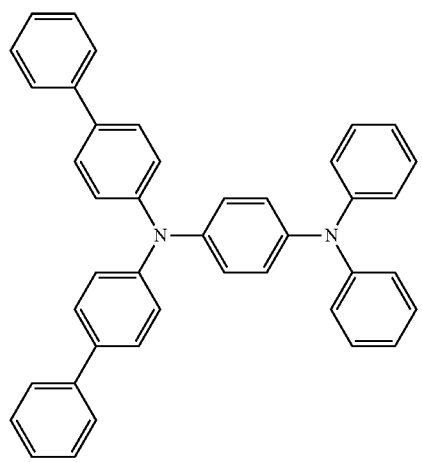
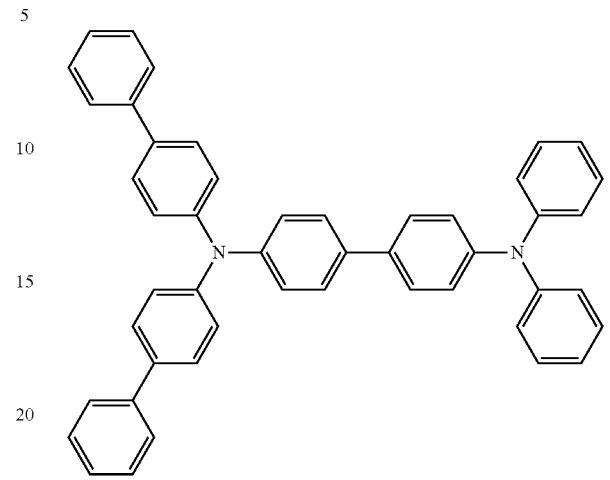
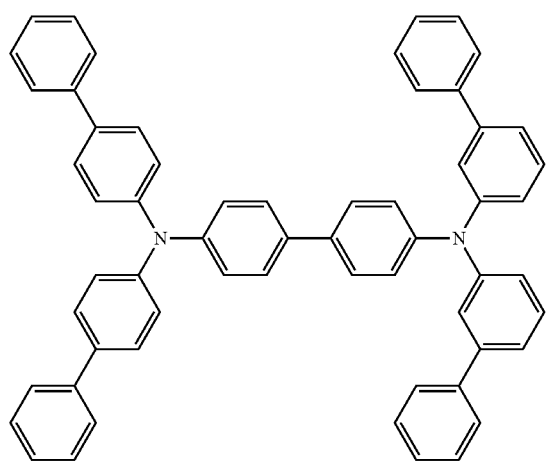
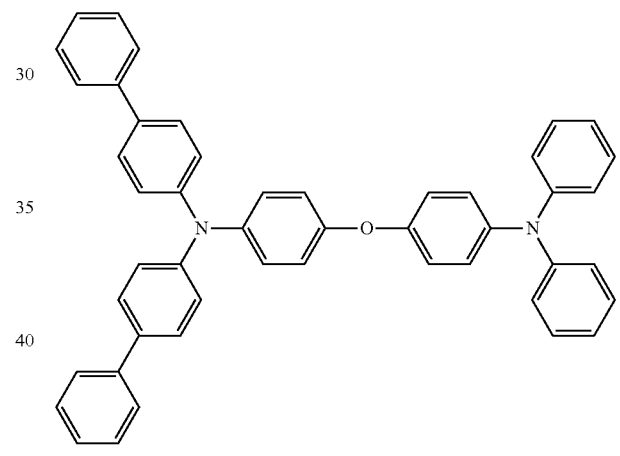
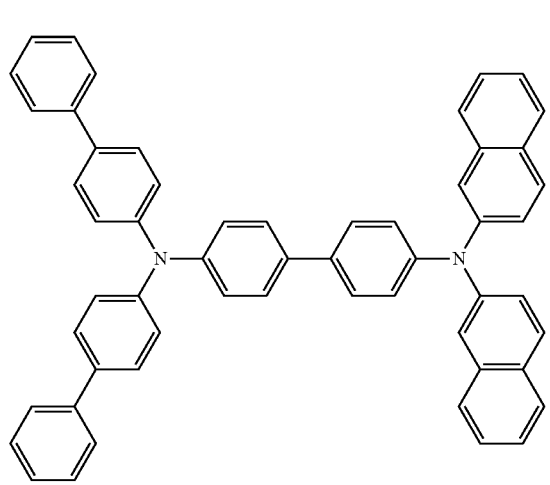
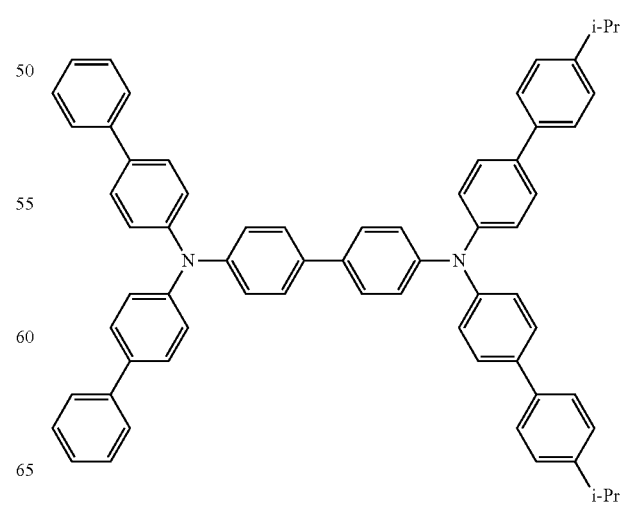

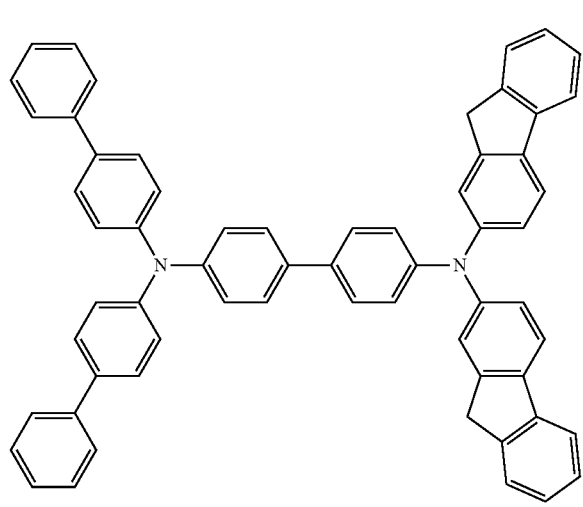
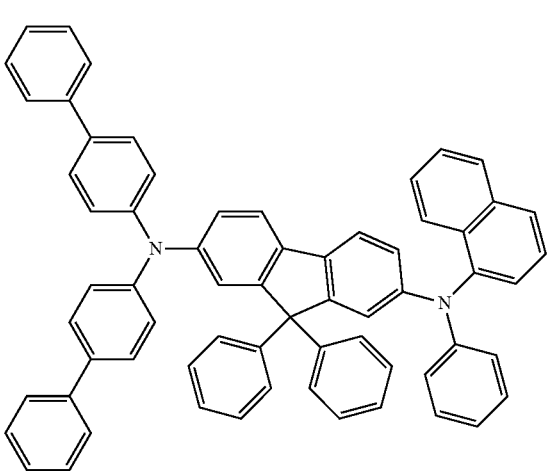
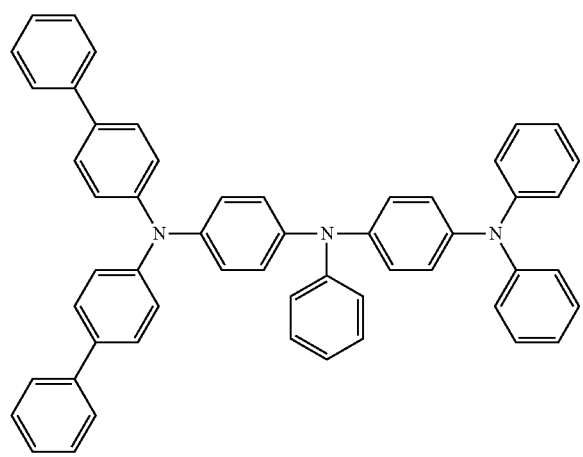
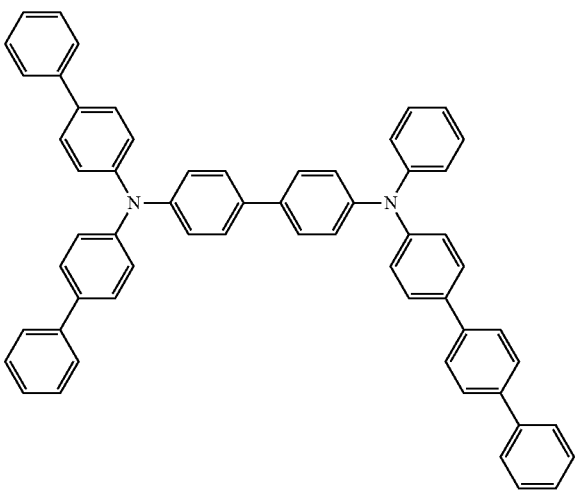
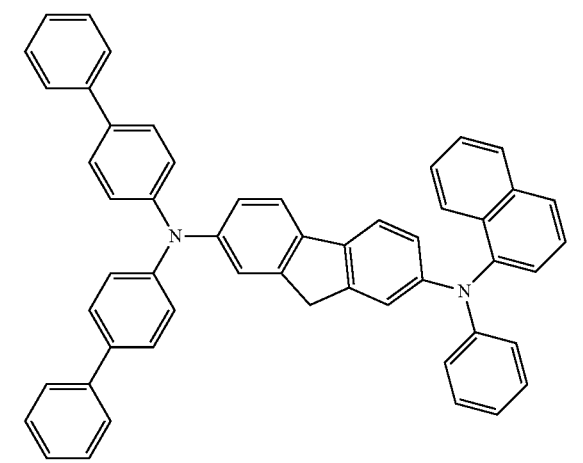
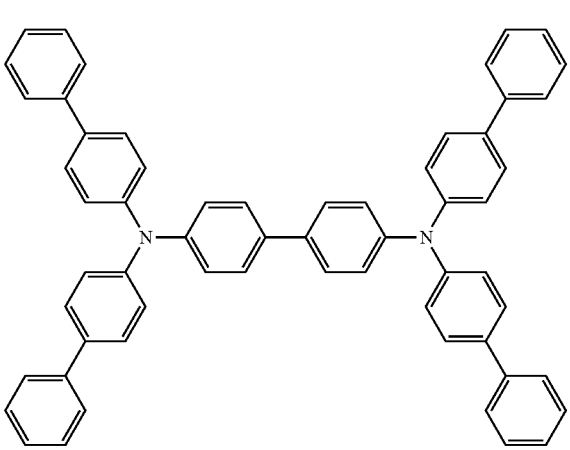

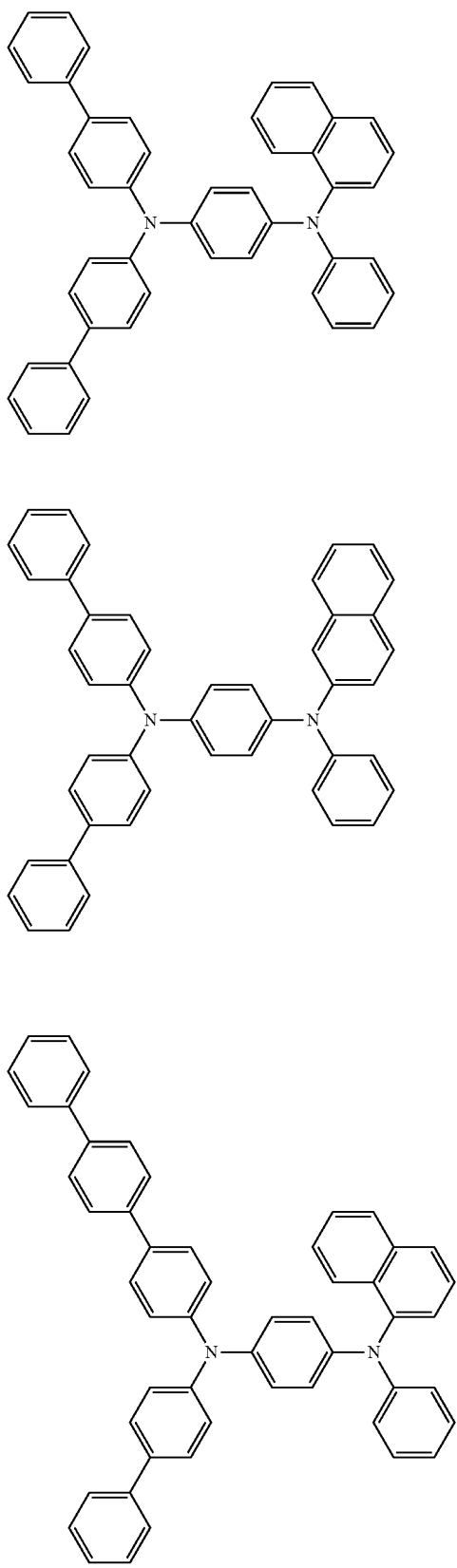
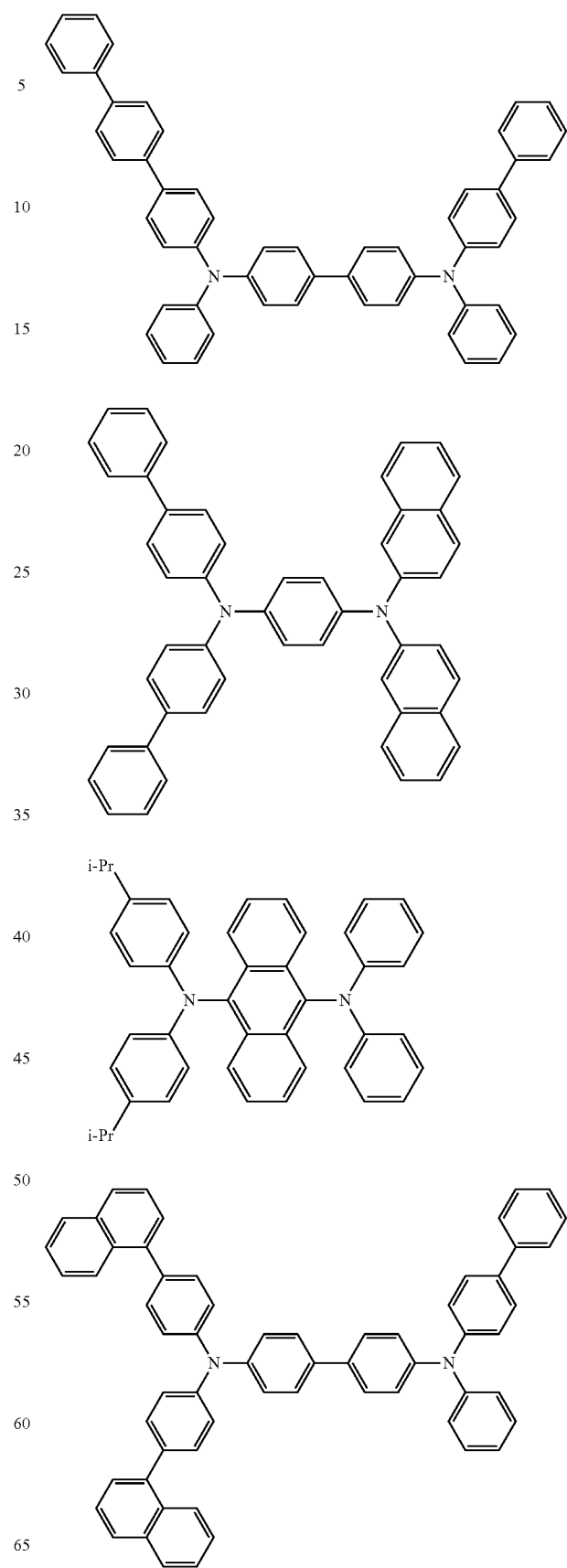

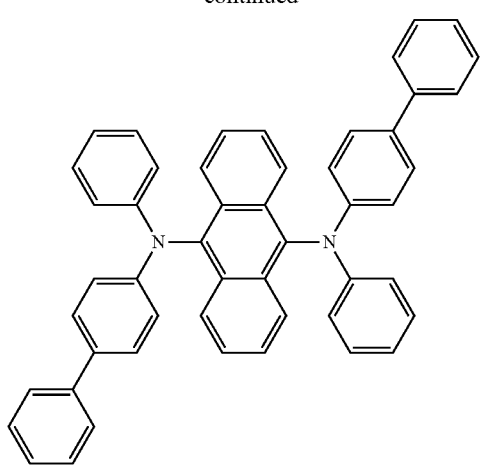
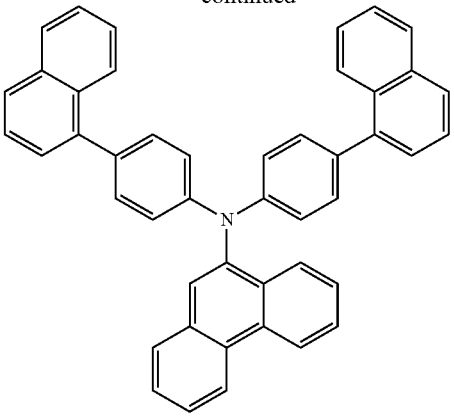
An aromatic amine represented by the following formula (II) is also preferably used to form the hole injecting layer or the hole transporting layer.
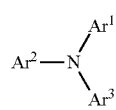 (II)
In formula (II), $Ar^1$ to $Ar^3$ are the same as defined in $Ar^1$ to $Ar^4$ of formula (I). Examples of the compound represented by formula (II) are shown below, although not limited thereto.
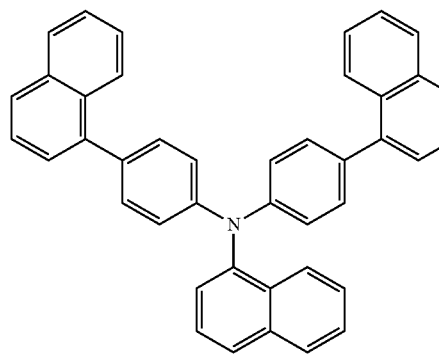
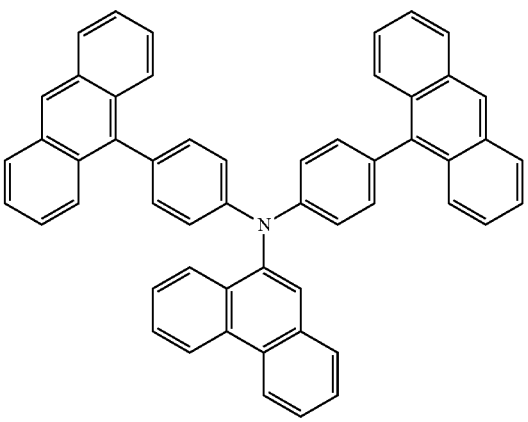
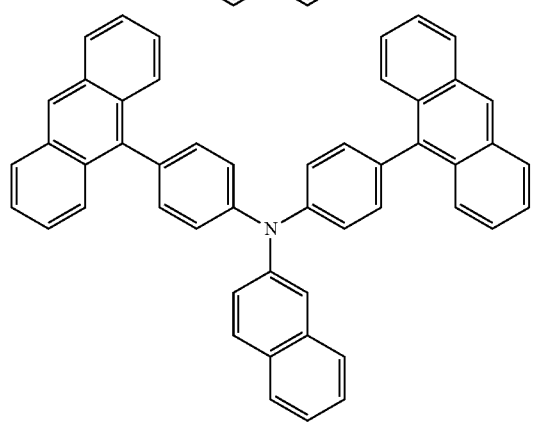
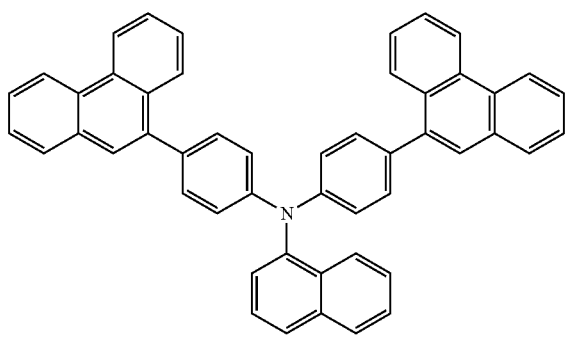
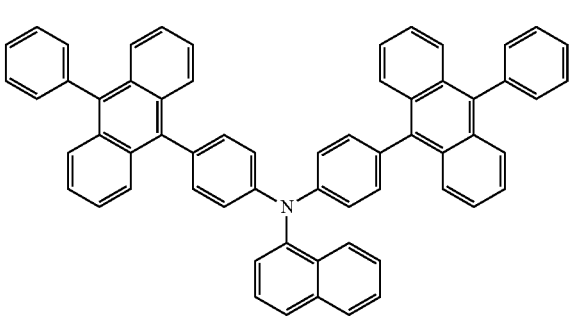

171
-continued
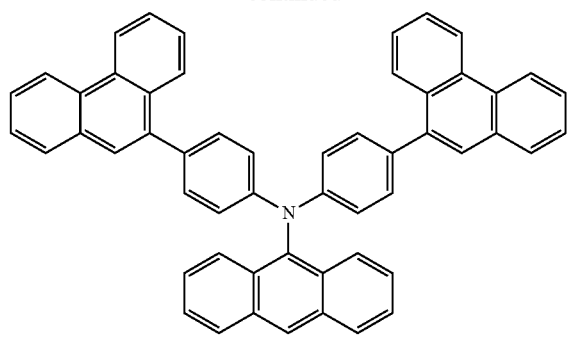
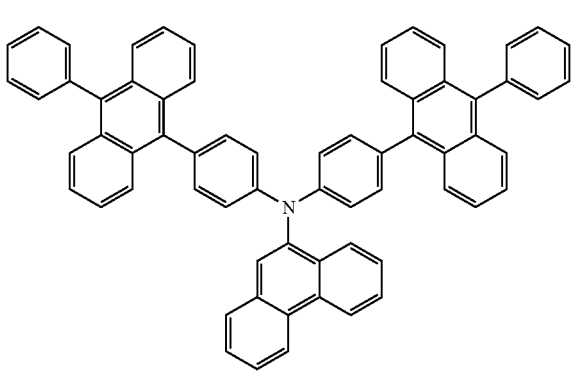
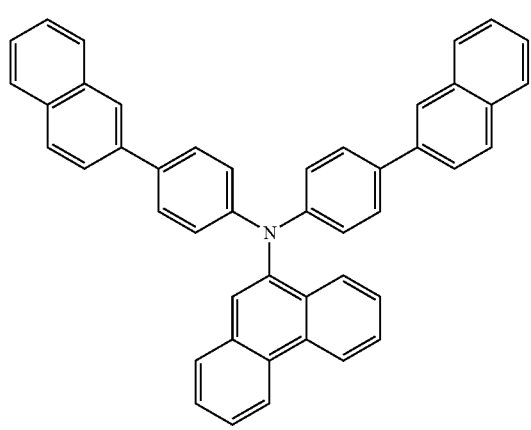
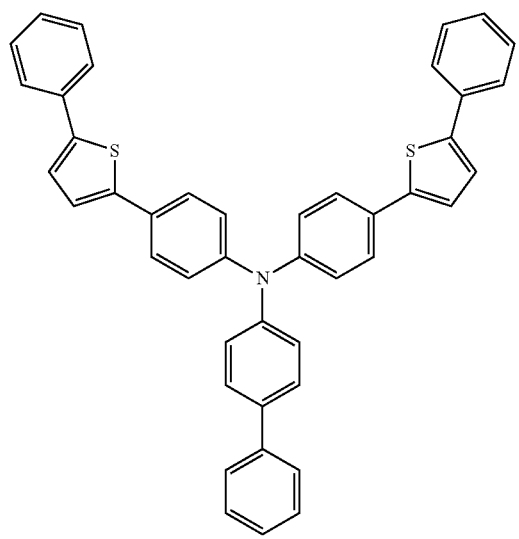
172
-continued
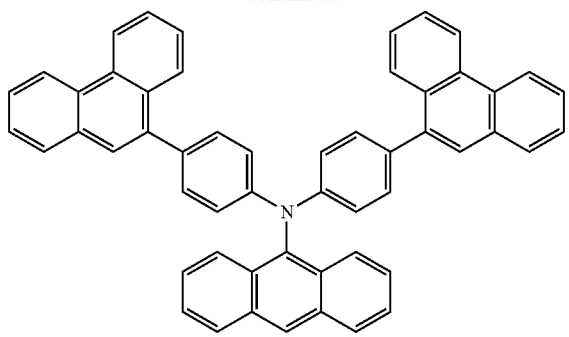
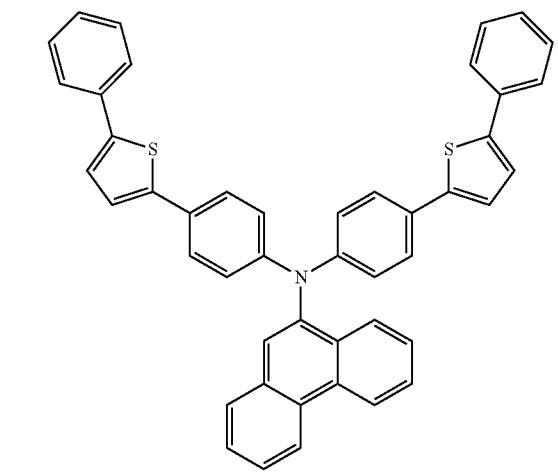
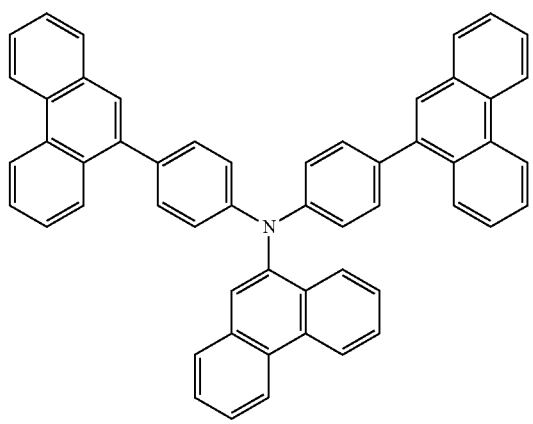
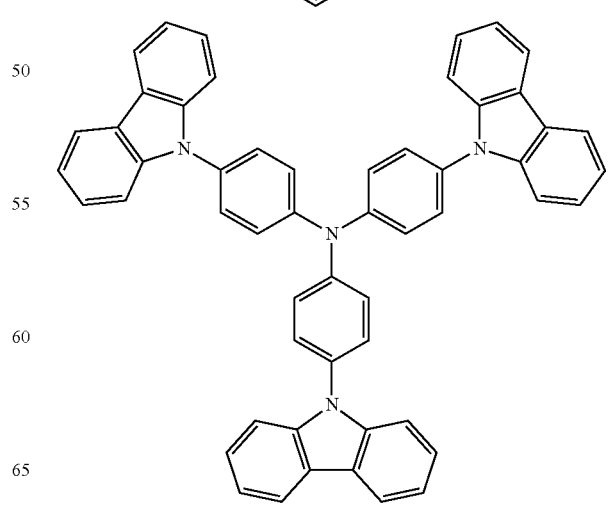

173
-continued
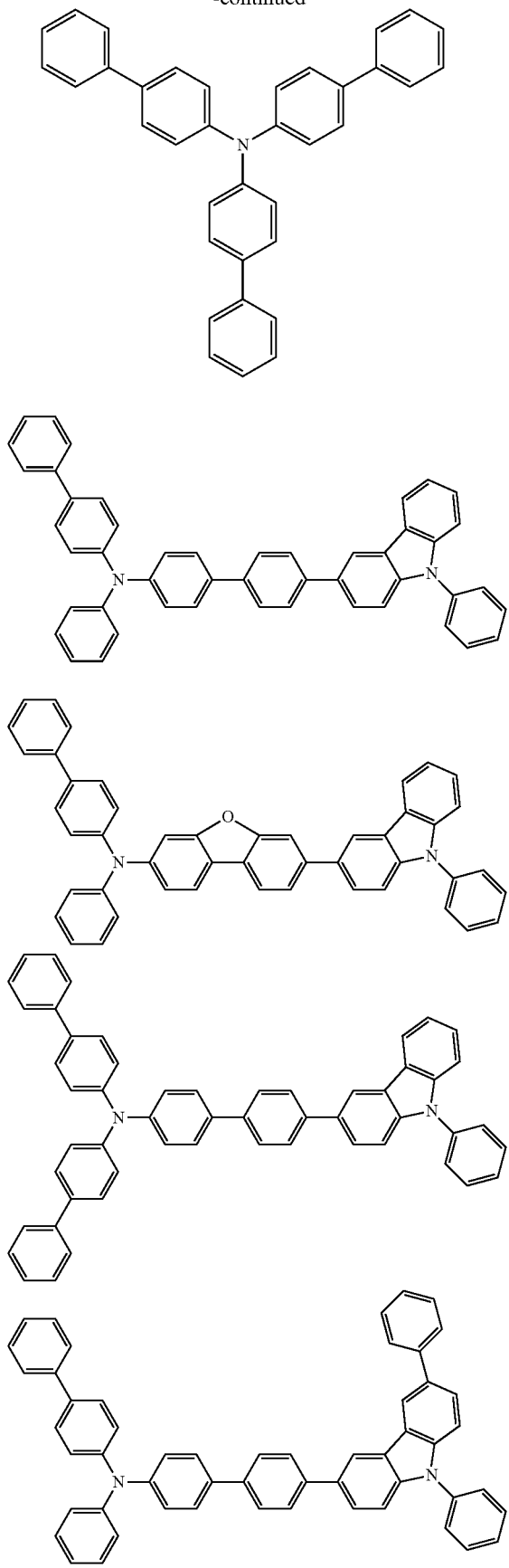
174
-continued
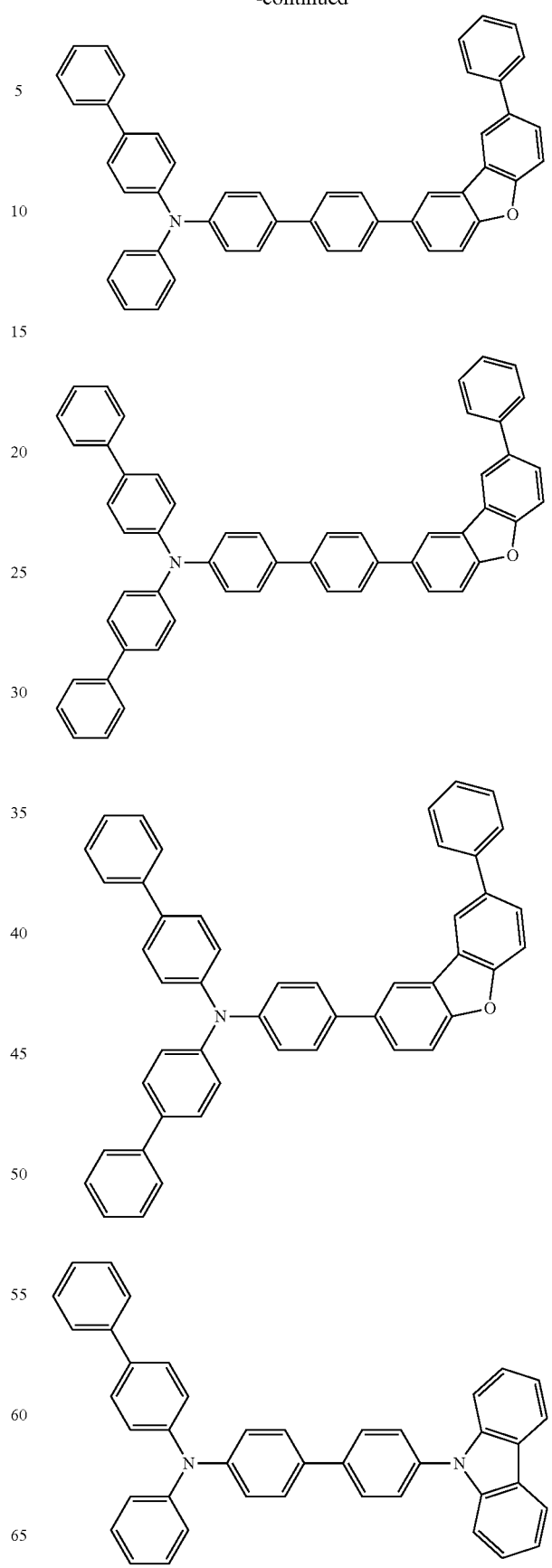

-continued

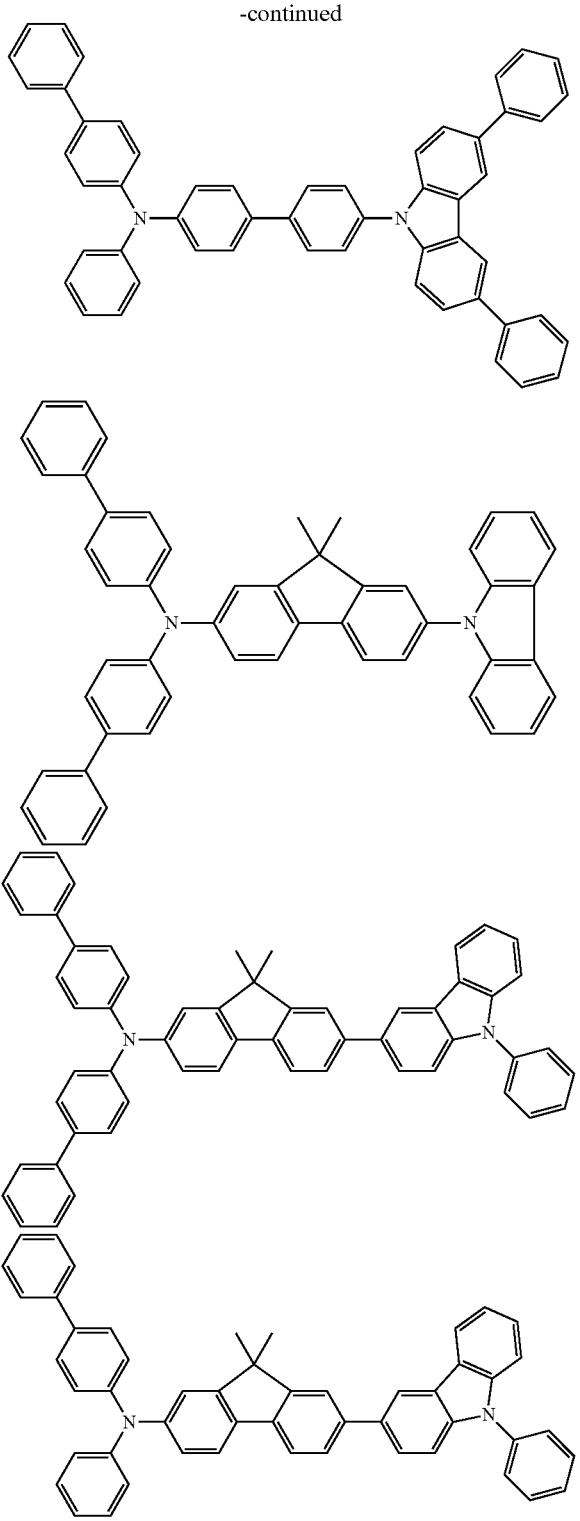

The present invention is not limited to the embodiments described above, and variations and modifications can be effected within the spirit and scope of the invention.

For example, the following modification is a preferred embodiment of the invention.

It is also preferred that the light emitting layer of the invention contains a charge injecting aid.

When the light emitting layer is formed by using a host material having a wide energy gap, the difference between the ionization potential (Ip) of the host material and Ip of the hole injecting/transporting layer, etc., this being likely to make the injection of holes into the light emitting layer difficult to increase the driving voltage for obtaining sufficient luminance.

In this case, by incorporating a hole injecting/transporting charge injecting aid into the light emitting layer, the injection of holes into the light emitting layer is facilitated and the driving voltage is reduced.

For example, a hole injecting/transporting material generally known is usable as the charge injecting aid.

Examples thereof include triazole derivatives (U.S. Pat. No. 3,112,197), oxadiazole derivatives (U.S. Pat. No. 3,189,447), imidazole derivatives (JP 37-16096B), polyarylalkane derivatives (U.S. Pat. No. 3,615,402, U.S. Pat. No. 3,820,989, U.S. Pat. No. 3,542,544, JP 45-555B, JP 51-10983B, JP 51-93224A, JP 55-17105A, JP 56-4148A, JP 55-108667A, JP 55-156953A, JP 56-36656A), pyrazoline derivatives and pyrazolone derivatives (U.S. Pat. No. 3,180,729, U.S. Pat. No. 4,278,746, JP 55-88064A, JP 55-88065A, JP 49-105537A, JP 55-51086A, JP 56-80051A, JP 56-88141A, JP 57-45545A, JP 54-112637A, JP 55-74546A), phenylenediamine derivatives (U.S. Pat. No. 3,615,404, JP 51-10105B, JP 46-3712B, JP 47-25336B, JP 54-53435A, JP 54-110536A, JP 54-119925A), arylamine derivatives (U.S. Pat. No. 3,567,450, U.S. Pat. No. 3,180,703, U.S. Pat. No. 3,240,597, U.S. Pat. No. 3,658,520, U.S. Pat. No. 4,232,103, U.S. Pat. No. 4,175,961, U.S. Pat. No. 4,012,376, JP 49-35702B, JP 39-27577B, JP 55-144250A, JP 56-119132A, JP 56-22437A, DE 1,110,518), amino-substituted chalcone derivatives (U.S. Pat. No. 3,526,501), oxazole derivatives (U.S. Pat. No. 3,257,203), styrylanthracene derivative (JP 56-46234A), fluorenone derivatives (JP 54-110837A), hydrazone derivatives (U.S. Pat. No. 3,717,462, JP 54-59143A, JP 55-52063A, JP 55-52064A, JP 55-46760A, JP 55-85495A, JP 57-11350A, JP 57-148749A, JP 2-311591A), stilbene derivatives (JP 61-210363A, JP 61-228451A, JP 61-14642A, JP 61-72255A, JP 62-47646A, JP 62-36674A, JP 62-10652A, JP 62-30255A, JP 60-93455A, JP 60-94462A, JP 60-174749A, JP 60-175052A), silazane derivatives (U.S. Pat. No. 4,950,950), polysilanes (JP 2-204996A), aniline-based copolymer (JP 2-282263A), and electroconductive high molecular weight oligomer (particularly, thiophene oligomer) disclosed in JP 1-211399A.

In addition to the hole injecting material mentioned above, porphyrin compounds (JP 63-295695A), and aromatic tertiary amines and styryl amine compounds (U.S. Pat. No. 4,127,412, JP 53-27033A, JP 54-58445A, JP 54-149634A, JP 54-64299A, JP 55-79450A, JP 55-144250A, JP 56-119132A, JP 61-295558A, JP 61-98353A, JP 63-295695A) are usable, with the aromatic tertiary amines being particularly preferred.

A compound having two condensed aromatic rings in its molecule described in U.S. Pat. No. 5,061,569, for example, 4,4'-bis(N-(1-naphthyl)-N-phenylamino)biphenyl(NPD), and 4,4',4"-tris(N-(3-methylphenyl)-N-phenylamino)triphenylamine (MTDATA) in which three triphenylamine units are linked to each other in starburst configuration are also usable.

Further, hexaazatriphenylene derivatives described in JP 3614405, JP 3571977, or U.S. Pat. No. 4,780,536 are preferably used as the hole injecting material.

An organic compound, such as p-type Si and p-type SiC, is also usable as the hole injecting material.

The method of forming each layer of the organic electroluminescence device of the invention is not particularly limited, and each layer can be formed by a known method, such as a vacuum vapor deposition method and a spin coating method. The organic thin film layer in the organic electroluminescence device of the invention may be formed by a known method, for example, by a vacuum vapor deposition method, a molecular beam evaporation method (MBE method), and a coating method, such as a dipping method, a spin coating method, a casting method, a bar coating method and a roll coating method, each using a solvent solution.

The film thickness of each organic layer in the organic electroluminescence device of the invention is not particularly limited. Since detects, such as pinholes, are likely to be caused if the film thickness is excessively small and high applied voltage is required to reduce the efficiency if the film thickness is excessively large, the film thickness is preferably from several nanometers to 1 µm.

EXAMPLES

The present invention will be described in more detail with reference to examples and comparative examples. However, it should be noted that the scope of the present invention is not limited to the following examples.

The physical properties of each material shown in Tables were measured as follows.

The triplet energy gap Eg was determined from the phosphorescent emission spectrum as described below.

A sample for phosphorescent measurement was prepared by dissolving each material in EPA solvent (diethyl ether:isopentane:ethanol=5:5:2 by volume) at 10 µmol/L.

The sample for phosphorescent measurement was charged into a quartz cell, cooled to 77 K, and irradiated with exciting light, and the intensity of emitted phosphorescent light was measured at each wavelength.

A line tangent to the rising portion at the short-wavelength side of the obtained phosphorescent emission spectrum was drawn, and the wavelength at the intersection of the tangent line and the base line was converted to a value of energy unit, employing the converted value as the triplet energy gap Eg(T).

The measurement was conducted by using a commercially available measuring apparatus F-4500 (manufactured by Hitachi, Ltd.).

Synthesis Example 1

Synthesis of Compound (1-1)

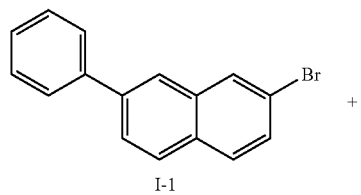

I-1

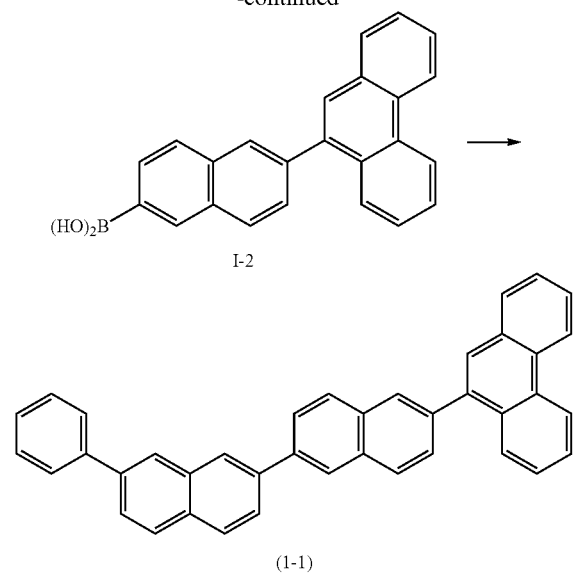

In argon atmosphere, a mixture of 5.0 g (18 mmol) of bromide I-1, 6.2 g (18 mmol) of boronic acid I-2, 420 mg (0.36 mmol) of tetrakis(triphenylphosphine)palladium(0), 120 ml of toluene, 40 ml of dimethoxyethane, and 26 ml of 2 M aqueous solution of sodium carbonate was stirred at 90° C. for 10 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 6.4 g (yield: 70%) of compound (1-1).

FD mass spectrometric analysis showed a peak at m/e=506 to the calculated molecular weight of 506.

Synthesis Example 2

Synthesis of Compound (1-3)

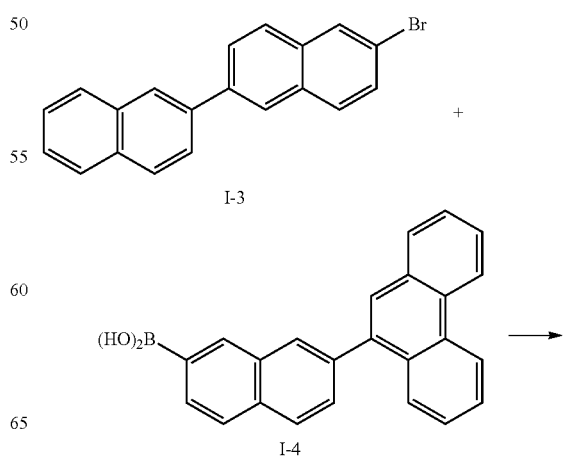

-continued

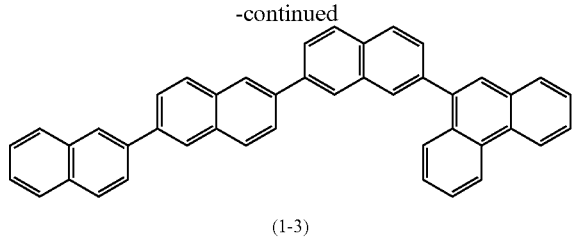

(1-3)

In argon atmosphere, a mixture of 5.0 g (15 mmol) of bromide I-3, 5.3 g (15 mmol) of boronic acid I-4, 350 mg (0.30 mmol) of tetrakis(triphenylphosphine)palladium(0), 100 ml of toluene, 30 ml of dimethoxyethane, and 22 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 5.5 g (yield: 66%) of compound (1-3).

FD mass spectrometric analysis showed a peak at m/e=556 to the calculated molecular weight of 556.

Synthesis Example 3

Synthesis of Compound (1-6)

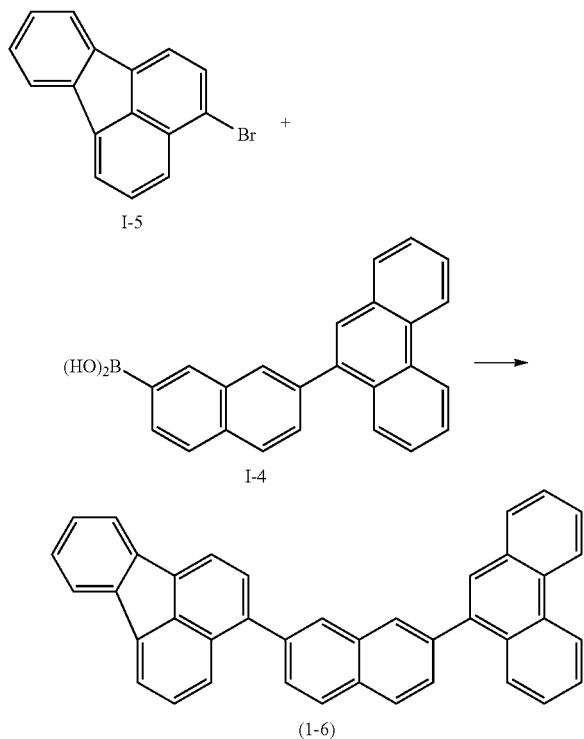

In argon atmosphere, a mixture of 5.0 g (18 mmol) of bromide I-5, 6.2 g (18 mmol) of boronic acid I-4, 420 mg (0.36 mmol) of tetrakis(triphenylphosphine)palladium(0), 120 ml of toluene, 40 ml of dimethoxyethane, and 26 ml of 2 M aqueous solution of sodium carbonate was stirred at 90° C. for 15 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 6.2 g (yield: 68%) of compound (1-6).

FD mass spectrometric analysis showed a peak at m/e=504 to the calculated molecular weight of 504.

Synthesis Example 4

Synthesis of Compound (1-7)

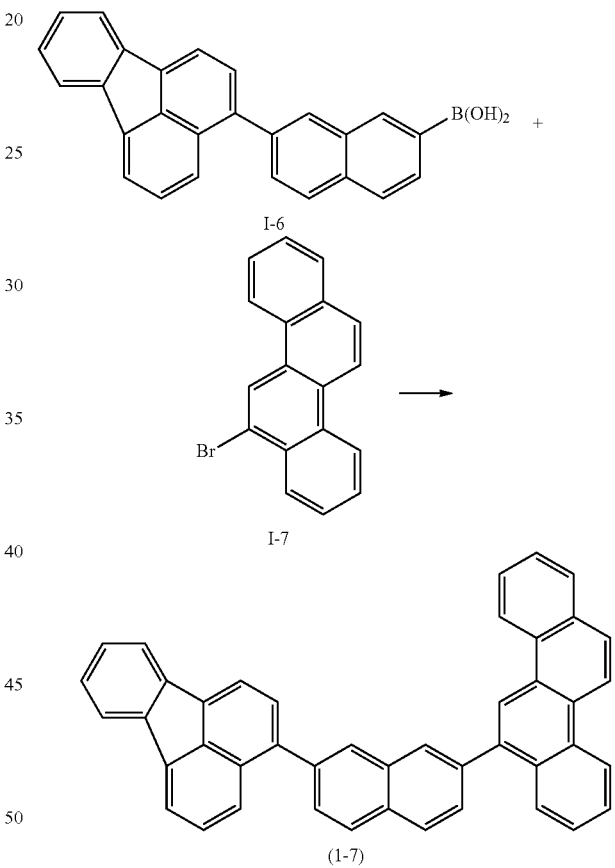

In argon atmosphere, a mixture of 5.2 g (14 mmol) of boronic acid I-6, 4.3 g (14 mmol) of bromide I-7, 330 mg (0.28 mmol) of tetrakis(triphenylphosphine)palladium(0), 120 ml of toluene, 40 ml of dimethoxyethane, and 20 ml of 2 M aqueous solution of sodium carbonate was stirred at 90° C. for 15 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 4.9 g (yield: 63%) of compound (1-7).

FD mass spectrometric analysis showed a peak at m/e=554 to the calculated molecular weight of 554.

Synthesis Example 5

Synthesis of Compound (1-11)

Synthesis Example 6

Synthesis of Compound (1-13)

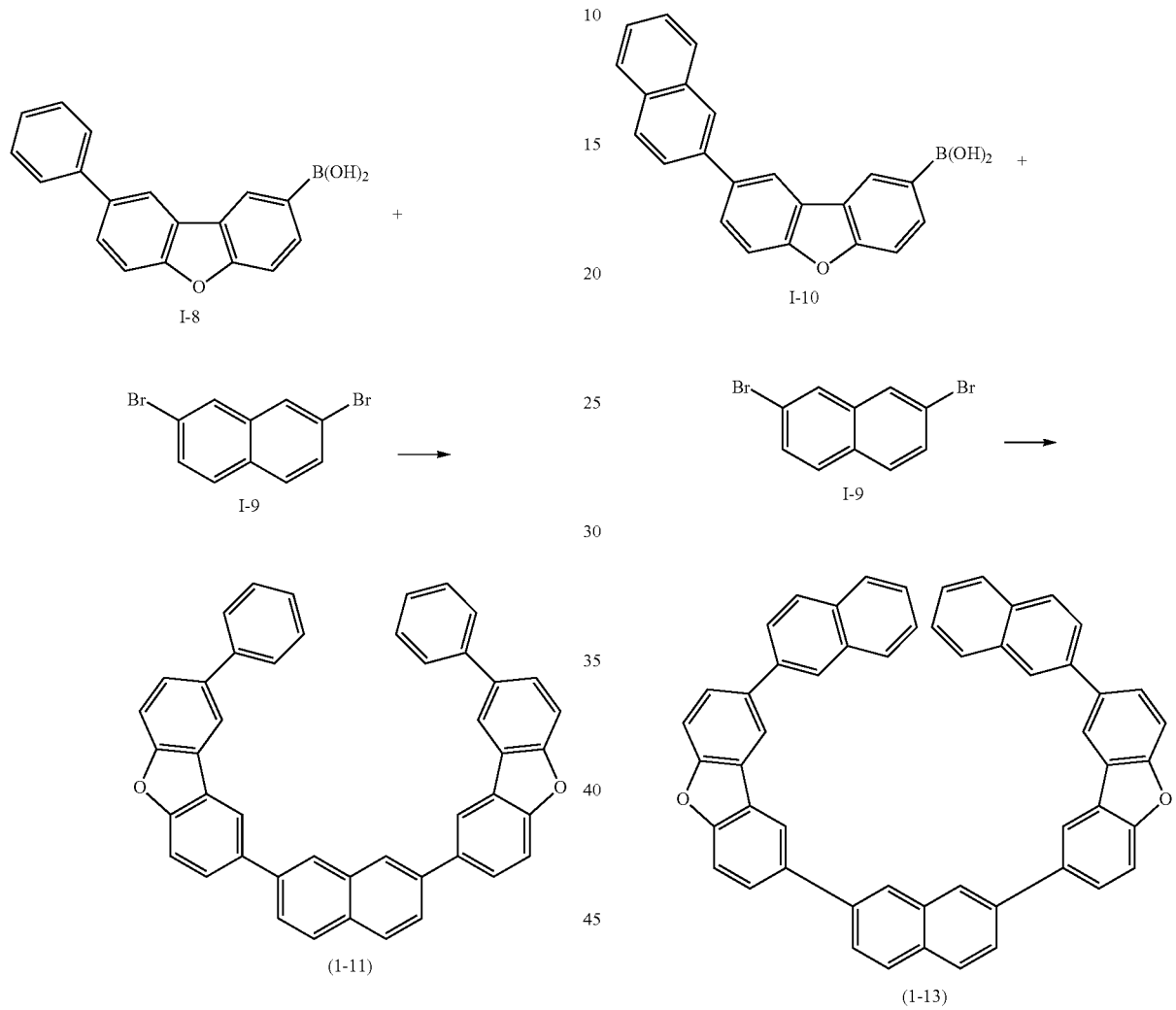

In argon atmosphere, a mixture of 5.2 g (18 mmol) of boronic acid I-8, 5.1 g (18 mmol) of dibromide I-9, 420 mg (0.36 mmol) of tetrakis(triphenylphosphine)palladium(0), 120 ml of toluene, 40 ml of dimethoxyethane, and 26 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 6.3 g (yield: 57%) of compound (1-11).

FD mass spectrometric analysis showed a peak at m/e=612 to the calculated molecular weight of 612.

In argon atmosphere, a mixture of 5.0 g (15 mmol) of boronic acid I-10, 4.2 g (15 mmol) of dibromide I-9, 350 mg (0.30 mmol) of tetrakis(triphenylphosphine)palladium(0), 100 ml of toluene, 35 ml of dimethoxyethane, and 22 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 6.4 g (yield: 50%) of compound (1-13).

FD mass spectrometric analysis showed a peak at m/e=712 to the calculated molecular weight of 712.

Synthesis Example 7

Synthesis of Compound (2-1)

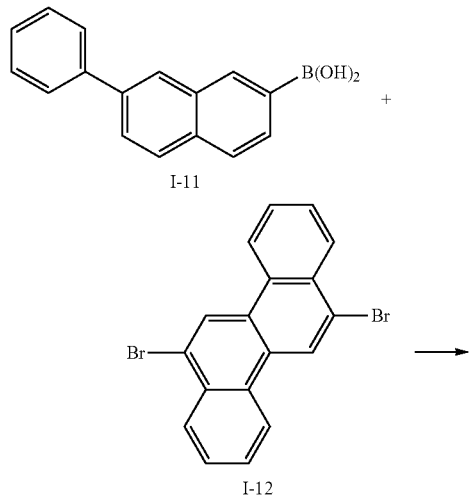

In argon atmosphere, a mixture of 5.0 g (20 mmol) of boronic acid I-11, 7.7 g (20 mmol) of dibromide I-12, 470 mg (0.40 mmol) of tetrakis(triphenylphosphine)palladium(0), 150 ml of toluene, 50 ml of dimethoxyethane, and 30 ml of 2 M aqueous solution of sodium carbonate was stirred at 90° C. for 15 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene and then tetrahydrofuran, to obtain 5.2 g (yield: 49%) of compound (2-1).

FD mass spectrometric analysis showed a peak at m/e=632 to the calculated molecular weight of 632.

Synthesis Example 8

Synthesis of Compound (2-5)

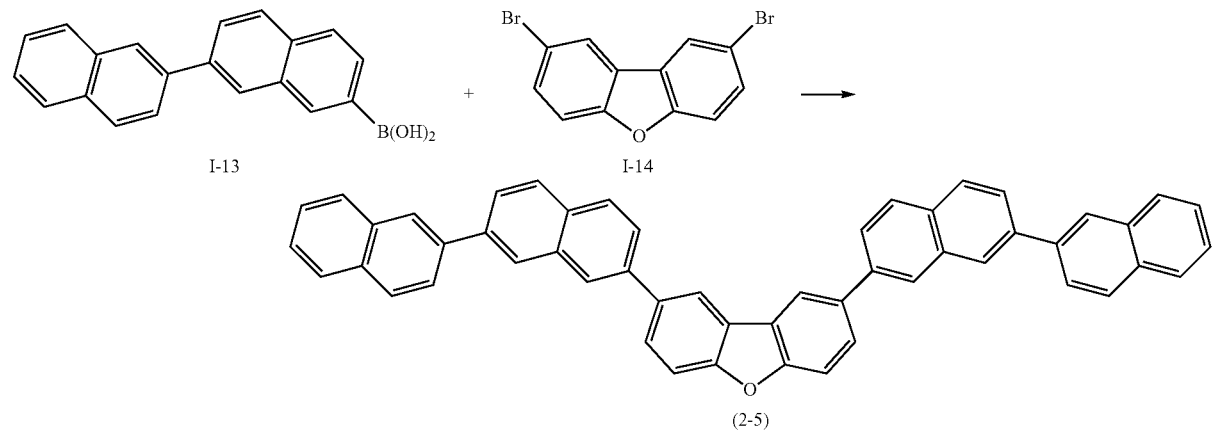

-continued

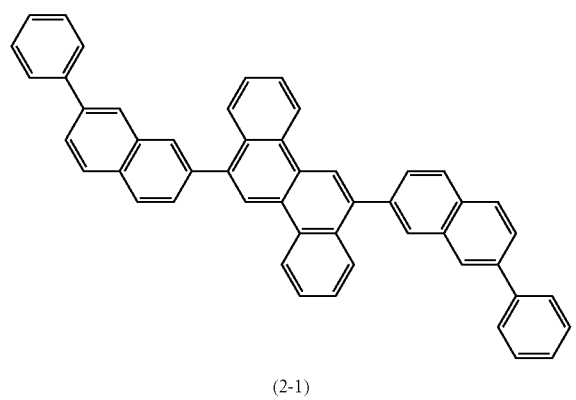

In argon atmosphere, a mixture of 5.4 g (18 mmol) of boronic acid I-13, 5.8 g (18 mmol) of dibromide I-14, 420 mg (0.36 mmol) of tetrakis(triphenylphosphine)palladium(0), 120 ml of toluene, 40 ml of dimethoxyethane, and 26 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 6.5 g (yield: 54%) of compound (2-5).

FD mass spectrometric analysis showed a peak at m/e=672 to the calculated molecular weight of 672.

Synthesis Example 9

Synthesis of Compound (1-17)

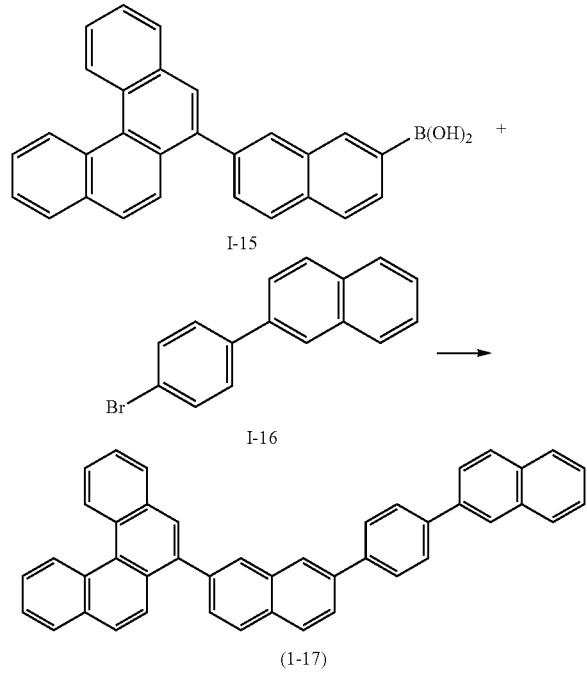

In argon atmosphere, a mixture of 5.2 g (13 mmol) of boronic acid I-15, 3.7 g (13 mmol) of bromide I-16, 305 mg (0.26 mmol) of tetrakis(triphenylphosphine)palladium(0), 100 ml of toluene, 30 ml of dimethoxyethane, and 19 ml of 2 M aqueous solution of sodium carbonate was stirred at 90° C. for 11 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 4.0 g (yield: 55%) of compound (1-17).

FD mass spectrometric analysis showed a peak at m/e=556 to the calculated molecular weight of 556.

Synthesis Example 10

Synthesis of Compound (1-20)

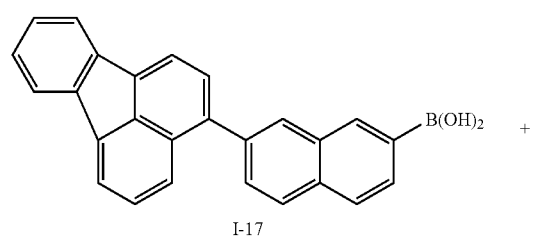

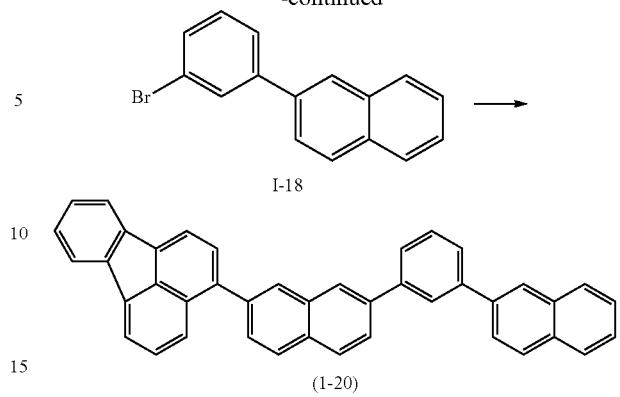

In argon atmosphere, a mixture of 4.8 g (13 mmol) of boronic acid I-17, 3.7 g (13 mmol) of bromide I-18, 305 mg (0.26 mmol) of tetrakis(triphenylphosphine)palladium(0), 90 ml of toluene, 30 ml of dimethoxyethane, and 19 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 3.6 g (yield: 52%) of compound (1-20).

FD mass spectrometric analysis showed a peak at m/e=530 to the calculated molecular weight of 530.

Synthesis Example 11

Synthesis of Compound (1-25)

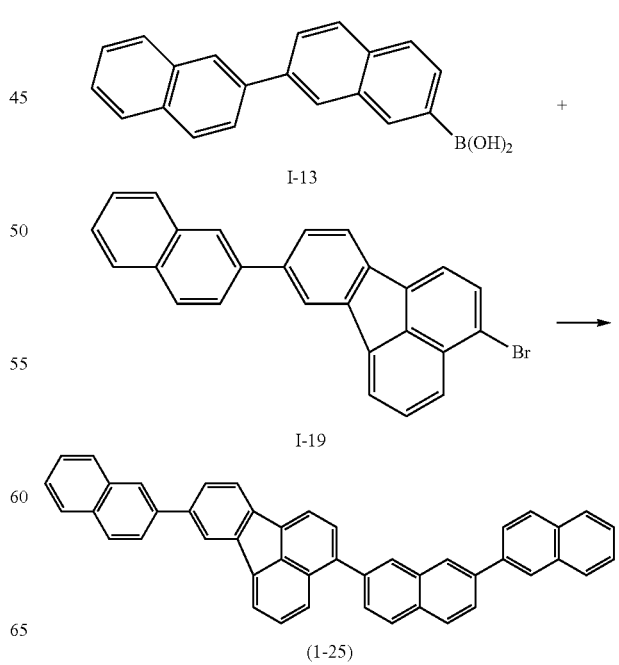

In argon atmosphere, a mixture of 5.1 g (17 mmol) of boronic acid I-13, 6.9 g (17 mmol) of bromide I-19, 400 mg (0.34 mmol) of tetrakis(triphenylphosphine)palladium(0), 120 ml of toluene, 40 ml of dimethoxyethane, and 25 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 5.2 g (yield: 53%) of compound (1-25).

FD mass spectrometric analysis showed a peak at m/e=580 to the calculated molecular weight of 580.

Synthesis Example 12

Synthesis of Compound (1-27)

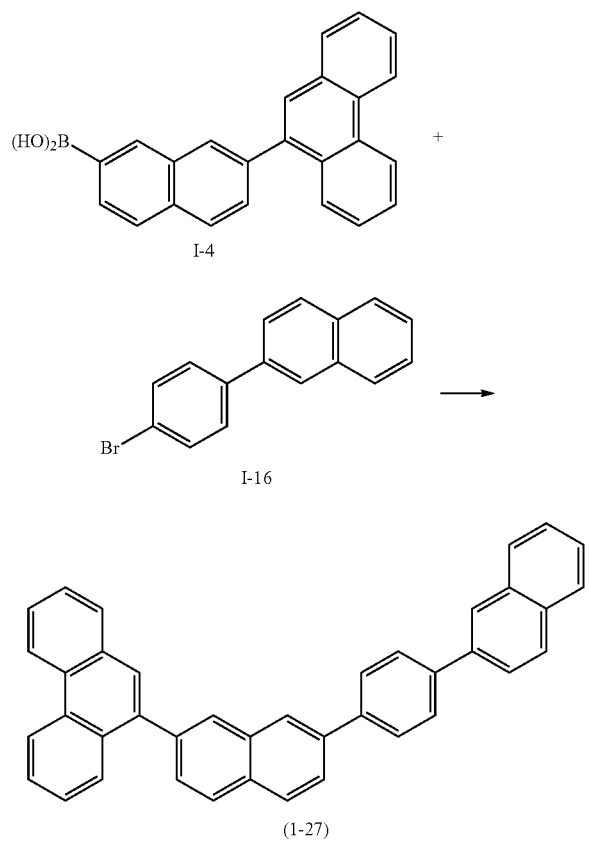

In argon atmosphere, a mixture of 5.6 g (16 mmol) of boronic acid I-4, 4.5 g (16 mmol) of bromide I-16, 375 mg (0.32 mmol) of tetrakis(triphenylphosphine)palladium(0), 100 ml of toluene, 40 ml of dimethoxyethane, and 23 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 5.5 g (yield: 68%) of compound (1-27).

FD mass spectrometric analysis showed a peak at m/e=506 to the calculated molecular weight of 506.

Synthesis Example 13

Synthesis of Compound (1-36)

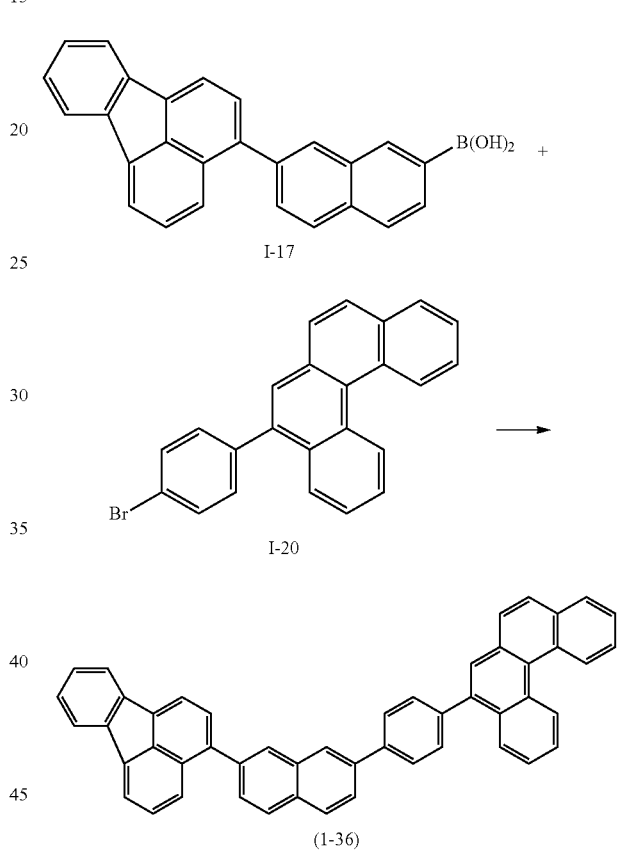

In argon atmosphere, a mixture of 5.6 g (15 mmol) of boronic acid I-17, 5.8 g (15 mmol) of bromide I-16, 350 mg (0.30 mmol) of tetrakis(triphenylphosphine)palladium(0), 100 ml of toluene, 40 ml of dimethoxyethane, and 22 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 5.1 g (yield: 54%) of compound (1-36).

FD mass spectrometric analysis showed a peak at m/e=630 to the calculated molecular weight of 630.

Synthesis Example 14

Synthesis of Compound (1-2)

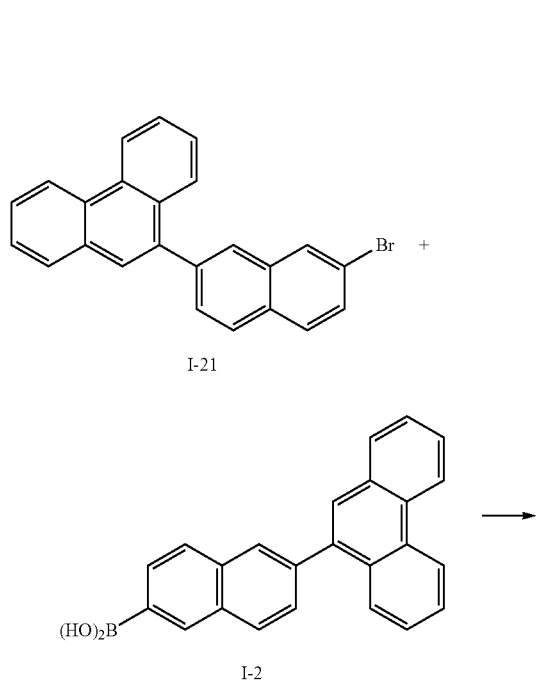

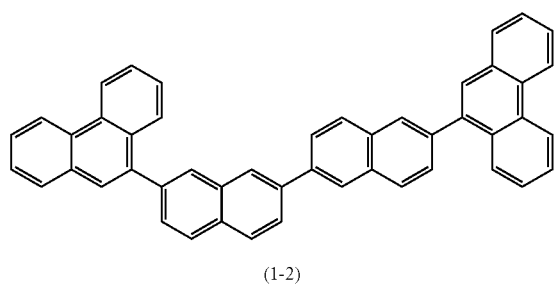

In argon atmosphere, a mixture of 6.9 g (18 mmol) of bromide I-21, 6.2 g (18 mmol) of boronic acid I-2, 420 mg (0.36 mmol) of tetrakis(triphenylphosphine)palladium(0), 120 ml of toluene, 40 ml of dimethoxyethane, and 26 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 6.8 g (yield: 62%) of compound (1-2).

FD mass spectrometric analysis showed a peak at m/e=606 to the calculated molecular weight of 606.

Synthesis Example 15

Synthesis of Compound (1-50)

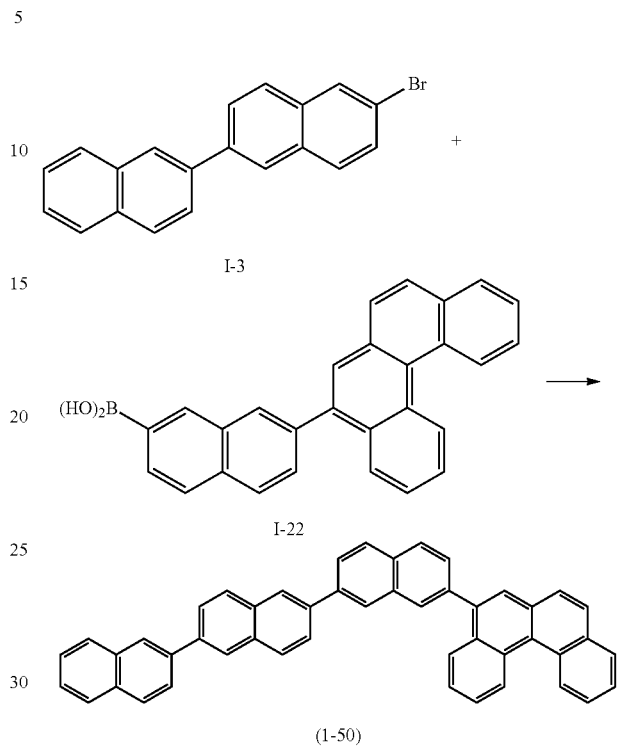

In argon atmosphere, a mixture of 5.0 g (15 mmol) of bromide I-3, 6.0 g (15 mmol) of boronic acid I-22, 350 mg (0.30 mmol) of tetrakis(triphenylphosphine)palladium(0), 100 ml of toluene, 30 ml of dimethoxyethane, and 22 ml of 2 M aqueous solution of sodium carbonate was stirred at 90° C. for 14 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 5.8 g (yield: 64%) of compound (1-50).

FD mass spectrometric analysis showed a peak at m/e=606 to the calculated molecular weight of 606.

Synthesis Example 16

Synthesis of Compound (1-51)

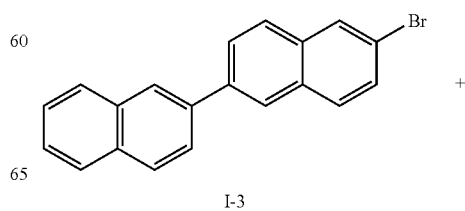

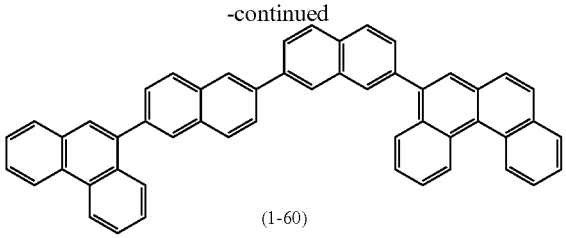

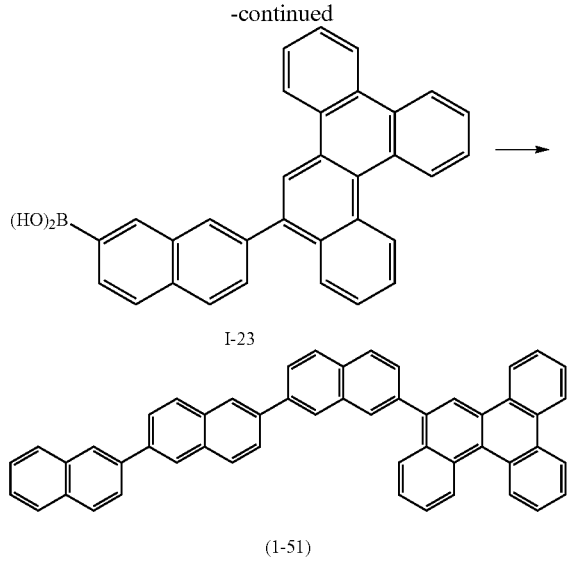

In argon atmosphere, a mixture of 5.0 g (15 mmol) of bromide I-3, 6.7 g (15 mmol) of boronic acid I-23, 350 mg (0.30 mmol) of tetrakis(triphenylphosphine)palladium(0), 100 ml of toluene, 30 ml of dimethoxyethane, and 22 ml of 2 M aqueous solution of sodium carbonate was stirred at 90° C. for 14 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 5.5 g (yield: 56%) of compound (1-51).

FD mass spectrometric analysis showed a peak at m/e=656 to the calculated molecular weight of 656.

Synthesis Example 17

Synthesis of Compound (1-60)

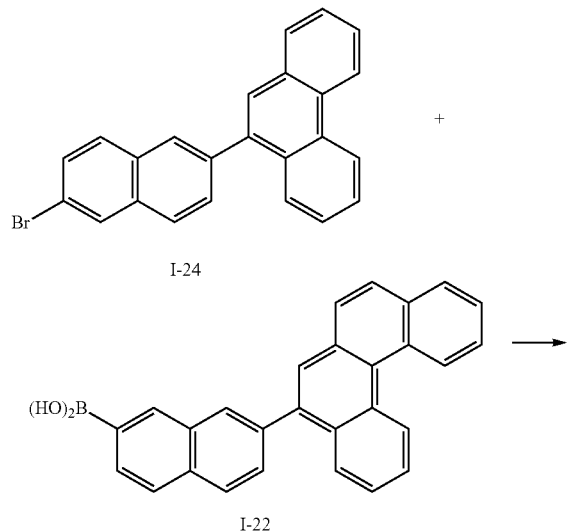

In argon atmosphere, a mixture of 5.7 g (15 mmol) of bromide I-24, 6.0 g (15 mmol) of boronic acid I-22, 350 mg (0.30 mmol) of tetrakis(triphenylphosphine)palladium(0), 100 ml of toluene, 30 ml of dimethoxyethane, and 22 ml of 2 M aqueous solution of sodium carbonate was stirred at 90° C. for 14 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 5.4 g (yield: 55%) of compound (1-60).

FD mass spectrometric analysis showed a peak at m/e=656 to the calculated molecular weight of 656.

Synthesis Example 18

Synthesis of Compound (1-69)

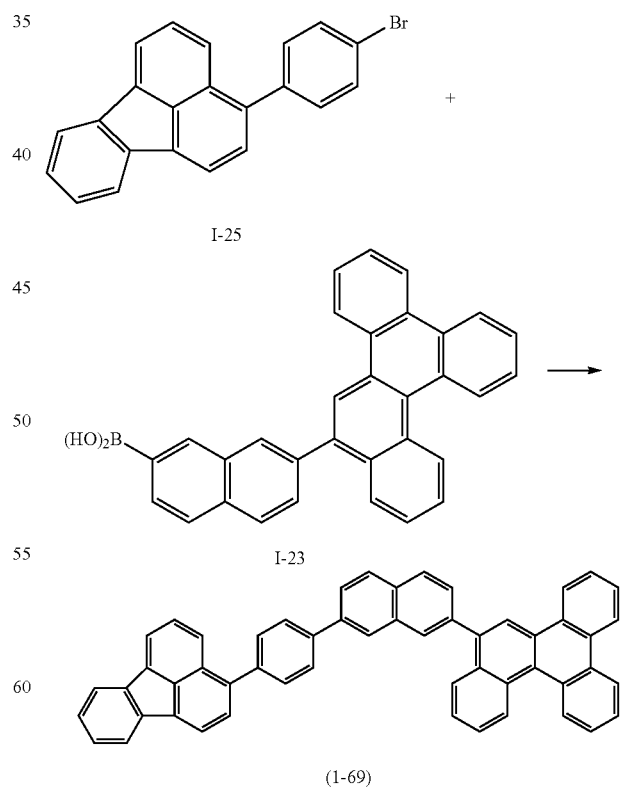

In argon atmosphere, a mixture of 6.1 g (17 mmol) of bromide I-25, 7.7 g (17 mmol) of boronic acid I-23, 400 mg (0.34 mmol) of tetrakis(triphenylphosphine)palladium(0), 120 ml of toluene, 40 ml of dimethoxyethane, and 26 ml of 2 M aqueous solution of sodium carbonate was stirred at 90° C. for 14 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 6.0 g (yield: 52%) of compound (1-69).

FD mass spectrometric analysis showed a peak at m/e=680 to the calculated molecular weight of 680.

Synthesis Example 19

Synthesis of Compound (2-17)

(0.30 mmol) of tetrakis(triphenylphosphine)palladium(0), 100 ml of toluene, 30 ml of dimethoxyethane, and 22 ml of 2 M aqueous solution of sodium carbonate was stirred at 90° C. for 12 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 3.1 g (yield: 62%) of compound (2-17).

FD mass spectrometric analysis showed a peak at m/e=732 to the calculated molecular weight of 732.

Synthesis Example 20

Synthesis of Compound (2-18)

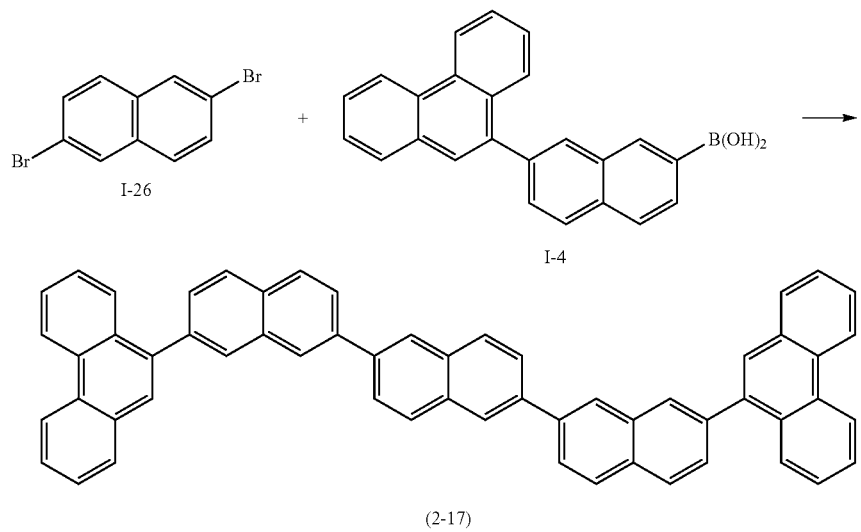

In argon atmosphere, a mixture of 2.1 g (7.3 mmol) of dibromide I-26, 5.3 g (15 mmol) of boronic acid I-4, 400 mg

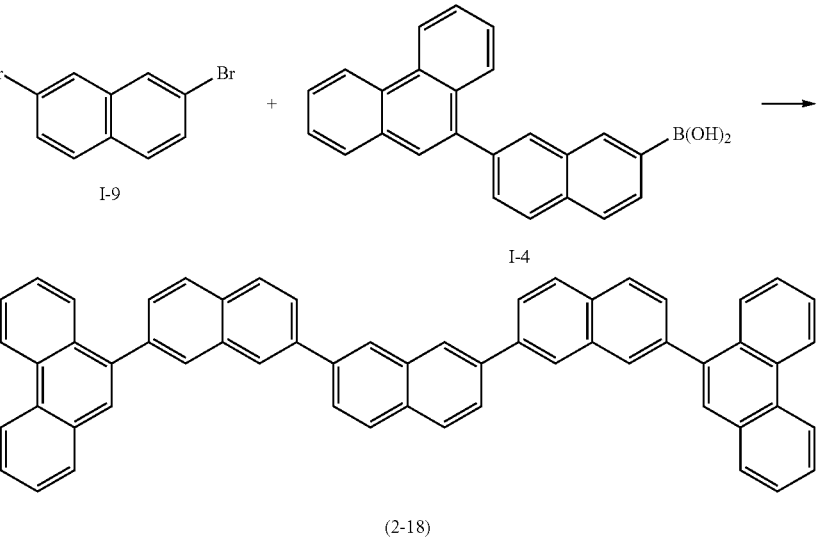

In argon atmosphere, a mixture of 2.1 g (7.3 mmol) of dibromide I-9, 5.3 g (15 mmol) of boronic acid I-4, 400 mg (0.30 mmol) of tetrakis(triphenylphosphine)palladium(0), 100 ml of toluene, 30 ml of dimethoxyethane, and 22 ml of 2 M aqueous solution of sodium carbonate was stirred at 90° C. for 14 h. The reaction mixture was allowed to cool to room temperature, added with water, stirred for one hour at room temperature, and then, extracted with toluene. After liquid-liquid separation, the organic phase was washed with saturated sodium chloride solution and dried over anhydrous sodium sulfate. The solvent was evaporated off under reduced pressure, and the residue was purified by silica gel column chromatography and recrystallized from toluene, to obtain 3.4 g (yield: 64%) of compound (2-18).

FD mass spectrometric analysis showed a peak at m/e=732 to the calculated molecular weight of 732.

Example 1

Production of Organic EL Device

A glass substrate of 25 mm×75 mm×0.7 mm thickness having ITO transparent electrode (product of Asahi Glass Company Ltd.) was cleaned by ultrasonic cleaning in isopropyl alcohol for 5 min and then UV ozone cleaning for 30 min. The cleaned glass substrate was mounted to a substrate holder of a vacuum vapor deposition apparatus. HT1 was deposited into a film of 50 nm thick so as to cover the transparent electrode. The HT1 film worked as a hole injecting/transporting layer. Successively, compound (1-1) and 10% by mass of Ir(piq)$_3$ as a phosphorescent dopant were co-deposited into a film of 40 nm thick on the hole injecting/transporting layer by resistance heating method. The obtained film worked as a light emitting layer (phosphorescent emitting layer). Successively, ET1 was deposited into a film of 40 nm thick on the light emitting layer. The obtained film worked as an electron transporting layer. An electron injection electrode (cathode) was formed by depositing LiF into a film of 0.5 nm thick at a film-forming speed of 0.1 nm/min. Then, a metal cathode was formed on the LiF layer by vapor-depositing metallic Al into a film of 150 nm thick, thereby producing an organic electroluminescence device.

Examples 2 to 23 and Comparative Examples 1 to 7

Each organic electroluminescence device was produced in the same manner as in Example 1 except for using each compound shown in Table 1 in place of compound (1-1).

Example 24

An organic electroluminescence device was produced in the same manner as in Example 14 except for using the following Complex A as the phosphorescent dopant in place of Ir(piq)$_3$.

Complex A

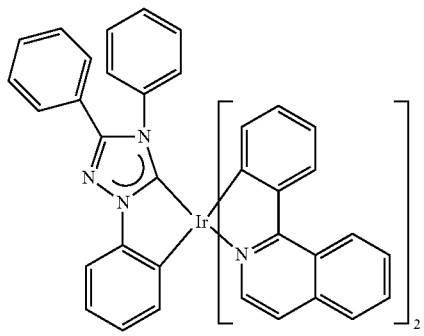

Example 25

An organic electroluminescence device was produced in the same manner as in Example 14 except for using the following Complex B as the phosphorescent dopant in place of Ir(piq)$_3$.

Complex B

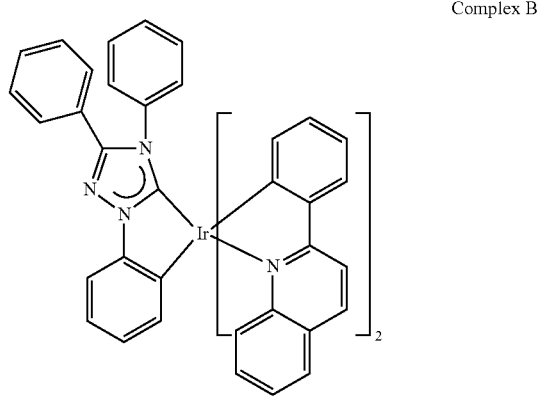

Comparative Example 8

An organic electroluminescence device was produced in the same manner as in Example 24 except for using CBP in place of compound (1-2).

Comparative Example 9

An organic electroluminescence device was produced in the same manner as in Example 25 except for using BAlq in place of compound (1-2).

Evaluation of Emission Performance of Organic Electroluminescence Devices

The organic EL devices produced in Examples 1 to 25 and Comparative Examples 1 to 9 were allowed to emit light by DC driving to measure the voltage, current efficiency and half lifetime of luminance (initial luminance: 3000 cd/m$^2$) at a current density of 10 mA/cm$^2$. Further, the uniformity of pixel at 70° C. driving was visually evaluated, and rated as A when uniform and B when partly not uniform. Separately, the phosphorescent emission spectrum of each sample was measured (10 μmol/L in EPA solution (diethyl ether:isopentane:isopropyl alcohol=5:5:2 by volume), 77 K, quartz cell, FLUOROLOG II available from SPEX). A line tangent to the rising portion at the short-wavelength side of the obtained phosphorescent emission spectrum was drawn, and the wavelength at the intersection of the tangent line and the axis of abscissa (emission end) was determined. The wavelength was converted to a value of energy unit, to obtain the excited triplet energy (Eg(T)) of the material for organic EL device. The samples used were purified by sublimation, etc. Results of evaluation are shown in Tables 1 and 2.

197                                              198
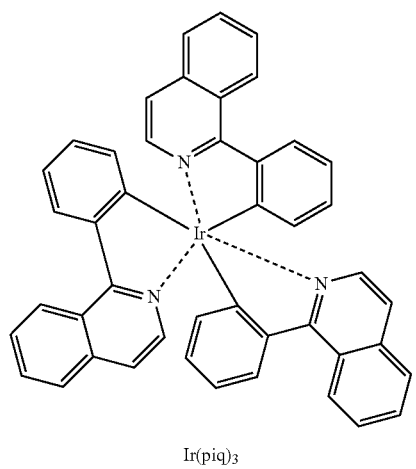
Ir(piq)₃
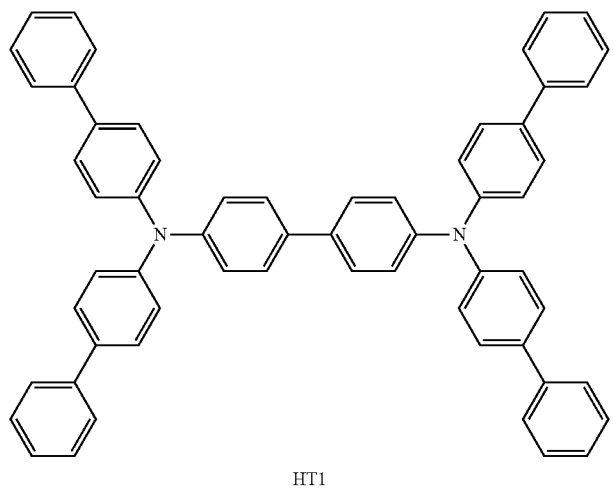
HT1
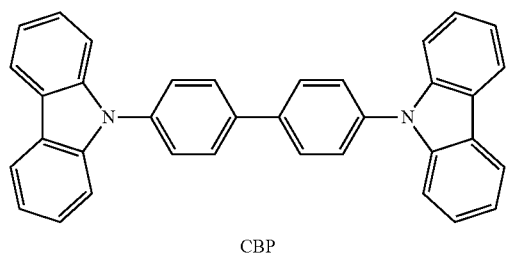
CBP
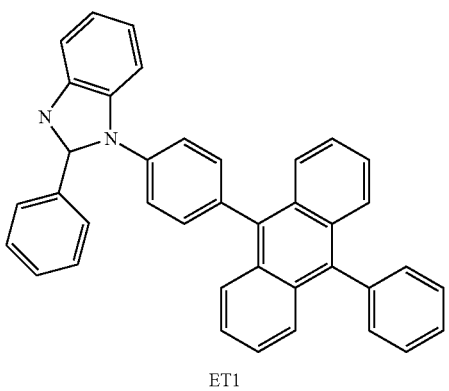
ET1
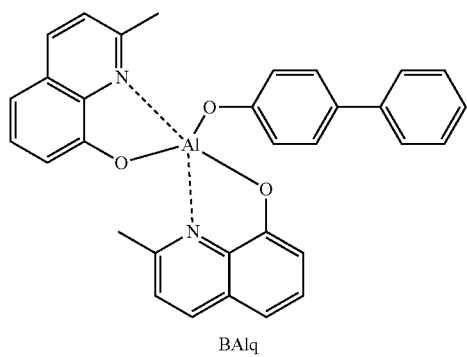
BAlq
(A)
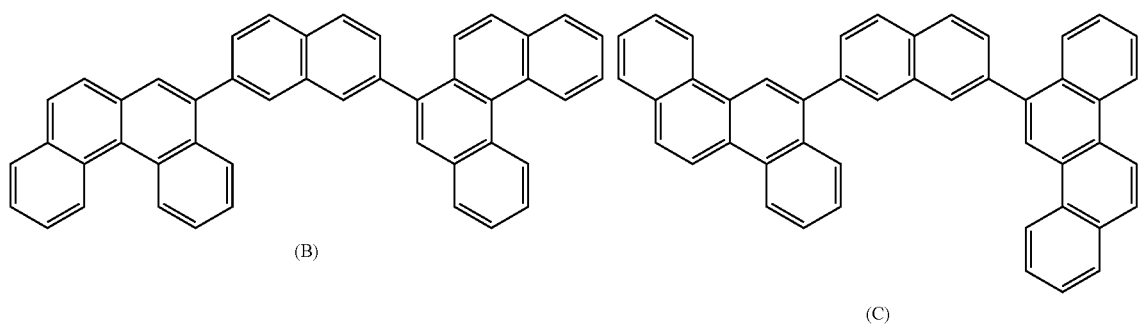
(B)                                              (C)

-continued
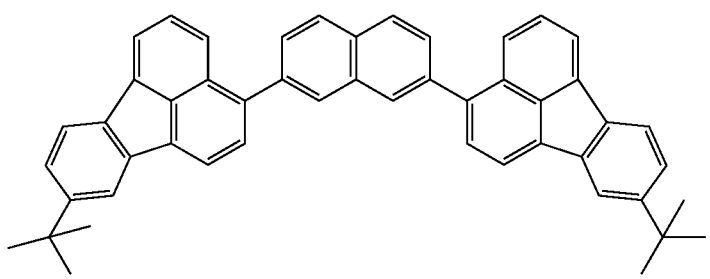
(D)
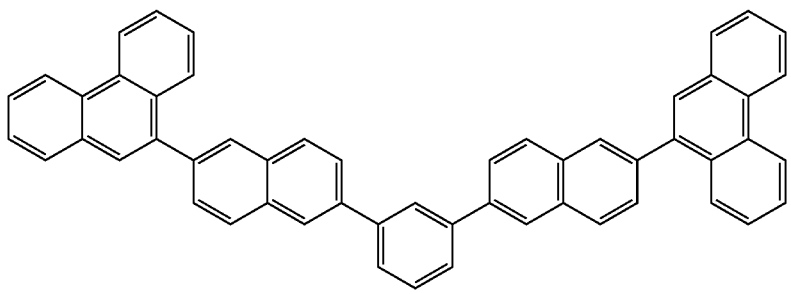
(E)
TABLE 1
| | Compound | Eg(T) of compound (eV) | Voltage (V) | Current efficiency (cd/A) | Half lifetime of luminance (h) | Pixel uniformity upon driving at 70° C. |
|---|---|---|---|---|---|---|
| Examples | | | | | | |
| 1 | (1-1) | 2.46 | 4.2 | 11.6 | 8,100 | A |
| 2 | (1-3) | 2.44 | 3.9 | 13.0 | 9,000 | A |
| 3 | (1-6) | 2.28 | 4.1 | 11.1 | 7,200 | A |
| 4 | (1-7) | 2.26 | 4.0 | 11.3 | 8,000 | A |
| 5 | (1-11) | 2.50 | 4.3 | 10.3 | 7,500 | A |
| 6 | (1-13) | 2.44 | 4.3 | 10.2 | 7,300 | A |
| 7 | (1-17) | 2.43 | 4.0 | 11.2 | 8,400 | A |
| 8 | (1-20) | 2.25 | 4.1 | 11.6 | 8,600 | A |
| 9 | (1-25) | 2.22 | 4.2 | 11.3 | 8,400 | A |
| 10 | (1-27) | 2.46 | 4.3 | 10.9 | 8,300 | A |
| 11 | (1-36) | 2.28 | 3.8 | 12.5 | 8,800 | A |
| 12 | (2-1) | 2.48 | 4.2 | 10.3 | 7,600 | A |
| 13 | (2-5) | 2.48 | 4.3 | 10.4 | 7,000 | A |
| Comparative Examples | | | | | | |
| 1 | CBP | 2.81 | 5.7 | 6.3 | 1,200 | B |
| 2 | BAlq | 2.28 | 5.3 | 7.0 | 2,300 | B |
| 3 | (A) | 2.21 | 4.6 | 8.4 | 4,000 | B |
| 4 | (B) | 2.50 | 4.5 | 8.7 | 3,300 | B |
| 5 | (C) | 2.40 | 4.8 | 7.4 | 3,500 | B |
| 6 | (D) | 2.20 | 4.7 | 7.0 | 3,100 | B |
| Examples | | | | | | |
| 14 | (1-2) | 2.50 | 4.3 | 11.4 | 7,800 | A |
| 15 | (1-50) | 2.41 | 4.0 | 11.7 | 8,800 | A |
| 16 | (1-51) | 2.37 | 4.1 | 10.8 | 7,400 | A |
| 17 | (1-60) | 2.41 | 4.2 | 11.6 | 8,500 | A |
| 18 | (1-69) | 2.31 | 4.1 | 10.9 | 7,200 | A |
| 19 | (2-17) | 2.48 | 4.3 | 10.5 | 7,000 | A |
| 20 | (2-18) | 2.49 | 4.3 | 10.2 | 6,800 | A |
| 21 | (2-19) | 2.50 | 4.5 | 10.7 | 6,600 | A |
| 22 | (2-20) | 2.44 | 4.2 | 11.6 | 7,000 | A |
| 23 | (2-21) | 2.39 | 4.4 | 11.3 | 7,500 | A |
| Comparative Example | | | | | | |
| 7 | (E) | 2.50 | 4.8 | 9.1 | 2,700 | B |

TABLE 2

| | Dopant | Material for organic EL devices | Voltage (V) | Current efficiency (cd/A) | Half lifetime of luminance (h) | Pixel uniformity upon driving at 70° C. |
|---|---|---|---|---|---|---|
| Examples | | | | | | |
| 24 | Complex A | (1-2) | 4.6 | 9.0 | 6,000 | A |
| 25 | Complex B | (1-2) | 4.5 | 8.2 | 6,200 | A |
| Comparative Examples | | | | | | |
| 8 | Complex A | CBP | 5.9 | 4.3 | 1,000 | B |
| 9 | Complex B | BAlq | 5.1 | 5.1 | 1,800 | B |

The results of Tables 1 and 2 show that the organic electroluminescence devices of Examples 1 to 25 employing the material for organic EL devices of the invention have high external quantum efficiency and extremely long lifetime.

In contrast, the devices of Comparative Examples 1 to 9 require relative high voltage and have low current efficiency and short lifetimes. Particularly, the device of Comparative Example 1 has low current efficiency and short lifetimes. The device of Comparative Example 2 also has short lifetime. The devices of Comparative Examples 3 to 6 have relatively high current efficiency, but poor in the lifetime as compared with those of examples. In addition, the devices of comparative examples are poor in uniformity of the emission surface at 70° C.

The characteristic features of the combinations in the present invention are that:

the triplet energy gap of host and the triplet energy gap of dopant are suited to improve the current efficiency;

since the material for organic EL devices is not substituted with a nitrogen-containing ring and a nitrogen atom, the light emitting material is highly resistant to holes and electrons, allowing the lifetime to be extended more than those of the combinations ever known; and the device is driven stably even at 70° C. because the thin film has good heat stability.

INDUSTRIAL APPLICABILITY

The present invention can be utilized as a high-efficiency, long-lifetime, phosphorescent organic electroluminescence device.

What is claimed is:
1. A material of formula (1):

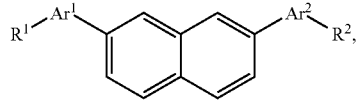

(1)

wherein,
$R^2$ represents a hydrogen atom, a benzene ring, a condensed aromatic hydrocarbon ring, a dibenzofuran ring or a group represented by $—Ar^3—R^3$;
$Ar^1$ to $Ar^2$ each independently represent a condensed aromatic hydrocarbon ring or a benzofuran ring;
$Ar^3$ represents a benzene ring, a condensed aromatic hydrocarbon ring, or a dibenzofuran ring;
$R^1$ and $R^3$ each independently represent a hydrogen atom, a benzene ring, a condensed aromatic hydrocarbon ring, or a dibenzofuran ring;
the condensed aromatic hydrocarbon ring of $R^1$ to $R^3$ and $Ar^1$ to $Ar^3$ is selected from the group consisting of a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring; and
$R^1$ to $R^3$ and $Ar^1$ to $Ar^3$ each independently optionally have one or more substituents, and the 2,7-disubstituted naphthalene ring has no other substituents;
with the proviso that:
when $Ar^1$ represents a naphthalene ring, $R^1$ cannot be a benzene ring;
when $Ar^2$ represents a naphthalene ring, $R^2$ cannot be a benzene ring;
when $Ar^2$ represents the group represented by $—Ar^3—R^3$ and $Ar^3$ represents a naphthalene ring, $R^3$ cannot be a benzene ring;
when each of $Ar^1$ and $Ar^2$ represents a condensed aromatic hydrocarbon constituted by four or more rings, $Ar^1$ and $Ar^2$ are different from each other;
when each of $R^1$ and $R^2$ represents a hydrogen atom, $Ar^1$ and $Ar^2$ cannot be a naphthalene ring; and
a material represented by any one of formulae (x-1) to (x-16) is excluded:

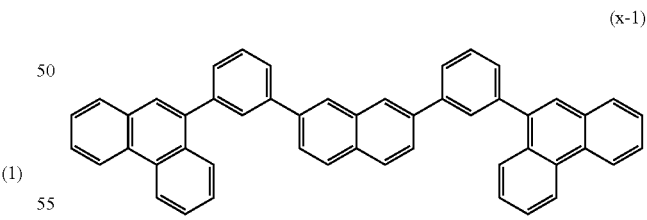

(x-1)

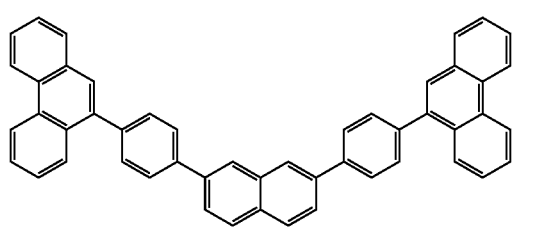

(x-2)

-continued
(x-3)
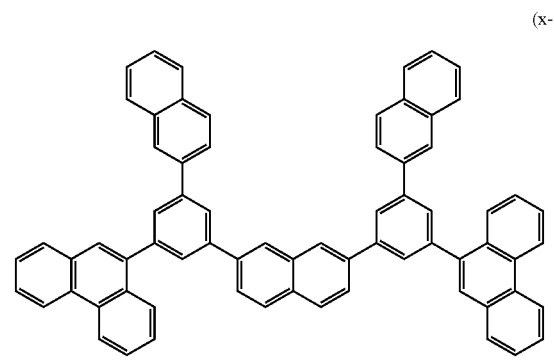
(x-4)
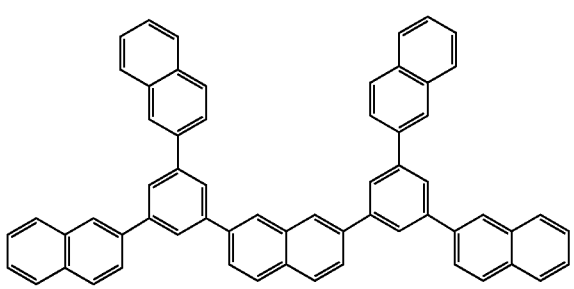
(x-5)
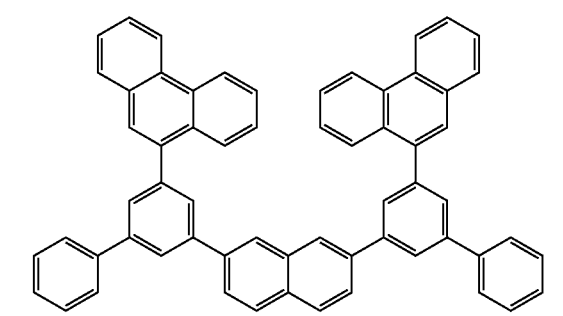
(x-6)
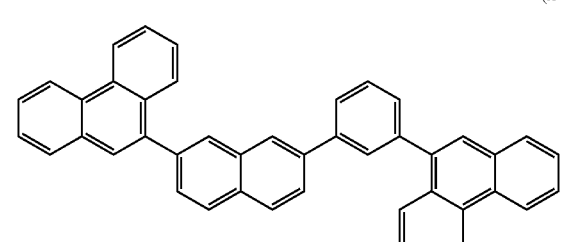
(x-7)
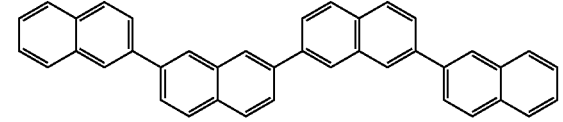
-continued
(x-8)
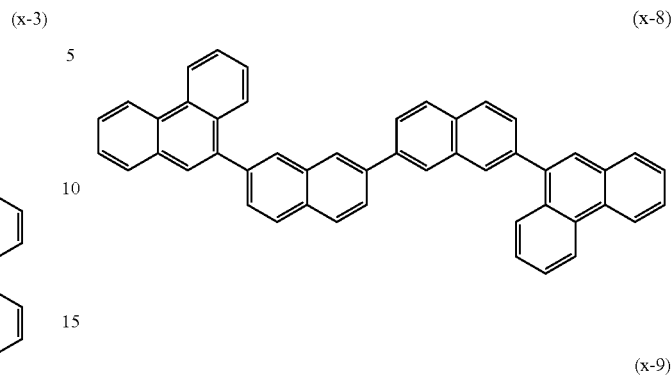
(x-9)
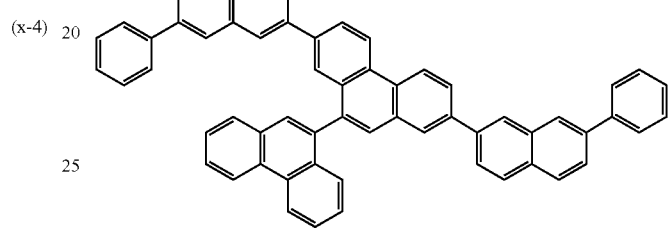
(x-10)
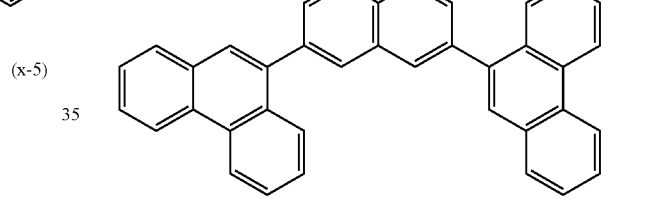
(x-11)
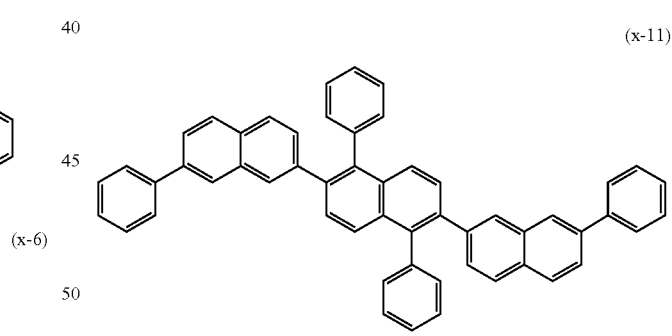
(x-12)

(x-13)
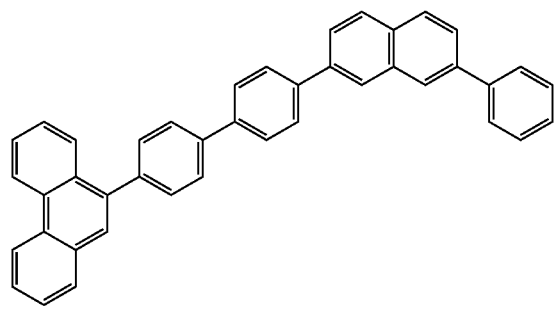

(x-14)
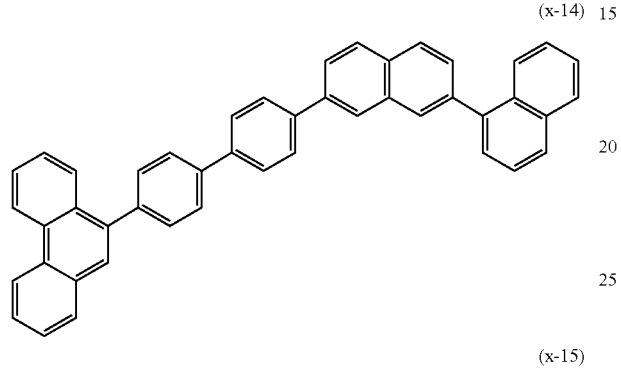

(x-15)
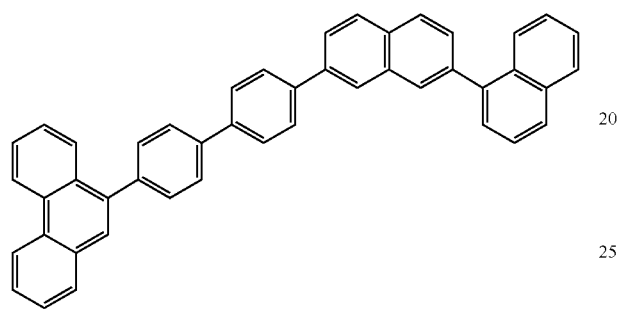

(x-16)
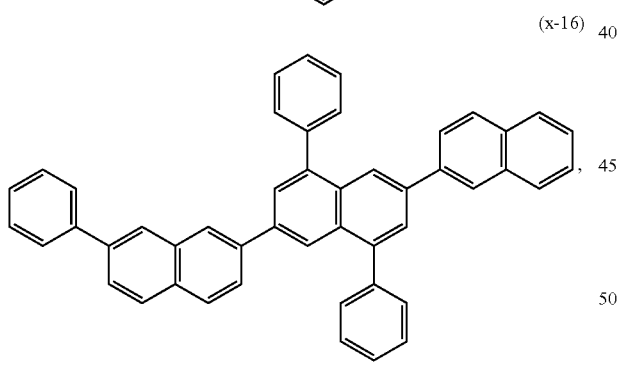

wherein the material is suitable for an organic electroluminescence device.

2. The material of claim 1, wherein the optional substituent of $R^1$ to $R^3$ and $Ar^1$ to $Ar^3$ is an aryl group having 6 to 14 carbon atoms other than an anthracene ring, an alkyl group having 1 to 20 carbon atoms, a haloalkyl group having 1 to 20 carbon atoms, a cycloalkyl group having 5 to 18 carbon atoms, or a silyl group having 3 to 20 carbon atoms.

3. The material of claim 1, wherein $Ar^1$ and $Ar^2$ each independently represent the condensed aromatic hydrocarbon ring.

4. The material of claim 3, wherein $Ar^1$ and $Ar^2$ represent condensed aromatic hydrocarbon rings different from each other.

5. A material of formula (2):

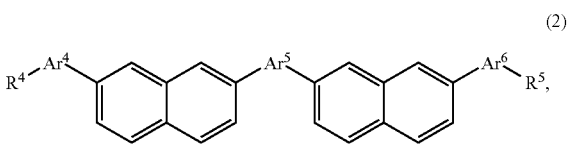
(2)

wherein $Ar^4$ and $Ar^6$ each independently represent a condensed aromatic hydrocarbon ring, or a dibenzofuran ring;

$Ar^5$ represents a benzene ring, a condensed aromatic hydrocarbon ring, or a dibenzofuran ring;

$R^4$ and $R^5$ each independently represent a hydrogen atom, a benzene ring, a condensed aromatic hydrocarbon ring, or a dibenzofuran ring;

the condensed aromatic hydrocarbon rings of $R^4$, $R^5$, and $Ar^4$ to $Ar^6$ are each independently selected from a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring;

$R^4$, $R^5$ and $Ar^4$ to $Ar^6$ optionally each independently have one or more substituents, and both 2,7-disubstituted naphthalene rings have no other substituents; and when $Ar^4$ represents a naphthalene ring, $R^4$ cannot be a benzene ring;

when $Ar^6$ represents a naphthalene ring, $R^6$ cannot be a benzene ring;

wherein the material is suitable for an electroluminescence device.

6. The material of claim 5, wherein, when $Ar^5$ of formula (2) represents a benzene ring, $Ar^4$ and $Ar^6$ each independently represent a condensed aromatic hydrocarbon ring selected from a chrysene ring, a fluoranthene ring, a benzophenanthrene ring, a dibenzophenanthrene ring, a benzotriphenylene ring, a benzochrysene ring, a benzo[b]fluoranthene ring, and a picene ring.

7. An organic electroluminescence device, comprising:
an organic thin film layer formed of one or more layers between a cathode and an anode,
wherein the organic thin film layer comprises a material for organic electroluminescence devices and at least one kind of a phosphorescent emitting material,
wherein the material is of formula (1):

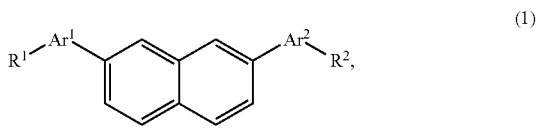
(1)

wherein $R^2$ represents a hydrogen atom, a benzene ring, a condensed aromatic hydrocarbon ring, a dibenzofuran ring or a group represented by —$Ar^3$—$R^3$;

$Ar^1$ and $Ar^2$ each independently represent a condensed aromatic hydrocarbon ring or a dibenzofuran ring;

$Ar^3$ represents a benzene ring, a condensed aromatic hydrocarbon ring, or a dibenzofuran ring;

R¹ and R³ each independently represent a hydrogen atom, a benzene ring, a condensed aromatic hydrocarbon ring, or a dibenzofuran ring;

the condensed aromatic hydrocarbon ring of R¹ to R³ and Ar¹ to Ar³ is selected from the group consisting of a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring;

R¹ to R³ and Ar¹ to Ar³ each independently optionally have one or more substituents, and the 2,7-disubstituted naphthalene ring has no other substituents; and wherein Ar¹ and Ar² represent condensed aromatic hydrocarbon rings different from each other;

with the proviso that:

when Ar¹ represents a naphthalene ring, R¹ cannot be a benzene ring;

when Ar² represents a naphthalene ring, R² cannot be a benzene ring;

when Ar² represents the group represented by —Ar³—R³ and Ar³ represents a naphthalene ring, R³ cannot be a benzene ring;

when each of Ar¹ and Ar² represents a benzene ring, R¹ and R² cannot both be a hydrogen atom or a naphthalene ring at the same time;

when each of R¹ and R² represents a hydrogen atom, one of Ar¹ and Ar² cannot be a naphthalene ring; and a material represented by any one of formulae (x-1) to (x-16) is excluded:

(x-1)

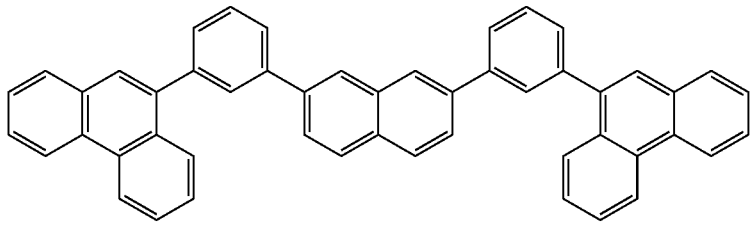

(x-2)

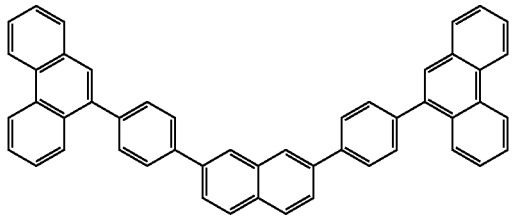

(x-3)

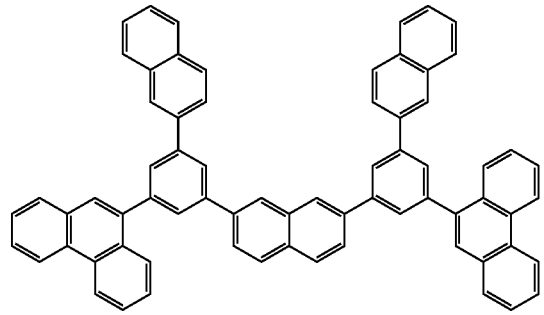

(x-4)

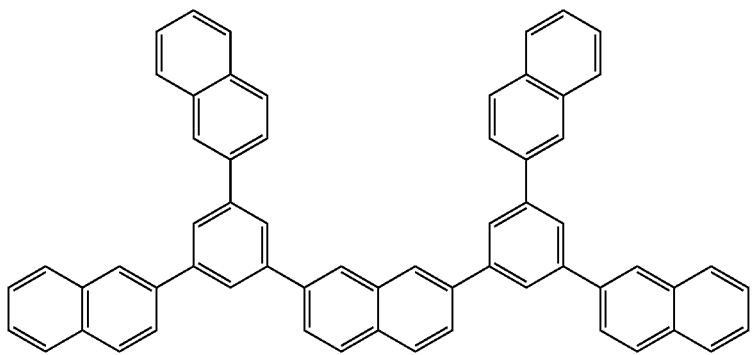

(x-5)

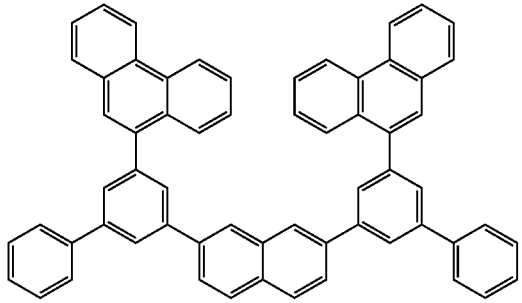

(x-6)

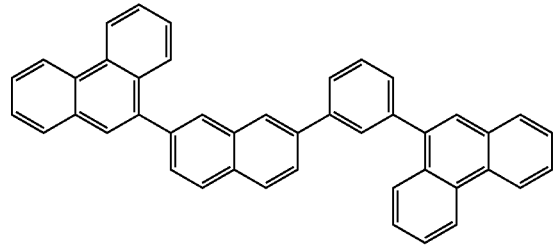

(x-7)
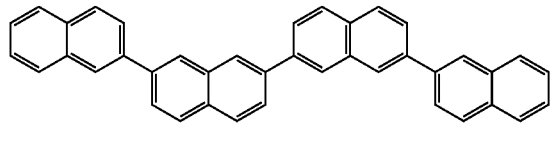
(x-8)
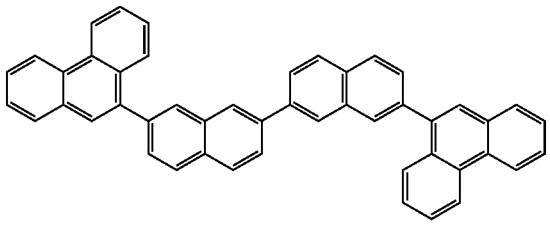
(x-9)
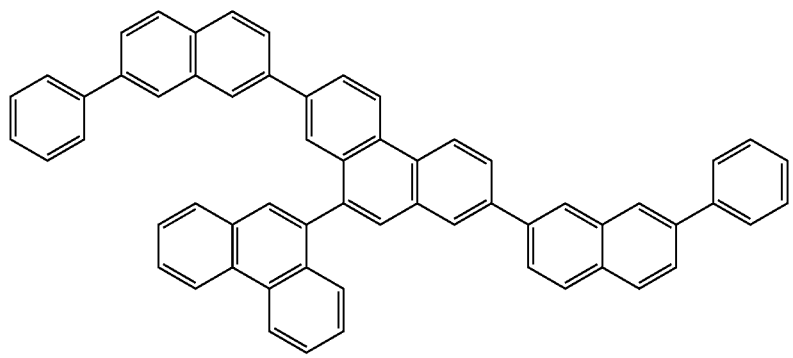
(x-10)
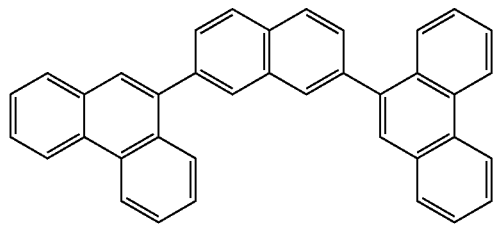
(x-11)
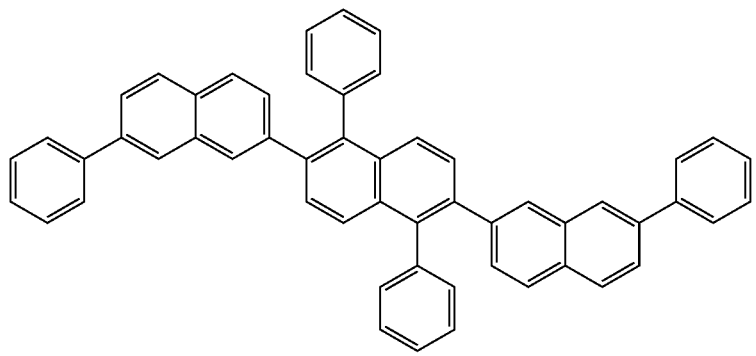
(x-12)
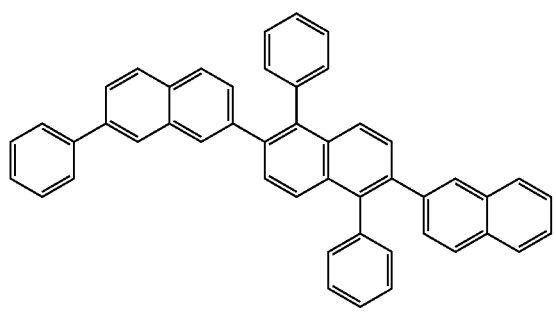
(x-13)
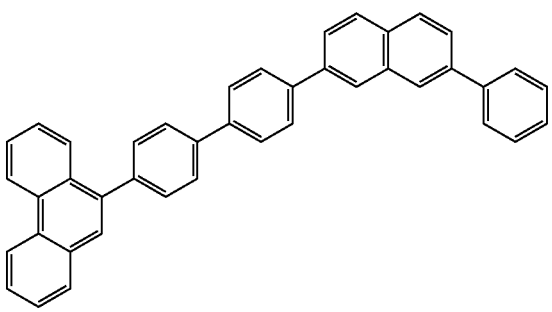

-continued

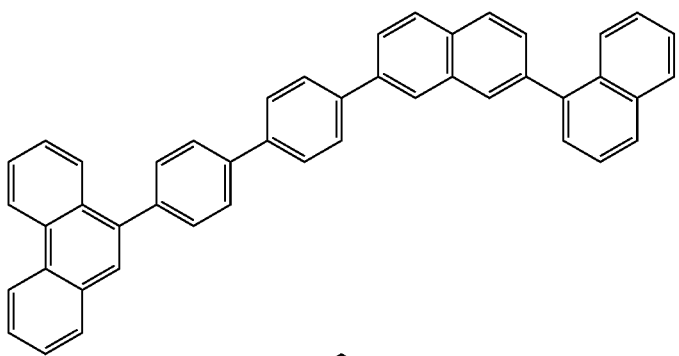
(x-14)

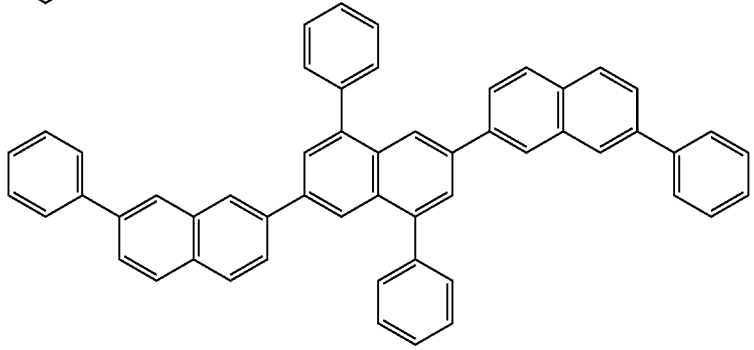
(x-15)

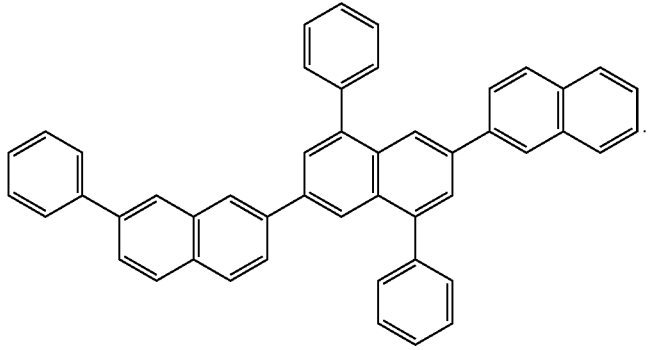
(x-16)

8. The device of claim 7, wherein the optional substituent of $R^1$ to $R^3$ and $Ar^1$ to $Ar^3$ is an aryl group having 6 to 14 carbon atoms other than an anthracene ring, an alkyl group having 1 to 20 carbon atoms, a haloalkyl group having 1 to 20 carbon atoms, a cycloalkyl group having 5 to 18 carbon atoms, or a silyl group having 3 to 20 carbon atoms.

9. The device of claim 7, wherein $Ar^1$ and $Ar^2$ each independently represent the condensed aromatic hydrocarbon ring.

10. An organic electroluminescence device, comprising:
an organic thin film layer formed of one or more layers between a cathode and an anode,
wherein the organic thin film layer comprises a material for organic electroluminescence devices and at least one kind of a phosphorescent emitting material,
wherein the material is of formula (2):

(2)

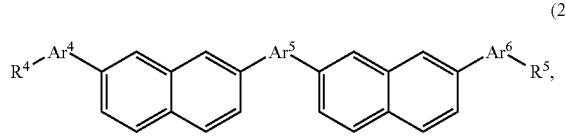

wherein
$Ar^4$ and $Ar^6$ each independently represent a condensed aromatic hydrocarbon ring, or a dibenzofuran ring;
$Ar^5$ represents a benzene ring, a condensed aromatic hydrocarbon ring, or a dibenzofuran ring;
$R^4$ and $R^5$ each independently represent a hydrogen atom, a benzene ring, a condensed aromatic hydrocarbon ring, or a dibenzofuran ring;
the condensed aromatic hydrocarbon rings represented by $R^4$, $R^5$, and $Ar^4$ to $Ar^6$ are each independently selected from a naphthalene ring, a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring, and a picene ring;
$R^4$, $R^5$ and $Ar^4$ to $Ar^6$ optionally each independently have one or more substituents, and both 2,7-disubstituted naphthalene rings have no other substituents; and
when $Ar^4$ represents a naphthalene ring, $R^4$ cannot be a benzene ring; and
when $Ar^6$ represents a naphthalene ring, $R^6$ cannot be a benzene ring.

11. The device of claim 10, wherein, when $Ar^5$ of formula (2) represents a benzene ring, $Ar^4$ and $Ar^6$ each independently represent a condensed aromatic hydrocarbon ring selected from a chrysene ring, a fluoranthene ring, a benzophenanthrene ring, a dibenzophenanthrene ring, a benzotriphenylene ring, a benzochrysene ring, a benzo[b]fluoranthene ring, and a picene ring.

12. The device of claim 7, wherein the material for organic electroluminescence devices represented by formula (1) has an excited triplet energy of 2.0 eV or more and 2.8 eV or less.

13. The device of claim 7, wherein the organic thin film layer comprises a light emitting layer, and
at least one light emitting layer comprises the material for organic electroluminescence devices represented by formula (1) and at least one phosphorescent emitting material.

14. The device of claim 13, wherein the phosphorescent emitting material comprises a metal complex, and
the metal complex comprises a metal atom selected from the group consisting of Ir, Pt, Os, Au, Cu, Re, and Ru, and a ligand.

15. The device of claim 7, wherein the organic thin film layer comprises a light emitting layer and an electron transporting layer or an electron injecting layer between the cathode and the light emitting layer, and
the electron transporting layer or the electron injecting layer comprises the materials for organic electroluminescence devices.

16. The device of claim 10, wherein the material for organic electroluminescence devices represented by formula (2) has an excited triplet energy of 2.0 eV or more and 2.8 eV or less.

17. The device of claim 10, wherein the organic thin film layer comprises a light emitting layer, and
at least one light emitting layer comprises the material for organic electroluminescence devices represented by formula (2) and at least one kind of a phosphorescent emitting material.

18. The device of claim 17, wherein the phosphorescent emitting material comprises a metal complex, and
the metal complex comprises a metal atom selected from the group consisting of Ir, Pt, Os, Au, Cu, Re, and Ru, and a ligand.

19. The device of claim 10, wherein the organic thin film layer comprises a light emitting layer and an electron transporting layer or an electron injecting layer between the cathode and the light emitting layer, and
the electron transporting layer or the electron injecting layer comprises the materials for organic electroluminescence devices.

20. The material of claim 1, wherein $Ar^1$ and $Ar^2$ each independently represent the condensed aromatic hydrocarbon ring selected from the group consisting of a chrysene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring and a picene ring.

21. The material of claim 1, wherein $Ar^1$ represents a phenanthrene ring and $Ar^e$ represents a fluoranthene ring.

22. The device of claim 7, wherein $Ar^1$ and $Ar^2$ each independently represent a dibenzofuran ring or the condensed aromatic hydrocarbon ring selected from
the group consisting of a chrysene ring, a fluoranthene ring, a triphenylene ring, a phenanthrene ring, a benzophenanthrene ring, a dibenoqphenanthrene ring, a benzotriphenylene ring, a benzochrysene ring, a benzo[b]fluoranthene ring and a picene ring.

23. The device of claim 7, wherein $Ar^1$ represents a phenanthrene ring and $Ar^2$ represents a fluoranthene ring.

24. The material of claim 5, wherein $Ar^4$ and $Ar^6$ each independently represent the condensed aromatic hydrocarbon ring selected from the group consisting of a chrysene ring, a flopranthene ring, a triphenylene ring, a phenanthrene ring, a benzophenanthrene ring, a dibenzophenanthrene ring, a benzotriphenylene ring, a benzochrysene ring, a benzo[b]fluoranthene ring and a picene ring.

25. The material of claim 5, wherein $Ar^4$ represents a phenanthrene ring and $Ar^6$ represents a fluoranthene ring.

26. The device of claim 10, wherein $Ar^4$ and $Ar^6$ each independently represent the condensed aromatic hydrocarbon ring selected from the group consisting of a chrvsene ring, a fluoranthene ring, a triphenylene ring, a phenanthrene ring, a benzophenanthrene ring, a dibenzophenanthrene ring, a benzotriphenylene ring, a benzochrysene ring, a benzo[b]fluoranthene ring and a picene ring.

27. The device of claim 10, wherein $Ar^4$ represents a phenanthrene ring and $Ar^6$ represents a fluoranthene ring.

* * * * *